US012060331B2

(12) United States Patent
Ling et al.

(10) Patent No.: US 12,060,331 B2
(45) Date of Patent: Aug. 13, 2024

(54) HERBICIDAL COMPOUNDS

(71) Applicant: SYNGENTA PARTICIPATIONS AG, Basel (CH)

(72) Inventors: Kenneth Bruce Ling, Bracknell (GB); Christopher John Mathews, Bracknell (GB); Timothy Jeremiah Cornelius O'Riordan, Bracknell (GB); Stephen Edward Shanahan, Bracknell (GB); Joseph Andrew Tate, Bracknell (GB); Christiana Kitsiou, Bracknell (GB); Peter Timothy Seden, Bracknell (GB)

(73) Assignee: SYNGENTA PARTICIPATIONS AG, Basel (CH)

( * ) Notice: Subject to any disclaimer, the term of this patent is extended or adjusted under 35 U.S.C. 154(b) by 1070 days.

(21) Appl. No.: 16/960,980

(22) PCT Filed: Jan. 4, 2019

(86) PCT No.: PCT/EP2019/050140
§ 371 (c)(1),
(2) Date: Jul. 9, 2020

(87) PCT Pub. No.: WO2019/137851
PCT Pub. Date: Jul. 18, 2019

(65) Prior Publication Data
US 2021/0009530 A1 Jan. 14, 2021

(30) Foreign Application Priority Data
Jan. 9, 2018 (GB) ..................................... 1800305

(51) Int. Cl.
*C07D 237/04* (2006.01)
*A01N 43/58* (2006.01)
*A01N 43/78* (2006.01)
*C07D 237/16* (2006.01)
*C07D 401/10* (2006.01)
*C07D 403/10* (2006.01)
*C07D 409/10* (2006.01)
*C07D 417/10* (2006.01)

(52) U.S. Cl.
CPC ........... *C07D 237/04* (2013.01); *A01N 43/58* (2013.01); *A01N 43/78* (2013.01); *C07D 237/16* (2013.01); *C07D 401/10* (2013.01); *C07D 403/10* (2013.01); *C07D 409/10* (2013.01); *C07D 417/10* (2013.01)

(58) Field of Classification Search
None
See application file for complete search history.

(56) References Cited

U.S. PATENT DOCUMENTS

| 8,188,008 | B2 | 5/2012 | Lehr et al. |
| 9,029,295 | B2 | 5/2015 | Kuragano et al. |
| 9,944,608 | B2 | 4/2018 | Shanahan et al. |
| 2022/0119353 | A1* | 4/2022 | Ling ................... C07D 401/10 |
| 2022/0281827 | A1* | 9/2022 | Ling ..................... A01N 25/32 |
| 2022/0281837 | A1* | 9/2022 | Ling ..................... A01N 43/58 |

FOREIGN PATENT DOCUMENTS

| CN | 106536486 | A | 3/2017 |
| JP | 2012149044 | A | 8/2012 |
| JP | 2017522318 | A | 8/2017 |
| WO | 2009035150 | A2 | 3/2009 |
| WO | 2009086041 | A1 | 7/2009 |
| WO | 2010069525 | A1 | 6/2010 |
| WO | 2011045271 | A1 | 4/2011 |
| WO | 2012091156 | A1 | 7/2012 |
| WO | 2013160126 | A1 | 10/2013 |
| WO | 2016008816 | A1 | 1/2016 |
| WO | 2016174072 | A1 | 11/2016 |

OTHER PUBLICATIONS

International Search Report and Written Opinion of the International Searching Authority issued in International Patent Application No. PCT/EP2019/050140 dated Feb. 14, 2019.

* cited by examiner

*Primary Examiner* — John Pak
(74) *Attorney, Agent, or Firm* — BakerHostetler; Toni-Junell Herbert

(57) ABSTRACT

The present invention relates to herbicidal substituted phenyl-pyridazine-diones and substituted phenyl-pyridazinone derivatives of formula (I), as well as to processes and intermediates used for the preparation of such derivatives. The invention further extends to herbicidal compositions comprising such derivatives, as well as to the use of such compounds and compositions in controlling undesirable plant growth: in particular the use in controlling weeds, such as broad-leaved dicotyledonous weeds, in crops of useful plants.

19 Claims, No Drawings

HERBICIDAL COMPOUNDS

CROSS-REFERENCE TO RELATED APPLICATIONS

This application is a 371 National Stage application of International Application No. PCT/EP2019/050140 filed Jan. 4, 2019, which claims priority to GB 1800305.3 filed Jan. 9, 2018, the entire contents of which applications are hereby incorporated by reference.

The present invention relates to herbicidal substituted phenyl-pyridazine-diones and substituted phenyl-pyridazinone derivatives of formula (I), as well as to processes and intermediates used for the preparation of such derivatives. The invention further extends to herbicidal compositions comprising such derivatives, as well as to the use of such compounds and compositions in controlling undesirable plant growth: in particular the use in controlling weeds, such as broad-leaved dicotyledonous weeds, in crops of useful plants.

Herbicidal pyridazinones are known from WO2009/086041. In addition, herbicidal 5/6 membered heterocyclyl-substituted pyridazinones are known from WO 2011/045271. Whilst WO2013/160126 describes indolyl-pyridazinone derivatives, which exhibit herbicidal activity.

The present invention is based on the finding substituted phenyl-pyridazine-diones and substituted phenyl-pyridazinone derivatives of formula (I), exhibit surprisingly good herbicidal activity.

Thus, in a first aspect there is provided a compound of formula (I)

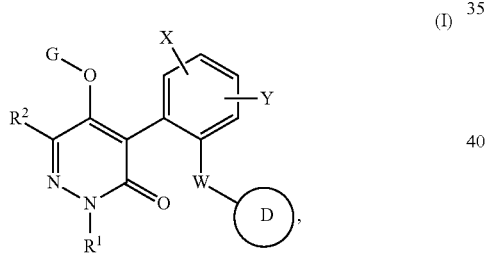

(I)

or a salt or N-oxide thereof, wherein $R^1$ is selected from the group consisting of $C_1$-$C_4$ alkyl, $C_3$-$C_6$cycloalkyl, $C_3$-$C_6$alkoxy, $C_1$-$C_2$alkoxy-$C_1$-$C_2$ alkyl, $C_2$-$C_4$ alkenyl, $C_1$-$C_4$ haloalkyl, cyano-$C_1$-$C_4$alkyl, $C_2$-$C_4$ haloalkenyl, $C_2$-$C_4$ alkynyl and $C_2$-$C_4$ haloalkynyl;

$R^2$ is selected from the group consisting of hydrogen, halogen, cyano, $C_1$-$C_6$alkyl, $C_1$-$C_6$haloalkyl, $C_1$-$C_6$haloalkoxy, $C_1$-$C_3$haloalkoxy-$C_1$-$C_3$alkyl-, $C_1$-$C_6$alkoxy, $C_1$-$C_3$alkoxy-$C_1$-$C_3$alkyl, $C_1$-$C_3$alkoxy-$C_1$-$C_3$alkoxy-$C_1$-$C_3$alkyl-, $C_3$-$C_6$cycloalkyl, $C_2$-$C_6$ alkenyl, $C_2$-$C_6$ haloalkenyl, $C_2$-$C_6$ alkynyl, $C_1$-$C_6$hydroxyalkyl-, —$C_1$-$C_6$alkylcarbonyl-, —$S(O)_m C_1$-$C_6$alkyl, amino, —$C_1$-$C_6$alkylamino, $C_1$-$C_6$dialkylamino, —$C(C_1$-$C_3$alkyl)=N—O—$C_1$-$C_3$alkyl and $C_2$-$C_6$ haloalkynyl;

G is hydrogen, or $C(O)R^3$;

$R^3$ is selected from the group consisting of $C_1$-$C_6$alkyl, $C_2$-$C_6$alkenyl, $C_2$-$C_6$alkynyl, $C_1$-$C_6$alkyl-S—, $C_1$-$C_6$alkoxy, —$NR^4R^5$ and phenyl optionally substituted by one or more $R^6$;

$R^4$ and $R^5$ are independently selected from the group consisting of $C_1$-$C_6$ alkyl and $C_1$-$C_6$ alkoxy, or $R^4$ and $R^5$ together can form a morpholinyl ring;

$R^6$ is selected from the group consisting of halogen, cyano, nitro, $C_1$-$C_3$alkyl, $C_1$-$C_3$haloalkyl, $C_1$-$C_3$alkoxy and $C_1$-$C_3$haloalkoxy, X and Y are each independently hydrogen, $C_1$-$C_3$ alkyl, $C_1$-$C_3$ alkoxy, $C_1$-$C_3$haloalkyl, $C_1$-$C_3$haloalkoxy, or halogen;

D is a substituted or unsubstituted monocyclic heteroaryl ring containing 1, 2, or 3 heteroatoms independently selected from oxygen, nitrogen and sulphur, and wherein when D is substituted it is substituted on at least one ring carbon atom with $R^8$ and/or on a ring nitrogen atom with $R^9$;

each $R^8$ is independently oxygen, hydroxyl, halogen, cyano, $C_1$-$C_6$alkyl, $C_1$-$C_6$haloalkyl, $C_1$-$C_6$haloalkoxy, $C_1$-$C_3$haloalkoxy-$C_1$-$C_3$alkyl-, $C_1$-$C_6$alkoxy, $C_1$-$C_3$alkoxy-$C_1$-$C_3$alkyl, $C_1$-$C_3$alkoxy-$C_1$-$C_3$alkoxy-$C_1$-$C_3$alkyl-, $C_3$-$C_6$cycloalkyl, $C_2$-$C_6$ alkenyl, $C_2$-$C_6$ haloalkenyl, $C_2$-$C_6$ alkynyl, $C_1$-$C_6$hydroxyalkyl-, $C_1$-$C_6$alkylcarbonyl-, $C_1$-$C_6$alkyl-$S(O)_m$—, amino, $C_1$-$C_6$alkylamino, $C_1$-$C_6$dialkylamino, —$C(C_1$-$C_3$alkyl)=N—O—$C_1$-$C_3$alkyl and $C_2$-$C_6$ haloalkynyl;

m is an integer of 0, 1, or 2; and each $R^9$ is independently, $C_1$-$C_4$ alkyl, $C_3$-$C_6$alkoxy, $C_1$-$C_2$alkoxy-$C_1$-$C_2$ alkyl, $C_2$-$C_4$ alkenyl, $C_1$-$C_4$ haloalkyl, $C_2$-$C_4$ haloalkenyl, $C_2$-$C_4$ alkynyl or $C_2$-$C_4$ haloalkynyl;

or D is a substituted or unsubstituted phenyl ring (Dp),

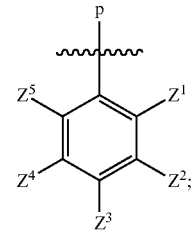

(Dp)

wherein p denotes the point of attachment of (Dp) to the rest of the molecule;

$Z^1$, $Z^2$, $Z^3$, $Z^4$, and $Z^5$ are each independently selected from the group consisting of hydrogen, cyano, amino, $C_1$-$C_3$-dialkylamino, hydroxy, $C_1$-$C_3$ alkyl, $C_1$-$C_4$ alkoxy, $C_1$-$C_3$haloalkyl, $C_1$-$C_3$haloalkoxy, and halogen;

and

W is either

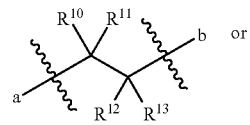

W1 or

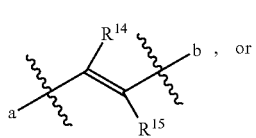

W2

-continued

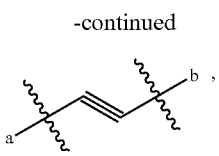

wherein
"a" denotes the point of attachment to the phenyl-pyridazinone/phenyl-pyridazine dione moiety,
"b" denotes the point of attachment to ring D,
$R^{10}$, $R^{12}$, $R^{14}$ and $R^{15}$ are each independently hydrogen, $C_1$-$C_3$alkyl, or $C_1$-$C_3$haloalkyl; or $R^{10}$ and $R^{12}$ together with the carbon atoms to which they are joined form a $C_3$-$C_6$ carbocyclic ring;
$R^{11}$ and $R^{13}$ are each independently hydrogen, halogen, $C_1$-$C_3$alkyl, or $C_1$-$C_3$haloalkyl, provided that when one of $R^{11}$ or $R^{13}$ is halogen, $C_1$-$C_3$alkyl or $C_1$-$C_3$ haloalkyl, the other is hydrogen.

Compounds of Formula (I) may contain asymmetric centres and may be present as a single enantiomer, pairs of enantiomers in any proportion or, where more than one asymmetric centre are present, contain diastereoisomers in all possible ratios. Typically one of the enantiomers has enhanced biological activity compared to the other possibilities.

Similarly, where there are di-substituted alkenes, these may be present in E or Z form or as mixtures of both in any proportion.

Furthermore, compounds of formula (I) may be in equilibrium with alternative tautomeric forms. For example, a compound of formula (I-i), i.e. a compound of formula (I) wherein $R^2$ is hydrogen and G is hydrogen, can be drawn in at least three tautomeric forms:

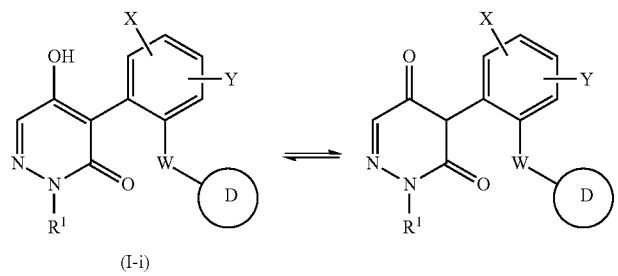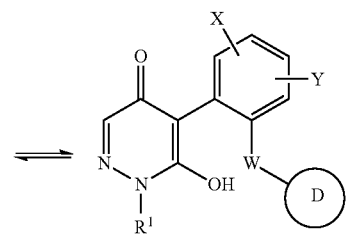

(I-i)

It should be appreciated that all tautomeric forms (single tautomer or mixtures thereof), racemic mixtures and single isomers are included within the scope of the present invention.

Each alkyl moiety either alone or as part of a larger group (such as alkoxy, alkylthio, alkoxycarbonyl, alkylcarbonyl, alkylaminocarbonyl, or dialkylaminocarbonyl, et al.) may be straight-chained or branched. Typically, the alkyl is, for example, methyl, ethyl, n-propyl, isopropyl, n-butyl, sec-butyl, isobutyl, tert-butyl, n-pentyl, neopentyl, or n-hexyl. The alkyl groups are generally $C_1$-$C_6$alkyl groups (except where already defined more narrowly), but are preferably $C_1$-$C_4$alkyl or $C_1$-$C_3$alkyl groups, and, more preferably, are $C_1$-$C_2$alkyl groups (such as methyl).

Alkenyl and alkynyl moieties can be in the form of straight or branched chains, and the alkenyl moieties, where appropriate, can be of either the (E)- or (Z)-configuration. The alkenyl or alkynyl moieties are typically $C_2$-$C_4$alkenyl or $C_2$-$C_4$alkynyl, more specifically vinyl, allyl, ethynyl, propargyl or prop-1-ynyl. Alkenyl and alkynyl moieties can contain one or more double and/or triple bonds in any combination; but preferably contain only one double bond (for alkenyl) or only one triple bond (for alkynyl).

Preferably, the term cycloalkyl refers to cyclopropyl, cyclobutyl, cyclopentyl or cyclohexyl.

In the context of the present specification the term "aryl" preferably means phenyl. The term "heteroaryl" as used herein means an aromatic ring system containing at least one ring heteroatom and consists of a single ring. Preferably, single rings will contain 1, 2 or 3 ring heteroatoms selected independently from nitrogen, oxygen and sulfur. Typically "heteroaryl" is furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, or 1,3,5-triazinyl.

Heterocyclyl groups and heterocyclic rings (either alone or as part of a larger group, such as heterocyclyl-alkyl-) are ring systems containing at least one heteroatom and can be in mono- or bi-cyclic form. Preferably, heterocyclyl groups will contain up to two heteroatoms which will preferably be chosen from nitrogen, oxygen and sulfur. Examples of heterocyclic groups include oxetanyl, thietanyl, azetidinyl and 7-oxa-bicyclo[2.2.1]hept-2-yl. Heterocyclyl groups containing a single oxygen atom as heteroatom are most preferred. The heterocyclyl groups are preferably 3- to 8-membered, more preferably 3- to 6-membered rings.

Halogen (or halo) encompasses fluorine, chlorine, bromine or iodine. The same correspondingly applies to halogen in the context of other definitions, such as haloalkyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or a pentyloxy or hexyloxy isomer, preferably methoxy and ethoxy. It should also be appreciated that two alkoxy substituents may be present on the same carbon atom.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

$C_1$-$C_6$alkyl-S— (alkylthio) is, for example, methylthio, ethylthio, propylthio, isopropylthio, n-butylthio, isobutylthio, sec-butylthio or tert-butylthio, preferably methylthio or ethylthio.

$C_1$-$C_6$alkyl-S(O)— (alkylsulfinyl) is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_6$alkyl-S(O)$_2$— (alkylsulfonyl) is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

The group Q

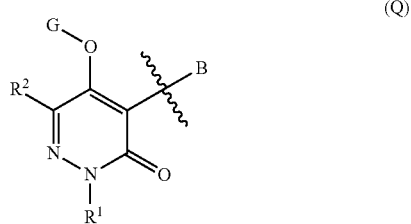

(Q)

is referred to herein as the pyridazine dione/pyridazinone moiety, wherein B denotes the point of attachment to the rest of the molecule (i.e. to the optionally substituted phenyl-W-D moiety).

The present invention also includes agronomically acceptable salts that the compounds of formula (I) may form with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used. The compounds of formula (I) according to the invention also include hydrates which may be formed during the salt formation.

Preferred values of $R^1$, $R^2$, $R^3$, $R^4$, $R^5$, $R^6$, $R^8$, $R^9$, $R^{10}$, $R^{11}$, $R^{12}$, $R^{13}$, $R^{14}$, $R^{15}$, W, D, Dp, G, X, Y, $Z^1$, $Z^2$, $Z^3$, $Z^4$, $Z^5$, and m are as set out below, and a compound of formula (I) according to the invention may comprise any combination of said values. The skilled man will appreciate that values for any specified set of embodiments may combined with values for any other set of embodiments where such combinations are not mutually exclusive.

Preferably $R^1$ is selected from the group consisting of methyl, ethyl, propyl (in particular n- or c-propyl), propargyl or $C_1$haloalkyl. More preferably $R^1$ is methyl, ethyl, cyclopropyl, propargyl or $C_1$fluoroalkyl. More preferably still $R^1$ is methyl, ethyl, cyclopropyl or propargyl.

Preferably $R^2$ is selected from the group consisting of hydrogen, $C_1$-$C_6$alkyl, $C_1$-$C_6$haloalkyl, $C_1$-$C_6$alkoxy, $C_1$-$C_3$alkoxy-$C_1$-$C_3$alkyl, $C_3$-$C_6$cycloalkyl, $C_2$-$C_0$ alkenyl, $C_2$-$C_6$ haloalkenyl, $C_2$-$C_6$ alkynyl and $C_2$-$C_6$ haloalkynyl. More preferably $R^2$ is selected from the group consisting of methyl, ethyl, cyclopropyl, trifluoromethyl and methoxymethyl, more preferably still cyclopropyl, trifluoromethyl or methyl, most preferably cyclopropyl or methyl. In one set of embodiments of the present invention $R^2$ is hydrogen. In a further set of embodiments $R^2$ is cyclopropyl, in a third set of embodiments $R^2$ is methyl, and in a fourth set of embodiments $R^2$ is trifluoromethyl.

As described herein, G may be hydrogen or —C(O)—$R^3$, and $R^3$ is selected from the group consisting of $C_1$-$C_6$alkyl, $C_2$-$C_6$alkenyl, $C_2$-$C_6$alkynyl, $C_1$-$C_6$alkyl-S—, $C_1$-$C_6$alkoxy, —NR$^4$R$^5$ and phenyl optionally substituted by one or more $R^6$. As defined herein, $R^4$ and $R^5$ are independently selected from the group consisting of $C_1$-$C_6$ alkyl, $C_1$-$C_6$ alkoxy-; or they can together form a morpholinyl ring. Preferably $R^4$ and $R^5$ are each independently selected from the group consisting of methyl, ethyl, propyl, methoxy, ethoxy and propoxy. $R^6$ is selected from the group consisting of halogen, cyano, nitro, $C_1$-$C_3$alkyl, $C_1$-$C_3$haloalkyl, $C_1$-$C_3$alkoxy and $C_1$-$C_3$haloalkoxy.

Preferably $R^3$ is $C_1$-$C_4$ alkyl, $C_2$-$C_3$alkenyl, $C_2$-$C_3$alkynyl, —$C_1$-$C_4$alkoxy, —NR$^4$R$^5$ wherein $R^4$ and $R^5$ together form a morpholinyl ring, or phenyl. More preferably $R^3$ is isopropyl, t-butyl, methyl, ethyl, propargyl, tert-butoxy or methoxy. More preferably $R^3$ is isopropyl, t-butyl, methyl, ethyl, propargyl, or methoxy.

In one set of embodiments G is hydrogen or —C(O)—$R^3$, wherein $R^3$ is $C_1$-$C_4$ alkyl, $C_2$-$C_3$alkenyl, $C_2$-$C_3$alkynyl or —$C_1$-$C_4$alkoxy. In a further set of embodiments G is hydrogen or —C(O)—$R^3$, wherein $R^3$ is isopropyl, t-butyl, methyl, ethyl, propargyl or methoxy. However, it is particularly preferred that G is hydrogen, or —C(O)—$R^3$ wherein $R^3$ is isopropyl.

X is preferably hydrogen, halogen, or $C_1$haloalkyl, more preferably hydrogen, fluoro, chloro, bromo, or $C_1$fluoroalkyl and more preferably still, hydrogen, fluoro, chloro or trifluoromethyl. In one set of embodiments it is preferred that X is ortho with respect to the pyridazinone/pyridazine-dione moiety (group Q). It is particularly preferred that X is fluoro, chloro or $C_1$-haloalkyl (in particular $C_1$fluoroalkyl) and is ortho with respect to pyridazinone/pyridazine-dione moiety (group Q).

Y is preferably hydrogen, $C_1$-$C_3$ alkyl, $C_1$-$C_3$haloalkyl, or halogen. More preferably Y is hydrogen, chloro, fluoro, or bromo.

In one set of embodiments it is preferred that Y is ortho with respect to the —W-D moiety. In a further set of embodiments, Y is para with respect to the pyridazinone/pyridazine-dione moiety (group Q).

It is particularly preferred that Y is ortho with respect to the —W-D moiety and is halogen, in particular chloro or fluoro; more preferably chloro.

As described herein, D is an substituted or unsubstituted phenyl ring (Dp) or is a substituted or unsubstituted 5- or 6-membered monocyclic heteroaryl ring containing 1, 2, or 3 heteroatoms independently selected from oxygen, nitrogen and sulphur, and wherein when D is a substituted heteroaryl ring it is substituted on at least one ring carbon atom with $R^8$ and/or on a ring nitrogen atom with $R^9$. Where D is a substituted or unsubstituted 5- or 6-membered monocyclic heteroaryl ring, it is preferably a substituted (as described herein) or unsubstituted furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyridonyl, pyrimidinyl, pyridazinyl, pyrazinyl, 1,2,3-triazinyl, 1,2,4-triazinyl, or 1,3,5-triazinyl ring.

In such embodiments, D is preferably a substituted (as described herein) or unsubstituted pyridyl, pyrazolyl, thiazolyl, pyrimidinyl, thienyl, triazolyl or oxadiazolyl ring, and more preferably a pyridyl ring.

In one set of embodiments, D is a substituted (as described herein) or unsubstituted pyrazolyl, imidazolyl, oxazolyl, isoxazolyl, thiazolyl, isothiazolyl, pyridyl, pyridonyl, pyrimidinyl, pyridazinyl, or pyrazinyl ring.

In a further set of such embodiments, D is a substituted (as described herein) or unsubstituted, oxazolyl, thiazolyl, or, pyridyl, ring. In certain embodiments, D is a substituted or unsubstituted pyridyl-, or substituted or unsubstituted thiazolyl ring.

Where D is substituted, it is preferably substituted by 1 or 2 $R^8$ and/or 1 $R^9$, more preferably by 1 or 2 $R^8$. Where D is a 5-membered substituted heteroaryl ring, it is most preferably substituted by 1 $R^8$.

Preferably, each $R^8$ is independently oxo, $C_1$-$C_4$alkyl, $C_1$-$C_4$haloalkyl, halogen, cyano, amino, —NHC(O)CH$_3$, hydroxyl, $C_1$-$C_4$alkoxy, or $C_1$-$C_4$alkylthio. More preferably each $R^8$ is independently oxo, $C_1$-$C_4$alkyl, $C_1$-$C_4$haloalkyl, halogen, cyano, hydroxyl, $C_1$-$C_4$alkoxy, or $C_1$-$C_4$alkylthio, most preferably each $R^8$ is independently halogen, or $C_1$-$C_4$haloalkyl.

Preferably each $R^9$ is independently $C_1$-$C_4$alkyl, $C_1$-$C_4$haloalkyl, hydroxyl, $C_1$-$C_4$alkoxy, or $C_1$-$C_4$alkylthio.

In particular embodiments where D is a substituted or unsubstituted 5- or 6-membered monocyclic heteroaryl ring as described above, D is selected from the group consisting of 4-chloro-3-pyridyl, 4-trifluoromethylpyridyl, 3-pyridyl, and 2-chloro-thiazo-5-yl, 2-chloro-3-pyridyl, 3-chloro-4-pyridyl, 1-methyl-3-(trifluoromethyl)-pyrazol-4-yl, thiazol-2-yl, thiazol-5-yl, pyrimidin-5-yl, 4-(tert-butoxy)phenyl, 2-chloro-4-pyridyl, 2-methyl-4-pyridyl, 2-trifluoromethyl-4-pyridyl, 4-pyridyl, 2-amino-4-pyridyl, thiophen-3-yl, 1-methyl-pyrazol-4-yl, 2-methyl-triazol-4-yl, 5-methyl-1,3,4-oxadiazol-2-yl, 5-methyl-3-pyridyl, 5-methyl-2-pyridyl, 6-methyl-2-pyridyl, 3-methyl-2-pyridyl, 6-choro-3-pyridyl, 3-trifluoromethyl-3-pyridyl, 4-methyl-2-pyridyl, 2-acetamidothiazol-5-yl, 2-fluoro-4-pyridyl, and 2-trifluoromethyl-3-pyridyl. In a subset of these embodiments D is selected from the group consisting of 4-chloro-3-pyridyl, 4-trifluoromethylpyridyl, 3-pyridyl, and 2-chloro-thiazo-5-yl, 2-chloro-3-pyridyl, 3-chloro-4-pyridyl, 1-methyl-3-(trifluoromethyl)-pyrazol-4-yl, thiazol-2-yl, thiazol-5-yl, pyrimidin-5-yl, 4-(tert-butoxy)phenyl, 2-chloro-4-pyridyl, 2-methyl-4-pyridyl, 2-trifluoromethyl-4-pyridyl, 4-pyridyl, thiophen-3-yl, 5-methyl-3-pyridyl, 5-methyl-2-pyridyl, 6-methyl-2-pyridyl, 3-trifluoromethyl-3-pyridyl, 2-fluoro-4-pyridyl, and 2-trifluoromethyl-3-pyridyl. In a further subset of these embodiments, D is selected from the group consisting of 4-chloro-3-pyridyl, 4-trifluoromethylpyridyl, 3-pyridyl, and 2-chloro-thiazo-5-yl.

However, as also stated above D may alternatively be a substituted or unsubstituted phenyl ring (Dp)

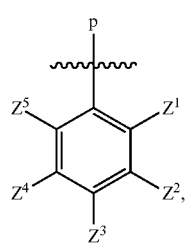
(Dp)

wherein $Z^1$, $Z^2$, $Z^3$, $Z^4$, and $Z^5$ are each independently selected from the group consisting of hydrogen, cyano, amino, $C_1$-$C_3$ dialkylamino, hydroxy, $C_1$-$C_3$ alkyl, $C_1$-$C_4$ alkoxy, $C_1$-$C_3$haloalkyl, $C_1$-$C_3$haloalkoxy, and halogen, and p is the point of attachment to the rest of the molecule.

In one set of embodiments, $Z^1$, $Z^2$, $Z^3$, $Z^4$, and $Z^5$ are each independently selected from hydrogen, cyano, $C_1$-$C_3$ alkyl, $C_1$-$C_4$ alkoxy, $C_1$-$C_3$haloalkyl, $C_1$-$C_3$haloalkoxy, or halogen. Preferably $Z^1$, $Z^2$, $Z^3$, $Z^4$, and $Z^5$ are each independently selected from hydrogen, cyano, halogen (in particular chloro or fluoro), methyl, methoxy, and trifluoromethyl.

In yet another set of embodiments each of $Z^1$, $Z^2$, $Z^4$, and $Z^5$ are hydrogen, and $Z^3$ is not hydrogen. Preferably in this set of embodiments, $Z^3$ is halogen, more preferably chloro.

In a further set of embodiments still, each of $Z^1$, $Z^4$ and $Z^5$ are hydrogen, and $Z^2$ and $Z^3$ are not hydrogen. In this set of embodiments it is particularly preferred that $Z^2$ and $Z^3$ are each independently halogen, and more preferred that $Z^2$ and $Z^3$ are both chloro.

In one particularly preferred set of embodiments $Z^1$, $Z^2$, $Z^3$, $Z^4$ and $Z^5$ all carry hydrogen.

In further embodiments, where D is Dp, Dp is selected from the group consisting of 4-chloro-phenyl, 4-trifluoromethyl-phenyl, 4-cyanophenyl, 4-fluoro-phenyl, 3,4-difluoro-phenyl, 2-trifluoromethyl-phenyl and 4-tolyl.

W acts as a linker moiety, linking ring D to the rest of the molecule (i.e. to the phenyl-pyridazinone/phenyl-pyridazine dione moiety). Compounds of formula (I) wherein the linker is W1 are herbicidal, whereas compounds of formula (I) wherein the linker is W2 may be not only herbicidal, but also useful intermediates in the production of compounds of formula (I) bearing W1 linkers. Thus, in one set of embodiments, W is W1, whereas in a second set of embodiments, W is W2. In a third set of embodiments, W is —C≡C—.

Preferably $R^{10}$, $R^{11}$, $R^{12}$ and $R^{13}$ are each independently selected from hydrogen or $C_1$-$C_3$ alkyl. In one set of embodiments $R^{10}$, $R^{11}$, $R^{12}$, and $R^{13}$ are all hydrogen.

Preferably $R^{14}$ and $R^{15}$ are each independently selected from hydrogen or $C_1$-$C_3$alkyl. In one set of embodiments $R^{14}$ and $R^{15}$ are both hydrogen.

Specific examples of W include —CH$_2$—CH$_2$—, and —CH═CH—, cis

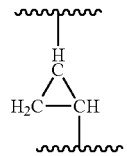

and trans

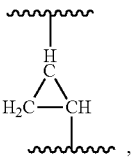

and —C≡C—. In more preferred embodiments W is either —CH$_2$—CH$_2$—, or —CH═CH— (in particular (E) —CH═CH—), more preferably still —CH$_2$—CH$_2$—.

Table 1 below provides 1656 specific examples of compounds of formula (I) of the invention.

TABLE 1

Herbicidal compounds of the present invention. The numbering system used to describe the
positions of X and Y is shown for the purposes of clarity only.

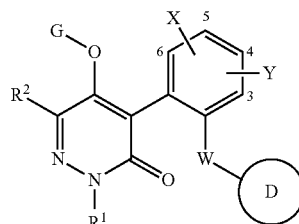

(I)

| Cmpd. No. | R¹ | R² | G | X | Y | W | D |
|---|---|---|---|---|---|---|---|
| 1.0001 | —Me | —Me | —H | 6-F | 3-Cl | —CH₂—CH₂— | —Ph |
| 1.0002 | —Me | —Me | —H | 6-F | 3-Cl | (E)—CH═CH— | —Ph |
| 1.0003 | —Me | —Me | —H | 6-F | 3-Cl | trans cyclopropyl | —Ph |
| 1.0004 | —Me | —Me | —H | 6-F | 3-Cl | cis cyclopropyl | —Ph |
| 1.0005 | —Me | —Me | —H | 6-Cl | 3-Cl | —CH₂—CH₂— | —Ph |
| 1.0006 | —Me | —Me | —H | 6-Cl | 3-Cl | trans cyclopropyl | —Ph |
| 1.0007 | —Me | —Me | —H | 6-Cl | 3-Cl | cis cyclopropyl | —Ph |
| 1.0008 | —CH₂—C≡CH | —Me | —H | 6-F | 3-Cl | —CH₂—CH₂— | —Ph |
| 1.0009 | —cyclopropyl | —Me | —H | 6-F | 3-Cl | —CH₂—CH₂— | —Ph |
| 1.0010 | —CH₂—C≡CH | —Me | —H | 6-Cl | 3-Cl | —CH₂—CH₂— | —Ph |
| 1.0011 | —cyclopropyl | —Me | —H | 6-Cl | 3-Cl | —CH₂—CH₂— | —Ph |
| 1.0012 | —Me | —Me | —H | 6-F | 3-Cl | —CH₂—CH₂— | 4-chloro-phenyl— |
| 1.0013 | —CH₂—C≡CH | —Me | —H | 6-F | 3-Cl | —CH₂—CH₂— | 4-chloro-phenyl— |
| 1.0014 | —cyclopropyl | —Me | —H | 6-F | 3-Cl | —CH₂—CH₂— | 4-chloro-phenyl— |
| 1.0015 | —Me | —Me | —H | 6-Cl | 3-Cl | —CH₂—CH₂— | 4-chloro-phenyl— |
| 1.0016 | —CH₂—C≡CH | —Me | —H | 6-Cl | 3-Cl | —CH₂—CH₂— | 4-chloro-phenyl— |
| 1.0017 | —cyclopropyl | —Me | —H | 6-Cl | 3-Cl | —CH₂—CH₂— | 4-chloro-phenyl— |
| 1.0018 | —Me | —Me | —H | 6-F | 3-Cl | —CH₂—CH₂— | 4-trifluoromethyl-phenyl— |
| 1.0019 | —CH₂—C≡CH | —Me | —H | 6-F | 3-Cl | —CH₂—CH₂— | 4-trifluoromethyl-phenyl— |
| 1.0020 | —cyclopropyl | —Me | —H | 6-F | 3-Cl | —CH₂—CH₂— | 4-trifluoromethyl-phenyl— |
| 1.0021 | —Me | —Me | —H | 6-Cl | 3-Cl | —CH₂—CH₂— | 4-trifluoromethyl-phenyl— |
| 1.0022 | —CH₂—C≡CH | —Me | —H | 6-Cl | 3-Cl | —CH₂—CH₂— | 4-trifluoromethyl-phenyl— |
| 1.0023 | —cyclopropyl | —Me | —H | 6-Cl | 3-Cl | —CH₂—CH₂— | 4-trifluoromethyl-phenyl— |
| 1.0024 | —Me | —Me | —H | 6-F | 3-Cl | —CH₂—CH₂— | 4-cyano-phenyl— |

TABLE 1-continued

Herbicidal compounds of the present invention. The numbering system used to describe the positions of X and Y is shown for the purposes of clarity only.

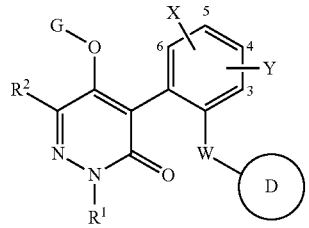

(I)

| Cmpd. No. | R¹ | R² | G | X | Y | W | D |
|---|---|---|---|---|---|---|---|
| 1.0025 | —CH₂—C≡CH | —Me | —H | 6-F | 3-Cl | —CH₂—CH₂— | 4-cyano-phenyl— |
| 1.0026 | —cyclopropyl | —Me | —H | 6-F | 3-Cl | —CH₂—CH₂— | 4-cyano-phenyl— |
| 1.0027 | —Me | —Me | —H | 6-Cl | 3-Cl | —CH₂—CH₂— | 4-cyano-phenyl— |
| 1.0028 | —CH₂—C≡CH | —Me | —H | 6-Cl | 3-Cl | —CH₂—CH₂— | 4-cyano-phenyl— |
| 1.0029 | —cyclopropyl | —Me | —H | 6-Cl | 3-Cl | —CH₂—CH₂— | 4-cyano-phenyl— |
| 1.0030 | —Me | —Me | —H | 6-F | 3-Cl | —CH₂—CH₂— | 4-chloro-3-pyridyl— |
| 1.0031 | —CH₂—C≡CH | —Me | —H | 6-F | 3-Cl | —CH₂—CH₂— | 4-chloro-3-pyridyl— |
| 1.0032 | —cyclopropyl | —Me | —H | 6-F | 3-Cl | —CH₂—CH₂— | 4-chloro-3-pyridyl— |
| 1.0033 | —Me | —Me | —H | 6-Cl | 3-Cl | —CH₂—CH₂— | 4-chloro-3-pyridyl— |
| 1.0034 | —CH₂—C≡CH | —Me | —H | 6-Cl | 3-Cl | —CH₂—CH₂— | 4-chloro-3-pyridyl— |
| 1.0035 | —cyclopropyl | —Me | —H | 6-Cl | 3-Cl | —CH₂—CH₂— | 4-chloro-3-pyridyl— |
| 1.0036 | —Me | —Me | —H | 6-F | 3-Cl | —CH₂—CH₂— | 2-chlorothiazol-5-yl— |
| 1.0037 | —CH₂—C≡CH | —Me | —H | 6-F | 3-Cl | —CH₂—CH₂— | 2-chlorothiazol-5-yl— |
| 1.0038 | —cyclopropyl | —Me | —H | 6-F | 3-Cl | —CH₂—CH₂— | 2-chlorothiazol-5-yl— |
| 1.0039 | —Me | —Me | —H | 6-Cl | 3-Cl | —CH₂—CH₂— | 2-chlorothiazol-5-yl— |
| 1.0040 | —CH₂—C≡CH | —Me | —H | 6-Cl | 3-Cl | —CH₂—CH₂— | 2-chlorothiazol-5-yl— |
| 1.0041 | —cyclopropyl | —Me | —H | 6-Cl | 3-Cl | —CH₂—CH₂— | 2-chlorothiazol-5-yl— |
| 1.0042 | —Me | —Me | —H | 6-F | 3-Cl | —CH₂—CH₂— | 4-trifluoromethyl-3-pyridyl— |
| 1.0043 | —CH₂—C≡CH | —Me | —H | 6-F | 3-Cl | —CH₂—CH₂— | 4-trifluoromethyl-3-pyridyl— |
| 1.0044 | —cyclopropyl | —Me | —H | 6-F | 3-Cl | —CH₂—CH₂— | 4-trifluoromethyl-3-pyridyl— |
| 1.0045 | —Me | —Me | —H | 6-Cl | 3-Cl | —CH₂—CH₂— | 4-trifluoromethyl-3-pyridyl— |
| 1.0046 | —CH₂—C≡CH | —Me | —H | 6-Cl | 3-Cl | —CH₂—CH₂— | 4-trifluoromethyl-3-pyridyl— |
| 1.0047 | —cyclopropyl | —Me | —H | 6-Cl | 3-Cl | —CH₂—CH₂— | 4-trifluoromethyl-3-pyridyl— |
| 1.0048 | —Me | —Me | —H | 6-F | 3-Cl | —CH₂—CH₂— | 4-fluoro-phenyl— |
| 1.0049 | —CH₂—C≡CH | —Me | —H | 6-F | 3-Cl | —CH₂—CH₂— | 4-fluoro-phenyl— |
| 1.0050 | —cyclopropyl | —Me | —H | 6-F | 3-Cl | —CH₂—CH₂— | 4-fluoro-phenyl— |
| 1.0051 | —Me | —Me | —H | 6-Cl | 3-Cl | —CH₂—CH₂— | 4-fluoro-phenyl— |
| 1.0052 | —CH₂—C≡CH | —Me | —H | 6-Cl | 3-Cl | —CH₂—CH₂— | 4-fluoro-phenyl— |
| 1.0053 | —cyclopropyl | —Me | —H | 6-Cl | 3-Cl | —CH₂—CH₂— | 4-fluoro-phenyl— |
| 1.0054 | —Me | —Me | —H | 6-F | 3-Cl | —CH₂—CH₂— | 3-pyridyl— |
| 1.0055 | —CH₂—C≡CH | —Me | —H | 6-F | 3-Cl | —CH₂—CH₂— | 3-pyridyl— |
| 1.0056 | —cyclopropyl | —Me | —H | 6-F | 3-Cl | —CH₂—CH₂— | 3-pyridyl— |
| 1.0057 | —Me | —Me | —H | 6-Cl | 3-Cl | —CH₂—CH₂— | 3-pyridyl— |
| 1.0058 | —CH₂—C≡CH | —Me | —H | 6-Cl | 3-Cl | —CH₂—CH₂— | 3-pyridyl— |
| 1.0059 | —cyclopropyl | —Me | —H | 6-Cl | 3-Cl | —CH₂—CH₂— | 3-pyridyl— |
| 1.0060 | —Me | —Me | —H | 6-F | 3-Cl | —CH₂—CH₂— | 3,4-difluoro-phenyl— |
| 1.0061 | —CH₂—C≡CH | —Me | —H | 6-F | 3-Cl | —CH₂—CH₂— | 3,4-difluoro-phenyl— |
| 1.0062 | —cyclopropyl | —Me | —H | 6-F | 3-Cl | —CH₂—CH₂— | 3,4-difluoro-phenyl— |
| 1.0063 | —Me | —Me | —H | 6-Cl | 3-Cl | —CH₂—CH₂— | 3,4-difluoro-phenyl— |
| 1.0064 | —CH₂—C≡CH | —Me | —H | 6-Cl | 3-Cl | —CH₂—CH₂— | 3,4-difluoro-phenyl— |
| 1.0065 | —cyclopropyl | —Me | —H | 6-Cl | 3-Cl | —CH₂—CH₂— | 3,4-difluoro-phenyl— |
| 1.0066 | —Me | —Me | —H | 6-F | 3-Cl | —CH₂—CH₂— | 2-trifluoromethyl-phenyl— |
| 1.0067 | —CH₂—C≡CH | —Me | —H | 6-F | 3-Cl | —CH₂—CH₂— | 2-trifluoromethyl-phenyl— |
| 1.0068 | —cyclopropyl | —Me | —H | 6-F | 3-Cl | —CH₂—CH₂— | 2-trifluoromethyl-phenyl— |
| 1.0069 | —Me | —Me | —H | 6-Cl | 3-Cl | —CH₂—CH₂— | 2-trifluoromethyl-phenyl— |
| 1.0070 | —CH₂—C≡CH | —Me | —H | 6-Cl | 3-Cl | —CH₂—CH₂— | 2-trifluoromethyl-phenyl— |
| 1.0071 | —cyclopropyl | —Me | —H | 6-Cl | 3-Cl | —CH₂—CH₂— | 2-trifluoromethyl-phenyl— |
| 1.0072 | —Me | —Me | —H | 6-F | 3-Cl | —CH₂—CH₂— | 4-tolyl— |
| 1.0073 | —CH₂—C≡CH | —Me | —H | 6-F | 3-Cl | —CH₂—CH₂— | 4-tolyl— |
| 1.0074 | —cyclopropyl | —Me | —H | 6-F | 3-Cl | —CH₂—CH₂— | 4-tolyl— |
| 1.0075 | —Me | —Me | —H | 6-Cl | 3-Cl | —CH₂—CH₂— | 4-tolyl— |
| 1.0076 | —CH₂—C≡CH | —Me | —H | 6-Cl | 3-Cl | —CH₂—CH₂— | 4-tolyl— |
| 1.0077 | —cyclopropyl | —Me | —H | 6-Cl | 3-Cl | —CH₂—CH₂— | 4-tolyl— |
| 1.0078 | —Me | —Me | —(C=O)$^i$Pr | 6-F | 3-Cl | —CH₂—CH₂— | —Ph |
| 1.0079 | —Me | —Me | —(C=O)$^i$Pr | 6-F | 3-Cl | (E)—CH=CH— | —Ph |

TABLE 1-continued

Herbicidal compounds of the present invention. The numbering system used to describe the
positions of X and Y is shown for the purposes of clarity only.

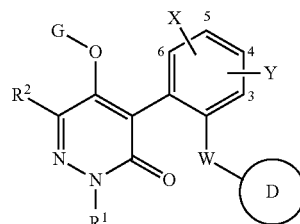

(I)

| Cmpd. No. | R¹ | R² | G | X | Y | W | D |
|---|---|---|---|---|---|---|---|
| 1.0080 | —Me | —Me | —(C═O)$^i$Pr | 6-F | 3-Cl | trans cyclopropyl | —Ph |
| 1.0081 | —Me | —Me | —(C═O)$^i$Pr | 6-F | 3-Cl | cis cyclopropyl | —Ph |
| 1.0082 | —Me | —Me | —(C═O)$^i$Pr | 6-Cl | 3-Cl | —CH₂—CH₂— | —Ph |
| 1.0083 | —Me | —Me | —(C═O)$^i$Pr | 6-Cl | 3-Cl | trans cyclopropyl | —Ph |
| 1.0084 | —Me | —Me | —(C═O)$^i$Pr | 6-Cl | 3-Cl | cis cyclopropyl | —Ph |
| 1.0085 | —CH₂—C≡CH | —Me | —(C═O)$^i$Pr | 6-F | 3-Cl | —CH₂—CH₂— | —Ph |
| 1.0086 | —cyclopropyl | —Me | —(C═O)$^i$Pr | 6-F | 3-Cl | —CH₂—CH₂— | —Ph |
| 1.0087 | —CH₂—C≡CH | —Me | —(C═O)$^i$Pr | 6-Cl | 3-Cl | —CH₂—CH₂— | —Ph |
| 1.0088 | —cyclopropyl | —Me | —(C═O)$^i$Pr | 6-Cl | 3-Cl | —CH₂—CH₂— | —Ph |
| 1.0089 | —Me | —Me | —(C═O)$^i$Pr | 6-F | 3-Cl | —CH₂—CH₂— | 4-chloro-phenyl— |
| 1.0090 | —CH₂—C≡CH | —Me | —(C═O)$^i$Pr | 6-F | 3-Cl | —CH₂—CH₂— | 4-chloro-phenyl— |
| 1.0091 | —cyclopropyl | —Me | —(C═O)$^i$Pr | 6-F | 3-Cl | —CH₂—CH₂— | 4-chloro-phenyl— |
| 1.0092 | —Me | —Me | —(C═O)$^i$Pr | 6-Cl | 3-Cl | —CH₂—CH₂— | 4-chloro-phenyl— |
| 1.0093 | —CH₂—C≡CH | —Me | —(C═O)$^i$Pr | 6-Cl | 3-Cl | —CH₂—CH₂— | 4-chloro-phenyl— |
| 1.0094 | —cyclopropyl | —Me | —(C═O)$^i$Pr | 6-Cl | 3-Cl | —CH₂—CH₂— | 4-chloro-phenyl— |
| 1.0095 | —Me | —Me | —(C═O)$^i$Pr | 6-F | 3-Cl | —CH₂—CH₂— | 4-trifluoromethyl-phenyl— |
| 1.0096 | —CH₂—C≡CH | —Me | —(C═O)$^i$Pr | 6-F | 3-Cl | —CH₂—CH₂— | 4-trifluoromethyl-phenyl— |
| 1.0097 | —cyclopropyl | —Me | —(C═O)$^i$Pr | 6-F | 3-Cl | —CH₂—CH₂— | 4-trifluoromethyl-phenyl— |
| 1.0098 | —Me | —Me | —(C═O)$^i$Pr | 6-Cl | 3-Cl | —CH₂—CH₂— | 4-trifluoromethyl-phenyl— |
| 1.0099 | —CH₂—C≡CH | —Me | —(C═O)$^i$Pr | 6-Cl | 3-Cl | —CH₂—CH₂— | 4-trifluoromethyl-phenyl— |
| 1.0100 | —cyclopropyl | —Me | —(C═O)$^i$Pr | 6-Cl | 3-Cl | —CH₂—CH₂— | 4-trifluoromethyl-phenyl— |
| 1.0101 | —Me | —Me | —(C═O)$^i$Pr | 6-F | 3-Cl | —CH₂—CH₂— | 4-cyano-phenyl— |
| 1.0102 | —CH₂—C≡CH | —Me | —(C═O)$^i$Pr | 6-F | 3-Cl | —CH₂—CH₂— | 4-cyano-phenyl— |
| 1.0103 | —cyclopropyl | —Me | —(C═O)$^i$Pr | 6-F | 3-Cl | —CH₂—CH₂— | 4-cyano-phenyl— |

TABLE 1-continued

Herbicidal compounds of the present invention. The numbering system used to describe the positions of X and Y is shown for the purposes of clarity only.

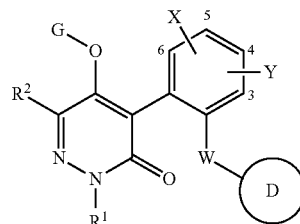

(I)

| Cmpd. No. | R$^1$ | R$^2$ | G | X | Y | W | D |
|---|---|---|---|---|---|---|---|
| 1.0104 | —Me | —Me | —(C=O)$^i$Pr | 6-Cl | 3-Cl | —CH$_2$—CH$_2$— | 4-cyano-phenyl— |
| 1.0105 | —CH$_2$—C≡CH | —Me | —(C=O)$^i$Pr | 6-Cl | 3-Cl | —CH$_2$—CH$_2$— | 4-cyano-phenyl— |
| 1.0106 | —cyclopropyl | —Me | —(C=O)$^i$Pr | 6-Cl | 3-Cl | —CH$_2$—CH$_2$— | 4-cyano-phenyl— |
| 1.0107 | —Me | —Me | —(C=O)$^i$Pr | 6-F | 3-Cl | —CH$_2$—CH$_2$— | 4-chloro-3-pyridyl— |
| 1.0108 | —CH$_2$—C≡CH | —Me | —(C=O)$^i$Pr | 6-F | 3-Cl | —CH$_2$—CH$_2$— | 4-chloro-3-pyridyl— |
| 1.0109 | —cyclopropyl | —Me | —(C=O)$^i$Pr | 6-F | 3-Cl | —CH$_2$—CH$_2$— | 4-chloro-3-pyridyl— |
| 1.0110 | —Me | —Me | —(C=O)$^i$Pr | 6-Cl | 3-Cl | —CH$_2$—CH$_2$— | 4-chloro-3-pyridyl— |
| 1.0111 | —CH$_2$—C≡CH | —Me | —(C=O)$^i$Pr | 6-Cl | 3-Cl | —CH$_2$—CH$_2$— | 4-chloro-3-pyridyl— |
| 1.0112 | —cyclopropyl | —Me | —(C=O)$^i$Pr | 6-Cl | 3-Cl | —CH$_2$—CH$_2$— | 4-chloro-3-pyridyl— |
| 1.0113 | —Me | —Me | —(C=O)$^i$Pr | 6-F | 3-Cl | —CH$_2$—CH$_2$— | 2-chlorothiazol-5-yl— |
| 1.0114 | —CH$_2$—C≡CH | —Me | —(C=O)$^i$Pr | 6-F | 3-Cl | —CH$_2$—CH$_2$— | 2-chlorothiazol-5-yl— |
| 1.0115 | —cyclopropyl | —Me | —(C=O)$^i$Pr | 6-F | 3-Cl | —CH$_2$—CH$_2$— | 2-chlorothiazol-5-yl— |
| 1.0116 | —Me | —Me | —(C=O)$^i$Pr | 6-Cl | 3-Cl | —CH$_2$—CH$_2$— | 2-chlorothiazol-5-yl— |
| 1.0117 | —CH$_2$—C≡CH | —Me | —(C=O)$^i$Pr | 6-Cl | 3-Cl | —CH$_2$—CH$_2$— | 2-chlorothiazol-5-yl— |
| 1.0118 | —cyclopropyl | —Me | —(C=O)$^i$Pr | 6-Cl | 3-Cl | —CH$_2$—CH$_2$— | 2-chlorothiazol-5-yl— |
| 1.0119 | —Me | —Me | —(C=O)$^i$Pr | 6-F | 3-Cl | —CH$_2$—CH$_2$— | 4-trifluoromethyl-3-pyridyl— |
| 1.0120 | —CH$_2$—C≡CH | —Me | —(C=O)$^i$Pr | 6-F | 3-Cl | —CH$_2$—CH$_2$— | 4-trifluoromethyl-3-pyridyl— |
| 1.0121 | —cyclopropyl | —Me | —(C=O)$^i$Pr | 6-F | 3-Cl | —CH$_2$—CH$_2$— | 4-trifluoromethyl-3-pyridyl— |
| 1.0122 | —Me | —Me | —(C=O)$^i$Pr | 6-Cl | 3-Cl | —CH$_2$—CH$_2$— | 4-trifluoromethyl-3-pyridyl— |
| 1.0123 | —CH$_2$—C≡CH | —Me | —(C=O)$^i$Pr | 6-Cl | 3-Cl | —CH$_2$—CH$_2$— | 4-trifluoromethyl-3-pyridyl— |
| 1.0124 | —cyclopropyl | —Me | —(C=O)$^i$Pr | 6-Cl | 3-Cl | —CH$_2$—CH$_2$— | 4-trifluoromethyl-3-pyridyl— |
| 1.0125 | —Me | —Me | —(C=O)$^i$Pr | 6-F | 3-Cl | —CH$_2$—CH$_2$— | 4-fluoro-phenyl— |
| 1.0126 | —CH$_2$—C≡CH | —Me | —(C=O)$^i$Pr | 6-F | 3-Cl | —CH$_2$—CH$_2$— | 4-fluoro-phenyl— |
| 1.0127 | —cyclopropyl | —Me | —(C=O)$^i$Pr | 6-F | 3-Cl | —CH$_2$—CH$_2$— | 4-fluoro-phenyl— |
| 1.0128 | —Me | —Me | —(C=O)$^i$Pr | 6-Cl | 3-Cl | —CH$_2$—CH$_2$— | 4-fluoro-phenyl— |
| 1.0129 | —CH$_2$—C≡CH | —Me | —(C=O)$^i$Pr | 6-Cl | 3-Cl | —CH$_2$—CH$_2$— | 4-fluoro-phenyl— |
| 1.0130 | —cyclopropyl | —Me | —(C=O)$^i$Pr | 6-Cl | 3-Cl | —CH$_2$—CH$_2$— | 4-fluoro-phenyl— |
| 1.0131 | —Me | —Me | —(C=O)$^i$Pr | 6-F | 3-Cl | —CH$_2$—CH$_2$— | 3-pyridyl— |
| 1.0132 | —CH$_2$—C≡CH | —Me | —(C=O)$^i$Pr | 6-F | 3-Cl | —CH$_2$—CH$_2$— | 3-pyridyl— |
| 1.0133 | —cyclopropyl | —Me | —(C=O)$^i$Pr | 6-F | 3-Cl | —CH$_2$—CH$_2$— | 3-pyridyl— |
| 1.0134 | —Me | —Me | —(C=O)$^i$Pr | 6-Cl | 3-Cl | —CH$_2$—CH$_2$— | 3-pyridyl— |
| 1.0135 | —CH$_2$—C≡CH | —Me | —(C=O)$^i$Pr | 6-Cl | 3-Cl | —CH$_2$—CH$_2$— | 3-pyridyl— |
| 1.0136 | —cyclopropyl | —Me | —(C=O)$^i$Pr | 6-Cl | 3-Cl | —CH$_2$—CH$_2$— | 3-pyridyl— |
| 1.0137 | —Me | —Me | —(C=O)$^i$Pr | 6-F | 3-Cl | —CH$_2$—CH$_2$— | 3,4-difluoro-phenyl— |
| 1.0138 | —CH$_2$—C≡CH | —Me | —(C=O)$^i$Pr | 6-F | 3-Cl | —CH$_2$—CH$_2$— | 3,4-difluoro-phenyl— |
| 1.0139 | —cyclopropyl | —Me | —(C=O)$^i$Pr | 6-F | 3-Cl | —CH$_2$—CH$_2$— | 3,4-difluoro-phenyl— |
| 1.0140 | —Me | —Me | —(C=O)$^i$Pr | 6-Cl | 3-Cl | —CH$_2$—CH$_2$— | 3,4-difluoro-phenyl— |
| 1.0141 | —CH$_2$—C≡CH | —Me | —(C=O)$^i$Pr | 6-Cl | 3-Cl | —CH$_2$—CH$_2$— | 3,4-difluoro-phenyl— |
| 1.0142 | —cyclopropyl | —Me | —(C=O)$^i$Pr | 6-Cl | 3-Cl | —CH$_2$—CH$_2$— | 3,4-difluoro-phenyl— |
| 1.0143 | —Me | —Me | —(C=O)$^i$Pr | 6-F | 3-Cl | —CH$_2$—CH$_2$— | 2-trifluoromethyl-phenyl— |
| 1.0144 | —CH$_2$—C≡CH | —Me | —(C=O)$^i$Pr | 6-F | 3-Cl | —CH$_2$—CH$_2$— | 2-trifluoromethyl-phenyl— |
| 1.0145 | —cyclopropyl | —Me | —(C=O)$^i$Pr | 6-F | 3-Cl | —CH$_2$—CH$_2$— | 2-trifluoromethyl-phenyl— |
| 1.0146 | —Me | —Me | —(C=O)$^i$Pr | 6-Cl | 3-Cl | —CH$_2$—CH$_2$— | 2-trifluoromethyl-phenyl— |
| 1.0147 | —CH$_2$—C≡CH | —Me | —(C=O)$^i$Pr | 6-Cl | 3-Cl | —CH$_2$—CH$_2$— | 2-trifluoromethyl-phenyl— |
| 1.0148 | —cyclopropyl | —Me | —(C=O)$^i$Pr | 6-Cl | 3-Cl | —CH$_2$—CH$_2$— | 2-trifluoromethyl-phenyl— |
| 1.0149 | —Me | —Me | —(C=O)$^i$Pr | 6-F | 3-Cl | —CH$_2$—CH$_2$— | 4-tolyl— |
| 1.0150 | —CH$_2$—C≡CH | —Me | —(C=O)$^i$Pr | 6-F | 3-Cl | —CH$_2$—CH$_2$— | 4-tolyl— |
| 1.0151 | —cyclopropyl | —Me | —(C=O)$^i$Pr | 6-F | 3-Cl | —CH$_2$—CH$_2$— | 4-tolyl— |
| 1.0152 | —Me | —Me | —(C=O)$^i$Pr | 6-Cl | 3-Cl | —CH$_2$—CH$_2$— | 4-tolyl— |
| 1.0153 | —CH$_2$—C≡CH | —Me | —(C=O)$^i$Pr | 6-Cl | 3-Cl | —CH$_2$—CH$_2$— | 4-tolyl— |
| 1.0154 | —cyclopropyl | —Me | —(C=O)$^i$Pr | 6-Cl | 3-Cl | —CH$_2$—CH$_2$— | 4-tolyl— |
| 1.0155 | —Me | —Me | —H | 6-F | —H | —CH$_2$—CH$_2$— | —Ph |
| 1.0156 | —Me | —Me | —H | 6-F | —H | (E)—CH=CH— | —Ph |

TABLE 1-continued

Herbicidal compounds of the present invention. The numbering system used to describe the positions of X and Y is shown for the purposes of clarity only.

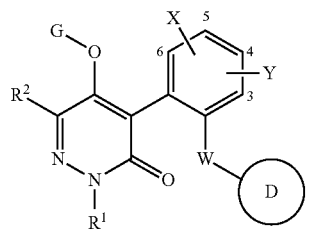

(I)

| Cmpd. No. | R¹ | R² | G | X | Y | W | D |
|---|---|---|---|---|---|---|---|
| 1.0157 | —Me | —Me | —H | 6-F | —H | trans cyclopropyl | —Ph |
| 1.0158 | —Me | —Me | —H | 6-F | —H | cis cyclopropyl | —Ph |
| 1.0159 | —Me | —Me | —H | 6-Cl | —H | —CH₂—CH₂— | —Ph |
| 1.0160 | —Me | —Me | —H | 6-Cl | —H | trans cyclopropyl | —Ph |
| 1.0161 | —Me | —Me | —H | 6-Cl | —H | cis cyclopropyl | —Ph |
| 1.0162 | —CH₂—C≡CH | —Me | —H | 6-F | —H | —CH₂—CH₂— | —Ph |
| 1.0163 | —cyclopropyl | —Me | —H | 6-F | —H | —CH₂—CH₂— | —Ph |
| 1.0164 | —CH₂—C≡CH | —Me | —H | 6-Cl | —H | —CH₂—CH₂— | —Ph |
| 1.0165 | —cyclopropyl | —Me | —H | 6-Cl | —H | —CH₂—CH₂— | —Ph |
| 1.0166 | —Me | —Me | —H | 6-F | —H | —CH₂—CH₂— | 4-chloro-phenyl— |
| 1.0167 | —CH₂—C≡CH | —Me | —H | 6-F | —H | —CH₂—CH₂— | 4-chloro-phenyl— |
| 1.0168 | —cyclopropyl | —Me | —H | 6-F | —H | —CH₂—CH₂— | 4-chloro-phenyl— |
| 1.0169 | —Me | —Me | —H | 6-Cl | —H | —CH₂—CH₂— | 4-chloro-phenyl— |
| 1.0170 | —CH₂—C≡CH | —Me | —H | 6-Cl | —H | —CH₂—CH₂— | 4-chloro-phenyl— |
| 1.0171 | —cyclopropyl | —Me | —H | 6-Cl | —H | —CH₂—CH₂— | 4-chloro-phenyl— |
| 1.0172 | —Me | —Me | —H | 6-F | —H | —CH₂—CH₂— | 4-trifluoromethyl-phenyl— |
| 1.0173 | —CH₂—C≡CH | —Me | —H | 6-F | —H | —CH₂—CH₂— | 4-trifluoromethyl-phenyl— |
| 1.0174 | —cyclopropyl | —Me | —H | 6-F | —H | —CH₂—CH₂— | 4-trifluoromethyl-phenyl— |
| 1.0175 | —Me | —Me | —H | 6-Cl | —H | —CH₂—CH₂— | 4-trifluoromethyl-phenyl— |
| 1.0176 | —CH₂—C≡CH | —Me | —H | 6-Cl | —H | —CH₂—CH₂— | 4-trifluoromethyl-phenyl— |
| 1.0177 | —cyclopropyl | —Me | —H | 6-Cl | —H | —CH₂—CH₂— | 4-trifluoromethyl-phenyl— |
| 1.0178 | —Me | —Me | —H | 6-F | —H | —CH₂—CH₂— | 4-cyano-phenyl— |
| 1.0179 | —CH₂—C≡CH | —Me | —H | 6-F | —H | —CH₂—CH₂— | 4-cyano-phenyl— |
| 1.0180 | —cyclopropyl | —Me | —H | 6-F | —H | —CH₂—CH₂— | 4-cyano-phenyl— |

TABLE 1-continued

Herbicidal compounds of the present invention. The numbering system used to describe the positions of X and Y is shown for the purposes of clarity only.

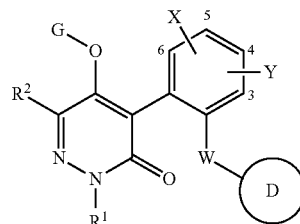

(I)

| Cmpd. No. | $R^1$ | $R^2$ | G | X | Y | W | D |
|---|---|---|---|---|---|---|---|
| 1.0181 | —Me | —Me | —H | 6-Cl | —H | —CH$_2$—CH$_2$— | 4-cyano-phenyl— |
| 1.0182 | —CH$_2$—C≡CH | —Me | —H | 6-Cl | —H | —CH$_2$—CH$_2$— | 4-cyano-phenyl— |
| 1.0183 | —cyclopropyl | —Me | —H | 6-Cl | —H | —CH$_2$—CH$_2$— | 4-cyano-phenyl— |
| 1.0184 | —Me | —Me | —H | 6-F | —H | —CH$_2$—CH$_2$— | 4-chloro-3-pyridyl— |
| 1.0185 | —CH$_2$—C≡CH | —Me | —H | 6-F | —H | —CH$_2$—CH$_2$— | 4-chloro-3-pyridyl— |
| 1.0186 | —cyclopropyl | —Me | —H | 6-F | —H | —CH$_2$—CH$_2$— | 4-chloro-3-pyridyl— |
| 1.0187 | —Me | —Me | —H | 6-Cl | —H | —CH$_2$—CH$_2$— | 4-chloro-3-pyridyl— |
| 1.0188 | —CH$_2$—C≡CH | —Me | —H | 6-Cl | —H | —CH$_2$—CH$_2$— | 4-chloro-3-pyridyl— |
| 1.0189 | —cyclopropyl | —Me | —H | 6-Cl | —H | —CH$_2$—CH$_2$— | 4-chloro-3-pyridyl— |
| 1.0190 | —Me | —Me | —H | 6-F | —H | —CH$_2$—CH$_2$— | 2-chlorothiazol-5-yl— |
| 1.0191 | —CH$_2$—C≡CH | —Me | —H | 6-F | —H | —CH$_2$—CH$_2$— | 2-chlorothiazol-5-yl— |
| 1.0192 | —cyclopropyl | —Me | —H | 6-F | —H | —CH$_2$—CH$_2$— | 2-chlorothiazol-5-yl— |
| 1.0193 | —Me | —Me | —H | 6-Cl | —H | —CH$_2$—CH$_2$— | 2-chlorothiazol-5-yl— |
| 1.0194 | —CH$_2$—C≡CH | —Me | —H | 6-Cl | —H | —CH$_2$—CH$_2$— | 2-chlorothiazol-5-yl— |
| 1.0195 | —cyclopropyl | —Me | —H | 6-Cl | —H | —CH$_2$—CH$_2$— | 2-chlorothiazol-5-yl— |
| 1.0196 | —Me | —Me | —H | 6-F | —H | —CH$_2$—CH$_2$— | 4-trifluoromethyl-3-pyridyl— |
| 1.0197 | —CH$_2$—C≡CH | —Me | —H | 6-F | —H | —CH$_2$—CH$_2$— | 4-trifluoromethyl-3-pyridyl— |
| 1.0198 | —cyclopropyl | —Me | —H | 6-F | —H | —CH$_2$—CH$_2$— | 4-trifluoromethyl-3-pyridyl— |
| 1.0199 | —Me | —Me | —H | 6-Cl | —H | —CH$_2$—CH$_2$— | 4-trifluoromethyl-3-pyridyl— |
| 1.0200 | —CH$_2$—C≡CH | —Me | —H | 6-Cl | —H | —CH$_2$—CH$_2$— | 4-trifluoromethyl-3-pyridyl— |
| 1.0201 | —cyclopropyl | —Me | —H | 6-Cl | —H | —CH$_2$—CH$_2$— | 4-trifluoromethyl-3-pyridyl— |
| 1.0202 | —Me | —Me | —H | 6-F | —H | —CH$_2$—CH$_2$— | 4-fluoro-phenyl— |
| 1.0203 | —CH$_2$—C≡CH | —Me | —H | 6-F | —H | —CH$_2$—CH$_2$— | 4-fluoro-phenyl— |
| 1.0204 | —cyclopropyl | —Me | —H | 6-F | —H | —CH$_2$—CH$_2$— | 4-fluoro-phenyl— |
| 1.0205 | —Me | —Me | —H | 6-Cl | —H | —CH$_2$—CH$_2$— | 4-fluoro-phenyl— |
| 1.0206 | —CH$_2$—C≡CH | —Me | —H | 6-Cl | —H | —CH$_2$—CH$_2$— | 4-fluoro-phenyl— |
| 1.0207 | —cyclopropyl | —Me | —H | 6-Cl | —H | —CH$_2$—CH$_2$— | 4-fluoro-phenyl— |
| 1.0208 | —Me | —Me | —H | 6-F | —H | —CH$_2$—CH$_2$— | 3-pyridyl— |
| 1.0209 | —CH$_2$—C≡CH | —Me | —H | 6-F | —H | —CH$_2$—CH$_2$— | 3-pyridyl— |
| 1.0210 | —cyclopropyl | —Me | —H | 6-F | —H | —CH$_2$—CH$_2$— | 3-pyridyl— |
| 1.0211 | —Me | —Me | —H | 6-Cl | —H | —CH$_2$—CH$_2$— | 3-pyridyl— |
| 1.0212 | —CH$_2$—C≡CH | —Me | —H | 6-Cl | —H | —CH$_2$—CH$_2$— | 3-pyridyl— |
| 1.0213 | —cyclopropyl | —Me | —H | 6-Cl | —H | —CH$_2$—CH$_2$— | 3-pyridyl— |
| 1.0214 | —Me | —Me | —H | 6-F | —H | —CH$_2$—CH$_2$— | 3,4-difluoro-phenyl— |
| 1.0215 | —CH$_2$—C≡CH | —Me | —H | 6-F | —H | —CH$_2$—CH$_2$— | 3,4-difluoro-phenyl— |
| 1.0216 | —cyclopropyl | —Me | —H | 6-F | —H | —CH$_2$—CH$_2$— | 3,4-difluoro-phenyl— |
| 1.0217 | —Me | —Me | —H | 6-Cl | —H | —CH$_2$—CH$_2$— | 3,4-difluoro-phenyl— |
| 1.0218 | —CH$_2$—C≡CH | —Me | —H | 6-Cl | —H | —CH$_2$—CH$_2$— | 3,4-difluoro-phenyl— |
| 1.0219 | —cyclopropyl | —Me | —H | 6-Cl | —H | —CH$_2$—CH$_2$— | 3,4-difluoro-phenyl— |
| 1.0220 | —Me | —Me | —H | 6-F | —H | —CH$_2$—CH$_2$— | 2-trifluoromethyl-phenyl— |
| 1.0221 | —CH$_2$—C≡CH | —Me | —H | 6-F | —H | —CH$_2$—CH$_2$— | 2-trifluoromethyl-phenyl— |
| 1.0222 | —cyclopropyl | —Me | —H | 6-F | —H | —CH$_2$—CH$_2$— | 2-trifluoromethyl-phenyl— |
| 1.0223 | —Me | —Me | —H | 6-Cl | —H | —CH$_2$—CH$_2$— | 2-trifluoromethyl-phenyl— |
| 1.0224 | —CH$_2$—C≡CH | —Me | —H | 6-Cl | —H | —CH$_2$—CH$_2$— | 2-trifluoromethyl-phenyl— |
| 1.0225 | —cyclopropyl | —Me | —H | 6-Cl | —H | —CH$_2$—CH$_2$— | 2-trifluoromethyl-phenyl— |
| 1.0226 | —Me | —Me | —H | 6-F | —H | —CH$_2$—CH$_2$— | 4-tolyl— |
| 1.0227 | —CH$_2$—C≡CH | —Me | —H | 6-F | —H | —CH$_2$—CH$_2$— | 4-tolyl— |
| 1.0228 | —cyclopropyl | —Me | —H | 6-F | —H | —CH$_2$—CH$_2$— | 4-tolyl— |
| 1.0229 | —Me | —Me | —H | 6-Cl | —H | —CH$_2$—CH$_2$— | 4-tolyl— |
| 1.0230 | —CH$_2$—C≡CH | —Me | —H | 6-Cl | —H | —CH$_2$—CH$_2$— | 4-tolyl— |
| 1.0231 | —cyclopropyl | —Me | —H | 6-Cl | —H | —CH$_2$—CH$_2$— | 4-tolyl— |
| 1.0232 | —Me | —Me | —(C=O)$^i$Pr | 6-F | —H | —CH$_2$—CH$_2$— | —Ph |
| 1.0233 | —Me | —Me | —(C=O)$^i$Pr | 6-F | —H | (E)—CH=CH— | —Ph |

TABLE 1-continued

Herbicidal compounds of the present invention. The numbering system used to describe the positions of X and Y is shown for the purposes of clarity only.

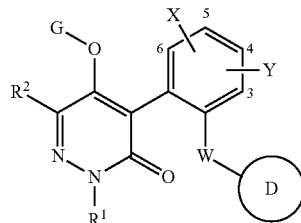

(I)

| Cmpd. No. | R¹ | R² | G | X | Y | W | D |
|---|---|---|---|---|---|---|---|
| 1.0234 | —Me | —Me | —(C=O)$^i$Pr | 6-F | —H | trans (cyclopropyl) | —Ph |
| 1.0235 | —Me | —Me | —(C=O)$^i$Pr | 6-F | —H | cis (cyclopropyl) | —Ph |
| 1.0236 | —Me | —Me | —(C=O)$^i$Pr | 6-Cl | —H | —CH$_2$—CH$_2$— | —Ph |
| 1.0237 | —Me | —Me | —(C=O)$^i$Pr | 6-Cl | —H | trans (cyclopropyl) | —Ph |
| 1.0238 | —Me | —Me | —(C=O)$^i$Pr | 6-Cl | —H | cis (cyclopropyl) | —Ph |
| 1.0239 | —CH$_2$—C≡CH | —Me | —(C=O)$^i$Pr | 6-F | —H | —CH$_2$—CH$_2$— | —Ph |
| 1.0240 | —cyclopropyl | —Me | —(C=O)$^i$Pr | 6-F | —H | —CH$_2$—CH$_2$— | —Ph |
| 1.0241 | —CH$_2$—C≡CH | —Me | —(C=O)$^i$Pr | 6-Cl | —H | —CH$_2$—CH$_2$— | —Ph |
| 1.0242 | —cyclopropyl | —Me | —(C=O)$^i$Pr | 6-Cl | —H | —CH$_2$—CH$_2$— | —Ph |
| 1.0243 | —Me | —Me | —(C=O)$^i$Pr | 6-F | —H | —CH$_2$—CH$_2$— | 4-chloro-phenyl— |
| 1.0244 | —CH$_2$—C≡CH | —Me | —(C=O)$^i$Pr | 6-F | —H | —CH$_2$—CH$_2$— | 4-chloro-phenyl— |
| 1.0245 | —cyclopropyl | —Me | —(C=O)$^i$Pr | 6-F | —H | —CH$_2$—CH$_2$— | 4-chloro-phenyl— |
| 1.0246 | —Me | —Me | —(C=O)$^i$Pr | 6-Cl | —H | —CH$_2$—CH$_2$— | 4-chloro-phenyl— |
| 1.0247 | —CH$_2$—C≡CH | —Me | —(C=O)$^i$Pr | 6-Cl | —H | —CH$_2$—CH$_2$— | 4-chloro-phenyl— |
| 1.0248 | —cyclopropyl | —Me | —(C=O)$^i$Pr | 6-Cl | —H | —CH$_2$—CH$_2$— | 4-chloro-phenyl— |
| 1.0249 | —Me | —Me | —(C=O)$^i$Pr | 6-F | —H | —CH$_2$—CH$_2$— | 4-trifluoromethyl-phenyl— |
| 1.0250 | —CH$_2$—C≡CH | —Me | —(C=O)$^i$Pr | 6-F | —H | —CH$_2$—CH$_2$— | 4-trifluoromethyl-phenyl— |
| 1.0251 | —cyclopropyl | —Me | —(C=O)$^i$Pr | 6-F | —H | —CH$_2$—CH$_2$— | 4-trifluoromethyl-phenyl— |
| 1.0252 | —Me | —Me | —(C=O)$^i$Pr | 6-Cl | —H | —CH$_2$—CH$_2$— | 4-trifluoromethyl-phenyl— |
| 1.0253 | —CH$_2$—C≡CH | —Me | —(C=O)$^i$Pr | 6-Cl | —H | —CH$_2$—CH$_2$— | 4-trifluoromethyl-phenyl— |
| 1.0254 | —cyclopropyl | —Me | —(C=O)$^i$Pr | 6-Cl | —H | —CH$_2$—CH$_2$— | 4-trifluoromethyl-phenyl— |
| 1.0255 | —Me | —Me | —(C=O)$^i$Pr | 6-F | —H | —CH$_2$—CH$_2$— | 4-cyano-phenyl— |
| 1.0256 | —CH$_2$—C≡CH | —Me | —(C=O)$^i$Pr | 6-F | —H | —CH$_2$—CH$_2$— | 4-cyano-phenyl— |
| 1.0257 | —cyclopropyl | —Me | —(C=O)$^i$Pr | 6-F | —H | —CH$_2$—CH$_2$— | 4-cyano-phenyl— |

TABLE 1-continued

Herbicidal compounds of the present invention. The numbering system used to describe the
positions of X and Y is shown for the purposes of clarity only.

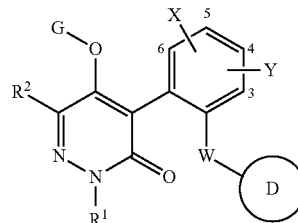

(I)

| Cmpd. No. | R¹ | R² | G | X | Y | W | D |
|---|---|---|---|---|---|---|---|
| 1.0258 | —Me | —Me | —(C=O)ⁱPr | 6-Cl | —H | —CH₂—CH₂— | 4-cyano-phenyl— |
| 1.0259 | —CH₂—C≡CH | —Me | —(C=O)ⁱPr | 6-Cl | —H | —CH₂—CH₂— | 4-cyano-phenyl— |
| 1.0260 | —cyclopropyl | —Me | —(C=O)ⁱPr | 6-Cl | —H | —CH₂—CH₂— | 4-cyano-phenyl— |
| 1.0261 | —Me | —Me | —(C=O)ⁱPr | 6-F | —H | —CH₂—CH₂— | 4-chloro-3-pyridyl— |
| 1.0262 | —CH₂—C≡CH | —Me | —(C=O)ⁱPr | 6-F | —H | —CH₂—CH₂— | 4-chloro-3-pyridyl— |
| 1.0263 | —cyclopropyl | —Me | —(C=O)ⁱPr | 6-F | —H | —CH₂—CH₂— | 4-chloro-3-pyridyl— |
| 1.0264 | —Me | —Me | —(C=O)ⁱPr | 6-Cl | —H | —CH₂—CH₂— | 4-chloro-3-pyridyl— |
| 1.0265 | —CH₂—C≡CH | —Me | —(C=O)ⁱPr | 6-Cl | —H | —CH₂—CH₂— | 4-chloro-3-pyridyl— |
| 1.0266 | —cyclopropyl | —Me | —(C=O)ⁱPr | 6-Cl | —H | —CH₂—CH₂— | 4-chloro-3-pyridyl— |
| 1.0267 | —Me | —Me | —(C=O)ⁱPr | 6-F | —H | —CH₂—CH₂— | 2-chlorothiazol-5-yl— |
| 1.0268 | —CH₂—C≡CH | —Me | —(C=O)ⁱPr | 6-F | —H | —CH₂—CH₂— | 2-chlorothiazol-5-yl— |
| 1.0269 | —cyclopropyl | —Me | —(C=O)ⁱPr | 6-F | —H | —CH₂—CH₂— | 2-chlorothiazol-5-yl— |
| 1.0270 | —Me | —Me | —(C=O)ⁱPr | 6-Cl | —H | —CH₂—CH₂— | 2-chlorothiazol-5-yl— |
| 1.0271 | —CH₂—C≡CH | —Me | —(C=O)ⁱPr | 6-Cl | —H | —CH₂—CH₂— | 2-chlorothiazol-5-yl— |
| 1.0272 | —cyclopropyl | —Me | —(C=O)ⁱPr | 6-Cl | —H | —CH₂—CH₂— | 2-chlorothiazol-5-yl— |
| 1.0273 | —Me | —Me | —(C=O)ⁱPr | 6-F | —H | —CH₂—CH₂— | 4-trifluoromethyl-3-pyridyl— |
| 1.0274 | —CH₂—C≡CH | —Me | —(C=O)ⁱPr | 6-F | —H | —CH₂—CH₂— | 4-trifluoromethyl-3-pyridyl— |
| 1.0275 | —cyclopropyl | —Me | —(C=O)ⁱPr | 6-F | —H | —CH₂—CH₂— | 4-trifluoromethyl-3-pyridyl— |
| 1.0276 | —Me | —Me | —(C=O)ⁱPr | 6-Cl | —H | —CH₂—CH₂— | 4-trifluoromethyl-3-pyridyl— |
| 1.0277 | —CH₂—C≡CH | —Me | —(C=O)ⁱPr | 6-Cl | —H | —CH₂—CH₂— | 4-trifluoromethyl-3-pyridyl— |
| 1.0278 | —cyclopropyl | —Me | —(C=O)ⁱPr | 6-Cl | —H | —CH₂—CH₂— | 4-trifluoromethyl-3-pyridyl— |
| 1.0279 | —Me | —Me | —(C=O)ⁱPr | 6-F | —H | —CH₂—CH₂— | 4-fluoro-phenyl— |
| 1.0280 | —CH₂—C≡CH | —Me | —(C=O)ⁱPr | 6-F | —H | —CH₂—CH₂— | 4-fluoro-phenyl— |
| 1.0281 | —cyclopropyl | —Me | —(C=O)ⁱPr | 6-F | —H | —CH₂—CH₂— | 4-fluoro-phenyl— |
| 1.0282 | —Me | —Me | —(C=O)ⁱPr | 6-Cl | —H | —CH₂—CH₂— | 4-fluoro-phenyl— |
| 1.0283 | —CH₂—C≡CH | —Me | —(C=O)ⁱPr | 6-Cl | —H | —CH₂—CH₂— | 4-fluoro-phenyl— |
| 1.0284 | —cyclopropyl | —Me | —(C=O)ⁱPr | 6-Cl | —H | —CH₂—CH₂— | 4-fluoro-phenyl— |
| 1.0285 | —Me | —Me | —(C=O)ⁱPr | 6-F | —H | —CH₂—CH₂— | 3-pyridyl— |
| 1.0286 | —CH₂—C≡CH | —Me | —(C=O)ⁱPr | 6-F | —H | —CH₂—CH₂— | 3-pyridyl— |
| 1.0287 | —cyclopropyl | —Me | —(C=O)ⁱPr | 6-F | —H | —CH₂—CH₂— | 3-pyridyl— |
| 1.0288 | —Me | —Me | —(C=O)ⁱPr | 6-Cl | —H | —CH₂—CH₂— | 3-pyridyl— |
| 1.0289 | —CH₂—C≡CH | —Me | —(C=O)ⁱPr | 6-Cl | —H | —CH₂—CH₂— | 3-pyridyl— |
| 1.0290 | —cyclopropyl | —Me | —(C=O)ⁱPr | 6-Cl | —H | —CH₂—CH₂— | 3-pyridyl— |
| 1.0291 | —Me | —Me | —(C=O)ⁱPr | 6-F | —H | —CH₂—CH₂— | 3,4-difluoro-phenyl— |
| 1.0292 | —CH₂—C≡CH | —Me | —(C=O)ⁱPr | 6-F | —H | —CH₂—CH₂— | 3,4-difluoro-phenyl— |
| 1.0293 | —cyclopropyl | —Me | —(C=O)ⁱPr | 6-F | —H | —CH₂—CH₂— | 3,4-difluoro-phenyl— |
| 1.0294 | —Me | —Me | —(C=O)ⁱPr | 6-Cl | —H | —CH₂—CH₂— | 3,4-difluoro-phenyl— |
| 1.0295 | —CH₂—C≡CH | —Me | —(C=O)ⁱPr | 6-Cl | —H | —CH₂—CH₂— | 3,4-difluoro-phenyl— |
| 1.0296 | —cyclopropyl | —Me | —(C=O)ⁱPr | 6-Cl | —H | —CH₂—CH₂— | 3,4-difluoro-phenyl— |
| 1.0297 | —Me | —Me | —(C=O)ⁱPr | 6-F | —H | —CH₂—CH₂— | 2-trifluoromethyl-phenyl— |
| 1.0298 | —CH₂—C≡CH | —Me | —(C=O)ⁱPr | 6-F | —H | —CH₂—CH₂— | 2-trifluoromethyl-phenyl— |
| 1.0299 | —cyclopropyl | —Me | —(C=O)ⁱPr | 6-F | —H | —CH₂—CH₂— | 2-trifluoromethyl-phenyl— |
| 1.0300 | —Me | —Me | —(C=O)ⁱPr | 6-Cl | —H | —CH₂—CH₂— | 2-trifluoromethyl-phenyl— |
| 1.0301 | —CH₂—C≡CH | —Me | —(C=O)ⁱPr | 6-Cl | —H | —CH₂—CH₂— | 2-trifluoromethyl-phenyl— |
| 1.0302 | —cyclopropyl | —Me | —(C=O)ⁱPr | 6-Cl | —H | —CH₂—CH₂— | 2-trifluoromethyl-phenyl— |
| 1.0303 | —Me | —Me | —(C=O)ⁱPr | 6-F | —H | —CH₂—CH₂— | 4-tolyl— |
| 1.0304 | —CH₂—C≡CH | —Me | —(C=O)ⁱPr | 6-F | —H | —CH₂—CH₂— | 4-tolyl— |
| 1.0305 | —cyclopropyl | —Me | —(C=O)ⁱPr | 6-F | —H | —CH₂—CH₂— | 4-tolyl— |
| 1.0306 | —Me | —Me | —(C=O)ⁱPr | 6-Cl | —H | —CH₂—CH₂— | 4-tolyl— |
| 1.0307 | —CH₂—C≡CH | —Me | —(C=O)ⁱPr | 6-Cl | —H | —CH₂—CH₂— | 4-tolyl— |
| 1.0308 | —cyclopropyl | —Me | —(C=O)ⁱPr | 6-Cl | —H | —CH₂—CH₂— | 4-tolyl— |
| 1.0309 | —Me | —Me | —H | 6-F | 3-Cl | —CH₂—CH₂— | 4-(trifluoromethoxy)-phenyl— |
| 1.0310 | —Me | —Me | —H | 6-Cl | 3-Cl | —CH₂—CH₂— | 4-(trifluoromethoxy)-phenyl— |
| 1.0311 | —CH₂—C≡CH | —Me | —H | 6-F | 3-Cl | —CH₂—CH₂— | 4-(trifluoromethoxy)-phenyl— |
| 1.0312 | —cyclopropyl | —Me | —H | 6-F | 3-Cl | —CH₂—CH₂— | 4-(trifluoromethoxy)-phenyl— |
| 1.0313 | —CH₂—C≡CH | —Me | —H | 6-Cl | 3-Cl | —CH₂—CH₂— | 4-(trifluoromethoxy)-phenyl— |
| 1.0314 | —cyclopropyl | —Me | —H | 6-Cl | 3-Cl | —CH₂—CH₂— | 4-(trifluoromethoxy)-phenyl— |
| 1.0315 | —Me | —Me | —H | 6-F | 3-Cl | —CH₂—CH₂— | 2-chloro-3-pyridyl— |
| 1.0316 | —CH₂—C≡CH | —Me | —H | 6-F | 3-Cl | —CH₂—CH₂— | 2-chloro-3-pyridyl— |
| 1.0317 | —cyclopropyl | —Me | —H | 6-F | 3-Cl | —CH₂—CH₂— | 2-chloro-3-pyridyl— |
| 1.0318 | —Me | —Me | —H | 6-Cl | 3-Cl | —CH₂—CH₂— | 2-chloro-3-pyridyl— |
| 1.0319 | —CH₂—C≡CH | —Me | —H | 6-Cl | 3-Cl | —CH₂—CH₂— | 2-chloro-3-pyridyl— |

TABLE 1-continued

Herbicidal compounds of the present invention. The numbering system used to describe the positions of X and Y is shown for the purposes of clarity only.

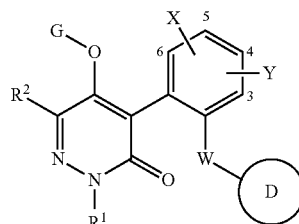

(I)

| Cmpd. No. | R¹ | R² | G | X | Y | W | D |
|---|---|---|---|---|---|---|---|
| 1.0320 | —cyclopropyl | —Me | —H | 6-Cl | 3-Cl | —CH₂—CH₂— | 2-chloro-3-pyridyl— |
| 1.0321 | —Me | —Me | —H | 6-F | 3-Cl | —CH₂—CH₂— | 2-chloro-4-pyridyl— |
| 1.0322 | —CH₂—C≡CH | —Me | —H | 6-F | 3-Cl | —CH₂—CH₂— | 2-chloro-4-pyridyl— |
| 1.0323 | —cyclopropyl | —Me | —H | 6-F | 3-Cl | —CH₂—CH₂— | 2-chloro-4-pyridyl— |
| 1.0324 | —Me | —Me | —H | 6-Cl | 3-Cl | —CH₂—CH₂— | 2-chloro-4-pyridyl— |
| 1.0325 | —CH₂—C≡CH | —Me | —H | 6-Cl | 3-Cl | —CH₂—CH₂— | 2-chloro-4-pyridyl— |
| 1.0326 | —cyclopropyl | —Me | —H | 6-Cl | 3-Cl | —CH₂—CH₂— | 2-chloro-4-pyridyl— |
| 1.0327 | —Me | —Me | —H | 6-F | 3-Cl | —CH₂—CH₂— | 3-chloro-4-fluoro-phenyl— |
| 1.0328 | —CH₂—C≡CH | —Me | —H | 6-F | 3-Cl | —CH₂—CH₂— | 3-chloro-4-fluoro-phenyl— |
| 1.0329 | —cyclopropyl | —Me | —H | 6-F | 3-Cl | —CH₂—CH₂— | 3-chloro-4-fluoro-phenyl— |
| 1.0330 | —Me | —Me | —H | 6-Cl | 3-Cl | —CH₂—CH₂— | 3-chloro-4-fluoro-phenyl— |
| 1.0331 | —CH₂—C≡CH | —Me | —H | 6-Cl | 3-Cl | —CH₂—CH₂— | 3-chloro-4-fluoro-phenyl— |
| 1.0332 | —cyclopropyl | —Me | —H | 6-Cl | 3-Cl | —CH₂—CH₂— | 3-chloro-4-fluoro-phenyl— |
| 1.0333 | —Me | —Me | —H | 6-F | 3-Cl | —CH₂—CH₂— | 3-chloro-4-pyridyl— |
| 1.0334 | —CH₂—C≡CH | —Me | —H | 6-F | 3-Cl | —CH₂—CH₂— | 3-chloro-4-pyridyl— |
| 1.0335 | —cyclopropyl | —Me | —H | 6-F | 3-Cl | —CH₂—CH₂— | 3-chloro-4-pyridyl— |
| 1.0336 | —Me | —Me | —H | 6-Cl | 3-Cl | —CH₂—CH₂— | 3-chloro-4-pyridyl— |
| 1.0337 | —CH₂—C≡CH | —Me | —H | 6-Cl | 3-Cl | —CH₂—CH₂— | 3-chloro-4-pyridyl— |
| 1.0338 | —cyclopropyl | —Me | —H | 6-Cl | 3-Cl | —CH₂—CH₂— | 3-chloro-4-pyridyl— |
| 1.0339 | —Me | —Me | —H | 6-F | 3-Cl | —CH₂—CH₂— | 4-hydroxy-phenyl— |
| 1.0340 | —CH₂—C≡CH | —Me | —H | 6-F | 3-Cl | —CH₂—CH₂— | 4-hydroxy-phenyl— |
| 1.0341 | —cyclopropyl | —Me | —H | 6-F | 3-Cl | —CH₂—CH₂— | 4-hydroxy-phenyl— |
| 1.0342 | —Me | —Me | —H | 6-Cl | 3-Cl | —CH₂—CH₂— | 4-hydroxy-phenyl— |
| 1.0343 | —CH₂—C≡CH | —Me | —H | 6-Cl | 3-Cl | —CH₂—CH₂— | 4-hydroxy-phenyl— |
| 1.0344 | —cyclopropyl | —Me | —H | 6-Cl | 3-Cl | —CH₂—CH₂— | 4-hydroxy-phenyl— |
| 1.0345 | —Me | —Me | —H | 6-F | 3-Cl | —CH₂—CH₂— | 4-cyclopropyl-phenyl— |
| 1.0346 | —CH₂—C≡CH | —Me | —H | 6-F | 3-Cl | —CH₂—CH₂— | 4-cyclopropyl-phenyl— |
| 1.0347 | —cyclopropyl | —Me | —H | 6-F | 3-Cl | —CH₂—CH₂— | 4-cyclopropyl-phenyl— |
| 1.0348 | —Me | —Me | —H | 6-Cl | 3-Cl | —CH₂—CH₂— | 4-cyclopropyl-phenyl— |
| 1.0349 | —CH₂—C≡CH | —Me | —H | 6-Cl | 3-Cl | —CH₂—CH₂— | 4-cyclopropyl-phenyl— |
| 1.0350 | —cyclopropyl | —Me | —H | 6-Cl | 3-Cl | —CH₂—CH₂— | 4-cyclopropyl-phenyl— |
| 1.0351 | —Me | —Me | —H | 6-F | 3-Cl | —CH₂—CH₂— | 1-methyl-3-(trifluoromethyl)pyrazol-4-yl— |
| 1.0352 | —CH₂—C≡CH | —Me | —H | 6-F | 3-Cl | —CH₂—CH₂— | 1-methyl-3-(trifluoromethyl)pyrazol-4-yl— |
| 1.0353 | —cyclopropyl | —Me | —H | 6-F | 3-Cl | —CH₂—CH₂— | 1-methyl-3-(trifluoromethyl)pyrazol-4-yl— |
| 1.0354 | —Me | —Me | —H | 6-Cl | 3-Cl | —CH₂—CH₂— | 1-methyl-3-(trifluoromethyl)pyrazol-4-yl— |
| 1.0355 | —CH₂—C≡CH | —Me | —H | 6-Cl | 3-Cl | —CH₂—CH₂— | 1-methyl-3-(trifluoromethyl)pyrazol-4-yl— |
| 1.0356 | —cyclopropyl | —Me | —H | 6-Cl | 3-Cl | —CH₂—CH₂— | 1-methyl-3-(trifluoromethyl)pyrazol-4-yl— |
| 1.0357 | —Me | —Me | —H | 6-F | 3-Cl | —CH₂—CH₂— | thiazol-2-yl— |
| 1.0358 | —CH₂—C≡CH | —Me | —H | 6-F | 3-Cl | —CH₂—CH₂— | thiazol-2-yl— |
| 1.0359 | —cyclopropyl | —Me | —H | 6-F | 3-Cl | —CH₂—CH₂— | thiazol-2-yl— |
| 1.0360 | —Me | —Me | —H | 6-Cl | 3-Cl | —CH₂—CH₂— | thiazol-2-yl— |
| 1.0361 | —CH₂—C≡CH | —Me | —H | 6-Cl | 3-Cl | —CH₂—CH₂— | thiazol-2-yl— |
| 1.0362 | —cyclopropyl | —Me | —H | 6-Cl | 3-Cl | —CH₂—CH₂— | thiazol-2-yl— |
| 1.0363 | —Me | —Me | —H | 6-F | 3-Cl | —CH₂—CH₂— | pyrimidin-5-yl— |
| 1.0364 | —CH₂—C≡CH | —Me | —H | 6-F | 3-Cl | —CH₂—CH₂— | pyrimidin-5-yl— |
| 1.0365 | —cyclopropyl | —Me | —H | 6-F | 3-Cl | —CH₂—CH₂— | pyrimidin-5-yl— |
| 1.0366 | —Me | —Me | —H | 6-Cl | 3-Cl | —CH₂—CH₂— | pyrimidin-5-yl— |
| 1.0367 | —CH₂—C≡CH | —Me | —H | 6-Cl | 3-Cl | —CH₂—CH₂— | pyrimidin-5-yl— |
| 1.0368 | —cyclopropyl | —Me | —H | 6-Cl | 3-Cl | —CH₂—CH₂— | pyrimidin-5-yl— |
| 1.0369 | —Me | —Me | —H | 6-F | 3-Cl | —CH₂—CH₂— | 4-(tert-butoxy)-phenyl— |
| 1.0370 | —CH₂—C≡CH | —Me | —H | 6-F | 3-Cl | —CH₂—CH₂— | 4-(tert-butoxy)-phenyl— |
| 1.0371 | —cyclopropyl | —Me | —H | 6-F | 3-Cl | —CH₂—CH₂— | 4-(tert-butoxy)-phenyl— |
| 1.0372 | —Me | —Me | —H | 6-Cl | 3-Cl | —CH₂—CH₂— | 4-(tert-butoxy)-phenyl— |
| 1.0373 | —CH₂—C≡CH | —Me | —H | 6-Cl | 3-Cl | —CH₂—CH₂— | 4-(tert-butoxy)-phenyl— |
| 1.0374 | —cyclopropyl | —Me | —H | 6-Cl | 3-Cl | —CH₂—CH₂— | 4-(tert-butoxy)-phenyl— |
| 1.0375 | —Me | —Me | —H | 6-F | 3-Cl | —CH₂—CH₂— | thiazol-5-yl— |

TABLE 1-continued

Herbicidal compounds of the present invention. The numbering system used to describe the positions of X and Y is shown for the purposes of clarity only.

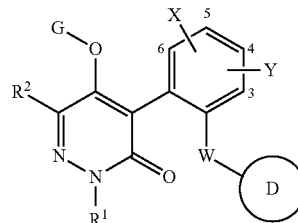

(I)

| Cmpd. No. | R$^1$ | R$^2$ | G | X | Y | W | D |
|---|---|---|---|---|---|---|---|
| 1.0376 | —CH$_2$—C≡CH | —Me | —H | 6-F | 3-Cl | —CH$_2$—CH$_2$— | thiazol-5-yl— |
| 1.0377 | —cyclopropyl | —Me | —H | 6-F | 3-Cl | —CH$_2$—CH$_2$— | thiazol-5-yl— |
| 1.0378 | —Me | —Me | —H | 6-Cl | 3-Cl | —CH$_2$—CH$_2$— | thiazol-5-yl— |
| 1.0379 | —CH$_2$—C≡CH | —Me | —H | 6-Cl | 3-Cl | —CH$_2$—CH$_2$— | thiazol-5-yl— |
| 1.0380 | —cyclopropyl | —Me | —H | 6-Cl | 3-Cl | —CH$_2$—CH$_2$— | thiazol-5-yl— |
| 1.0381 | —Me | —Me | —(C=O)$^i$Pr | 6-F | 3-Cl | —CH$_2$—CH$_2$— | 4-(trifluoromethoxy)-phenyl— |
| 1.0382 | —Me | —Me | —(C=O)$^i$Pr | 6-Cl | 3-Cl | —CH$_2$—CH$_2$— | 4-(trifluoromethoxy)-phenyl— |
| 1.0383 | —CH$_2$—C≡CH | —Me | —(C=O)$^i$Pr | 6-F | 3-Cl | —CH$_2$—CH$_2$— | 4-(trifluoromethoxy)-phenyl— |
| 1.0384 | —cyclopropyl | —Me | —(C=O)$^i$Pr | 6-F | 3-Cl | —CH$_2$—CH$_2$— | 4-(trifluoromethoxy)-phenyl— |
| 1.0385 | —CH$_2$—C≡CH | —Me | —(C=O)$^i$Pr | 6-Cl | 3-Cl | —CH$_2$—CH$_2$— | 4-(trifluoromethoxy)-phenyl— |
| 1.0386 | —cyclopropyl | —Me | —(C=O)$^i$Pr | 6-Cl | 3-Cl | —CH$_2$—CH$_2$— | 4-(trifluoromethoxy)-phenyl— |
| 1.0387 | —Me | —Me | —(C=O)$^i$Pr | 6-F | 3-Cl | —CH$_2$—CH$_2$— | 2-chloro-3-pyridyl— |
| 1.0388 | —CH$_2$—C≡CH | —Me | —(C=O)$^i$Pr | 6-F | 3-Cl | —CH$_2$—CH$_2$— | 2-chloro-3-pyridyl— |
| 1.0389 | —cyclopropyl | —Me | —(C=O)$^i$Pr | 6-F | 3-Cl | —CH$_2$—CH$_2$— | 2-chloro-3-pyridyl— |
| 1.0390 | —Me | —Me | —(C=O)$^i$Pr | 6-Cl | 3-Cl | —CH$_2$—CH$_2$— | 2-chloro-3-pyridyl— |
| 1.0391 | —CH$_2$—C≡CH | —Me | —(C=O)$^i$Pr | 6-Cl | 3-Cl | —CH$_2$—CH$_2$— | 2-chloro-3-pyridyl— |
| 1.0392 | —cyclopropyl | —Me | —(C=O)$^i$Pr | 6-Cl | 3-Cl | —CH$_2$—CH$_2$— | 2-chloro-3-pyridyl— |
| 1.0393 | —Me | —Me | —(C=O)$^i$Pr | 6-F | 3-Cl | —CH$_2$—CH$_2$— | 2-chloro-4-pyridyl— |
| 1.0394 | —CH$_2$—C≡CH | —Me | —(C=O)$^i$Pr | 6-F | 3-Cl | —CH$_2$—CH$_2$— | 2-chloro-4-pyridyl— |
| 1.0395 | —cyclopropyl | —Me | —(C=O)$^i$Pr | 6-F | 3-Cl | —CH$_2$—CH$_2$— | 2-chloro-4-pyridyl— |
| 1.0396 | —Me | —Me | —(C=O)$^i$Pr | 6-Cl | 3-Cl | —CH$_2$—CH$_2$— | 2-chloro-4-pyridyl— |
| 1.0397 | —CH$_2$—C≡CH | —Me | —(C=O)$^i$Pr | 6-Cl | 3-Cl | —CH$_2$—CH$_2$— | 2-chloro-4-pyridyl— |
| 1.0398 | —cyclopropyl | —Me | —(C=O)$^i$Pr | 6-Cl | 3-Cl | —CH$_2$—CH$_2$— | 2-chloro-4-pyridyl— |
| 1.0399 | —Me | —Me | —(C=O)$^i$Pr | 6-F | 3-Cl | —CH$_2$—CH$_2$— | 3-chloro-4-fluoro-phenyl— |
| 1.0400 | —CH$_2$—C≡CH | —Me | —(C=O)$^i$Pr | 6-F | 3-Cl | —CH$_2$—CH$_2$— | 3-chloro-4-fluoro-phenyl— |
| 1.0401 | —cyclopropyl | —Me | —(C=O)$^i$Pr | 6-F | 3-Cl | —CH$_2$—CH$_2$— | 3-chloro-4-fluoro-phenyl— |
| 1.0402 | —Me | —Me | —(C=O)$^i$Pr | 6-Cl | 3-Cl | —CH$_2$—CH$_2$— | 3-chloro-4-fluoro-phenyl— |
| 1.0403 | —CH$_2$—C≡CH | —Me | —(C=O)$^i$Pr | 6-Cl | 3-Cl | —CH$_2$—CH$_2$— | 3-chloro-4-fluoro-phenyl— |
| 1.0404 | —cyclopropyl | —Me | —(C=O)$^i$Pr | 6-Cl | 3-Cl | —CH$_2$—CH$_2$— | 3-chloro-4-fluoro-phenyl— |
| 1.0405 | —Me | —Me | —(C=O)$^i$Pr | 6-F | 3-Cl | —CH$_2$—CH$_2$— | 3-chloro-4-pyridyl— |
| 1.0406 | —CH$_2$—C≡CH | —Me | —(C=O)$^i$Pr | 6-F | 3-Cl | —CH$_2$—CH$_2$— | 3-chloro-4-pyridyl— |
| 1.0407 | —cyclopropyl | —Me | —(C=O)$^i$Pr | 6-F | 3-Cl | —CH$_2$—CH$_2$— | 3-chloro-4-pyridyl— |
| 1.0408 | —Me | —Me | —(C=O)$^i$Pr | 6-Cl | 3-Cl | —CH$_2$—CH$_2$— | 3-chloro-4-pyridyl— |
| 1.0409 | —CH$_2$—C≡CH | —Me | —(C=O)$^i$Pr | 6-Cl | 3-Cl | —CH$_2$—CH$_2$— | 3-chloro-4-pyridyl— |
| 1.0410 | —cyclopropyl | —Me | —(C=O)$^i$Pr | 6-Cl | 3-Cl | —CH$_2$—CH$_2$— | 3-chloro-4-pyridyl— |
| 1.0411 | —Me | —Me | —(C=O)$^i$Pr | 6-F | 3-Cl | —CH$_2$—CH$_2$— | 4-hydroxy-phenyl— |
| 1.0412 | —CH$_2$—C≡CH | —Me | —(C=O)$^i$Pr | 6-F | 3-Cl | —CH$_2$—CH$_2$— | 4-hydroxy-phenyl— |
| 1.0413 | —cyclopropyl | —Me | —(C=O)$^i$Pr | 6-F | 3-Cl | —CH$_2$—CH$_2$— | 4-hydroxy-phenyl— |
| 1.0414 | —Me | —Me | —(C=O)$^i$Pr | 6-Cl | 3-Cl | —CH$_2$—CH$_2$— | 4-hydroxy-phenyl— |
| 1.0415 | —CH$_2$—C≡CH | —Me | —(C=O)$^i$Pr | 6-Cl | 3-Cl | —CH$_2$—CH$_2$— | 4-hydroxy-phenyl— |
| 1.0416 | —cyclopropyl | —Me | —(C=O)$^i$Pr | 6-Cl | 3-Cl | —CH$_2$—CH$_2$— | 4-hydroxy-phenyl— |
| 1.0417 | —Me | —Me | —(C=O)$^i$Pr | 6-F | 3-Cl | —CH$_2$—CH$_2$— | 4-cyclopropyl-phenyl— |
| 1.0418 | —CH$_2$—C≡CH | —Me | —(C=O)$^i$Pr | 6-F | 3-Cl | —CH$_2$—CH$_2$— | 4-cyclopropyl-phenyl— |
| 1.0419 | —cyclopropyl | —Me | —(C=O)$^i$Pr | 6-F | 3-Cl | —CH$_2$—CH$_2$— | 4-cyclopropyl-phenyl— |
| 1.0420 | —Me | —Me | —(C=O)$^i$Pr | 6-Cl | 3-Cl | —CH$_2$—CH$_2$— | 4-cyclopropyl-phenyl— |
| 1.0421 | —CH$_2$—C≡CH | —Me | —(C=O)$^i$Pr | 6-Cl | 3-Cl | —CH$_2$—CH$_2$— | 4-cyclopropyl-phenyl— |
| 1.0422 | —cyclopropyl | —Me | —(C=O)$^i$Pr | 6-Cl | 3-Cl | —CH$_2$—CH$_2$— | 4-cyclopropyl-phenyl— |
| 1.0423 | —Me | —Me | —(C=O)$^i$Pr | 6-F | 3-Cl | —CH$_2$—CH$_2$— | 1-methyl-3-(trifluoromethyl)pyrazol-4-yl— |
| 1.0424 | —CH$_2$—C≡CH | —Me | —(C=O)$^i$Pr | 6-F | 3-Cl | —CH$_2$—CH$_2$— | 1-methyl-3-(trifluoromethyl)pyrazol-4-yl— |
| 1.0425 | —cyclopropyl | —Me | —(C=O)$^i$Pr | 6-F | 3-Cl | —CH$_2$—CH$_2$— | 1-methyl-3-(trifluoromethyl)pyrazol-4-yl— |
| 1.0426 | —Me | —Me | —(C=O)$^i$Pr | 6-Cl | 3-Cl | —CH$_2$—CH$_2$— | 1-methyl-3-(trifluoromethyl)pyrazol-4-yl— |
| 1.0427 | —CH$_2$—C≡CH | —Me | —(C=O)$^i$Pr | 6-Cl | 3-Cl | —CH$_2$—CH$_2$— | 1-methyl-3-(trifluoromethyl)pyrazol-4-yl— |
| 1.0428 | —cyclopropyl | —Me | —(C=O)$^i$Pr | 6-Cl | 3-Cl | —CH$_2$—CH$_2$— | 1-methyl-3-(trifluoromethyl)pyrazol-4-yl— |
| 1.0429 | —Me | —Me | —(C=O)$^i$Pr | 6-F | 3-Cl | —CH$_2$—CH$_2$— | thiazol-2-yl— |
| 1.0430 | —CH$_2$—C≡CH | —Me | —(C=O)$^i$Pr | 6-F | 3-Cl | —CH$_2$—CH$_2$— | thiazol-2-yl— |
| 1.0431 | —cyclopropyl | —Me | —(C=O)$^i$Pr | 6-F | 3-Cl | —CH$_2$—CH$_2$— | thiazol-2-yl— |

TABLE 1-continued

Herbicidal compounds of the present invention. The numbering system used to describe the positions of X and Y is shown for the purposes of clarity only.

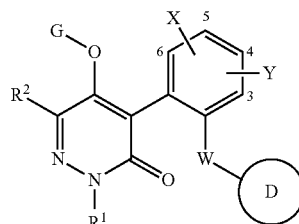

(I)

| Cmpd. No. | R$^1$ | R$^2$ | G | X | Y | W | D |
|---|---|---|---|---|---|---|---|
| 1.0432 | —Me | —Me | —(C═O)$^i$Pr | 6-Cl | 3-Cl | —CH$_2$—CH$_2$— | thiazol-2-yl— |
| 1.0433 | —CH$_2$—C≡CH | —Me | —(C═O)$^i$Pr | 6-Cl | 3-Cl | —CH$_2$—CH$_2$— | thiazol-2-yl— |
| 1.0434 | —cyclopropyl | —Me | —(C═O)$^i$Pr | 6-Cl | 3-Cl | —CH$_2$—CH$_2$— | thiazol-2-yl— |
| 1.0435 | —Me | —Me | —(C═O)$^i$Pr | 6-F | 3-Cl | —CH$_2$—CH$_2$— | pyrimidin-5-yl— |
| 1.0436 | —CH$_2$—C≡CH | —Me | —(C═O)$^i$Pr | 6-F | 3-Cl | —CH$_2$—CH$_2$— | pyrimidin-5-yl— |
| 1.0437 | —cyclopropyl | —Me | —(C═O)$^i$Pr | 6-F | 3-Cl | —CH$_2$—CH$_2$— | pyrimidin-5-yl— |
| 1.0438 | —Me | —Me | —(C═O)$^i$Pr | 6-Cl | 3-Cl | —CH$_2$—CH$_2$— | pyrimidin-5-yl— |
| 1.0439 | —CH$_2$—C≡CH | —Me | —(C═O)$^i$Pr | 6-Cl | 3-Cl | —CH$_2$—CH$_2$— | pyrimidin-5-yl— |
| 1.0440 | —cyclopropyl | —Me | —(C═O)$^i$Pr | 6-Cl | 3-Cl | —CH$_2$—CH$_2$— | pyrimidin-5-yl— |
| 1.0441 | —Me | —Me | —(C═O)$^i$Pr | 6-F | 3-Cl | —CH$_2$—CH$_2$— | 4-(tert-butoxy)-phenyl— |
| 1.0442 | —CH$_2$—C≡CH | —Me | —(C═O)$^i$Pr | 6-F | 3-Cl | —CH$_2$—CH$_2$— | 4-(tert-butoxy)-phenyl— |
| 1.0443 | —cyclopropyl | —Me | —(C═O)$^i$Pr | 6-F | 3-Cl | —CH$_2$—CH$_2$— | 4-(tert-butoxy)-phenyl— |
| 1.0444 | —Me | —Me | —(C═O)$^i$Pr | 6-Cl | 3-Cl | —CH$_2$—CH$_2$— | 4-(tert-butoxy)-phenyl— |
| 1.0445 | —CH$_2$—C≡CH | —Me | —(C═O)$^i$Pr | 6-Cl | 3-Cl | —CH$_2$—CH$_2$— | 4-(tert-butoxy)-phenyl— |
| 1.0446 | —cyclopropyl | —Me | —(C═O)$^i$Pr | 6-Cl | 3-Cl | —CH$_2$—CH$_2$— | 4-(tert-butoxy)-phenyl— |
| 1.0447 | —Me | —Me | —(C═O)$^i$Pr | 6-F | 3-Cl | —CH$_2$—CH$_2$— | thiazol-5-yl— |
| 1.0448 | —CH$_2$—C≡CH | —Me | —(C═O)$^i$Pr | 6-F | 3-Cl | —CH$_2$—CH$_2$— | thiazol-5-yl— |
| 1.0449 | —cyclopropyl | —Me | —(C═O)$^i$Pr | 6-F | 3-Cl | —CH$_2$—CH$_2$— | thiazol-5-yl— |
| 1.0450 | —Me | —Me | —(C═O)$^i$Pr | 6-Cl | 3-Cl | —CH$_2$—CH$_2$— | thiazol-5-yl— |
| 1.0451 | —CH$_2$—C≡CH | —Me | —(C═O)$^i$Pr | 6-Cl | 3-Cl | —CH$_2$—CH$_2$— | thiazol-5-yl— |
| 1.0452 | —cyclopropyl | —Me | —(C═O)$^i$Pr | 6-Cl | 3-Cl | —CH$_2$—CH$_2$— | thiazol-5-yl— |
| 1.0453 | —Me | —Me | —H | 6-F | —H | —CH$_2$—CH$_2$— | 4-(trifluoromethoxy)-phenyl— |
| 1.0454 | —Me | —Me | —H | 6-Cl | —H | —CH$_2$—CH$_2$— | 4-(trifluoromethoxy)-phenyl— |
| 1.0455 | —CH$_2$—C≡CH | —Me | —H | 6-F | —H | —CH$_2$—CH$_2$— | 4-(trifluoromethoxy)-phenyl— |
| 1.0456 | —cyclopropyl | —Me | —H | 6-F | —H | —CH$_2$—CH$_2$— | 4-(trifluoromethoxy)-phenyl— |
| 1.0457 | —CH$_2$—C≡CH | —Me | —H | 6-Cl | —H | —CH$_2$—CH$_2$— | 4-(trifluoromethoxy)-phenyl— |
| 1.0458 | —cyclopropyl | —Me | —H | 6-Cl | —H | —CH$_2$—CH$_2$— | 4-(trifluoromethoxy)-phenyl— |
| 1.0459 | —Me | —Me | —H | 6-F | —H | —CH$_2$—CH$_2$— | 2-chloro-3-pyridyl— |
| 1.0460 | —CH$_2$—C≡CH | —Me | —H | 6-F | —H | —CH$_2$—CH$_2$— | 2-chloro-3-pyridyl— |
| 1.0461 | —cyclopropyl | —Me | —H | 6-F | —H | —CH$_2$—CH$_2$— | 2-chloro-3-pyridyl— |
| 1.0462 | —Me | —Me | —H | 6-Cl | —H | —CH$_2$—CH$_2$— | 2-chloro-3-pyridyl— |
| 1.0463 | —CH$_2$—C≡CH | —Me | —H | 6-Cl | —H | —CH$_2$—CH$_2$— | 2-chloro-3-pyridyl— |
| 1.0464 | —cyclopropyl | —Me | —H | 6-Cl | —H | —CH$_2$—CH$_2$— | 2-chloro-3-pyridyl— |
| 1.0465 | —Me | —Me | —H | 6-F | —H | —CH$_2$—CH$_2$— | 2-chloro-4-pyridyl— |
| 1.0466 | —CH$_2$—C≡CH | —Me | —H | 6-F | —H | —CH$_2$—CH$_2$— | 2-chloro-4-pyridyl— |
| 1.0467 | —cyclopropyl | —Me | —H | 6-F | —H | —CH$_2$—CH$_2$— | 2-chloro-4-pyridyl— |
| 1.0468 | —Me | —Me | —H | 6-Cl | —H | —CH$_2$—CH$_2$— | 2-chloro-4-pyridyl— |
| 1.0469 | —CH$_2$—C≡CH | —Me | —H | 6-Cl | —H | —CH$_2$—CH$_2$— | 2-chloro-4-pyridyl— |
| 1.0470 | —cyclopropyl | —Me | —H | 6-Cl | —H | —CH$_2$—CH$_2$— | 2-chloro-4-pyridyl— |
| 1.0471 | —Me | —Me | —H | 6-F | —H | —CH$_2$—CH$_2$— | 3-chloro-4-fluoro-phenyl— |
| 1.0472 | —CH$_2$—C≡CH | —Me | —H | 6-F | —H | —CH$_2$—CH$_2$— | 3-chloro-4-fluoro-phenyl— |
| 1.0473 | —cyclopropyl | —Me | —H | 6-F | —H | —CH$_2$—CH$_2$— | 3-chloro-4-fluoro-phenyl— |
| 1.0474 | —Me | —Me | —H | 6-Cl | —H | —CH$_2$—CH$_2$— | 3-chloro-4-fluoro-phenyl— |
| 1.0475 | —CH$_2$—C≡CH | —Me | —H | 6-Cl | —H | —CH$_2$—CH$_2$— | 3-chloro-4-fluoro-phenyl— |
| 1.0476 | —cyclopropyl | —Me | —H | 6-Cl | —H | —CH$_2$—CH$_2$— | 3-chloro-4-fluoro-phenyl— |
| 1.0477 | —Me | —Me | —H | 6-F | —H | —CH$_2$—CH$_2$— | 3-chloro-4-pyridyl— |
| 1.0478 | —CH$_2$—C≡CH | —Me | —H | 6-F | —H | —CH$_2$—CH$_2$— | 3-chloro-4-pyridyl— |
| 1.0479 | —cyclopropyl | —Me | —H | 6-F | —H | —CH$_2$—CH$_2$— | 3-chloro-4-pyridyl— |
| 1.0480 | —Me | —Me | —H | 6-Cl | —H | —CH$_2$—CH$_2$— | 3-chloro-4-pyridyl— |
| 1.0481 | —CH$_2$—C≡CH | —Me | —H | 6-Cl | —H | —CH$_2$—CH$_2$— | 3-chloro-4-pyridyl— |
| 1.0482 | —cyclopropyl | —Me | —H | 6-Cl | —H | —CH$_2$—CH$_2$— | 3-chloro-4-pyridyl— |
| 1.0483 | —Me | —Me | —H | 6-F | —H | —CH$_2$—CH$_2$— | 4-hydroxy-phenyl— |
| 1.0484 | —CH$_2$—C≡CH | —Me | —H | 6-F | —H | —CH$_2$—CH$_2$— | 4-hydroxy-phenyl— |
| 1.0485 | —cyclopropyl | —Me | —H | 6-F | —H | —CH$_2$—CH$_2$— | 4-hydroxy-phenyl— |
| 1.0486 | —Me | —Me | —H | 6-Cl | —H | —CH$_2$—CH$_2$— | 4-hydroxy-phenyl— |
| 1.0487 | —CH$_2$—C≡CH | —Me | —H | 6-Cl | —H | —CH$_2$—CH$_2$— | 4-hydroxy-phenyl— |
| 1.0488 | —cyclopropyl | —Me | —H | 6-Cl | —H | —CH$_2$—CH$_2$— | 4-hydroxy-phenyl— |
| 1.0489 | —Me | —Me | —H | 6-F | —H | —CH$_2$—CH$_2$— | 4-cyclopropyl-phenyl— |
| 1.0490 | —CH$_2$—C≡CH | —Me | —H | 6-F | —H | —CH$_2$—CH$_2$— | 4-cyclopropyl-phenyl— |
| 1.0491 | —cyclopropyl | —Me | —H | 6-F | —H | —CH$_2$—CH$_2$— | 4-cyclopropyl-phenyl— |
| 1.0492 | —Me | —Me | —H | 6-Cl | —H | —CH$_2$—CH$_2$— | 4-cyclopropyl-phenyl— |
| 1.0493 | —CH$_2$—C≡CH | —Me | —H | 6-Cl | —H | —CH$_2$—CH$_2$— | 4-cyclopropyl-phenyl— |

TABLE 1-continued

Herbicidal compounds of the present invention. The numbering system used to describe the positions of X and Y is shown for the purposes of clarity only.

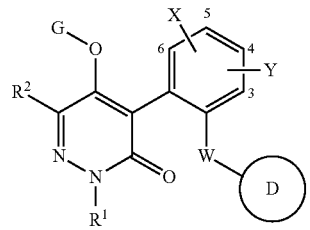

(I)

| Cmpd. No. | R$^1$ | R$^2$ | G | X | Y | W | D |
|---|---|---|---|---|---|---|---|
| 1.0494 | —cyclopropyl | —Me | —H | 6-Cl | —H | —CH$_2$—CH$_2$— | 4-cyclopropyl-phenyl— |
| 1.0495 | —Me | —Me | —H | 6-F | —H | —CH$_2$—CH$_2$— | 1-methyl-3-(trifluoromethyl)pyrazol-4-yl— |
| 1.0496 | —CH$_2$—C≡CH | —Me | —H | 6-F | —H | —CH$_2$—CH$_2$— | 1-methyl-3-(trifluoromethyl)pyrazol-4-yl— |
| 1.0497 | —cyclopropyl | —Me | —H | 6-F | —H | —CH$_2$—CH$_2$— | 1-methyl-3-(trifluoromethyl)pyrazol-4-yl— |
| 1.0498 | —Me | —Me | —H | 6-Cl | —H | —CH$_2$—CH$_2$— | 1-methyl-3-(trifluoromethyl)pyrazol-4-yl— |
| 1.0499 | —CH$_2$—C≡CH | —Me | —H | 6-Cl | —H | —CH$_2$—CH$_2$— | 1-methyl-3-(trifluoromethyl)pyrazol-4-yl— |
| 1.0500 | —cyclopropyl | —Me | —H | 6-Cl | —H | —CH$_2$—CH$_2$— | 1-methyl-3-(trifluoromethyl)pyrazol-4-yl— |
| 1.0501 | —Me | —Me | —H | 6-F | —H | —CH$_2$—CH$_2$— | thiazol-2-yl— |
| 1.0502 | —CH$_2$—C≡CH | —Me | —H | 6-F | —H | —CH$_2$—CH$_2$— | thiazol-2-yl— |
| 1.0503 | —cyclopropyl | —Me | —H | 6-F | —H | —CH$_2$—CH$_2$— | thiazol-2-yl— |
| 1.0504 | —Me | —Me | —H | 6-Cl | —H | —CH$_2$—CH$_2$— | thiazol-2-yl— |
| 1.0505 | —CH$_2$—C≡CH | —Me | —H | 6-Cl | —H | —CH$_2$—CH$_2$— | thiazol-2-yl— |
| 1.0506 | —cyclopropyl | —Me | —H | 6-Cl | —H | —CH$_2$—CH$_2$— | thiazol-2-yl— |
| 1.0507 | —Me | —Me | —H | 6-F | —H | —CH$_2$—CH$_2$— | pyrimidin-5-yl— |
| 1.0508 | —CH$_2$—C≡CH | —Me | —H | 6-F | —H | —CH$_2$—CH$_2$— | pyrimidin-5-yl— |
| 1.0509 | —cyclopropyl | —Me | —H | 6-F | —H | —CH$_2$—CH$_2$— | pyrimidin-5-yl— |
| 1.0510 | —Me | —Me | —H | 6-Cl | —H | —CH$_2$—CH$_2$— | pyrimidin-5-yl— |
| 1.0511 | —CH$_2$—C≡CH | —Me | —H | 6-Cl | —H | —CH$_2$—CH$_2$— | pyrimidin-5-yl— |
| 1.0512 | —cyclopropyl | —Me | —H | 6-Cl | —H | —CH$_2$—CH$_2$— | pyrimidin-5-yl— |
| 1.0513 | —Me | —Me | —H | 6-F | —H | —CH$_2$—CH$_2$— | 4-(tert-butoxy)-phenyl— |
| 1.0514 | —CH$_2$—C≡CH | —Me | —H | 6-F | —H | —CH$_2$—CH$_2$— | 4-(tert-butoxy)-phenyl— |
| 1.0515 | —cyclopropyl | —Me | —H | 6-F | —H | —CH$_2$—CH$_2$— | 4-(tert-butoxy)-phenyl— |
| 1.0516 | —Me | —Me | —H | 6-Cl | —H | —CH$_2$—CH$_2$— | 4-(tert-butoxy)-phenyl— |
| 1.0517 | —CH$_2$—C≡CH | —Me | —H | 6-Cl | —H | —CH$_2$—CH$_2$— | 4-(tert-butoxy)-phenyl— |
| 1.0518 | —cyclopropyl | —Me | —H | 6-Cl | —H | —CH$_2$—CH$_2$— | 4-(tert-butoxy)-phenyl— |
| 1.0519 | —Me | —Me | —H | 6-F | —H | —CH$_2$—CH$_2$— | thiazol-5-yl— |
| 1.0520 | —CH$_2$—C≡CH | —Me | —H | 6-F | —H | —CH$_2$—CH$_2$— | thiazol-5-yl— |
| 1.0521 | —cyclopropyl | —Me | —H | 6-F | —H | —CH$_2$—CH$_2$— | thiazol-5-yl— |
| 1.0522 | —Me | —Me | —H | 6-Cl | —H | —CH$_2$—CH$_2$— | thiazol-5-yl— |
| 1.0523 | —CH$_2$—C≡CH | —Me | —H | 6-Cl | —H | —CH$_2$—CH$_2$— | thiazol-5-yl— |
| 1.0524 | —cyclopropyl | —Me | —H | 6-Cl | —H | —CH$_2$—CH$_2$— | thiazol-5-yl— |
| 1.0525 | —Me | —Me | —(C=O)$^i$Pr | 6-F | —H | —CH$_2$—CH$_2$— | 4-(trifluoromethoxy)-phenyl— |
| 1.0526 | —Me | —Me | —(C=O)$^i$Pr | 6-Cl | —H | —CH$_2$—CH$_2$— | 4-(trifluoromethoxy)-phenyl— |
| 1.0527 | —CH$_2$—C≡CH | —Me | —(C=O)$^i$Pr | 6-F | —H | —CH$_2$—CH$_2$— | 4-(trifluoromethoxy)-phenyl— |
| 1.0528 | —cyclopropyl | —Me | —(C=O)$^i$Pr | 6-F | —H | —CH$_2$—CH$_2$— | 4-(trifluoromethoxy)-phenyl— |
| 1.0529 | —CH$_2$—C≡CH | —Me | —(C=O)$^i$Pr | 6-Cl | —H | —CH$_2$—CH$_2$— | 4-(trifluoromethoxy)-phenyl— |
| 1.0530 | —cyclopropyl | —Me | —(C=O)$^i$Pr | 6-Cl | —H | —CH$_2$—CH$_2$— | 4-(trifluoromethoxy)-phenyl— |
| 1.0531 | —Me | —Me | —(C=O)$^i$Pr | 6-F | —H | —CH$_2$—CH$_2$— | 2-chloro-3-pyridyl— |
| 1.0532 | —CH$_2$—C≡CH | —Me | —(C=O)$^i$Pr | 6-F | —H | —CH$_2$—CH$_2$— | 2-chloro-3-pyridyl— |
| 1.0533 | —cyclopropyl | —Me | —(C=O)$^i$Pr | 6-F | —H | —CH$_2$—CH$_2$— | 2-chloro-3-pyridyl— |
| 1.0534 | —Me | —Me | —(C=O)$^i$Pr | 6-Cl | —H | —CH$_2$—CH$_2$— | 2-chloro-3-pyridyl— |
| 1.0535 | —CH$_2$—C≡CH | —Me | —(C=O)$^i$Pr | 6-Cl | —H | —CH$_2$—CH$_2$— | 2-chloro-3-pyridyl— |
| 1.0536 | —cyclopropyl | —Me | —(C=O)$^i$Pr | 6-Cl | —H | —CH$_2$—CH$_2$— | 2-chloro-3-pyridyl— |
| 1.0537 | —Me | —Me | —(C=O)$^i$Pr | 6-F | —H | —CH$_2$—CH$_2$— | 2-chloro-4-pyridyl— |
| 1.0538 | —CH$_2$—C≡CH | —Me | —(C=O)$^i$Pr | 6-F | —H | —CH$_2$—CH$_2$— | 2-chloro-4-pyridyl— |
| 1.0539 | —cyclopropyl | —Me | —(C=O)$^i$Pr | 6-F | —H | —CH$_2$—CH$_2$— | 2-chloro-4-pyridyl— |
| 1.0540 | —Me | —Me | —(C=O)$^i$Pr | 6-Cl | —H | —CH$_2$—CH$_2$— | 2-chloro-4-pyridyl— |
| 1.0541 | —CH$_2$—C≡CH | —Me | —(C=O)$^i$Pr | 6-Cl | —H | —CH$_2$—CH$_2$— | 2-chloro-4-pyridyl— |
| 1.0542 | —cyclopropyl | —Me | —(C=O)$^i$Pr | 6-Cl | —H | —CH$_2$—CH$_2$— | 2-chloro-4-pyridyl— |
| 1.0543 | —Me | —Me | —(C=O)$^i$Pr | 6-F | —H | —CH$_2$—CH$_2$— | 3-chloro-4-fluoro-phenyl— |
| 1.0544 | —CH$_2$—C≡CH | —Me | —(C=O)$^i$Pr | 6-F | —H | —CH$_2$—CH$_2$— | 3-chloro-4-fluoro-phenyl— |
| 1.0545 | —cyclopropyl | —Me | —(C=O)$^i$Pr | 6-F | —H | —CH$_2$—CH$_2$— | 3-chloro-4-fluoro-phenyl— |
| 1.0546 | —Me | —Me | —(C=O)$^i$Pr | 6-Cl | —H | —CH$_2$—CH$_2$— | 3-chloro-4-fluoro-phenyl— |
| 1.0547 | —CH$_2$—C≡CH | —Me | —(C=O)$^i$Pr | 6-Cl | —H | —CH$_2$—CH$_2$— | 3-chloro-4-fluoro-phenyl— |
| 1.0548 | —cyclopropyl | —Me | —(C=O)$^i$Pr | 6-Cl | —H | —CH$_2$—CH$_2$— | 3-chloro-4-fluoro-phenyl— |
| 1.0549 | —Me | —Me | —(C=O)$^i$Pr | 6-F | —H | —CH$_2$—CH$_2$— | 3-chloro-4-pyridyl— |

TABLE 1-continued

Herbicidal compounds of the present invention. The numbering system used to describe the positions of X and Y is shown for the purposes of clarity only.

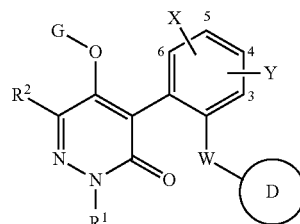

(I)

| Cmpd. No. | R¹ | R² | G | X | Y | W | D |
|---|---|---|---|---|---|---|---|
| 1.0550 | —CH₂—C≡CH | —Me | —(C=O)ⁱPr | 6-F | —H | —CH₂—CH₂— | 3-chloro-4-pyridyl— |
| 1.0551 | —cyclopropyl | —Me | —(C=O)ⁱPr | 6-F | —H | —CH₂—CH₂— | 3-chloro-4-pyridyl— |
| 1.0552 | —Me | —Me | —(C=O)ⁱPr | 6-Cl | —H | —CH₂—CH₂— | 3-chloro-4-pyridyl— |
| 1.0553 | —CH₂—C≡CH | —Me | —(C=O)ⁱPr | 6-Cl | —H | —CH₂—CH₂— | 3-chloro-4-pyridyl— |
| 1.0554 | —cyclopropyl | —Me | —(C=O)ⁱPr | 6-Cl | —H | —CH₂—CH₂— | 3-chloro-4-pyridyl— |
| 1.0555 | —Me | —Me | —(C=O)ⁱPr | 6-F | —H | —CH₂—CH₂— | 4-hydroxy-phenyl— |
| 1.0556 | —CH₂—C≡CH | —Me | —(C=O)ⁱPr | 6-F | —H | —CH₂—CH₂— | 4-hydroxy-phenyl— |
| 1.0557 | —cyclopropyl | —Me | —(C=O)ⁱPr | 6-F | —H | —CH₂—CH₂— | 4-hydroxy-phenyl— |
| 1.0558 | —Me | —Me | —(C=O)ⁱPr | 6-Cl | —H | —CH₂—CH₂— | 4-hydroxy-phenyl— |
| 1.0559 | —CH₂—C≡CH | —Me | —(C=O)ⁱPr | 6-Cl | —H | —CH₂—CH₂— | 4-hydroxy-phenyl— |
| 1.0560 | —cyclopropyl | —Me | —(C=O)ⁱPr | 6-Cl | —H | —CH₂—CH₂— | 4-hydroxy-phenyl— |
| 1.0561 | —Me | —Me | —(C=O)ⁱPr | 6-F | —H | —CH₂—CH₂— | 4-cyclopropyl-phenyl— |
| 1.0562 | —CH₂—C≡CH | —Me | —(C=O)ⁱPr | 6-F | —H | —CH₂—CH₂— | 4-cyclopropyl-phenyl— |
| 1.0563 | —cyclopropyl | —Me | —(C=O)ⁱPr | 6-F | —H | —CH₂—CH₂— | 4-cyclopropyl-phenyl— |
| 1.0564 | —Me | —Me | —(C=O)ⁱPr | 6-Cl | —H | —CH₂—CH₂— | 4-cyclopropyl-phenyl— |
| 1.0565 | —CH₂—C≡CH | —Me | —(C=O)ⁱPr | 6-Cl | —H | —CH₂—CH₂— | 4-cyclopropyl-phenyl— |
| 1.0566 | —cyclopropyl | —Me | —(C=O)ⁱPr | 6-Cl | —H | —CH₂—CH₂— | 4-cyclopropyl-phenyl— |
| 1.0567 | —Me | —Me | —(C=O)ⁱPr | 6-F | —H | —CH₂—CH₂— | 1-methyl-3-(trifluoromethyl)pyrazol-4-yl— |
| 1.0568 | —CH₂—C≡CH | —Me | —(C=O)ⁱPr | 6-F | —H | —CH₂—CH₂— | 1-methyl-3-(trifluoromethyl)pyrazol-4-yl— |
| 1.0569 | —cyclopropyl | —Me | —(C=O)ⁱPr | 6-F | —H | —CH₂—CH₂— | 1-methyl-3-(trifluoromethyl)pyrazol-4-yl— |
| 1.0570 | —Me | —Me | —(C=O)ⁱPr | 6-Cl | —H | —CH₂—CH₂— | 1-methyl-3-(trifluoromethyl)pyrazol-4-yl— |
| 1.0571 | —CH₂—C≡CH | —Me | —(C=O)ⁱPr | 6-Cl | —H | —CH₂—CH₂— | 1-methyl-3-(trifluoromethyl)pyrazol-4-yl— |
| 1.0572 | —cyclopropyl | —Me | —(C=O)ⁱPr | 6-Cl | —H | —CH₂—CH₂— | 1-methyl-3-(trifluoromethyl)pyrazol-4-yl— |
| 1.0573 | —Me | —Me | —(C=O)ⁱPr | 6-F | —H | —CH₂—CH₂— | thiazol-2-yl— |
| 1.0574 | —CH₂—C≡CH | —Me | —(C=O)ⁱPr | 6-F | —H | —CH₂—CH₂— | thiazol-2-yl— |
| 1.0575 | —cyclopropyl | —Me | —(C=O)ⁱPr | 6-F | —H | —CH₂—CH₂— | thiazol-2-yl— |
| 1.0576 | —Me | —Me | —(C=O)ⁱPr | 6-Cl | —H | —CH₂—CH₂— | thiazol-2-yl— |
| 1.0577 | —CH₂—C≡CH | —Me | —(C=O)ⁱPr | 6-Cl | —H | —CH₂—CH₂— | thiazol-2-yl— |
| 1.0578 | —cyclopropyl | —Me | —(C=O)ⁱPr | 6-Cl | —H | —CH₂—CH₂— | thiazol-2-yl— |
| 1.0579 | —Me | —Me | —(C=O)ⁱPr | 6-F | —H | —CH₂—CH₂— | pyrimidin-5-yl— |
| 1.0580 | —CH₂—C≡CH | —Me | —(C=O)ⁱPr | 6-F | —H | —CH₂—CH₂— | pyrimidin-5-yl— |
| 1.0581 | —cyclopropyl | —Me | —(C=O)ⁱPr | 6-F | —H | —CH₂—CH₂— | pyrimidin-5-yl— |
| 1.0582 | —Me | —Me | —(C=O)ⁱPr | 6-Cl | —H | —CH₂—CH₂— | pyrimidin-5-yl— |
| 1.0583 | —CH₂—C≡CH | —Me | —(C=O)ⁱPr | 6-Cl | —H | —CH₂—CH₂— | pyrimidin-5-yl— |
| 1.0584 | —cyclopropyl | —Me | —(C=O)ⁱPr | 6-Cl | —H | —CH₂—CH₂— | pyrimidin-5-yl— |
| 1.0585 | —Me | —Me | —(C=O)ⁱPr | 6-F | —H | —CH₂—CH₂— | 4-(tert-butoxy)-phenyl— |
| 1.0586 | —CH₂—C≡CH | —Me | —(C=O)ⁱPr | 6-F | —H | —CH₂—CH₂— | 4-(tert-butoxy)-phenyl— |
| 1.0587 | —cyclopropyl | —Me | —(C=O)ⁱPr | 6-F | —H | —CH₂—CH₂— | 4-(tert-butoxy)-phenyl— |
| 1.0588 | —Me | —Me | —(C=O)ⁱPr | 6-Cl | —H | —CH₂—CH₂— | 4-(tert-butoxy)-phenyl— |
| 1.0589 | —CH₂—C≡CH | —Me | —(C=O)ⁱPr | 6-Cl | —H | —CH₂—CH₂— | 4-(tert-butoxy)-phenyl— |
| 1.0590 | —cyclopropyl | —Me | —(C=O)ⁱPr | 6-Cl | —H | —CH₂—CH₂— | 4-(tert-butoxy)-phenyl— |
| 1.0591 | —Me | —Me | —(C=O)ⁱPr | 6-F | —H | —CH₂—CH₂— | thiazol-5-yl— |
| 1.0592 | —CH₂—C≡CH | —Me | —(C=O)ⁱPr | 6-F | —H | —CH₂—CH₂— | thiazol-5-yl— |
| 1.0593 | —cyclopropyl | —Me | —(C=O)ⁱPr | 6-F | —H | —CH₂—CH₂— | thiazol-5-yl— |
| 1.0594 | —Me | —Me | —(C=O)ⁱPr | 6-Cl | —H | —CH₂—CH₂— | thiazol-5-yl— |
| 1.0595 | —CH₂—C≡CH | —Me | —(C=O)ⁱPr | 6-Cl | —H | —CH₂—CH₂— | thiazol-5-yl— |
| 1.0596 | —cyclopropyl | —Me | —(C=O)ⁱPr | 6-Cl | —H | —CH₂—CH₂— | thiazol-5-yl— |
| 1.0597 | —Me | —Me | —H | 6-F | 3-Cl | —CH₂—CH₂— | 2-cyano-phenyl— |
| 1.0598 | —Me | —Me | —H | 6-Cl | 3-Cl | —CH₂—CH₂— | 2-cyano-phenyl— |
| 1.0599 | —CH₂—C≡CH | —Me | —H | 6-F | 3-Cl | —CH₂—CH₂— | 2-cyano-phenyl— |
| 1.0600 | —cyclopropyl | —Me | —H | 6-F | 3-Cl | —CH₂—CH₂— | 2-cyano-phenyl— |
| 1.0601 | —CH₂—C≡CH | —Me | —H | 6-Cl | 3-Cl | —CH₂—CH₂— | 2-cyano-phenyl— |
| 1.0602 | —cyclopropyl | —Me | —H | 6-Cl | 3-Cl | —CH₂—CH₂— | 2-cyano-phenyl— |
| 1.0603 | —Me | —Me | —H | 6-F | 3-Cl | —CH₂—CH₂— | 3-cyano-phenyl— |
| 1.0604 | —CH₂—C≡CH | —Me | —H | 6-F | 3-Cl | —CH₂—CH₂— | 3-cyano-phenyl— |
| 1.0605 | —cyclopropyl | —Me | —H | 6-F | 3-Cl | —CH₂—CH₂— | 3-cyano-phenyl— |

TABLE 1-continued

Herbicidal compounds of the present invention. The numbering system used to describe the
positions of X and Y is shown for the purposes of clarity only.

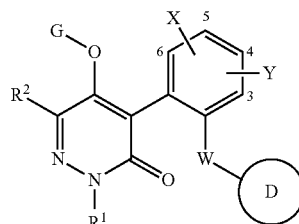

(I)

| Cmpd. No. | R¹ | R² | G | X | Y | W | D |
|---|---|---|---|---|---|---|---|
| 1.0606 | —Me | —Me | —H | 6-Cl | 3-Cl | —CH₂—CH₂— | 3-cyano-phenyl— |
| 1.0607 | —CH₂—C≡CH | —Me | —H | 6-Cl | 3-Cl | —CH₂—CH₂— | 3-cyano-phenyl— |
| 1.0608 | —cyclopropyl | —Me | —H | 6-Cl | 3-Cl | —CH₂—CH₂— | 3-cyano-phenyl— |
| 1.0609 | —Me | —Me | —H | 6-F | 3-Cl | —CH₂—CH₂— | 3-trifluoromethyl-phenyl— |
| 1.0610 | —CH₂—C≡CH | —Me | —H | 6-F | 3-Cl | —CH₂—CH₂— | 3-trifluoromethyl-phenyl— |
| 1.0611 | —cyclopropyl | —Me | —H | 6-F | 3-Cl | —CH₂—CH₂— | 3-trifluoromethyl-phenyl— |
| 1.0612 | —Me | —Me | —H | 6-Cl | 3-Cl | —CH₂—CH₂— | 3-trifluoromethyl-phenyl— |
| 1.0613 | —CH₂—C≡CH | —Me | —H | 6-Cl | 3-Cl | —CH₂—CH₂— | 3-trifluoromethyl-phenyl— |
| 1.0614 | —cyclopropyl | —Me | —H | 6-Cl | 3-Cl | —CH₂—CH₂— | 3-trifluoromethyl-phenyl— |
| 1.0615 | —Me | —Me | —H | 6-F | 3-Cl | —CH₂—CH₂— | 2-tolyl— |
| 1.0616 | —CH₂—C≡CH | —Me | —H | 6-F | 3-Cl | —CH₂—CH₂— | 2-tolyl— |
| 1.0617 | —cyclopropyl | —Me | —H | 6-F | 3-Cl | —CH₂—CH₂— | 2-tolyl— |
| 1.0618 | —Me | —Me | —H | 6-Cl | 3-Cl | —CH₂—CH₂— | 2-tolyl— |
| 1.0619 | —CH₂—C≡CH | —Me | —H | 6-Cl | 3-Cl | —CH₂—CH₂— | 2-tolyl— |
| 1.0620 | —cyclopropyl | —Me | —H | 6-Cl | 3-Cl | —CH₂—CH₂— | 2-tolyl— |
| 1.0621 | —Me | —Me | —H | 6-F | 3-Cl | —CH₂—CH₂— | 3-tolyl— |
| 1.0622 | —CH₂—C≡CH | —Me | —H | 6-F | 3-Cl | —CH₂—CH₂— | 3-tolyl— |
| 1.0623 | —cyclopropyl | —Me | —H | 6-F | 3-Cl | —CH₂—CH₂— | 3-tolyl— |
| 1.0624 | —Me | —Me | —H | 6-Cl | 3-Cl | —CH₂—CH₂— | 3-tolyl— |
| 1.0625 | —CH₂—C≡CH | —Me | —H | 6-Cl | 3-Cl | —CH₂—CH₂— | 3-tolyl— |
| 1.0626 | —cyclopropyl | —Me | —H | 6-Cl | 3-Cl | —CH₂—CH₂— | 3-tolyl— |
| 1.0627 | —Me | —Me | —H | 6-F | 3-Cl | —CH₂—CH₂— | 2-methyl-4-pyridyl— |
| 1.0628 | —CH₂—C≡CH | —Me | —H | 6-F | 3-Cl | —CH₂—CH₂— | 2-methyl-4-pyridyl— |
| 1.0629 | —cyclopropyl | —Me | —H | 6-F | 3-Cl | —CH₂—CH₂— | 2-methyl-4-pyridyl— |
| 1.0630 | —Me | —Me | —H | 6-Cl | 3-Cl | —CH₂—CH₂— | 2-methyl-4-pyridyl— |
| 1.0631 | —CH₂—C≡CH | —Me | —H | 6-Cl | 3-Cl | —CH₂—CH₂— | 2-methyl-4-pyridyl— |
| 1.0632 | —cyclopropyl | —Me | —H | 6-Cl | 3-Cl | —CH₂—CH₂— | 2-methyl-4-pyridyl— |
| 1.0633 | —Me | —Me | —H | 6-F | 3-Cl | —CH₂—CH₂— | 2-trifluoromethyl-4-pyridyl— |
| 1.0634 | —CH₂—C≡CH | —Me | —H | 6-F | 3-Cl | —CH₂—CH₂— | 2-trifluoromethyl-4-pyridyl— |
| 1.0635 | —cyclopropyl | —Me | —H | 6-F | 3-Cl | —CH₂—CH₂— | 2-trifluoromethyl-4-pyridyl— |
| 1.0636 | —Me | —Me | —H | 6-Cl | 3-Cl | —CH₂—CH₂— | 2-trifluoromethyl-4-pyridyl— |
| 1.0637 | —CH₂—C≡CH | —Me | —H | 6-Cl | 3-Cl | —CH₂—CH₂— | 2-trifluoromethyl-4-pyridyl— |
| 1.0638 | —cyclopropyl | —Me | —H | 6-Cl | 3-Cl | —CH₂—CH₂— | 2-trifluoromethyl-4-pyridyl— |
| 1.0639 | —Me | —Me | —H | 6-F | 3-Cl | —CH₂—CH₂— | 2-amino-4-pyridyl— |
| 1.0640 | —CH₂—C≡CH | —Me | —H | 6-F | 3-Cl | —CH₂—CH₂— | 2-amino-4-pyridyl— |
| 1.0641 | —cyclopropyl | —Me | —H | 6-F | 3-Cl | —CH₂—CH₂— | 2-amino-4-pyridyl— |
| 1.0642 | —Me | —Me | —H | 6-Cl | 3-Cl | —CH₂—CH₂— | 2-amino-4-pyridyl— |
| 1.0643 | —CH₂—C≡CH | —Me | —H | 6-Cl | 3-Cl | —CH₂—CH₂— | 2-amino-4-pyridyl— |
| 1.0644 | —cyclopropyl | —Me | —H | 6-Cl | 3-Cl | —CH₂—CH₂— | 2-amino-4-pyridyl— |
| 1.0645 | —Me | —Me | —H | 6-F | 3-Cl | —CH₂—CH₂— | 2-fluoro-4-pyridyl— |
| 1.0646 | —CH₂—C≡CH | —Me | —H | 6-F | 3-Cl | —CH₂—CH₂— | 2-fluoro-4-pyridyl— |
| 1.0647 | —cyclopropyl | —Me | —H | 6-F | 3-Cl | —CH₂—CH₂— | 2-fluoro-4-pyridyl— |
| 1.0648 | —Me | —Me | —H | 6-Cl | 3-Cl | —CH₂—CH₂— | 2-fluoro-4-pyridyl— |
| 1.0649 | —CH₂—C≡CH | —Me | —H | 6-Cl | 3-Cl | —CH₂—CH₂— | 2-fluoro-4-pyridyl— |
| 1.0650 | —cyclopropyl | —Me | —H | 6-Cl | 3-Cl | —CH₂—CH₂— | 2-fluoro-4-pyridyl— |
| 1.0651 | —Me | —Me | —H | 6-F | 3-Cl | —CH₂—CH₂— | 4-pyridyl— |
| 1.0652 | —CH₂—C≡CH | —Me | —H | 6-F | 3-Cl | —CH₂—CH₂— | 4-pyridyl— |
| 1.0653 | —cyclopropyl | —Me | —H | 6-F | 3-Cl | —CH₂—CH₂— | 4-pyridyl— |
| 1.0654 | —Me | —Me | —H | 6-Cl | 3-Cl | —CH₂—CH₂— | 4-pyridyl— |
| 1.0655 | —CH₂—C≡CH | —Me | —H | 6-Cl | 3-Cl | —CH₂—CH₂— | 4-pyridyl— |
| 1.0656 | —cyclopropyl | —Me | —H | 6-Cl | 3-Cl | —CH₂—CH₂— | 4-pyridyl— |
| 1.0657 | —Me | —Me | —H | 6-F | 3-Cl | —CH₂—CH₂— | 4-(methylamino)-phenyl— |
| 1.0658 | —CH₂—C≡CH | —Me | —H | 6-F | 3-Cl | —CH₂—CH₂— | 4-(methylamino)-phenyl— |
| 1.0659 | —cyclopropyl | —Me | —H | 6-F | 3-Cl | —CH₂—CH₂— | 4-(methylamino)-phenyl— |
| 1.0660 | —Me | —Me | —H | 6-Cl | 3-Cl | —CH₂—CH₂— | 4-(methylamino)-phenyl— |
| 1.0661 | —CH₂—C≡CH | —Me | —H | 6-Cl | 3-Cl | —CH₂—CH₂— | 4-(methylamino)-phenyl— |
| 1.0662 | —cyclopropyl | —Me | —H | 6-Cl | 3-Cl | —CH₂—CH₂— | 4-(methylamino)-phenyl— |
| 1.0663 | —Me | —Me | —H | 6-F | 3-Cl | —CH₂—CH₂— | 4-amino-phenyl— |
| 1.0664 | —CH₂—C≡CH | —Me | —H | 6-F | 3-Cl | —CH₂—CH₂— | 4-amino-phenyl— |
| 1.0665 | —cyclopropyl | —Me | —H | 6-F | 3-Cl | —CH₂—CH₂— | 4-amino-phenyl— |
| 1.0666 | —Me | —Me | —H | 6-Cl | 3-Cl | —CH₂—CH₂— | 4-amino-phenyl— |
| 1.0667 | —CH₂—C≡CH | —Me | —H | 6-Cl | 3-Cl | —CH₂—CH₂— | 4-amino-phenyl— |

TABLE 1-continued

Herbicidal compounds of the present invention. The numbering system used to describe the positions of X and Y is shown for the purposes of clarity only.

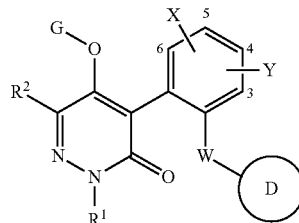

(I)

| Cmpd. No. | R¹ | R² | G | X | Y | W | D |
|---|---|---|---|---|---|---|---|
| 1.0668 | —cyclopropyl | —Me | —H | 6-Cl | 3-Cl | —CH₂—CH₂— | 4-amino-phenyl— |
| 1.0669 | —Me | —Me | —(C=O)ⁱPr | 6-F | 3-Cl | —CH₂—CH₂— | 2-cyano-phenyl— |
| 1.0670 | —Me | —Me | —(C=O)ⁱPr | 6-Cl | 3-Cl | —CH₂—CH₂— | 2-cyano-phenyl— |
| 1.0671 | —CH₂—C≡CH | —Me | —(C=O)ⁱPr | 6-F | 3-Cl | —CH₂—CH₂— | 2-cyano-phenyl— |
| 1.0672 | —cyclopropyl | —Me | —(C=O)ⁱPr | 6-F | 3-Cl | —CH₂—CH₂— | 2-cyano-phenyl— |
| 1.0673 | —CH₂—C≡CH | —Me | —(C=O)ⁱPr | 6-Cl | 3-Cl | —CH₂—CH₂— | 2-cyano-phenyl— |
| 1.0674 | —cyclopropyl | —Me | —(C=O)ⁱPr | 6-Cl | 3-Cl | —CH₂—CH₂— | 2-cyano-phenyl— |
| 1.0675 | —Me | —Me | —(C=O)ⁱPr | 6-F | 3-Cl | —CH₂—CH₂— | 3-cyano-phenyl— |
| 1.0676 | —CH₂—C≡CH | —Me | —(C=O)ⁱPr | 6-F | 3-Cl | —CH₂—CH₂— | 3-cyano-phenyl— |
| 1.0677 | —cyclopropyl | —Me | —(C=O)ⁱPr | 6-F | 3-Cl | —CH₂—CH₂— | 3-cyano-phenyl— |
| 1.0678 | —Me | —Me | —(C=O)ⁱPr | 6-Cl | 3-Cl | —CH₂—CH₂— | 3-cyano-phenyl— |
| 1.0679 | —CH₂—C≡CH | —Me | —(C=O)ⁱPr | 6-Cl | 3-Cl | —CH₂—CH₂— | 3-cyano-phenyl— |
| 1.0680 | —cyclopropyl | —Me | —(C=O)ⁱPr | 6-Cl | 3-Cl | —CH₂—CH₂— | 3-cyano-phenyl— |
| 1.0681 | —Me | —Me | —(C=O)ⁱPr | 6-F | 3-Cl | —CH₂—CH₂— | 3-trifluoromethyl-phenyl— |
| 1.0682 | —CH₂—C≡CH | —Me | —(C=O)ⁱPr | 6-F | 3-Cl | —CH₂—CH₂— | 3-trifluoromethyl-phenyl— |
| 1.0683 | —cyclopropyl | —Me | —(C=O)ⁱPr | 6-F | 3-Cl | —CH₂—CH₂— | 3-trifluoromethyl-phenyl— |
| 1.0684 | —Me | —Me | —(C=O)ⁱPr | 6-Cl | 3-Cl | —CH₂—CH₂— | 3-trifluoromethyl-phenyl— |
| 1.0685 | —CH₂—C≡CH | —Me | —(C=O)ⁱPr | 6-Cl | 3-Cl | —CH₂—CH₂— | 3-trifluoromethyl-phenyl— |
| 1.0686 | —cyclopropyl | —Me | —(C=O)ⁱPr | 6-Cl | 3-Cl | —CH₂—CH₂— | 3-trifluoromethyl-phenyl— |
| 1.0687 | —Me | —Me | —(C=O)ⁱPr | 6-F | 3-Cl | —CH₂—CH₂— | 2-tolyl— |
| 1.0688 | —CH₂—C≡CH | —Me | —(C=O)ⁱPr | 6-F | 3-Cl | —CH₂—CH₂— | 2-tolyl— |
| 1.0689 | —cyclopropyl | —Me | —(C=O)ⁱPr | 6-F | 3-Cl | —CH₂—CH₂— | 2-tolyl— |
| 1.0690 | —Me | —Me | —(C=O)ⁱPr | 6-Cl | 3-Cl | —CH₂—CH₂— | 2-tolyl— |
| 1.0691 | —CH₂—C≡CH | —Me | —(C=O)ⁱPr | 6-Cl | 3-Cl | —CH₂—CH₂— | 2-tolyl— |
| 1.0692 | —cyclopropyl | —Me | —(C=O)ⁱPr | 6-Cl | 3-Cl | —CH₂—CH₂— | 2-tolyl— |
| 1.0693 | —Me | —Me | —(C=O)ⁱPr | 6-F | 3-Cl | —CH₂—CH₂— | 3-tolyl— |
| 1.0694 | —CH₂—C≡CH | —Me | —(C=O)ⁱPr | 6-F | 3-Cl | —CH₂—CH₂— | 3-tolyl— |
| 1.0695 | —cyclopropyl | —Me | —(C=O)ⁱPr | 6-F | 3-Cl | —CH₂—CH₂— | 3-tolyl— |
| 1.0696 | —Me | —Me | —(C=O)ⁱPr | 6-Cl | 3-Cl | —CH₂—CH₂— | 3-tolyl— |
| 1.0697 | —CH₂—C≡CH | —Me | —(C=O)ⁱPr | 6-Cl | 3-Cl | —CH₂—CH₂— | 3-tolyl— |
| 1.0698 | —cyclopropyl | —Me | —(C=O)ⁱPr | 6-Cl | 3-Cl | —CH₂—CH₂— | 3-tolyl— |
| 1.0699 | —Me | —Me | —(C=O)ⁱPr | 6-F | 3-Cl | —CH₂—CH₂— | 2-methyl-4-pyridyl— |
| 1.0700 | —CH₂—C≡CH | —Me | —(C=O)ⁱPr | 6-F | 3-Cl | —CH₂—CH₂— | 2-methyl-4-pyridyl— |
| 1.0701 | —cyclopropyl | —Me | —(C=O)ⁱPr | 6-F | 3-Cl | —CH₂—CH₂— | 2-methyl-4-pyridyl— |
| 1.0702 | —Me | —Me | —(C=O)ⁱPr | 6-Cl | 3-Cl | —CH₂—CH₂— | 2-methyl-4-pyridyl— |
| 1.0703 | —CH₂—C≡CH | —Me | —(C=O)ⁱPr | 6-Cl | 3-Cl | —CH₂—CH₂— | 2-methyl-4-pyridyl— |
| 1.0704 | —cyclopropyl | —Me | —(C=O)ⁱPr | 6-Cl | 3-Cl | —CH₂—CH₂— | 2-methyl-4-pyridyl— |
| 1.0705 | —Me | —Me | —(C=O)ⁱPr | 6-F | 3-Cl | —CH₂—CH₂— | 2-trifluoromethyl-4-pyridyl— |
| 1.0706 | —CH₂—C≡CH | —Me | —(C=O)ⁱPr | 6-F | 3-Cl | —CH₂—CH₂— | 2-trifluoromethyl-4-pyridyl— |
| 1.0707 | —cyclopropyl | —Me | —(C=O)ⁱPr | 6-F | 3-Cl | —CH₂—CH₂— | 2-trifluoromethyl-4-pyridyl— |
| 1.0708 | —Me | —Me | —(C=O)ⁱPr | 6-Cl | 3-Cl | —CH₂—CH₂— | 2-trifluoromethyl-4-pyridyl— |
| 1.0709 | —CH₂—C≡CH | —Me | —(C=O)ⁱPr | 6-Cl | 3-Cl | —CH₂—CH₂— | 2-trifluoromethyl-4-pyridyl— |
| 1.0710 | —cyclopropyl | —Me | —(C=O)ⁱPr | 6-Cl | 3-Cl | —CH₂—CH₂— | 2-trifluoromethyl-4-pyridyl— |
| 1.0711 | —Me | —Me | —(C=O)ⁱPr | 6-F | 3-Cl | —CH₂—CH₂— | 2-amino-4-pyridyl— |
| 1.0712 | —CH₂—C≡CH | —Me | —(C=O)ⁱPr | 6-F | 3-Cl | —CH₂—CH₂— | 2-amino-4-pyridyl— |
| 1.0713 | —cyclopropyl | —Me | —(C=O)ⁱPr | 6-F | 3-Cl | —CH₂—CH₂— | 2-amino-4-pyridyl— |
| 1.0714 | —Me | —Me | —(C=O)ⁱPr | 6-Cl | 3-Cl | —CH₂—CH₂— | 2-amino-4-pyridyl— |
| 1.0715 | —CH₂—C≡CH | —Me | —(C=O)ⁱPr | 6-Cl | 3-Cl | —CH₂—CH₂— | 2-amino-4-pyridyl— |
| 1.0716 | —cyclopropyl | —Me | —(C=O)ⁱPr | 6-Cl | 3-Cl | —CH₂—CH₂— | 2-amino-4-pyridyl— |
| 1.0717 | —Me | —Me | —(C=O)ⁱPr | 6-F | 3-Cl | —CH₂—CH₂— | 2-fluoro-4-pyridyl— |
| 1.0718 | —CH₂—C≡CH | —Me | —(C=O)ⁱPr | 6-F | 3-Cl | —CH₂—CH₂— | 2-fluoro-4-pyridyl— |
| 1.0719 | —cyclopropyl | —Me | —(C=O)ⁱPr | 6-F | 3-Cl | —CH₂—CH₂— | 2-fluoro-4-pyridyl— |
| 1.0720 | —Me | —Me | —(C=O)ⁱPr | 6-Cl | 3-Cl | —CH₂—CH₂— | 2-fluoro-4-pyridyl— |
| 1.0721 | —CH₂—C≡CH | —Me | —(C=O)ⁱPr | 6-Cl | 3-Cl | —CH₂—CH₂— | 2-fluoro-4-pyridyl— |
| 1.0722 | —cyclopropyl | —Me | —(C=O)ⁱPr | 6-Cl | 3-Cl | —CH₂—CH₂— | 2-fluoro-4-pyridyl— |
| 1.0723 | —Me | —Me | —(C=O)ⁱPr | 6-F | 3-Cl | —CH₂—CH₂— | 4-pyridyl— |
| 1.0724 | —CH₂—C≡CH | —Me | —(C=O)ⁱPr | 6-F | 3-Cl | —CH₂—CH₂— | 4-pyridyl— |
| 1.0725 | —cyclopropyl | —Me | —(C=O)ⁱPr | 6-F | 3-Cl | —CH₂—CH₂— | 4-pyridyl— |
| 1.0726 | —Me | —Me | —(C=O)ⁱPr | 6-Cl | 3-Cl | —CH₂—CH₂— | 4-pyridyl— |
| 1.0727 | —CH₂—C≡CH | —Me | —(C=O)ⁱPr | 6-Cl | 3-Cl | —CH₂—CH₂— | 4-pyridyl— |
| 1.0728 | —cyclopropyl | —Me | —(C=O)ⁱPr | 6-Cl | 3-Cl | —CH₂—CH₂— | 4-pyridyl— |
| 1.0729 | —Me | —Me | —(C=O)ⁱPr | 6-F | 3-Cl | —CH₂—CH₂— | 4-(methylamino)-phenyl— |

TABLE 1-continued

Herbicidal compounds of the present invention. The numbering system used to describe the positions of X and Y is shown for the purposes of clarity only.

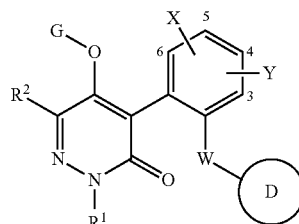

(I)

| Cmpd. No. | R¹ | R² | G | X | Y | W | D |
|---|---|---|---|---|---|---|---|
| 1.0730 | —CH₂—C≡CH | —Me | —(C=O)ⁱPr | 6-F | 3-Cl | —CH₂—CH₂— | 4-(methylamino)-phenyl— |
| 1.0731 | —cyclopropyl | —Me | —(C=O)ⁱPr | 6-F | 3-Cl | —CH₂—CH₂— | 4-(methylamino)-phenyl— |
| 1.0732 | —Me | —Me | —(C=O)ⁱPr | 6-Cl | 3-Cl | —CH₂—CH₂— | 4-(methylamino)-phenyl— |
| 1.0733 | —CH₂—C≡CH | —Me | —(C=O)ⁱPr | 6-Cl | 3-Cl | —CH₂—CH₂— | 4-(methylamino)-phenyl— |
| 1.0734 | —cyclopropyl | —Me | —(C=O)ⁱPr | 6-Cl | 3-Cl | —CH₂—CH₂— | 4-(methylamino)-phenyl— |
| 1.0735 | —Me | —Me | —(C=O)ⁱPr | 6-F | 3-Cl | —CH₂—CH₂— | 4-amino-phenyl— |
| 1.0736 | —CH₂—C≡CH | —Me | —(C=O)ⁱPr | 6-F | 3-Cl | —CH₂—CH₂— | 4-amino-phenyl— |
| 1.0737 | —cyclopropyl | —Me | —(C=O)ⁱPr | 6-F | 3-Cl | —CH₂—CH₂— | 4-amino-phenyl— |
| 1.0738 | —Me | —Me | —(C=O)ⁱPr | 6-Cl | 3-Cl | —CH₂—CH₂— | 4-amino-phenyl— |
| 1.0739 | —CH₂—C≡CH | —Me | —(C=O)ⁱPr | 6-Cl | 3-Cl | —CH₂—CH₂— | 4-amino-phenyl— |
| 1.0740 | —cyclopropyl | —Me | —(C=O)ⁱPr | 6-Cl | 3-Cl | —CH₂—CH₂— | 4-amino-phenyl— |
| 1.0741 | —Me | —Me | —H | 6-F | —H | —CH₂—CH₂— | 2-cyano-phenyl— |
| 1.0742 | —Me | —Me | —H | 6-Cl | —H | —CH₂—CH₂— | 2-cyano-phenyl— |
| 1.0743 | —CH₂—C≡CH | —Me | —H | 6-F | —H | —CH₂—CH₂— | 2-cyano-phenyl— |
| 1.0744 | —cyclopropyl | —Me | —H | 6-F | —H | —CH₂—CH₂— | 2-cyano-phenyl— |
| 1.0745 | —CH₂—C≡CH | —Me | —H | 6-Cl | —H | —CH₂—CH₂— | 2-cyano-phenyl— |
| 1.0746 | —cyclopropyl | —Me | —H | 6-Cl | —H | —CH₂—CH₂— | 2-cyano-phenyl— |
| 1.0747 | —Me | —Me | —H | 6-F | —H | —CH₂—CH₂— | 3-cyano-phenyl— |
| 1.0748 | —CH₂—C≡CH | —Me | —H | 6-F | —H | —CH₂—CH₂— | 3-cyano-phenyl— |
| 1.0749 | —cyclopropyl | —Me | —H | 6-F | —H | —CH₂—CH₂— | 3-cyano-phenyl— |
| 1.0750 | —Me | —Me | —H | 6-Cl | —H | —CH₂—CH₂— | 3-cyano-phenyl— |
| 1.0751 | —CH₂—C≡CH | —Me | —H | 6-Cl | —H | —CH₂—CH₂— | 3-cyano-phenyl— |
| 1.0752 | —cyclopropyl | —Me | —H | 6-Cl | —H | —CH₂—CH₂— | 3-cyano-phenyl— |
| 1.0753 | —Me | —Me | —H | 6-F | —H | —CH₂—CH₂— | 3-trifluoromethyl-phenyl— |
| 1.0754 | —CH₂—C≡CH | —Me | —H | 6-F | —H | —CH₂—CH₂— | 3-trifluoromethyl-phenyl— |
| 1.0755 | —cyclopropyl | —Me | —H | 6-F | —H | —CH₂—CH₂— | 3-trifluoromethyl-phenyl— |
| 1.0756 | —Me | —Me | —H | 6-Cl | —H | —CH₂—CH₂— | 3-trifluoromethyl-phenyl— |
| 1.0757 | —CH₂—C≡CH | —Me | —H | 6-Cl | —H | —CH₂—CH₂— | 3-trifluoromethyl-phenyl— |
| 1.0758 | —cyclopropyl | —Me | —H | 6-Cl | —H | —CH₂—CH₂— | 3-trifluoromethyl-phenyl— |
| 1.0759 | —Me | —Me | —H | 6-F | —H | —CH₂—CH₂— | 2-tolyl— |
| 1.0760 | —CH₂—C≡CH | —Me | —H | 6-F | —H | —CH₂—CH₂— | 2-tolyl— |
| 1.0761 | —cyclopropyl | —Me | —H | 6-F | —H | —CH₂—CH₂— | 2-tolyl— |
| 1.0762 | —Me | —Me | —H | 6-Cl | —H | —CH₂—CH₂— | 2-tolyl— |
| 1.0763 | —CH₂—C≡CH | —Me | —H | 6-Cl | —H | —CH₂—CH₂— | 2-tolyl— |
| 1.0764 | —cyclopropyl | —Me | —H | 6-Cl | —H | —CH₂—CH₂— | 2-tolyl— |
| 1.0765 | —Me | —Me | —H | 6-F | —H | —CH₂—CH₂— | 3-tolyl— |
| 1.0766 | —CH₂—C≡CH | —Me | —H | 6-F | —H | —CH₂—CH₂— | 3-tolyl— |
| 1.0767 | —cyclopropyl | —Me | —H | 6-F | —H | —CH₂—CH₂— | 3-tolyl— |
| 1.0768 | —Me | —Me | —H | 6-Cl | —H | —CH₂—CH₂— | 3-tolyl— |
| 1.0769 | —CH₂—C≡CH | —Me | —H | 6-Cl | —H | —CH₂—CH₂— | 3-tolyl— |
| 1.0770 | —cyclopropyl | —Me | —H | 6-Cl | —H | —CH₂—CH₂— | 3-tolyl— |
| 1.0771 | —Me | —Me | —H | 6-F | —H | —CH₂—CH₂— | 2-methyl-4-pyridyl— |
| 1.0772 | —CH₂—C≡CH | —Me | —H | 6-F | —H | —CH₂—CH₂— | 2-methyl-4-pyridyl— |
| 1.0773 | —cyclopropyl | —Me | —H | 6-F | —H | —CH₂—CH₂— | 2-methyl-4-pyridyl— |
| 1.0774 | —Me | —Me | —H | 6-Cl | —H | —CH₂—CH₂— | 2-methyl-4-pyridyl— |
| 1.0775 | —CH₂—C≡CH | —Me | —H | 6-Cl | —H | —CH₂—CH₂— | 2-methyl-4-pyridyl— |
| 1.0776 | —cyclopropyl | —Me | —H | 6-Cl | —H | —CH₂—CH₂— | 2-methyl-4-pyridyl— |
| 1.0777 | —Me | —Me | —H | 6-F | —H | —CH₂—CH₂— | 2-trifluoromethyl-4-pyridyl— |
| 1.0778 | —CH₂—C≡CH | —Me | —H | 6-F | —H | —CH₂—CH₂— | 2-trifluoromethyl-4-pyridyl— |
| 1.0779 | —cyclopropyl | —Me | —H | 6-F | —H | —CH₂—CH₂— | 2-trifluoromethyl-4-pyridyl— |
| 1.0780 | —Me | —Me | —H | 6-Cl | —H | —CH₂—CH₂— | 2-trifluoromethyl-4-pyridyl— |
| 1.0781 | —CH₂—C≡CH | —Me | —H | 6-Cl | —H | —CH₂—CH₂— | 2-trifluoromethyl-4-pyridyl— |
| 1.0782 | —cyclopropyl | —Me | —H | 6-Cl | —H | —CH₂—CH₂— | 2-trifluoromethyl-4-pyridyl— |
| 1.0783 | —Me | —Me | —H | 6-F | —H | —CH₂—CH₂— | 2-amino-4-pyridyl— |
| 1.0784 | —CH₂—C≡CH | —Me | —H | 6-F | —H | —CH₂—CH₂— | 2-amino-4-pyridyl— |
| 1.0785 | —cyclopropyl | —Me | —H | 6-F | —H | —CH₂—CH₂— | 2-amino-4-pyridyl— |
| 1.0786 | —Me | —Me | —H | 6-Cl | —H | —CH₂—CH₂— | 2-amino-4-pyridyl— |
| 1.0787 | —CH₂—C≡CH | —Me | —H | 6-Cl | —H | —CH₂—CH₂— | 2-amino-4-pyridyl— |
| 1.0788 | —cyclopropyl | —Me | —H | 6-Cl | —H | —CH₂—CH₂— | 2-amino-4-pyridyl— |
| 1.0789 | —Me | —Me | —H | 6-F | —H | —CH₂—CH₂— | 2-fluoro-4-pyridyl— |
| 1.0790 | —CH₂—C≡CH | —Me | —H | 6-F | —H | —CH₂—CH₂— | 2-fluoro-4-pyridyl— |
| 1.0791 | —cyclopropyl | —Me | —H | 6-F | —H | —CH₂—CH₂— | 2-fluoro-4-pyridyl— |

TABLE 1-continued

Herbicidal compounds of the present invention. The numbering system used to describe the positions of X and Y is shown for the purposes of clarity only.

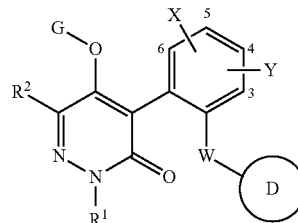

(I)

| Cmpd. No. | R¹ | R² | G | X | Y | W | D |
|---|---|---|---|---|---|---|---|
| 1.0792 | —Me | —Me | —H | 6-Cl | —H | —CH₂—CH₂— | 2-fluoro-4-pyridyl— |
| 1.0793 | —CH₂—C≡CH | —Me | —H | 6-Cl | —H | —CH₂—CH₂— | 2-fluoro-4-pyridyl— |
| 1.0794 | —cyclopropyl | —Me | —H | 6-Cl | —H | —CH₂—CH₂— | 2-fluoro-4-pyridyl— |
| 1.0795 | —Me | —Me | —H | 6-F | —H | —CH₂—CH₂— | 4-pyridyl— |
| 1.0796 | —CH₂—C≡CH | —Me | —H | 6-F | —H | —CH₂—CH₂— | 4-pyridyl— |
| 1.0797 | —cyclopropyl | —Me | —H | 6-F | —H | —CH₂—CH₂— | 4-pyridyl— |
| 1.0798 | —Me | —Me | —H | 6-Cl | —H | —CH₂—CH₂— | 4-pyridyl— |
| 1.0799 | —CH₂—C≡CH | —Me | —H | 6-Cl | —H | —CH₂—CH₂— | 4-pyridyl— |
| 1.0800 | —cyclopropyl | —Me | —H | 6-Cl | —H | —CH₂—CH₂— | 4-pyridyl— |
| 1.0801 | —Me | —Me | —H | 6-F | —H | —CH₂—CH₂— | 4-(methylamino)-phenyl— |
| 1.0802 | —CH₂—C≡CH | —Me | —H | 6-F | —H | —CH₂—CH₂— | 4-(methylamino)-phenyl— |
| 1.0803 | —cyclopropyl | —Me | —H | 6-F | —H | —CH₂—CH₂— | 4-(methylamino)-phenyl— |
| 1.0804 | —Me | —Me | —H | 6-Cl | —H | —CH₂—CH₂— | 4-(methylamino)-phenyl— |
| 1.0805 | —CH₂—C≡CH | —Me | —H | 6-Cl | —H | —CH₂—CH₂— | 4-(methylamino)-phenyl— |
| 1.0806 | —cyclopropyl | —Me | —H | 6-Cl | —H | —CH₂—CH₂— | 4-(methylamino)-phenyl— |
| 1.0807 | —Me | —Me | —H | 6-F | —H | —CH₂—CH₂— | 4-amino-phenyl— |
| 1.0808 | —CH₂—C≡CH | —Me | —H | 6-F | —H | —CH₂—CH₂— | 4-amino-phenyl— |
| 1.0809 | —cyclopropyl | —Me | —H | 6-F | —H | —CH₂—CH₂— | 4-amino-phenyl— |
| 1.0810 | —Me | —Me | —H | 6-Cl | —H | —CH₂—CH₂— | 4-amino-phenyl— |
| 1.0811 | —CH₂—C≡CH | —Me | —H | 6-Cl | —H | —CH₂—CH₂— | 4-amino-phenyl— |
| 1.0812 | —cyclopropyl | —Me | —H | 6-Cl | —H | —CH₂—CH₂— | 4-amino-phenyl— |
| 1.0813 | —Me | —Me | —(C=O)ⁱPr | 6-F | —H | —CH₂—CH₂— | 2-cyano-phenyl— |
| 1.0814 | —Me | —Me | —(C=O)ⁱPr | 6-Cl | —H | —CH₂—CH₂— | 2-cyano-phenyl— |
| 1.0815 | —CH₂—C≡CH | —Me | —(C=O)ⁱPr | 6-F | —H | —CH₂—CH₂— | 2-cyano-phenyl— |
| 1.0816 | —cyclopropyl | —Me | —(C=O)ⁱPr | 6-F | —H | —CH₂—CH₂— | 2-cyano-phenyl— |
| 1.0817 | —CH₂—C≡CH | —Me | —(C=O)ⁱPr | 6-Cl | —H | —CH₂—CH₂— | 2-cyano-phenyl— |
| 1.0818 | —cyclopropyl | —Me | —(C=O)ⁱPr | 6-Cl | —H | —CH₂—CH₂— | 2-cyano-phenyl— |
| 1.0819 | —Me | —Me | —(C=O)ⁱPr | 6-F | —H | —CH₂—CH₂— | 3-cyano-phenyl— |
| 1.0820 | —CH₂—C≡CH | —Me | —(C=O)ⁱPr | 6-F | —H | —CH₂—CH₂— | 3-cyano-phenyl— |
| 1.0821 | —cyclopropyl | —Me | —(C=O)ⁱPr | 6-F | —H | —CH₂—CH₂— | 3-cyano-phenyl— |
| 1.0822 | —Me | —Me | —(C=O)ⁱPr | 6-Cl | —H | —CH₂—CH₂— | 3-cyano-phenyl— |
| 1.0823 | —CH₂—C≡CH | —Me | —(C=O)ⁱPr | 6-Cl | —H | —CH₂—CH₂— | 3-cyano-phenyl— |
| 1.0824 | —cyclopropyl | —Me | —(C=O)ⁱPr | 6-Cl | —H | —CH₂—CH₂— | 3-cyano-phenyl— |
| 1.0825 | —Me | —Me | —(C=O)ⁱPr | 6-F | —H | —CH₂—CH₂— | 3-trifluoromethyl-phenyl— |
| 1.0826 | —CH₂—C≡CH | —Me | —(C=O)ⁱPr | 6-F | —H | —CH₂—CH₂— | 3-trifluoromethyl-phenyl— |
| 1.0827 | —cyclopropyl | —Me | —(C=O)ⁱPr | 6-F | —H | —CH₂—CH₂— | 3-trifluoromethyl-phenyl— |
| 1.0828 | —Me | —Me | —(C=O)ⁱPr | 6-Cl | —H | —CH₂—CH₂— | 3-trifluoromethyl-phenyl— |
| 1.0829 | —CH₂—C≡CH | —Me | —(C=O)ⁱPr | 6-Cl | —H | —CH₂—CH₂— | 3-trifluoromethyl-phenyl— |
| 1.0830 | —cyclopropyl | —Me | —(C=O)ⁱPr | 6-Cl | —H | —CH₂—CH₂— | 3-trifluoromethyl-phenyl— |
| 1.0831 | —Me | —Me | —(C=O)ⁱPr | 6-F | —H | —CH₂—CH₂— | 2-tolyl— |
| 1.0832 | —CH₂—C≡CH | —Me | —(C=O)ⁱPr | 6-F | —H | —CH₂—CH₂— | 2-tolyl— |
| 1.0833 | —cyclopropyl | —Me | —(C=O)ⁱPr | 6-F | —H | —CH₂—CH₂— | 2-tolyl— |
| 1.0834 | —Me | —Me | —(C=O)ⁱPr | 6-Cl | —H | —CH₂—CH₂— | 2-tolyl— |
| 1.0835 | —CH₂—C≡CH | —Me | —(C=O)ⁱPr | 6-Cl | —H | —CH₂—CH₂— | 2-tolyl— |
| 1.0836 | —cyclopropyl | —Me | —(C=O)ⁱPr | 6-Cl | —H | —CH₂—CH₂— | 2-tolyl— |
| 1.0837 | —Me | —Me | —(C=O)ⁱPr | 6-F | —H | —CH₂—CH₂— | 3-tolyl— |
| 1.0838 | —CH₂—C≡CH | —Me | —(C=O)ⁱPr | 6-F | —H | —CH₂—CH₂— | 3-tolyl— |
| 1.0839 | —cyclopropyl | —Me | —(C=O)ⁱPr | 6-F | —H | —CH₂—CH₂— | 3-tolyl— |
| 1.0840 | —Me | —Me | —(C=O)ⁱPr | 6-Cl | —H | —CH₂—CH₂— | 3-tolyl— |
| 1.0841 | —CH₂—C≡CH | —Me | —(C=O)ⁱPr | 6-Cl | —H | —CH₂—CH₂— | 3-tolyl— |
| 1.0842 | —cyclopropyl | —Me | —(C=O)ⁱPr | 6-Cl | —H | —CH₂—CH₂— | 3-tolyl— |
| 1.0843 | —Me | —Me | —(C=O)ⁱPr | 6-F | —H | —CH₂—CH₂— | 2-methyl-4-pyridyl— |
| 1.0844 | —CH₂—C≡CH | —Me | —(C=O)ⁱPr | 6-F | —H | —CH₂—CH₂— | 2-methyl-4-pyridyl— |
| 1.0845 | —cyclopropyl | —Me | —(C=O)ⁱPr | 6-F | —H | —CH₂—CH₂— | 2-methyl-4-pyridyl— |
| 1.0846 | —Me | —Me | —(C=O)ⁱPr | 6-Cl | —H | —CH₂—CH₂— | 2-methyl-4-pyridyl— |
| 1.0847 | —CH₂—C≡CH | —Me | —(C=O)ⁱPr | 6-Cl | —H | —CH₂—CH₂— | 2-methyl-4-pyridyl— |
| 1.0848 | —cyclopropyl | —Me | —(C=O)ⁱPr | 6-Cl | —H | —CH₂—CH₂— | 2-methyl-4-pyridyl— |
| 1.0849 | —Me | —Me | —(C=O)ⁱPr | 6-F | —H | —CH₂—CH₂— | 2-trifluoromethyl-4-pyridyl— |
| 1.0850 | —CH₂—C≡CH | —Me | —(C=O)ⁱPr | 6-F | —H | —CH₂—CH₂— | 2-trifluoromethyl-4-pyridyl— |
| 1.0851 | —cyclopropyl | —Me | —(C=O)ⁱPr | 6-F | —H | —CH₂—CH₂— | 2-trifluoromethyl-4-pyridyl— |
| 1.0852 | —Me | —Me | —(C=O)ⁱPr | 6-Cl | —H | —CH₂—CH₂— | 2-trifluoromethyl-4-pyridyl— |
| 1.0853 | —CH₂—C≡CH | —Me | —(C=O)ⁱPr | 6-Cl | —H | —CH₂—CH₂— | 2-trifluoromethyl-4-pyridyl— |

TABLE 1-continued

Herbicidal compounds of the present invention. The numbering system used to describe the positions of X and Y is shown for the purposes of clarity only.

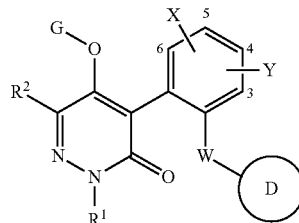

(I)

| Cmpd. No. | R¹ | R² | G | X | Y | W | D |
|---|---|---|---|---|---|---|---|
| 1.0854 | —cyclopropyl | —Me | —(C=O)ⁱPr | 6-Cl | —H | —CH₂—CH₂— | 2-trifluoromethyl-4-pyridyl— |
| 1.0855 | —Me | —Me | —(C=O)ⁱPr | 6-F | —H | —CH₂—CH₂— | 2-amino-4-pyridyl— |
| 1.0856 | —CH₂—C≡CH | —Me | —(C=O)ⁱPr | 6-F | —H | —CH₂—CH₂— | 2-amino-4-pyridyl— |
| 1.0857 | —cyclopropyl | —Me | —(C=O)ⁱPr | 6-F | —H | —CH₂—CH₂— | 2-amino-4-pyridyl— |
| 1.0858 | —Me | —Me | —(C=O)ⁱPr | 6-Cl | —H | —CH₂—CH₂— | 2-amino-4-pyridyl— |
| 1.0859 | —CH₂—C≡CH | —Me | —(C=O)ⁱPr | 6-Cl | —H | —CH₂—CH₂— | 2-amino-4-pyridyl— |
| 1.0860 | —cyclopropyl | —Me | —(C=O)ⁱPr | 6-Cl | —H | —CH₂—CH₂— | 2-amino-4-pyridyl— |
| 1.0861 | —Me | —Me | —(C=O)ⁱPr | 6-F | —H | —CH₂—CH₂— | 2-fluoro-4-pyridyl— |
| 1.0862 | —CH₂—C≡CH | —Me | —(C=O)ⁱPr | 6-F | —H | —CH₂—CH₂— | 2-fluoro-4-pyridyl— |
| 1.0863 | —cyclopropyl | —Me | —(C=O)ⁱPr | 6-F | —H | —CH₂—CH₂— | 2-fluoro-4-pyridyl— |
| 1.0864 | —Me | —Me | —(C=O)ⁱPr | 6-Cl | —H | —CH₂—CH₂— | 2-fluoro-4-pyridyl— |
| 1.0865 | —CH₂—C≡CH | —Me | —(C=O)ⁱPr | 6-Cl | —H | —CH₂—CH₂— | 2-fluoro-4-pyridyl— |
| 1.0866 | —cyclopropyl | —Me | —(C=O)ⁱPr | 6-Cl | —H | —CH₂—CH₂— | 2-fluoro-4-pyridyl— |
| 1.0867 | —Me | —Me | —(C=O)ⁱPr | 6-F | —H | —CH₂—CH₂— | 4-pyridyl— |
| 1.0868 | —CH₂—C≡CH | —Me | —(C=O)ⁱPr | 6-F | —H | —CH₂—CH₂— | 4-pyridyl— |
| 1.0869 | —cyclopropyl | —Me | —(C=O)ⁱPr | 6-F | —H | —CH₂—CH₂— | 4-pyridyl— |
| 1.0870 | —Me | —Me | —(C=O)ⁱPr | 6-Cl | —H | —CH₂—CH₂— | 4-pyridyl— |
| 1.0871 | —CH₂—C≡CH | —Me | —(C=O)ⁱPr | 6-Cl | —H | —CH₂—CH₂— | 4-pyridyl— |
| 1.0872 | —cyclopropyl | —Me | —(C=O)ⁱPr | 6-Cl | —H | —CH₂—CH₂— | 4-pyridyl— |
| 1.0873 | —Me | —Me | —(C=O)ⁱPr | 6-F | —H | —CH₂—CH₂— | 4-(methylamino)-phenyl— |
| 1.0874 | —CH₂—C≡CH | —Me | —(C=O)ⁱPr | 6-F | —H | —CH₂—CH₂— | 4-(methylamino)-phenyl— |
| 1.0875 | —cyclopropyl | —Me | —(C=O)ⁱPr | 6-F | —H | —CH₂—CH₂— | 4-(methylamino)-phenyl— |
| 1.0876 | —Me | —Me | —(C=O)ⁱPr | 6-Cl | —H | —CH₂—CH₂— | 4-(methylamino)-phenyl— |
| 1.0877 | —CH₂—C≡CH | —Me | —(C=O)ⁱPr | 6-Cl | —H | —CH₂—CH₂— | 4-(methylamino)-phenyl— |
| 1.0878 | —cyclopropyl | —Me | —(C=O)ⁱPr | 6-Cl | —H | —CH₂—CH₂— | 4-(methylamino)-phenyl— |
| 1.0879 | —Me | —Me | —(C=O)ⁱPr | 6-F | —H | —CH₂—CH₂— | 4-amino-phenyl— |
| 1.0880 | —CH₂—C≡CH | —Me | —(C=O)ⁱPr | 6-F | —H | —CH₂—CH₂— | 4-amino-phenyl— |
| 1.0881 | —cyclopropyl | —Me | —(C=O)ⁱPr | 6-F | —H | —CH₂—CH₂— | 4-amino-phenyl— |
| 1.0882 | —Me | —Me | —(C=O)ⁱPr | 6-Cl | —H | —CH₂—CH₂— | 4-amino-phenyl— |
| 1.0883 | —CH₂—C≡CH | —Me | —(C=O)ⁱPr | 6-Cl | —H | —CH₂—CH₂— | 4-amino-phenyl— |
| 1.0884 | —cyclopropyl | —Me | —(C=O)ⁱPr | 6-Cl | —H | —CH₂—CH₂— | 4-amino-phenyl— |
| 1.0885 | —Me | —Me | —H | 6-F | 3-Cl | —CH₂—CH₂— | 4-(dimethylamino)-phenyl— |
| 1.0886 | —Me | —Me | —H | 6-Cl | 3-Cl | —CH₂—CH₂— | 4-(dimethylamino)-phenyl— |
| 1.0887 | —CH₂—C≡CH | —Me | —H | 6-F | 3-Cl | —CH₂—CH₂— | 4-(dimethylamino)-phenyl— |
| 1.0888 | —cyclopropyl | —Me | —H | 6-F | 3-Cl | —CH₂—CH₂— | 4-(dimethylamino)-phenyl— |
| 1.0889 | —CH₂—C≡CH | —Me | —H | 6-Cl | 3-Cl | —CH₂—CH₂— | 4-(dimethylamino)-phenyl— |
| 1.0890 | —cyclopropyl | —Me | —H | 6-Cl | 3-Cl | —CH₂—CH₂— | 4-(dimethylamino)-phenyl— |
| 1.0891 | —Me | —Me | —H | 6-F | 3-Cl | —CH₂—CH₂— | 3-methyl-4-amino-phenyl— |
| 1.0892 | —CH₂—C≡CH | —Me | —H | 6-F | 3-Cl | —CH₂—CH₂— | 3-methyl-4-amino-phenyl— |
| 1.0893 | —cyclopropyl | —Me | —H | 6-F | 3-Cl | —CH₂—CH₂— | 3-methyl-4-amino-phenyl— |
| 1.0894 | —Me | —Me | —H | 6-Cl | 3-Cl | —CH₂—CH₂— | 3-methyl-4-amino-phenyl— |
| 1.0895 | —CH₂—C≡CH | —Me | —H | 6-Cl | 3-Cl | —CH₂—CH₂— | 3-methyl-4-amino-phenyl— |
| 1.0896 | —cyclopropyl | —Me | —H | 6-Cl | 3-Cl | —CH₂—CH₂— | 3-methyl-4-amino-phenyl— |
| 1.0897 | —Me | —Me | —H | 6-F | 3-Cl | —CH₂—CH₂— | thiophen-3-yl— |
| 1.0898 | —CH₂—C≡CH | —Me | —H | 6-F | 3-Cl | —CH₂—CH₂— | thiophen-3-yl— |
| 1.0899 | —cyclopropyl | —Me | —H | 6-F | 3-Cl | —CH₂—CH₂— | thiophen-3-yl— |
| 1.0900 | —Me | —Me | —H | 6-Cl | 3-Cl | —CH₂—CH₂— | thiophen-3-yl— |
| 1.0901 | —CH₂—C≡CH | —Me | —H | 6-Cl | 3-Cl | —CH₂—CH₂— | thiophen-3-yl— |
| 1.0902 | —cyclopropyl | —Me | —H | 6-Cl | 3-Cl | —CH₂—CH₂— | thiophen-3-yl— |
| 1.0903 | —Me | —Me | —H | 6-F | 3-Cl | —CH₂—CH₂— | 1-methyl-pyrazol-4-yl— |
| 1.0904 | —CH₂—C≡CH | —Me | —H | 6-F | 3-Cl | —CH₂—CH₂— | 1-methyl-pyrazol-4-yl— |
| 1.0905 | —cyclopropyl | —Me | —H | 6-F | 3-Cl | —CH₂—CH₂— | 1-methyl-pyrazol-4-yl— |
| 1.0906 | —Me | —Me | —H | 6-Cl | 3-Cl | —CH₂—CH₂— | 1-methyl-pyrazol-4-yl— |
| 1.0907 | —CH₂—C≡CH | —Me | —H | 6-Cl | 3-Cl | —CH₂—CH₂— | 1-methyl-pyrazol-4-yl— |
| 1.0908 | —cyclopropyl | —Me | —H | 6-Cl | 3-Cl | —CH₂—CH₂— | 1-methyl-pyrazol-4-yl— |
| 1.0909 | —Me | —Me | —H | 6-F | 3-Cl | —CH₂—CH₂— | 2-methyl-triazol-4-yl— |
| 1.0910 | —CH₂—C≡CH | —Me | —H | 6-F | 3-Cl | —CH₂—CH₂— | 2-methyl-triazol-4-yl— |
| 1.0911 | —cyclopropyl | —Me | —H | 6-F | 3-Cl | —CH₂—CH₂— | 2-methyl-triazol-4-yl— |
| 1.0912 | —Me | —Me | —H | 6-Cl | 3-Cl | —CH₂—CH₂— | 2-methyl-triazol-4-yl— |
| 1.0913 | —CH₂—C≡CH | —Me | —H | 6-Cl | 3-Cl | —CH₂—CH₂— | 2-methyl-triazol-4-yl— |
| 1.0914 | —cyclopropyl | —Me | —H | 6-Cl | 3-Cl | —CH₂—CH₂— | 2-methyl-triazol-4-yl— |
| 1.0915 | —Me | —Me | —H | 6-F | 3-Cl | —CH₂—CH₂— | 5-methyl-1,3,4-oxadiazol-2-yl— |

TABLE 1-continued

Herbicidal compounds of the present invention. The numbering system used to describe the positions of X and Y is shown for the purposes of clarity only.

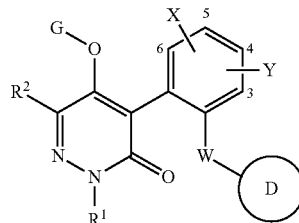

(I)

| Cmpd. No. | R¹ | R² | G | X | Y | W | D |
|---|---|---|---|---|---|---|---|
| 1.0916 | —CH₂—C≡CH | —Me | —H | 6-F | 3-Cl | —CH₂—CH₂— | 5-methyl-1,3,4-oxadiazol-2-yl— |
| 1.0917 | —cyclopropyl | —Me | —H | 6-F | 3-Cl | —CH₂—CH₂— | 5-methyl-1,3,4-oxadiazol-2-yl— |
| 1.0918 | —Me | —Me | —H | 6-Cl | 3-Cl | —CH₂—CH₂— | 5-methyl-1,3,4-oxadiazol-2-yl— |
| 1.0919 | —CH₂—C≡CH | —Me | —H | 6-Cl | 3-Cl | —CH₂—CH₂— | 5-methyl-1,3,4-oxadiazol-2-yl— |
| 1.0920 | —cyclopropyl | —Me | —H | 6-Cl | 3-Cl | —CH₂—CH₂— | 5-methyl-1,3,4-oxadiazol-2-yl— |
| 1.0921 | —Me | —Me | —H | 6-F | 3-Cl | —CH₂—CH₂— | 5-methyl-3-pyridyl— |
| 1.0922 | —CH₂—C≡CH | —Me | —H | 6-F | 3-Cl | —CH₂—CH₂— | 5-methyl-3-pyridyl— |
| 1.0923 | —cyclopropyl | —Me | —H | 6-F | 3-Cl | —CH₂—CH₂— | 5-methyl-3-pyridyl— |
| 1.0924 | —Me | —Me | —H | 6-Cl | 3-Cl | —CH₂—CH₂— | 5-methyl-3-pyridyl— |
| 1.0925 | —CH₂—C≡CH | —Me | —H | 6-Cl | 3-Cl | —CH₂—CH₂— | 5-methyl-3-pyridyl— |
| 1.0926 | —cyclopropyl | —Me | —H | 6-Cl | 3-Cl | —CH₂—CH₂— | 5-methyl-3-pyridyl— |
| 1.0927 | —Me | —Me | —H | 6-F | 3-Cl | —CH₂—CH₂— | 5-methyl-2-pyridyl— |
| 1.0928 | —CH₂—C≡CH | —Me | —H | 6-F | 3-Cl | —CH₂—CH₂— | 5-methyl-2-pyridyl— |
| 1.0929 | —cyclopropyl | —Me | —H | 6-F | 3-Cl | —CH₂—CH₂— | 5-methyl-2-pyridyl— |
| 1.0930 | —Me | —Me | —H | 6-Cl | 3-Cl | —CH₂—CH₂— | 5-methyl-2-pyridyl— |
| 1.0931 | —CH₂—C≡CH | —Me | —H | 6-Cl | 3-Cl | —CH₂—CH₂— | 5-methyl-2-pyridyl— |
| 1.0932 | —cyclopropyl | —Me | —H | 6-Cl | 3-Cl | —CH₂—CH₂— | 5-methyl-2-pyridyl— |
| 1.0933 | —Me | —Me | —H | 6-F | 3-Cl | —CH₂—CH₂— | 6-methyl-2-pyridyl— |
| 1.0934 | —CH₂—C≡CH | —Me | —H | 6-F | 3-Cl | —CH₂—CH₂— | 6-methyl-2-pyridyl— |
| 1.0935 | —cyclopropyl | —Me | —H | 6-F | 3-Cl | —CH₂—CH₂— | 6-methyl-2-pyridyl— |
| 1.0936 | —Me | —Me | —H | 6-Cl | 3-Cl | —CH₂—CH₂— | 6-methyl-2-pyridyl— |
| 1.0937 | —CH₂—C≡CH | —Me | —H | 6-Cl | 3-Cl | —CH₂—CH₂— | 6-methyl-2-pyridyl— |
| 1.0938 | —cyclopropyl | —Me | —H | 6-Cl | 3-Cl | —CH₂—CH₂— | 6-methyl-2-pyridyl— |
| 1.0939 | —Me | —Me | —H | 6-F | 3-Cl | —CH₂—CH₂— | 3-methyl-2-pyridyl— |
| 1.0940 | —CH₂—C≡CH | —Me | —H | 6-F | 3-Cl | —CH₂—CH₂— | 3-methyl-2-pyridyl— |
| 1.0941 | —cyclopropyl | —Me | —H | 6-F | 3-Cl | —CH₂—CH₂— | 3-methyl-2-pyridyl— |
| 1.0942 | —Me | —Me | —H | 6-Cl | 3-Cl | —CH₂—CH₂— | 3-methyl-2-pyridyl— |
| 1.0943 | —CH₂—C≡CH | —Me | —H | 6-Cl | 3-Cl | —CH₂—CH₂— | 3-methyl-2-pyridyl— |
| 1.0944 | —cyclopropyl | —Me | —H | 6-Cl | 3-Cl | —CH₂—CH₂— | 3-methyl-2-pyridyl— |
| 1.0945 | —Me | —Me | —H | 6-F | 3-Cl | —CH₂—CH₂— | 6-chloro-3-pyridyl— |
| 1.0946 | —CH₂—C≡CH | —Me | —H | 6-F | 3-Cl | —CH₂—CH₂— | 6-chloro-3-pyridyl— |
| 1.0947 | —cyclopropyl | —Me | —H | 6-F | 3-Cl | —CH₂—CH₂— | 6-chloro-3-pyridyl— |
| 1.0948 | —Me | —Me | —H | 6-Cl | 3-Cl | —CH₂—CH₂— | 6-chloro-3-pyridyl— |
| 1.0949 | —CH₂—C≡CH | —Me | —H | 6-Cl | 3-Cl | —CH₂—CH₂— | 6-chloro-3-pyridyl— |
| 1.0950 | —cyclopropyl | —Me | —H | 6-Cl | 3-Cl | —CH₂—CH₂— | 6-chloro-3-pyridyl— |
| 1.0951 | —Me | —Me | —H | 6-F | 3-Cl | —CH₂—CH₂— | 3-trifluoromethyl-3-pyridyl— |
| 1.0952 | —CH₂—C≡CH | —Me | —H | 6-F | 3-Cl | —CH₂—CH₂— | 3-trifluoromethyl-3-pyridyl— |
| 1.0953 | —cyclopropyl | —Me | —H | 6-F | 3-Cl | —CH₂—CH₂— | 3-trifluoromethyl-3-pyridyl— |
| 1.0954 | —Me | —Me | —H | 6-Cl | 3-Cl | —CH₂—CH₂— | 3-trifluoromethyl-3-pyridyl— |
| 1.0955 | —CH₂—C≡CH | —Me | —H | 6-Cl | 3-Cl | —CH₂—CH₂— | 3-trifluoromethyl-3-pyridyl— |
| 1.0956 | —cyclopropyl | —Me | —H | 6-Cl | 3-Cl | —CH₂—CH₂— | 3-trifluoromethyl-3-pyridyl— |
| 1.0957 | —Me | —Me | —(C=O)ⁱPr | 6-F | 3-Cl | —CH₂—CH₂— | 4-(dimethylamino)-phenyl— |
| 1.0958 | —Me | —Me | —(C=O)ⁱPr | 6-Cl | 3-Cl | —CH₂—CH₂— | 4-(dimethylamino)-phenyl— |
| 1.0959 | —CH₂—C≡CH | —Me | —(C=O)ⁱPr | 6-F | 3-Cl | —CH₂—CH₂— | 4-(dimethylamino)-phenyl— |
| 1.0960 | —cyclopropyl | —Me | —(C=O)ⁱPr | 6-F | 3-Cl | —CH₂—CH₂— | 4-(dimethylamino)-phenyl— |
| 1.0961 | —CH₂—C≡CH | —Me | —(C=O)ⁱPr | 6-Cl | 3-Cl | —CH₂—CH₂— | 4-(dimethylamino)-phenyl— |
| 1.0962 | —cyclopropyl | —Me | —(C=O)ⁱPr | 6-Cl | 3-Cl | —CH₂—CH₂— | 4-(dimethylamino)-phenyl— |
| 1.0963 | —Me | —Me | —(C=O)ⁱPr | 6-F | 3-Cl | —CH₂—CH₂— | 3-methyl-4-amino-phenyl— |
| 1.0964 | —CH₂—C≡CH | —Me | —(C=O)ⁱPr | 6-F | 3-Cl | —CH₂—CH₂— | 3-methyl-4-amino-phenyl— |
| 1.0965 | —cyclopropyl | —Me | —(C=O)ⁱPr | 6-F | 3-Cl | —CH₂—CH₂— | 3-methyl-4-amino-phenyl— |
| 1.0966 | —Me | —Me | —(C=O)ⁱPr | 6-Cl | 3-Cl | —CH₂—CH₂— | 3-methyl-4-amino-phenyl— |
| 1.0967 | —CH₂—C≡CH | —Me | —(C=O)ⁱPr | 6-Cl | 3-Cl | —CH₂—CH₂— | 3-methyl-4-amino-phenyl— |
| 1.0968 | —cyclopropyl | —Me | —(C=O)ⁱPr | 6-Cl | 3-Cl | —CH₂—CH₂— | 3-methyl-4-amino-phenyl— |
| 1.0969 | —Me | —Me | —(C=O)ⁱPr | 6-F | 3-Cl | —CH₂—CH₂— | thiophen-3-yl— |
| 1.0970 | —CH₂—C≡CH | —Me | —(C=O)ⁱPr | 6-F | 3-Cl | —CH₂—CH₂— | thiophen-3-yl— |
| 1.0971 | —cyclopropyl | —Me | —(C=O)ⁱPr | 6-F | 3-Cl | —CH₂—CH₂— | thiophen-3-yl— |
| 1.0972 | —Me | —Me | —(C=O)ⁱPr | 6-Cl | 3-Cl | —CH₂—CH₂— | thiophen-3-yl— |
| 1.0973 | —CH₂—C≡CH | —Me | —(C=O)ⁱPr | 6-Cl | 3-Cl | —CH₂—CH₂— | thiophen-3-yl— |
| 1.0974 | —cyclopropyl | —Me | —(C=O)ⁱPr | 6-Cl | 3-Cl | —CH₂—CH₂— | thiophen-3-yl— |
| 1.0975 | —Me | —Me | —(C=O)ⁱPr | 6-F | 3-Cl | —CH₂—CH₂— | 1-methyl-pyrazol-4-yl— |
| 1.0976 | —CH₂—C≡CH | —Me | —(C=O)ⁱPr | 6-F | 3-Cl | —CH₂—CH₂— | 1-methyl-pyrazol-4-yl— |
| 1.0977 | —cyclopropyl | —Me | —(C=O)ⁱPr | 6-F | 3-Cl | —CH₂—CH₂— | 1-methyl-pyrazol-4-yl— |

TABLE 1-continued

Herbicidal compounds of the present invention. The numbering system used to describe the positions of X and Y is shown for the purposes of clarity only.

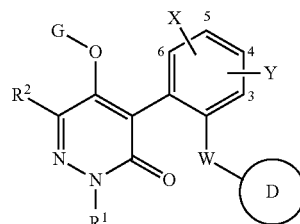

(I)

| Cmpd. No. | R¹ | R² | G | X | Y | W | D |
|---|---|---|---|---|---|---|---|
| 1.0978 | —Me | —Me | —(C=O)ⁱPr | 6-Cl | 3-Cl | —CH₂—CH₂— | 1-methyl-pyrazol-4-yl— |
| 1.0979 | —CH₂—C≡CH | —Me | —(C=O)ⁱPr | 6-Cl | 3-Cl | —CH₂—CH₂— | 1-methyl-pyrazol-4-yl— |
| 1.0980 | —cyclopropyl | —Me | —(C=O)ⁱPr | 6-Cl | 3-Cl | —CH₂—CH₂— | 1-methyl-pyrazol-4-yl— |
| 1.0981 | —Me | —Me | —(C=O)ⁱPr | 6-F | 3-Cl | —CH₂—CH₂— | 2-methyl-triazol-4-yl— |
| 1.0982 | —CH₂—C≡CH | —Me | —(C=O)ⁱPr | 6-F | 3-Cl | —CH₂—CH₂— | 2-methyl-triazol-4-yl— |
| 1.0983 | —cyclopropyl | —Me | —(C=O)ⁱPr | 6-F | 3-Cl | —CH₂—CH₂— | 2-methyl-triazol-4-yl— |
| 1.0984 | —Me | —Me | —(C=O)ⁱPr | 6-Cl | 3-Cl | —CH₂—CH₂— | 2-methyl-triazol-4-yl— |
| 1.0985 | —CH₂—C≡CH | —Me | —(C=O)ⁱPr | 6-Cl | 3-Cl | —CH₂—CH₂— | 2-methyl-triazol-4-yl— |
| 1.0986 | —cyclopropyl | —Me | —(C=O)ⁱPr | 6-Cl | 3-Cl | —CH₂—CH₂— | 2-methyl-triazol-4-yl— |
| 1.0987 | —Me | —Me | —(C=O)ⁱPr | 6-F | 3-Cl | —CH₂—CH₂— | 5-methyl-1,3,4-oxadiazol-2-yl— |
| 1.0988 | —CH₂—C≡CH | —Me | —(C=O)ⁱPr | 6-F | 3-Cl | —CH₂—CH₂— | 5-methyl-1,3,4-oxadiazol-2-yl— |
| 1.0989 | —cyclopropyl | —Me | —(C=O)ⁱPr | 6-F | 3-Cl | —CH₂—CH₂— | 5-methyl-1,3,4-oxadiazol-2-yl— |
| 1.0990 | —Me | —Me | —(C=O)ⁱPr | 6-Cl | 3-Cl | —CH₂—CH₂— | 5-methyl-1,3,4-oxadiazol-2-yl— |
| 1.0991 | —CH₂—C≡CH | —Me | —(C=O)ⁱPr | 6-Cl | 3-Cl | —CH₂—CH₂— | 5-methyl-1,3,4-oxadiazol-2-yl— |
| 1.0992 | —cyclopropyl | —Me | —(C=O)ⁱPr | 6-Cl | 3-Cl | —CH₂—CH₂— | 5-methyl-1,3,4-oxadiazol-2-yl— |
| 1.0993 | —Me | —Me | —(C=O)ⁱPr | 6-F | 3-Cl | —CH₂—CH₂— | 5-methyl-3-pyridyl— |
| 1.0994 | —CH₂—C≡CH | —Me | —(C=O)ⁱPr | 6-F | 3-Cl | —CH₂—CH₂— | 5-methyl-3-pyridyl— |
| 1.0995 | —cyclopropyl | —Me | —(C=O)ⁱPr | 6-F | 3-Cl | —CH₂—CH₂— | 5-methyl-3-pyridyl— |
| 1.0996 | —Me | —Me | —(C=O)ⁱPr | 6-Cl | 3-Cl | —CH₂—CH₂— | 5-methyl-3-pyridyl— |
| 1.0997 | —CH₂—C≡CH | —Me | —(C=O)ⁱPr | 6-Cl | 3-Cl | —CH₂—CH₂— | 5-methyl-3-pyridyl— |
| 1.0998 | —cyclopropyl | —Me | —(C=O)ⁱPr | 6-Cl | 3-Cl | —CH₂—CH₂— | 5-methyl-3-pyridyl— |
| 1.0999 | —Me | —Me | —(C=O)ⁱPr | 6-F | 3-Cl | —CH₂—CH₂— | 5-methyl-2-pyridyl— |
| 1.1000 | —CH₂—C≡CH | —Me | —(C=O)ⁱPr | 6-F | 3-Cl | —CH₂—CH₂— | 5-methyl-2-pyridyl— |
| 1.1001 | —cyclopropyl | —Me | —(C=O)ⁱPr | 6-F | 3-Cl | —CH₂—CH₂— | 5-methyl-2-pyridyl— |
| 1.1002 | —Me | —Me | —(C=O)ⁱPr | 6-Cl | 3-Cl | —CH₂—CH₂— | 5-methyl-2-pyridyl— |
| 1.1003 | —CH₂—C≡CH | —Me | —(C=O)ⁱPr | 6-Cl | 3-Cl | —CH₂—CH₂— | 5-methyl-2-pyridyl— |
| 1.1004 | —cyclopropyl | —Me | —(C=O)ⁱPr | 6-Cl | 3-Cl | —CH₂—CH₂— | 5-methyl-2-pyridyl— |
| 1.1005 | —Me | —Me | —(C=O)ⁱPr | 6-F | 3-Cl | —CH₂—CH₂— | 6-methyl-2-pyridyl— |
| 1.1006 | —CH₂—C≡CH | —Me | —(C=O)ⁱPr | 6-F | 3-Cl | —CH₂—CH₂— | 6-methyl-2-pyridyl— |
| 1.1007 | —cyclopropyl | —Me | —(C=O)ⁱPr | 6-F | 3-Cl | —CH₂—CH₂— | 6-methyl-2-pyridyl— |
| 1.1008 | —Me | —Me | —(C=O)ⁱPr | 6-Cl | 3-Cl | —CH₂—CH₂— | 6-methyl-2-pyridyl— |
| 1.1009 | —CH₂—C≡CH | —Me | —(C=O)ⁱPr | 6-Cl | 3-Cl | —CH₂—CH₂— | 6-methyl-2-pyridyl— |
| 1.1010 | —cyclopropyl | —Me | —(C=O)ⁱPr | 6-Cl | 3-Cl | —CH₂—CH₂— | 6-methyl-2-pyridyl— |
| 1.1011 | —Me | —Me | —(C=O)ⁱPr | 6-F | 3-Cl | —CH₂—CH₂— | 3-methyl-2-pyridyl— |
| 1.1012 | —CH₂—C≡CH | —Me | —(C=O)ⁱPr | 6-F | 3-Cl | —CH₂—CH₂— | 3-methyl-2-pyridyl— |
| 1.1013 | —cyclopropyl | —Me | —(C=O)ⁱPr | 6-F | 3-Cl | —CH₂—CH₂— | 3-methyl-2-pyridyl— |
| 1.1014 | —Me | —Me | —(C=O)ⁱPr | 6-Cl | 3-Cl | —CH₂—CH₂— | 3-methyl-2-pyridyl— |
| 1.1015 | —CH₂—C≡CH | —Me | —(C=O)ⁱPr | 6-Cl | 3-Cl | —CH₂—CH₂— | 3-methyl-2-pyridyl— |
| 1.1016 | —cyclopropyl | —Me | —(C=O)ⁱPr | 6-Cl | 3-Cl | —CH₂—CH₂— | 3-methyl-2-pyridyl— |
| 1.1017 | —Me | —Me | —(C=O)ⁱPr | 6-F | 3-Cl | —CH₂—CH₂— | 6-chloro-3-pyridyl— |
| 1.1018 | —CH₂—C≡CH | —Me | —(C=O)ⁱPr | 6-F | 3-Cl | —CH₂—CH₂— | 6-chloro-3-pyridyl— |
| 1.1019 | —cyclopropyl | —Me | —(C=O)ⁱPr | 6-F | 3-Cl | —CH₂—CH₂— | 6-chloro-3-pyridyl— |
| 1.1020 | —Me | —Me | —(C=O)ⁱPr | 6-Cl | 3-Cl | —CH₂—CH₂— | 6-chloro-3-pyridyl— |
| 1.1021 | —CH₂—C≡CH | —Me | —(C=O)ⁱPr | 6-Cl | 3-Cl | —CH₂—CH₂— | 6-chloro-3-pyridyl— |
| 1.1022 | —cyclopropyl | —Me | —(C=O)ⁱPr | 6-Cl | 3-Cl | —CH₂—CH₂— | 6-chloro-3-pyridyl— |
| 1.1023 | —Me | —Me | —(C=O)ⁱPr | 6-F | 3-Cl | —CH₂—CH₂— | 3-trifluoromethyl-3-pyridyl— |
| 1.1024 | —CH₂—C≡CH | —Me | —(C=O)ⁱPr | 6-F | 3-Cl | —CH₂—CH₂— | 3-trifluoromethyl-3-pyridyl— |
| 1.1025 | —cyclopropyl | —Me | —(C=O)ⁱPr | 6-F | 3-Cl | —CH₂—CH₂— | 3-trifluoromethyl-3-pyridyl— |
| 1.1026 | —Me | —Me | —(C=O)ⁱPr | 6-Cl | 3-Cl | —CH₂—CH₂— | 3-trifluoromethyl-3-pyridyl— |
| 1.1027 | —CH₂—C≡CH | —Me | —(C=O)ⁱPr | 6-Cl | 3-Cl | —CH₂—CH₂— | 3-trifluoromethyl-3-pyridyl— |
| 1.1028 | —cyclopropyl | —Me | —(C=O)ⁱPr | 6-Cl | 3-Cl | —CH₂—CH₂— | 3-trifluoromethyl-3-pyridyl— |
| 1.1029 | —Me | —Me | —H | 6-F | —H | —CH₂—CH₂— | 4-(dimethylamino)-phenyl— |
| 1.1030 | —Me | —Me | —H | 6-Cl | —H | —CH₂—CH₂— | 4-(dimethylamino)-phenyl— |
| 1.1031 | —CH₂—C≡CH | —Me | —H | 6-F | —H | —CH₂—CH₂— | 4-(dimethylamino)-phenyl— |
| 1.1032 | —cyclopropyl | —Me | —H | 6-F | —H | —CH₂—CH₂— | 4-(dimethylamino)-phenyl— |
| 1.1033 | —CH₂—C≡CH | —Me | —H | 6-Cl | —H | —CH₂—CH₂— | 4-(dimethylamino)-phenyl— |
| 1.1034 | —cyclopropyl | —Me | —H | 6-Cl | —H | —CH₂—CH₂— | 4-(dimethylamino)-phenyl— |
| 1.1035 | —Me | —Me | —H | 6-F | —H | —CH₂—CH₂— | 3-methyl-4-amino-phenyl— |
| 1.1036 | —CH₂—C≡CH | —Me | —H | 6-F | —H | —CH₂—CH₂— | 3-methyl-4-amino-phenyl— |
| 1.1037 | —cyclopropyl | —Me | —H | 6-F | —H | —CH₂—CH₂— | 3-methyl-4-amino-phenyl— |
| 1.1038 | —Me | —Me | —H | 6-Cl | —H | —CH₂—CH₂— | 3-methyl-4-amino-phenyl— |
| 1.1039 | —CH₂—C≡CH | —Me | —H | 6-Cl | —H | —CH₂—CH₂— | 3-methyl-4-amino-phenyl— |

TABLE 1-continued

Herbicidal compounds of the present invention. The numbering system used to describe the positions of X and Y is shown for the purposes of clarity only.

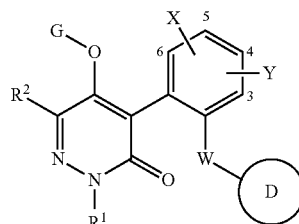

(I)

| Cmpd. No. | R$^1$ | R$^2$ | G | X | Y | W | D |
|---|---|---|---|---|---|---|---|
| 1.1040 | —cyclopropyl | —Me | —H | 6-Cl | —H | —CH$_2$—CH$_2$— | 3-methyl-4-amino-phenyl— |
| 1.1041 | —Me | —Me | —H | 6-F | —H | —CH$_2$—CH$_2$— | thiophen-3-yl— |
| 1.1042 | —CH$_2$—C≡CH | —Me | —H | 6-F | —H | —CH$_2$—CH$_2$— | thiophen-3-yl— |
| 1.1043 | —cyclopropyl | —Me | —H | 6-F | —H | —CH$_2$—CH$_2$— | thiophen-3-yl— |
| 1.1044 | —Me | —Me | —H | 6-Cl | —H | —CH$_2$—CH$_2$— | thiophen-3-yl— |
| 1.1045 | —CH$_2$—C≡CH | —Me | —H | 6-Cl | —H | —CH$_2$—CH$_2$— | thiophen-3-yl— |
| 1.1046 | —cyclopropyl | —Me | —H | 6-Cl | —H | —CH$_2$—CH$_2$— | thiophen-3-yl— |
| 1.1047 | —Me | —Me | —H | 6-F | —H | —CH$_2$—CH$_2$— | 1-methyl-pyrazol-4-yl— |
| 1.1048 | —CH$_2$—C≡CH | —Me | —H | 6-F | —H | —CH$_2$—CH$_2$— | 1-methyl-pyrazol-4-yl— |
| 1.1049 | —cyclopropyl | —Me | —H | 6-F | —H | —CH$_2$—CH$_2$— | 1-methyl-pyrazol-4-yl— |
| 1.1050 | —Me | —Me | —H | 6-Cl | —H | —CH$_2$—CH$_2$— | 1-methyl-pyrazol-4-yl— |
| 1.1051 | —CH$_2$—C≡CH | —Me | —H | 6-Cl | —H | —CH$_2$—CH$_2$— | 1-methyl-pyrazol-4-yl— |
| 1.1052 | —cyclopropyl | —Me | —H | 6-Cl | —H | —CH$_2$—CH$_2$— | 1-methyl-pyrazol-4-yl— |
| 1.1053 | —Me | —Me | —H | 6-F | —H | —CH$_2$—CH$_2$— | 2-methyl-triazol-4-yl— |
| 1.1054 | —CH$_2$—C≡CH | —Me | —H | 6-F | —H | —CH$_2$—CH$_2$— | 2-methyl-triazol-4-yl— |
| 1.1055 | —cyclopropyl | —Me | —H | 6-F | —H | —CH$_2$—CH$_2$— | 2-methyl-triazol-4-yl— |
| 1.1056 | —Me | —Me | —H | 6-Cl | —H | —CH$_2$—CH$_2$— | 2-methyl-triazol-4-yl— |
| 1.1057 | —CH$_2$—C≡CH | —Me | —H | 6-Cl | —H | —CH$_2$—CH$_2$— | 2-methyl-triazol-4-yl— |
| 1.1058 | —cyclopropyl | —Me | —H | 6-Cl | —H | —CH$_2$—CH$_2$— | 2-methyl-triazol-4-yl— |
| 1.1059 | —Me | —Me | —H | 6-F | —H | —CH$_2$—CH$_2$— | 5-methyl-1,3,4-oxadiazol-2-yl— |
| 1.1060 | —CH$_2$—C≡CH | —Me | —H | 6-F | —H | —CH$_2$—CH$_2$— | 5-methyl-1,3,4-oxadiazol-2-yl— |
| 1.1061 | —cyclopropyl | —Me | —H | 6-F | —H | —CH$_2$—CH$_2$— | 5-methyl-1,3,4-oxadiazol-2-yl— |
| 1.1062 | —Me | —Me | —H | 6-Cl | —H | —CH$_2$—CH$_2$— | 5-methyl-1,3,4-oxadiazol-2-yl— |
| 1.1063 | —CH$_2$—C≡CH | —Me | —H | 6-Cl | —H | —CH$_2$—CH$_2$— | 5-methyl-1,3,4-oxadiazol-2-yl— |
| 1.1064 | —cyclopropyl | —Me | —H | 6-Cl | —H | —CH$_2$—CH$_2$— | 5-methyl-1,3,4-oxadiazol-2-yl— |
| 1.1065 | —Me | —Me | —H | 6-F | —H | —CH$_2$—CH$_2$— | 5-methyl-3-pyridyl— |
| 1.1066 | —CH$_2$—C≡CH | —Me | —H | 6-F | —H | —CH$_2$—CH$_2$— | 5-methyl-3-pyridyl— |
| 1.1067 | —cyclopropyl | —Me | —H | 6-F | —H | —CH$_2$—CH$_2$— | 5-methyl-3-pyridyl— |
| 1.1068 | —Me | —Me | —H | 6-Cl | —H | —CH$_2$—CH$_2$— | 5-methyl-3-pyridyl— |
| 1.1069 | —CH$_2$—C≡CH | —Me | —H | 6-Cl | —H | —CH$_2$—CH$_2$— | 5-methyl-3-pyridyl— |
| 1.1070 | —cyclopropyl | —Me | —H | 6-Cl | —H | —CH$_2$—CH$_2$— | 5-methyl-3-pyridyl— |
| 1.1071 | —Me | —Me | —H | 6-F | —H | —CH$_2$—CH$_2$— | 5-methyl-2-pyridyl— |
| 1.1072 | —CH$_2$—C≡CH | —Me | —H | 6-F | —H | —CH$_2$—CH$_2$— | 5-methyl-2-pyridyl— |
| 1.1073 | —cyclopropyl | —Me | —H | 6-F | —H | —CH$_2$—CH$_2$— | 5-methyl-2-pyridyl— |
| 1.1074 | —Me | —Me | —H | 6-Cl | —H | —CH$_2$—CH$_2$— | 5-methyl-2-pyridyl— |
| 1.1075 | —CH$_2$—C≡CH | —Me | —H | 6-Cl | —H | —CH$_2$—CH$_2$— | 5-methyl-2-pyridyl— |
| 1.1076 | —cyclopropyl | —Me | —H | 6-Cl | —H | —CH$_2$—CH$_2$— | 5-methyl-2-pyridyl— |
| 1.1077 | —Me | —Me | —H | 6-F | —H | —CH$_2$—CH$_2$— | 6-methyl-2-pyridyl— |
| 1.1078 | —CH$_2$—C≡CH | —Me | —H | 6-F | —H | —CH$_2$—CH$_2$— | 6-methyl-2-pyridyl— |
| 1.1079 | —cyclopropyl | —Me | —H | 6-F | —H | —CH$_2$—CH$_2$— | 6-methyl-2-pyridyl— |
| 1.1080 | —Me | —Me | —H | 6-Cl | —H | —CH$_2$—CH$_2$— | 6-methyl-2-pyridyl— |
| 1.1081 | —CH$_2$—C≡CH | —Me | —H | 6-Cl | —H | —CH$_2$—CH$_2$— | 6-methyl-2-pyridyl— |
| 1.1082 | —cyclopropyl | —Me | —H | 6-Cl | —H | —CH$_2$—CH$_2$— | 6-methyl-2-pyridyl— |
| 1.1083 | —Me | —Me | —H | 6-F | —H | —CH$_2$—CH$_2$— | 3-methyl-2-pyridyl— |
| 1.1084 | —CH$_2$—C≡CH | —Me | —H | 6-F | —H | —CH$_2$—CH$_2$— | 3-methyl-2-pyridyl— |
| 1.1085 | —cyclopropyl | —Me | —H | 6-F | —H | —CH$_2$—CH$_2$— | 3-methyl-2-pyridyl— |
| 1.1086 | —Me | —Me | —H | 6-Cl | —H | —CH$_2$—CH$_2$— | 3-methyl-2-pyridyl— |
| 1.1087 | —CH$_2$—C≡CH | —Me | —H | 6-Cl | —H | —CH$_2$—CH$_2$— | 3-methyl-2-pyridyl— |
| 1.1088 | —cyclopropyl | —Me | —H | 6-Cl | —H | —CH$_2$—CH$_2$— | 3-methyl-2-pyridyl— |
| 1.1089 | —Me | —Me | —H | 6-F | —H | —CH$_2$—CH$_2$— | 6-chloro-3-pyridyl— |
| 1.1090 | —CH$_2$—C≡CH | —Me | —H | 6-F | —H | —CH$_2$—CH$_2$— | 6-chloro-3-pyridyl— |
| 1.1091 | —cyclopropyl | —Me | —H | 6-F | —H | —CH$_2$—CH$_2$— | 6-chloro-3-pyridyl— |
| 1.1092 | —Me | —Me | —H | 6-Cl | —H | —CH$_2$—CH$_2$— | 6-chloro-3-pyridyl— |
| 1.1093 | —CH$_2$—C≡CH | —Me | —H | 6-Cl | —H | —CH$_2$—CH$_2$— | 6-chloro-3-pyridyl— |
| 1.1094 | —cyclopropyl | —Me | —H | 6-Cl | —H | —CH$_2$—CH$_2$— | 6-chloro-3-pyridyl— |
| 1.1095 | —Me | —Me | —H | 6-F | —H | —CH$_2$—CH$_2$— | 3-trifluoromethyl-3-pyridyl— |
| 1.1096 | —CH$_2$—C≡CH | —Me | —H | 6-F | —H | —CH$_2$—CH$_2$— | 3-trifluoromethyl-3-pyridyl— |
| 1.1097 | —cyclopropyl | —Me | —H | 6-F | —H | —CH$_2$—CH$_2$— | 3-trifluoromethyl-3-pyridyl— |
| 1.1098 | —Me | —Me | —H | 6-Cl | —H | —CH$_2$—CH$_2$— | 3-trifluoromethyl-3-pyridyl— |
| 1.1099 | —CH$_2$—C≡CH | —Me | —H | 6-Cl | —H | —CH$_2$—CH$_2$— | 3-trifluoromethyl-3-pyridyl— |
| 1.1100 | —cyclopropyl | —Me | —H | 6-Cl | —H | —CH$_2$—CH$_2$— | 3-trifluoromethyl-3-pyridyl— |
| 1.1101 | —Me | —Me | —(C═O)$^i$Pr | 6-F | —H | —CH$_2$—CH$_2$— | 4-(dimethylamino)-phenyl— |

TABLE 1-continued

Herbicidal compounds of the present invention. The numbering system used to describe the positions of X and Y is shown for the purposes of clarity only.

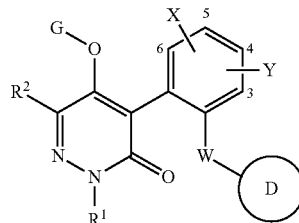

(I)

| Cmpd. No. | R$^1$ | R$^2$ | G | X | Y | W | D |
|---|---|---|---|---|---|---|---|
| 1.1102 | —Me | —Me | —(C=O)$^i$Pr | 6-Cl | —H | —CH$_2$—CH$_2$— | 4-(dimethylamino)-phenyl— |
| 1.1103 | —CH$_2$—C≡CH | —Me | —(C=O)$^i$Pr | 6-F | —H | —CH$_2$—CH$_2$— | 4-(dimethylamino)-phenyl— |
| 1.1104 | —cyclopropyl | —Me | —(C=O)$^i$Pr | 6-F | —H | —CH$_2$—CH$_2$— | 4-(dimethylamino)-phenyl— |
| 1.1105 | —CH$_2$—C≡CH | —Me | —(C=O)$^i$Pr | 6-Cl | —H | —CH$_2$—CH$_2$— | 4-(dimethylamino)-phenyl— |
| 1.1106 | —cyclopropyl | —Me | —(C=O)$^i$Pr | 6-Cl | —H | —CH$_2$—CH$_2$— | 4-(dimethylamino)-phenyl— |
| 1.1107 | —Me | —Me | —(C=O)$^i$Pr | 6-F | —H | —CH$_2$—CH$_2$— | 3-methyl-4-amino-phenyl— |
| 1.1108 | —CH$_2$—C≡CH | —Me | —(C=O)$^i$Pr | 6-F | —H | —CH$_2$—CH$_2$— | 3-methyl-4-amino-phenyl— |
| 1.1109 | —cyclopropyl | —Me | —(C=O)$^i$Pr | 6-F | —H | —CH$_2$—CH$_2$— | 3-methyl-4-amino-phenyl— |
| 1.1110 | —Me | —Me | —(C=O)$^i$Pr | 6-Cl | —H | —CH$_2$—CH$_2$— | 3-methyl-4-amino-phenyl— |
| 1.1111 | —CH$_2$—C≡CH | —Me | —(C=O)$^i$Pr | 6-Cl | —H | —CH$_2$—CH$_2$— | 3-methyl-4-amino-phenyl— |
| 1.1112 | —cyclopropyl | —Me | —(C=O)$^i$Pr | 6-Cl | —H | —CH$_2$—CH$_2$— | 3-methyl-4-amino-phenyl— |
| 1.1113 | —Me | —Me | —(C=O)$^i$Pr | 6-F | —H | —CH$_2$—CH$_2$— | thiophen-3-yl— |
| 1.1114 | —CH$_2$—C≡CH | —Me | —(C=O)$^i$Pr | 6-F | —H | —CH$_2$—CH$_2$— | thiophen-3-yl— |
| 1.1115 | —cyclopropyl | —Me | —(C=O)$^i$Pr | 6-F | —H | —CH$_2$—CH$_2$— | thiophen-3-yl— |
| 1.1116 | —Me | —Me | —(C=O)$^i$Pr | 6-Cl | —H | —CH$_2$—CH$_2$— | thiophen-3-yl— |
| 1.1117 | —CH$_2$—C≡CH | —Me | —(C=O)$^i$Pr | 6-Cl | —H | —CH$_2$—CH$_2$— | thiophen-3-yl— |
| 1.1118 | —cyclopropyl | —Me | —(C=O)$^i$Pr | 6-Cl | —H | —CH$_2$—CH$_2$— | thiophen-3-yl— |
| 1.1119 | —Me | —Me | —(C=O)$^i$Pr | 6-F | —H | —CH$_2$—CH$_2$— | 1-methyl-pyrazol-4-yl— |
| 1.1120 | —CH$_2$—C≡CH | —Me | —(C=O)$^i$Pr | 6-F | —H | —CH$_2$—CH$_2$— | 1-methyl-pyrazol-4-yl— |
| 1.1121 | —cyclopropyl | —Me | —(C=O)$^i$Pr | 6-F | —H | —CH$_2$—CH$_2$— | 1-methyl-pyrazol-4-yl— |
| 1.1122 | —Me | —Me | —(C=O)$^i$Pr | 6-Cl | —H | —CH$_2$—CH$_2$— | 1-methyl-pyrazol-4-yl— |
| 1.1123 | —CH$_2$—C≡CH | —Me | —(C=O)$^i$Pr | 6-Cl | —H | —CH$_2$—CH$_2$— | 1-methyl-pyrazol-4-yl— |
| 1.1124 | —cyclopropyl | —Me | —(C=O)$^i$Pr | 6-Cl | —H | —CH$_2$—CH$_2$— | 1-methyl-pyrazol-4-yl— |
| 1.1125 | —Me | —Me | —(C=O)$^i$Pr | 6-F | —H | —CH$_2$—CH$_2$— | 2-methyl-triazol-4-yl— |
| 1.1126 | —CH$_2$—C≡CH | —Me | —(C=O)$^i$Pr | 6-F | —H | —CH$_2$—CH$_2$— | 2-methyl-triazol-4-yl— |
| 1.1127 | —cyclopropyl | —Me | —(C=O)$^i$Pr | 6-F | —H | —CH$_2$—CH$_2$— | 2-methyl-triazol-4-yl— |
| 1.1128 | —Me | —Me | —(C=O)$^i$Pr | 6-Cl | —H | —CH$_2$—CH$_2$— | 2-methyl-triazol-4-yl— |
| 1.1129 | —CH$_2$—C≡CH | —Me | —(C=O)$^i$Pr | 6-Cl | —H | —CH$_2$—CH$_2$— | 2-methyl-triazol-4-yl— |
| 1.1130 | —cyclopropyl | —Me | —(C=O)$^i$Pr | 6-Cl | —H | —CH$_2$—CH$_2$— | 2-methyl-triazol-4-yl— |
| 1.1131 | —Me | —Me | —(C=O)$^i$Pr | 6-F | —H | —CH$_2$—CH$_2$— | 5-methyl-1,3,4-oxadiazol-2-yl— |
| 1.1132 | —CH$_2$—C≡CH | —Me | —(C=O)$^i$Pr | 6-F | —H | —CH$_2$—CH$_2$— | 5-methyl-1,3,4-oxadiazol-2-yl— |
| 1.1133 | —cyclopropyl | —Me | —(C=O)$^i$Pr | 6-F | —H | —CH$_2$—CH$_2$— | 5-methyl-1,3,4-oxadiazol-2-yl— |
| 1.1134 | —Me | —Me | —(C=O)$^i$Pr | 6-Cl | —H | —CH$_2$—CH$_2$— | 5-methyl-1,3,4-oxadiazol-2-yl— |
| 1.1135 | —CH$_2$—C≡CH | —Me | —(C=O)$^i$Pr | 6-Cl | —H | —CH$_2$—CH$_2$— | 5-methyl-1,3,4-oxadiazol-2-yl— |
| 1.1136 | —cyclopropyl | —Me | —(C=O)$^i$Pr | 6-Cl | —H | —CH$_2$—CH$_2$— | 5-methyl-1,3,4-oxadiazol-2-yl— |
| 1.1137 | —Me | —Me | —(C=O)$^i$Pr | 6-F | —H | —CH$_2$—CH$_2$— | 5-methyl-3-pyridyl— |
| 1.1138 | —CH$_2$—C≡CH | —Me | —(C=O)$^i$Pr | 6-F | —H | —CH$_2$—CH$_2$— | 5-methyl-3-pyridyl— |
| 1.1139 | —cyclopropyl | —Me | —(C=O)$^i$Pr | 6-F | —H | —CH$_2$—CH$_2$— | 5-methyl-3-pyridyl— |
| 1.1140 | —Me | —Me | —(C=O)$^i$Pr | 6-Cl | —H | —CH$_2$—CH$_2$— | 5-methyl-3-pyridyl— |
| 1.1141 | —CH$_2$—C≡CH | —Me | —(C=O)$^i$Pr | 6-Cl | —H | —CH$_2$—CH$_2$— | 5-methyl-3-pyridyl— |
| 1.1142 | —cyclopropyl | —Me | —(C=O)$^i$Pr | 6-Cl | —H | —CH$_2$—CH$_2$— | 5-methyl-3-pyridyl— |
| 1.1143 | —Me | —Me | —(C=O)$^i$Pr | 6-F | —H | —CH$_2$—CH$_2$— | 5-methyl-2-pyridyl— |
| 1.1144 | —CH$_2$—C≡CH | —Me | —(C=O)$^i$Pr | 6-F | —H | —CH$_2$—CH$_2$— | 5-methyl-2-pyridyl— |
| 1.1145 | —cyclopropyl | —Me | —(C=O)$^i$Pr | 6-F | —H | —CH$_2$—CH$_2$— | 5-methyl-2-pyridyl— |
| 1.1146 | —Me | —Me | —(C=O)$^i$Pr | 6-Cl | —H | —CH$_2$—CH$_2$— | 5-methyl-2-pyridyl— |
| 1.1147 | —CH$_2$—C≡CH | —Me | —(C=O)$^i$Pr | 6-Cl | —H | —CH$_2$—CH$_2$— | 5-methyl-2-pyridyl— |
| 1.1148 | —cyclopropyl | —Me | —(C=O)$^i$Pr | 6-Cl | —H | —CH$_2$—CH$_2$— | 5-methyl-2-pyridyl— |
| 1.1149 | —Me | —Me | —(C=O)$^i$Pr | 6-F | —H | —CH$_2$—CH$_2$— | 6-methyl-2-pyridyl— |
| 1.1150 | —CH$_2$—C≡CH | —Me | —(C=O)$^i$Pr | 6-F | —H | —CH$_2$—CH$_2$— | 6-methyl-2-pyridyl— |
| 1.1151 | —cyclopropyl | —Me | —(C=O)$^i$Pr | 6-F | —H | —CH$_2$—CH$_2$— | 6-methyl-2-pyridyl— |
| 1.1152 | —Me | —Me | —(C=O)$^i$Pr | 6-Cl | —H | —CH$_2$—CH$_2$— | 6-methyl-2-pyridyl— |
| 1.1153 | —CH$_2$—C≡CH | —Me | —(C=O)$^i$Pr | 6-Cl | —H | —CH$_2$—CH$_2$— | 6-methyl-2-pyridyl— |
| 1.1154 | —cyclopropyl | —Me | —(C=O)$^i$Pr | 6-Cl | —H | —CH$_2$—CH$_2$— | 6-methyl-2-pyridyl— |
| 1.1155 | —Me | —Me | —(C=O)$^i$Pr | 6-F | —H | —CH$_2$—CH$_2$— | 3-methyl-2-pyridyl— |
| 1.1156 | —CH$_2$—C≡CH | —Me | —(C=O)$^i$Pr | 6-F | —H | —CH$_2$—CH$_2$— | 3-methyl-2-pyridyl— |
| 1.1157 | —cyclopropyl | —Me | —(C=O)$^i$Pr | 6-F | —H | —CH$_2$—CH$_2$— | 3-methyl-2-pyridyl— |
| 1.1158 | —Me | —Me | —(C=O)$^i$Pr | 6-Cl | —H | —CH$_2$—CH$_2$— | 3-methyl-2-pyridyl— |
| 1.1159 | —CH$_2$—C≡CH | —Me | —(C=O)$^i$Pr | 6-Cl | —H | —CH$_2$—CH$_2$— | 3-methyl-2-pyridyl— |
| 1.1160 | —cyclopropyl | —Me | —(C=O)$^i$Pr | 6-Cl | —H | —CH$_2$—CH$_2$— | 3-methyl-2-pyridyl— |
| 1.1161 | —Me | —Me | —(C=O)$^i$Pr | 6-F | —H | —CH$_2$—CH$_2$— | 6-chloro-3-pyridyl— |
| 1.1162 | —CH$_2$—C≡CH | —Me | —(C=O)$^i$Pr | 6-F | —H | —CH$_2$—CH$_2$— | 6-chloro-3-pyridyl— |
| 1.1163 | —cyclopropyl | —Me | —(C=O)$^i$Pr | 6-F | —H | —CH$_2$—CH$_2$— | 6-chloro-3-pyridyl— |

TABLE 1-continued

Herbicidal compounds of the present invention. The numbering system used to describe the positions of X and Y is shown for the purposes of clarity only.

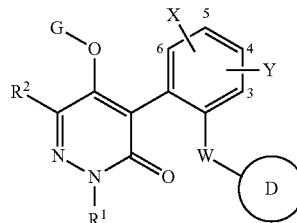

(I)

| Cmpd. No. | R¹ | R² | G | X | Y | W | D |
|---|---|---|---|---|---|---|---|
| 1.1164 | —Me | —Me | —(C=O)$^i$Pr | 6-Cl | —H | —CH$_2$—CH$_2$— | 6-chloro-3-pyridyl— |
| 1.1165 | —CH$_2$—C≡CH | —Me | —(C=O)$^i$Pr | 6-Cl | —H | —CH$_2$—CH$_2$— | 6-chloro-3-pyridyl— |
| 1.1166 | —cyclopropyl | —Me | —(C=O)$^i$Pr | 6-Cl | —H | —CH$_2$—CH$_2$— | 6-chloro-3-pyridyl— |
| 1.1167 | —Me | —Me | —(C=O)$^i$Pr | 6-F | —H | —CH$_2$—CH$_2$— | 3-trifluoromethyl-3-pyridyl— |
| 1.1168 | —CH$_2$—C≡CH | —Me | —(C=O)$^i$Pr | 6-F | —H | —CH$_2$—CH$_2$— | 3-trifluoromethyl-3-pyridyl— |
| 1.1169 | —cyclopropyl | —Me | —(C=O)$^i$Pr | 6-F | —H | —CH$_2$—CH$_2$— | 3-trifluoromethyl-3-pyridyl— |
| 1.1170 | —Me | —Me | —(C=O)$^i$Pr | 6-Cl | —H | —CH$_2$—CH$_2$— | 3-trifluoromethyl-3-pyridyl— |
| 1.1171 | —CH$_2$—C≡CH | —Me | —(C=O)$^i$Pr | 6-Cl | —H | —CH$_2$—CH$_2$— | 3-trifluoromethyl-3-pyridyl— |
| 1.1172 | —cyclopropyl | —Me | —(C=O)$^i$Pr | 6-Cl | —H | —CH$_2$—CH$_2$— | 3-trifluoromethyl-3-pyridyl— |
| 1.1173 | —Me | —Me | —H | 6-F | 3-Cl | —CH$_2$—CH$_2$— | 3,5-difluoro-phenyl— |
| 1.1174 | —Me | —Me | —H | 6-Cl | 3-Cl | —CH$_2$—CH$_2$— | 3,5-difluoro-phenyl— |
| 1.1175 | —CH$_2$—C≡CH | —Me | —H | 6-F | 3-Cl | —CH$_2$—CH$_2$— | 3,5-difluoro-phenyl— |
| 1.1176 | —cyclopropyl | —Me | —H | 6-F | 3-Cl | —CH$_2$—CH$_2$— | 3,5-difluoro-phenyl— |
| 1.1177 | —CH$_2$—C≡CH | —Me | —H | 6-Cl | 3-Cl | —CH$_2$—CH$_2$— | 3,5-difluoro-phenyl— |
| 1.1178 | —cyclopropyl | —Me | —H | 6-Cl | 3-Cl | —CH$_2$—CH$_2$— | 3,5-difluoro-phenyl— |
| 1.1179 | —Me | —Me | —H | 6-F | 3-Cl | —CH$_2$—CH$_2$— | 4-methyl-2-pyridyl— |
| 1.1180 | —CH$_2$—C≡CH | —Me | —H | 6-F | 3-Cl | —CH$_2$—CH$_2$— | 4-methyl-2-pyridyl— |
| 1.1181 | —cyclopropyl | —Me | —H | 6-F | 3-Cl | —CH$_2$—CH$_2$— | 4-methyl-2-pyridyl— |
| 1.1182 | —Me | —Me | —H | 6-Cl | 3-Cl | —CH$_2$—CH$_2$— | 4-methyl-2-pyridyl— |
| 1.1183 | —CH$_2$—C≡CH | —Me | —H | 6-Cl | 3-Cl | —CH$_2$—CH$_2$— | 4-methyl-2-pyridyl— |
| 1.1184 | —cyclopropyl | —Me | —H | 6-Cl | 3-Cl | —CH$_2$—CH$_2$— | 4-methyl-2-pyridyl— |
| 1.1185 | —Me | —Me | —H | 6-F | 3-Cl | —CH$_2$—CH$_2$— | 2-acetamidothiazol-5-yl— |
| 1.1186 | —CH$_2$—C≡CH | —Me | —H | 6-F | 3-Cl | —CH$_2$—CH$_2$— | 2-acetamidothiazol-5-yl— |
| 1.1187 | —cyclopropyl | —Me | —H | 6-F | 3-Cl | —CH$_2$—CH$_2$— | 2-acetamidothiazol-5-yl— |
| 1.1188 | —Me | —Me | —H | 6-Cl | 3-Cl | —CH$_2$—CH$_2$— | 2-acetamidothiazol-5-yl— |
| 1.1189 | —CH$_2$—C≡CH | —Me | —H | 6-Cl | 3-Cl | —CH$_2$—CH$_2$— | 2-acetamidothiazol-5-yl— |
| 1.1190 | —cyclopropyl | —Me | —H | 6-Cl | 3-Cl | —CH$_2$—CH$_2$— | 2-acetamidothiazol-5-yl— |
| 1.1191 | —Me | —Me | —(C=O)$^i$Pr | 6-F | 3-Cl | —CH$_2$—CH$_2$— | 3,5-difluoro-phenyl— |
| 1.1192 | —Me | —Me | —(C=O)$^i$Pr | 6-Cl | 3-Cl | —CH$_2$—CH$_2$— | 3,5-difluoro-phenyl— |
| 1.1193 | —CH$_2$—C≡CH | —Me | —(C=O)$^i$Pr | 6-F | 3-Cl | —CH$_2$—CH$_2$— | 3,5-difluoro-phenyl— |
| 1.1194 | —cyclopropyl | —Me | —(C=O)$^i$Pr | 6-F | 3-Cl | —CH$_2$—CH$_2$— | 3,5-difluoro-phenyl— |
| 1.1195 | —CH$_2$—C≡CH | —Me | —(C=O)$^i$Pr | 6-Cl | 3-Cl | —CH$_2$—CH$_2$— | 3,5-difluoro-phenyl— |
| 1.1196 | —cyclopropyl | —Me | —(C=O)$^i$Pr | 6-Cl | 3-Cl | —CH$_2$—CH$_2$— | 3,5-difluoro-phenyl— |
| 1.1197 | —Me | —Me | —(C=O)$^i$Pr | 6-F | 3-Cl | —CH$_2$—CH$_2$— | 4-methyl-2-pyridyl— |
| 1.1198 | —CH$_2$—C≡CH | —Me | —(C=O)$^i$Pr | 6-F | 3-Cl | —CH$_2$—CH$_2$— | 4-methyl-2-pyridyl— |
| 1.1199 | —cyclopropyl | —Me | —(C=O)$^i$Pr | 6-F | 3-Cl | —CH$_2$—CH$_2$— | 4-methyl-2-pyridyl— |
| 1.1200 | —Me | —Me | —(C=O)$^i$Pr | 6-Cl | 3-Cl | —CH$_2$—CH$_2$— | 4-methyl-2-pyridyl— |
| 1.1201 | —CH$_2$—C≡CH | —Me | —(C=O)$^i$Pr | 6-Cl | 3-Cl | —CH$_2$—CH$_2$— | 4-methyl-2-pyridyl— |
| 1.1202 | —cyclopropyl | —Me | —(C=O)$^i$Pr | 6-Cl | 3-Cl | —CH$_2$—CH$_2$— | 4-methyl-2-pyridyl— |
| 1.1203 | —Me | —Me | —(C=O)$^i$Pr | 6-F | 3-Cl | —CH$_2$—CH$_2$— | 2-acetamidothiazol-5-yl— |
| 1.1204 | —CH$_2$—C≡CH | —Me | —(C=O)$^i$Pr | 6-F | 3-Cl | —CH$_2$—CH$_2$— | 2-acetamidothiazol-5-yl— |
| 1.1205 | —cyclopropyl | —Me | —(C=O)$^i$Pr | 6-F | 3-Cl | —CH$_2$—CH$_2$— | 2-acetamidothiazol-5-yl— |
| 1.1206 | —Me | —Me | —(C=O)$^i$Pr | 6-Cl | 3-Cl | —CH$_2$—CH$_2$— | 2-acetamidothiazol-5-yl— |
| 1.1207 | —CH$_2$—C≡CH | —Me | —(C=O)$^i$Pr | 6-Cl | 3-Cl | —CH$_2$—CH$_2$— | 2-acetamidothiazol-5-yl— |
| 1.1208 | —cyclopropyl | —Me | —(C=O)$^i$Pr | 6-Cl | 3-Cl | —CH$_2$—CH$_2$— | 2-acetamidothiazol-5-yl— |
| 1.1209 | —Me | —Me | —H | 6-F | —H | —CH$_2$—CH$_2$— | 3,5-difluoro-phenyl— |
| 1.1210 | —Me | —Me | —H | 6-Cl | —H | —CH$_2$—CH$_2$— | 3,5-difluoro-phenyl— |
| 1.1211 | —CH$_2$—C≡CH | —Me | —H | 6-F | —H | —CH$_2$—CH$_2$— | 3,5-difluoro-phenyl— |
| 1.1212 | —cyclopropyl | —Me | —H | 6-F | —H | —CH$_2$—CH$_2$— | 3,5-difluoro-phenyl— |
| 1.1213 | —CH$_2$—C≡CH | —Me | —H | 6-Cl | —H | —CH$_2$—CH$_2$— | 3,5-difluoro-phenyl— |
| 1.1214 | —cyclopropyl | —Me | —H | 6-Cl | —H | —CH$_2$—CH$_2$— | 3,5-difluoro-phenyl— |
| 1.1215 | —Me | —Me | —H | 6-F | —H | —CH$_2$—CH$_2$— | 4-methyl-2-pyridyl— |
| 1.1216 | —CH$_2$—C≡CH | —Me | —H | 6-F | —H | —CH$_2$—CH$_2$— | 4-methyl-2-pyridyl— |
| 1.1217 | —cyclopropyl | —Me | —H | 6-F | —H | —CH$_2$—CH$_2$— | 4-methyl-2-pyridyl— |
| 1.1218 | —Me | —Me | —H | 6-Cl | —H | —CH$_2$—CH$_2$— | 4-methyl-2-pyridyl— |
| 1.1219 | —CH$_2$—C≡CH | —Me | —H | 6-Cl | —H | —CH$_2$—CH$_2$— | 4-methyl-2-pyridyl— |
| 1.1220 | —cyclopropyl | —Me | —H | 6-Cl | —H | —CH$_2$—CH$_2$— | 4-methyl-2-pyridyl— |
| 1.1221 | —Me | —Me | —H | 6-F | —H | —CH$_2$—CH$_2$— | 2-acetamidothiazol-5-yl— |
| 1.1222 | —CH$_2$—C≡CH | —Me | —H | 6-F | —H | —CH$_2$—CH$_2$— | 2-acetamidothiazol-5-yl— |
| 1.1223 | —cyclopropyl | —Me | —H | 6-F | —H | —CH$_2$—CH$_2$— | 2-acetamidothiazol-5-yl— |
| 1.1224 | —Me | —Me | —H | 6-Cl | —H | —CH$_2$—CH$_2$— | 2-acetamidothiazol-5-yl— |
| 1.1225 | —CH$_2$—C≡CH | —Me | —H | 6-Cl | —H | —CH$_2$—CH$_2$— | 2-acetamidothiazol-5-yl— |

TABLE 1-continued

Herbicidal compounds of the present invention. The numbering system used to describe the positions of X and Y is shown for the purposes of clarity only.

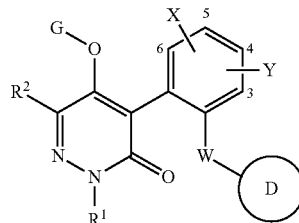

(I)

| Cmpd. No. | R¹ | R² | G | X | Y | W | D |
|---|---|---|---|---|---|---|---|
| 1.1226 | —cyclopropyl | —Me | —H | 6-Cl | —H | —CH₂—CH₂— | 2-acetamidothiazol-5-yl— |
| 1.1227 | —Me | —Me | —(C=O)ⁱPr | 6-F | —H | —CH₂—CH₂— | 3,5-difluoro-phenyl— |
| 1.1228 | —Me | —Me | —(C=O)ⁱPr | 6-Cl | —H | —CH₂—CH₂— | 3,5-difluoro-phenyl— |
| 1.1229 | —CH₂—C≡CH | —Me | —(C=O)ⁱPr | 6-F | —H | —CH₂—CH₂— | 3,5-difluoro-phenyl— |
| 1.1230 | —cyclopropyl | —Me | —(C=O)ⁱPr | 6-F | —H | —CH₂—CH₂— | 3,5-difluoro-phenyl— |
| 1.1231 | —CH₂—C≡CH | —Me | —(C=O)ⁱPr | 6-Cl | —H | —CH₂—CH₂— | 3,5-difluoro-phenyl— |
| 1.1232 | —cyclopropyl | —Me | —(C=O)ⁱPr | 6-Cl | —H | —CH₂—CH₂— | 3,5-difluoro-phenyl— |
| 1.1233 | —Me | —Me | —(C=O)ⁱPr | 6-F | —H | —CH₂—CH₂— | 4-methyl-2-pyridyl— |
| 1.1234 | —CH₂—C≡CH | —Me | —(C=O)ⁱPr | 6-F | —H | —CH₂—CH₂— | 4-methyl-2-pyridyl— |
| 1.1235 | —cyclopropyl | —Me | —(C=O)ⁱPr | 6-F | —H | —CH₂—CH₂— | 4-methyl-2-pyridyl— |
| 1.1236 | —Me | —Me | —(C=O)ⁱPr | 6-Cl | —H | —CH₂—CH₂— | 4-methyl-2-pyridyl— |
| 1.1237 | —CH₂—C≡CH | —Me | —(C=O)ⁱPr | 6-Cl | —H | —CH₂—CH₂— | 4-methyl-2-pyridyl— |
| 1.1238 | —cyclopropyl | —Me | —(C=O)ⁱPr | 6-Cl | —H | —CH₂—CH₂— | 4-methyl-2-pyridyl— |
| 1.1239 | —Me | —Me | —(C=O)ⁱPr | 6-F | —H | —CH₂—CH₂— | 2-acetamidothiazol-5-yl— |
| 1.1240 | —CH₂—C≡CH | —Me | —(C=O)ⁱPr | 6-F | —H | —CH₂—CH₂— | 2-acetamidothiazol-5-yl— |
| 1.1241 | —cyclopropyl | —Me | —(C=O)ⁱPr | 6-F | —H | —CH₂—CH₂— | 2-acetamidothiazol-5-yl— |
| 1.1242 | —Me | —Me | —(C=O)ⁱPr | 6-Cl | —H | —CH₂—CH₂— | 2-acetamidothiazol-5-yl— |
| 1.1243 | —CH₂—C≡CH | —Me | —(C=O)ⁱPr | 6-Cl | —H | —CH₂—CH₂— | 2-acetamidothiazol-5-yl— |
| 1.1244 | —cyclopropyl | —Me | —(C=O)ⁱPr | 6-Cl | —H | —CH₂—CH₂— | 2-acetamidothiazol-5-yl— |
| 1.1245 | —Me | —Me | —H | 6-F | 3-Cl | (E)—CH=CH— | 4-chloro-phenyl— |
| 1.1246 | —Me | —Me | —H | 6-F | 3-Cl | (E)—CH=CH— | 4-trifluoromethyl-phenyl— |
| 1.1247 | —Me | —Me | —H | 6-F | 3-Cl | (E)—CH=CH— | 4-cyano-phenyl— |
| 1.1248 | —Me | —Me | —H | 6-F | 3-Cl | (E)—CH=CH— | 4-chloro-3-pyridyl— |
| 1.1249 | —Me | —Me | —H | 6-F | 3-Cl | (E)—CH=CH— | 2-chlorothiazol-5-yl— |
| 1.1250 | —Me | —Me | —H | 6-F | 3-Cl | (E)—CH=CH— | 4-trifluoromethyl-3-pyridyl— |
| 1.1251 | —Me | —Me | —H | 6-F | 3-Cl | (E)—CH=CH— | 4-fluoro-phenyl— |
| 1.1252 | —Me | —Me | —H | 6-F | 3-Cl | (E)—CH=CH— | 3-pyridyl— |
| 1.1253 | —Me | —Me | —H | 6-F | 3-Cl | (E)—CH=CH— | 3,4-difluoro-phenyl— |
| 1.1254 | —Me | —Me | —H | 6-F | 3-Cl | (E)—CH=CH— | 2-trifluoromethyl-phenyl— |
| 1.1255 | —Me | —Me | —H | 6-F | 3-Cl | (E)—CH=CH— | 4-tolyl— |
| 1.1256 | —Me | —Me | —H | 6-F | 3-Cl | (E)—CH=CH— | 4-(trifluoromethoxy)-phenyl— |
| 1.1257 | —Me | —Me | —H | 6-F | 3-Cl | (E)—CH=CH— | 2-chloro-3-pyridyl— |
| 1.1258 | —Me | —Me | —H | 6-F | 3-Cl | (E)—CH=CH— | 2-chloro-4-pyridyl— |
| 1.1259 | —Me | —Me | —H | 6-F | 3-Cl | (E)—CH=CH— | 3-chloro-4-fluoro-phenyl— |
| 1.1260 | —Me | —Me | —H | 6-F | 3-Cl | (E)—CH=CH— | 3-chloro-4-pyridyl— |
| 1.1261 | —Me | —Me | —H | 6-F | 3-Cl | (E)—CH=CH— | 4-hydroxy-phenyl— |
| 1.1262 | —Me | —Me | —H | 6-F | 3-Cl | (E)—CH=CH— | 4-cyclopropyl-phenyl— |
| 1.1263 | —Me | —Me | —H | 6-F | 3-Cl | (E)—CH=CH— | 1-methyl-3-(trifluoromethyl)pyrazol-4-yl— |
| 1.1264 | —Me | —Me | —H | 6-F | 3-Cl | (E)—CH=CH— | thiazol-2-yl— |
| 1.1265 | —Me | —Me | —H | 6-F | 3-Cl | (E)—CH=CH— | pyrimidin-5-yl— |
| 1.1266 | —Me | —Me | —H | 6-F | 3-Cl | (E)—CH=CH— | 4-(tert-butoxy)-phenyl— |
| 1.1267 | —Me | —Me | —H | 6-F | 3-Cl | (E)—CH=CH— | thiazol-5-yl— |
| 1.1268 | —Me | —Me | —H | 6-F | 3-Cl | (E)—CH=CH— | 2-cyano-phenyl— |
| 1.1269 | —Me | —Me | —H | 6-F | 3-Cl | (E)—CH=CH— | 3-cyano-phenyl— |
| 1.1270 | —Me | —Me | —H | 6-F | 3-Cl | (E)—CH=CH— | 3-trifluoromethyl-phenyl— |
| 1.1271 | —Me | —Me | —H | 6-F | 3-Cl | (E)—CH=CH— | 2-tolyl— |
| 1.1272 | —Me | —Me | —H | 6-F | 3-Cl | (E)—CH=CH— | 3-tolyl— |
| 1.1273 | —Me | —Me | —H | 6-F | 3-Cl | (E)—CH=CH— | 2-methyl-4-pyridyl— |
| 1.1274 | —Me | —Me | —H | 6-F | 3-Cl | (E)—CH=CH— | 2-trifluoromethyl-4-pyridyl— |
| 1.1275 | —Me | —Me | —H | 6-F | 3-Cl | (E)—CH=CH— | 2-amino-4-pyridyl— |
| 1.1276 | —Me | —Me | —H | 6-F | 3-Cl | (E)—CH=CH— | 2-fluoro-4-pyridyl— |
| 1.1277 | —Me | —Me | —H | 6-F | 3-Cl | (E)—CH=CH— | 4-pyridyl— |
| 1.1278 | —Me | —Me | —H | 6-F | 3-Cl | (E)—CH=CH— | 4-(methylamino)-phenyl— |
| 1.1279 | —Me | —Me | —H | 6-F | 3-Cl | (E)—CH=CH— | 4-amino-phenyl— |
| 1.1280 | —Me | —Me | —H | 6-F | 3-Cl | (E)—CH=CH— | 4-(dimethylamino)-phenyl— |
| 1.1281 | —Me | —Me | —H | 6-F | 3-Cl | (E)—CH=CH— | 3-methyl-4-amino-phenyl— |
| 1.1282 | —Me | —Me | —H | 6-F | 3-Cl | (E)—CH=CH— | thiophen-3-yl— |
| 1.1283 | —Me | —Me | —H | 6-F | 3-Cl | (E)—CH=CH— | 1-methyl-pyrazol-4-yl— |
| 1.1284 | —Me | —Me | —H | 6-F | 3-Cl | (E)—CH=CH— | 2-methyl-triazol-4-yl— |
| 1.1285 | —Me | —Me | —H | 6-F | 3-Cl | (E)—CH=CH— | 5-methyl-1,3,4-oxadiazol-2-yl— |
| 1.1286 | —Me | —Me | —H | 6-F | 3-Cl | (E)—CH=CH— | 5-methyl-3-pyridyl— |

TABLE 1-continued

Herbicidal compounds of the present invention. The numbering system used to describe the positions of X and Y is shown for the purposes of clarity only.

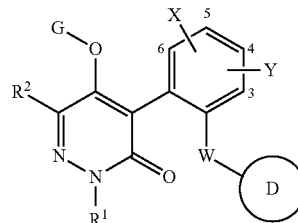

(I)

| Cmpd. No. | R¹ | R² | G | X | Y | W | D |
|---|---|---|---|---|---|---|---|
| 1.1287 | —Me | —Me | —H | 6-F | 3-Cl | (E)—CH=CH— | 5-methyl-2-pyridyl— |
| 1.1288 | —Me | —Me | —H | 6-F | 3-Cl | (E)—CH=CH— | 6-methyl-2-pyridyl— |
| 1.1289 | —Me | —Me | —H | 6-F | 3-Cl | (E)—CH=CH— | 3-methyl-2-pyridyl— |
| 1.1290 | —Me | —Me | —H | 6-F | 3-Cl | (E)—CH=CH— | 6-chloro-3-pyridyl— |
| 1.1291 | —Me | —Me | —H | 6-F | 3-Cl | (E)—CH=CH— | 3-trifluoromethyl-3-pyridyl— |
| 1.1292 | —Me | —Me | —H | 6-F | 3-Cl | (E)—CH=CH— | 3,5-difluoro-phenyl— |
| 1.1293 | —Me | —Me | —H | 6-F | 3-Cl | (E)—CH=CH— | 4-methyl-2-pyridyl— |
| 1.1294 | —Me | —Me | —H | 6-F | 3-Cl | (E)—CH=CH— | 2-acetamidothiazol-5-yl— |
| 1.1295 | —Me | —Me | —H | 6-Cl | 3-Cl | (E)—CH=CH— | —Ph |
| 1.1296 | —Me | —Me | —H | 6-Cl | 3-Cl | (E)—CH=CH— | 4-chloro-phenyl— |
| 1.1297 | —Me | —Me | —H | 6-Cl | 3-Cl | (E)—CH=CH— | 4-trifluoromethyl-phenyl— |
| 1.1298 | —Me | —Me | —H | 6-Cl | 3-Cl | (E)—CH=CH— | 4-cyano-phenyl— |
| 1.1299 | —Me | —Me | —H | 6-Cl | 3-Cl | (E)—CH=CH— | 4-chloro-3-pyridyl— |
| 1.1300 | —Me | —Me | —H | 6-Cl | 3-Cl | (E)—CH=CH— | 2-chlorothiazol-5-yl— |
| 1.1301 | —Me | —Me | —H | 6-Cl | 3-Cl | (E)—CH=CH— | 4-trifluoromethyl-3-pyridyl— |
| 1.1302 | —Me | —Me | —H | 6-Cl | 3-Cl | (E)—CH=CH— | 4-fluoro-phenyl— |
| 1.1303 | —Me | —Me | —H | 6-Cl | 3-Cl | (E)—CH=CH— | 3-pyridyl— |
| 1.1304 | —Me | —Me | —H | 6-Cl | 3-Cl | (E)—CH=CH— | 3,4-difluoro-phenyl— |
| 1.1305 | —Me | —Me | —H | 6-Cl | 3-Cl | (E)—CH=CH— | 2-trifluoromethyl-phenyl— |
| 1.1306 | —Me | —Me | —H | 6-Cl | 3-Cl | (E)—CH=CH— | 4-tolyl— |
| 1.1307 | —Me | —Me | —H | 6-Cl | 3-Cl | (E)—CH=CH— | 4-(trifluoromethoxy)-phenyl— |
| 1.1308 | —Me | —Me | —H | 6-Cl | 3-Cl | (E)—CH=CH— | 2-chloro-3-pyridyl— |
| 1.1309 | —Me | —Me | —H | 6-Cl | 3-Cl | (E)—CH=CH— | 2-chloro-4-pyridyl— |
| 1.1310 | —Me | —Me | —H | 6-Cl | 3-Cl | (E)—CH=CH— | 3-chloro-4-fluoro-phenyl— |
| 1.1311 | —Me | —Me | —H | 6-Cl | 3-Cl | (E)—CH=CH— | 3-chloro-4-pyridyl— |
| 1.1312 | —Me | —Me | —H | 6-Cl | 3-Cl | (E)—CH=CH— | 4-hydroxy-phenyl— |
| 1.1313 | —Me | —Me | —H | 6-Cl | 3-Cl | (E)—CH=CH— | 4-cyclopropyl-phenyl— |
| 1.1314 | —Me | —Me | —H | 6-Cl | 3-Cl | (E)—CH=CH— | 1-methyl-3-(trifluoromethyl)pyrazol-4-yl— |
| 1.1315 | —Me | —Me | —H | 6-Cl | 3-Cl | (E)—CH=CH— | thiazol-2-yl— |
| 1.1316 | —Me | —Me | —H | 6-Cl | 3-Cl | (E)—CH=CH— | pyrimidin-5-yl— |
| 1.1317 | —Me | —Me | —H | 6-Cl | 3-Cl | (E)—CH=CH— | 4-(tert-butoxy)-phenyl— |
| 1.1318 | —Me | —Me | —H | 6-Cl | 3-Cl | (E)—CH=CH— | thiazol-5-yl— |
| 1.1319 | —Me | —Me | —H | 6-Cl | 3-Cl | (E)—CH=CH— | 2-cyano-phenyl— |
| 1.1320 | —Me | —Me | —H | 6-Cl | 3-Cl | (E)—CH=CH— | 3-cyano-phenyl— |
| 1.1321 | —Me | —Me | —H | 6-Cl | 3-Cl | (E)—CH=CH— | 3-trifluoromethyl-phenyl— |
| 1.1322 | —Me | —Me | —H | 6-Cl | 3-Cl | (E)—CH=CH— | 2-tolyl— |
| 1.1323 | —Me | —Me | —H | 6-Cl | 3-Cl | (E)—CH=CH— | 3-tolyl— |
| 1.1324 | —Me | —Me | —H | 6-Cl | 3-Cl | (E)—CH=CH— | 2-methyl-4-pyridyl— |
| 1.1325 | —Me | —Me | —H | 6-Cl | 3-Cl | (E)—CH=CH— | 2-trifluoromethyl-4-pyridyl— |
| 1.1326 | —Me | —Me | —H | 6-Cl | 3-Cl | (E)—CH=CH— | 2-amino-4-pyridyl— |
| 1.1327 | —Me | —Me | —H | 6-Cl | 3-Cl | (E)—CH=CH— | 2-fluoro-4-pyridyl— |
| 1.1328 | —Me | —Me | —H | 6-Cl | 3-Cl | (E)—CH=CH— | 4-pyridyl— |
| 1.1329 | —Me | —Me | —H | 6-Cl | 3-Cl | (E)—CH=CH— | 4-(methylamino)-phenyl— |
| 1.1330 | —Me | —Me | —H | 6-Cl | 3-Cl | (E)—CH=CH— | 4-amino-phenyl— |
| 1.1331 | —Me | —Me | —H | 6-Cl | 3-Cl | (E)—CH=CH— | 4-(dimethylamino)-phenyl— |
| 1.1332 | —Me | —Me | —H | 6-Cl | 3-Cl | (E)—CH=CH— | 3-methyl-4-amino-phenyl— |
| 1.1333 | —Me | —Me | —H | 6-Cl | 3-Cl | (E)—CH=CH— | thiophen-3-yl— |
| 1.1334 | —Me | —Me | —H | 6-Cl | 3-Cl | (E)—CH=CH— | 1-methyl-pyrazol-4-yl— |
| 1.1335 | —Me | —Me | —H | 6-Cl | 3-Cl | (E)—CH=CH— | 2-methyl-triazol-4-yl— |
| 1.1336 | —Me | —Me | —H | 6-Cl | 3-Cl | (E)—CH=CH— | 5-methyl-1,3,4-oxadiazol-2-yl— |
| 1.1337 | —Me | —Me | —H | 6-Cl | 3-Cl | (E)—CH=CH— | 5-methyl-3-pyridyl— |
| 1.1338 | —Me | —Me | —H | 6-Cl | 3-Cl | (E)—CH=CH— | 5-methyl-2-pyridyl— |
| 1.1339 | —Me | —Me | —H | 6-Cl | 3-Cl | (E)—CH=CH— | 6-methyl-2-pyridyl— |
| 1.1340 | —Me | —Me | —H | 6-Cl | 3-Cl | (E)—CH=CH— | 3-methyl-2-pyridyl— |
| 1.1341 | —Me | —Me | —H | 6-Cl | 3-Cl | (E)—CH=CH— | 6-chloro-3-pyridyl— |
| 1.1342 | —Me | —Me | —H | 6-Cl | 3-Cl | (E)—CH=CH— | 3-trifluoromethyl-3-pyridyl— |
| 1.1343 | —Me | —Me | —H | 6-Cl | 3-Cl | (E)—CH=CH— | 3,5-difluoro-phenyl— |
| 1.1344 | —Me | —Me | —H | 6-Cl | 3-Cl | (E)—CH=CH— | 4-methyl-2-pyridyl— |
| 1.1345 | —Me | —Me | —H | 6-Cl | 3-Cl | (E)—CH=CH— | 2-acetamidothiazol-5-yl— |
| 1.1346 | —Me | —Me | —(C=O)ⁱPr | 6-F | 3-Cl | (E)—CH=CH— | 4-chloro-phenyl— |
| 1.1347 | —Me | —Me | —(C=O)ⁱPr | 6-F | 3-Cl | (E)—CH=CH— | 4-trifluoromethyl-phenyl— |

TABLE 1-continued

Herbicidal compounds of the present invention. The numbering system used to describe the positions of X and Y is shown for the purposes of clarity only.

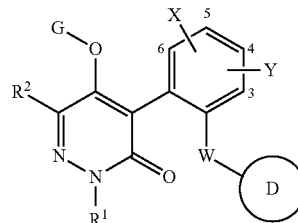

(I)

| Cmpd. No. | R¹ | R² | G | X | Y | W | D |
|---|---|---|---|---|---|---|---|
| 1.1348 | —Me | —Me | —(C=O)$^i$Pr | 6-F | 3-Cl | (E)—CH=CH— | 4-cyano-phenyl— |
| 1.1349 | —Me | —Me | —(C=O)$^i$Pr | 6-F | 3-Cl | (E)—CH=CH— | 4-chloro-3-pyridyl— |
| 1.1350 | —Me | —Me | —(C=O)$^i$Pr | 6-F | 3-Cl | (E)—CH=CH— | 2-chlorothiazol-5-yl— |
| 1.1351 | —Me | —Me | —(C=O)$^i$Pr | 6-F | 3-Cl | (E)—CH=CH— | 4-trifluoromethyl-3-pyridyl— |
| 1.1352 | —Me | —Me | —(C=O)$^i$Pr | 6-F | 3-Cl | (E)—CH=CH— | 4-fluoro-phenyl— |
| 1.1353 | —Me | —Me | —(C=O)$^i$Pr | 6-F | 3-Cl | (E)—CH=CH— | 3-pyridyl— |
| 1.1354 | —Me | —Me | —(C=O)$^i$Pr | 6-F | 3-Cl | (E)—CH=CH— | 3,4-difluoro-phenyl— |
| 1.1355 | —Me | —Me | —(C=O)$^i$Pr | 6-F | 3-Cl | (E)—CH=CH— | 2-trifluoromethyl-phenyl— |
| 1.1356 | —Me | —Me | —(C=O)$^i$Pr | 6-F | 3-Cl | (E)—CH=CH— | 4-tolyl— |
| 1.1357 | —Me | —Me | —(C=O)$^i$Pr | 6-F | 3-Cl | (E)—CH=CH— | 4-(trifluoromethoxy)-phenyl— |
| 1.1358 | —Me | —Me | —(C=O)$^i$Pr | 6-F | 3-Cl | (E)—CH=CH— | 2-chloro-3-pyridyl— |
| 1.1359 | —Me | —Me | —(C=O)$^i$Pr | 6-F | 3-Cl | (E)—CH=CH— | 2-chloro-4-pyridyl— |
| 1.1360 | —Me | —Me | —(C=O)$^i$Pr | 6-F | 3-Cl | (E)—CH=CH— | 3-chloro-4-fluoro-phenyl— |
| 1.1361 | —Me | —Me | —(C=O)$^i$Pr | 6-F | 3-Cl | (E)—CH=CH— | 3-chloro-4-pyridyl— |
| 1.1362 | —Me | —Me | —(C=O)$^i$Pr | 6-F | 3-Cl | (E)—CH=CH— | 4-hydroxy-phenyl— |
| 1.1363 | —Me | —Me | —(C=O)$^i$Pr | 6-F | 3-Cl | (E)—CH=CH— | 4-cyclopropyl-phenyl— |
| 1.1364 | —Me | —Me | —(C=O)$^i$Pr | 6-F | 3-Cl | (E)—CH=CH— | 1-methyl-3-(trifluoromethyl)pyrazol-4-yl— |
| 1.1365 | —Me | —Me | —(C=O)$^i$Pr | 6-F | 3-Cl | (E)—CH=CH— | thiazol-2-yl— |
| 1.1366 | —Me | —Me | —(C=O)$^i$Pr | 6-F | 3-Cl | (E)—CH=CH— | pyrimidin-5-yl— |
| 1.1367 | —Me | —Me | —(C=O)$^i$Pr | 6-F | 3-Cl | (E)—CH=CH— | 4-(tert-butoxy)-phenyl— |
| 1.1368 | —Me | —Me | —(C=O)$^i$Pr | 6-F | 3-Cl | (E)—CH=CH— | thiazol-5-yl— |
| 1.1369 | —Me | —Me | —(C=O)$^i$Pr | 6-F | 3-Cl | (E)—CH=CH— | 2-cyano-phenyl— |
| 1.1370 | —Me | —Me | —(C=O)$^i$Pr | 6-F | 3-Cl | (E)—CH=CH— | 3-cyano-phenyl— |
| 1.1371 | —Me | —Me | —(C=O)$^i$Pr | 6-F | 3-Cl | (E)—CH=CH— | 3-trifluoromethyl-phenyl— |
| 1.1372 | —Me | —Me | —(C=O)$^i$Pr | 6-F | 3-Cl | (E)—CH=CH— | 2-tolyl— |
| 1.1373 | —Me | —Me | —(C=O)$^i$Pr | 6-F | 3-Cl | (E)—CH=CH— | 3-tolyl— |
| 1.1374 | —Me | —Me | —(C=O)$^i$Pr | 6-F | 3-Cl | (E)—CH=CH— | 2-methyl-4-pyridyl— |
| 1.1375 | —Me | —Me | —(C=O)$^i$Pr | 6-F | 3-Cl | (E)—CH=CH— | 2-trifluoromethyl-4-pyridyl— |
| 1.1376 | —Me | —Me | —(C=O)$^i$Pr | 6-F | 3-Cl | (E)—CH=CH— | 2-amino-4-pyridyl— |
| 1.1377 | —Me | —Me | —(C=O)$^i$Pr | 6-F | 3-Cl | (E)—CH=CH— | 2-fluoro-4-pyridyl— |
| 1.1378 | —Me | —Me | —(C=O)$^i$Pr | 6-F | 3-Cl | (E)—CH=CH— | 4-pyridyl— |
| 1.1379 | —Me | —Me | —(C=O)$^i$Pr | 6-F | 3-Cl | (E)—CH=CH— | 4-(methylamino)-phenyl— |
| 1.1380 | —Me | —Me | —(C=O)$^i$Pr | 6-F | 3-Cl | (E)—CH=CH— | 4-amino-phenyl— |
| 1.1381 | —Me | —Me | —(C=O)$^i$Pr | 6-F | 3-Cl | (E)—CH=CH— | 4-(dimethylamino)-phenyl— |
| 1.1382 | —Me | —Me | —(C=O)$^i$Pr | 6-F | 3-Cl | (E)—CH=CH— | 3-methyl-4-amino-phenyl— |
| 1.1383 | —Me | —Me | —(C=O)$^i$Pr | 6-F | 3-Cl | (E)—CH=CH— | thiophen-3-yl— |
| 1.1384 | —Me | —Me | —(C=O)$^i$Pr | 6-F | 3-Cl | (E)—CH=CH— | 1-methyl-pyrazol-4-yl— |
| 1.1385 | —Me | —Me | —(C=O)$^i$Pr | 6-F | 3-Cl | (E)—CH=CH— | 2-methyl-triazol-4-yl— |
| 1.1386 | —Me | —Me | —(C=O)$^i$Pr | 6-F | 3-Cl | (E)—CH=CH— | 5-methyl-1,3,4-oxadiazol-2-yl— |
| 1.1387 | —Me | —Me | —(C=O)$^i$Pr | 6-F | 3-Cl | (E)—CH=CH— | 5-methyl-3-pyridyl— |
| 1.1388 | —Me | —Me | —(C=O)$^i$Pr | 6-F | 3-Cl | (E)—CH=CH— | 5-methyl-2-pyridyl— |
| 1.1389 | —Me | —Me | —(C=O)$^i$Pr | 6-F | 3-Cl | (E)—CH=CH— | 6-methyl-2-pyridyl— |
| 1.1390 | —Me | —Me | —(C=O)$^i$Pr | 6-F | 3-Cl | (E)—CH=CH— | 3-methyl-2-pyridyl— |
| 1.1391 | —Me | —Me | —(C=O)$^i$Pr | 6-F | 3-Cl | (E)—CH=CH— | 6-chloro-3-pyridyl— |
| 1.1392 | —Me | —Me | —(C=O)$^i$Pr | 6-F | 3-Cl | (E)—CH=CH— | 3-trifluoromethyl-3-pyridyl— |
| 1.1393 | —Me | —Me | —(C=O)$^i$Pr | 6-F | 3-Cl | (E)—CH=CH— | 3,5-difluoro-phenyl— |
| 1.1394 | —Me | —Me | —(C=O)$^i$Pr | 6-F | 3-Cl | (E)—CH=CH— | 4-methyl-2-pyridyl— |
| 1.1395 | —Me | —Me | —(C=O)$^i$Pr | 6-F | 3-Cl | (E)—CH=CH— | 2-acetamidothiazol-5-yl— |
| 1.1396 | —Me | —Me | —(C=O)$^i$Pr | 6-Cl | 3-Cl | (E)—CH=CH— | —Ph |
| 1.1397 | —Me | —Me | —(C=O)$^i$Pr | 6-Cl | 3-Cl | (E)—CH=CH— | 4-chloro-phenyl— |
| 1.1398 | —Me | —Me | —(C=O)$^i$Pr | 6-Cl | 3-Cl | (E)—CH=CH— | 4-trifluoromethyl-phenyl— |
| 1.1399 | —Me | —Me | —(C=O)$^i$Pr | 6-Cl | 3-Cl | (E)—CH=CH— | 4-cyano-phenyl— |
| 1.1400 | —Me | —Me | —(C=O)$^i$Pr | 6-Cl | 3-Cl | (E)—CH=CH— | 4-chloro-3-pyridyl— |
| 1.1401 | —Me | —Me | —(C=O)$^i$Pr | 6-Cl | 3-Cl | (E)—CH=CH— | 2-chlorothiazol-5-yl— |
| 1.1402 | —Me | —Me | —(C=O)$^i$Pr | 6-Cl | 3-Cl | (E)—CH=CH— | 4-trifluoromethyl-3-pyridyl— |
| 1.1403 | —Me | —Me | —(C=O)$^i$Pr | 6-Cl | 3-Cl | (E)—CH=CH— | 4-fluoro-phenyl— |
| 1.1404 | —Me | —Me | —(C=O)$^i$Pr | 6-Cl | 3-Cl | (E)—CH=CH— | 3-pyridyl— |
| 1.1405 | —Me | —Me | —(C=O)$^i$Pr | 6-Cl | 3-Cl | (E)—CH=CH— | 3,4-difluoro-phenyl— |
| 1.1406 | —Me | —Me | —(C=O)$^i$Pr | 6-Cl | 3-Cl | (E)—CH=CH— | 2-trifluoromethyl-phenyl— |
| 1.1407 | —Me | —Me | —(C=O)$^i$Pr | 6-Cl | 3-Cl | (E)—CH=CH— | 4-tolyl— |
| 1.1408 | —Me | —Me | —(C=O)$^i$Pr | 6-Cl | 3-Cl | (E)—CH=CH— | 4-(trifluoromethoxy)-phenyl— |

TABLE 1-continued

Herbicidal compounds of the present invention. The numbering system used to describe the positions of X and Y is shown for the purposes of clarity only.

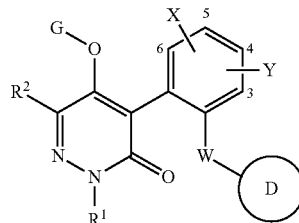

(I)

| Cmpd. No. | R¹ | R² | G | X | Y | W | D |
|---|---|---|---|---|---|---|---|
| 1.1409 | —Me | —Me | —(C=O)ⁱPr | 6-Cl | 3-Cl | (E)—CH=CH— | 2-chloro-3-pyridyl— |
| 1.1410 | —Me | —Me | —(C=O)ⁱPr | 6-Cl | 3-Cl | (E)—CH=CH— | 2-chloro-4-pyridyl— |
| 1.1411 | —Me | —Me | —(C=O)ⁱPr | 6-Cl | 3-Cl | (E)—CH=CH— | 3-chloro-4-fluoro-phenyl— |
| 1.1412 | —Me | —Me | —(C=O)ⁱPr | 6-Cl | 3-Cl | (E)—CH=CH— | 3-chloro-4-pyridyl— |
| 1.1413 | —Me | —Me | —(C=O)ⁱPr | 6-Cl | 3-Cl | (E)—CH=CH— | 4-hydroxy-phenyl— |
| 1.1414 | —Me | —Me | —(C=O)ⁱPr | 6-Cl | 3-Cl | (E)—CH=CH— | 4-cyclopropyl-phenyl— |
| 1.1415 | —Me | —Me | —(C=O)ⁱPr | 6-Cl | 3-Cl | (E)—CH=CH— | 1-methyl-3-(trifluoromethyl)pyrazol-4-yl— |
| 1.1416 | —Me | —Me | —(C=O)ⁱPr | 6-Cl | 3-Cl | (E)—CH=CH— | thiazol-2-yl— |
| 1.1417 | —Me | —Me | —(C=O)ⁱPr | 6-Cl | 3-Cl | (E)—CH=CH— | pyrimidin-5-yl— |
| 1.1418 | —Me | —Me | —(C=O)ⁱPr | 6-Cl | 3-Cl | (E)—CH=CH— | 4-(tert-butoxy)-phenyl— |
| 1.1419 | —Me | —Me | —(C=O)ⁱPr | 6-Cl | 3-Cl | (E)—CH=CH— | thiazol-5-yl— |
| 1.1420 | —Me | —Me | —(C=O)ⁱPr | 6-Cl | 3-Cl | (E)—CH=CH— | 2-cyano-phenyl— |
| 1.1421 | —Me | —Me | —(C=O)ⁱPr | 6-Cl | 3-Cl | (E)—CH=CH— | 3-cyano-phenyl— |
| 1.1422 | —Me | —Me | —(C=O)ⁱPr | 6-Cl | 3-Cl | (E)—CH=CH— | 3-trifluoromethyl-phenyl— |
| 1.1423 | —Me | —Me | —(C=O)ⁱPr | 6-Cl | 3-Cl | (E)—CH=CH— | 2-tolyl— |
| 1.1424 | —Me | —Me | —(C=O)ⁱPr | 6-Cl | 3-Cl | (E)—CH=CH— | 3-tolyl— |
| 1.1425 | —Me | —Me | —(C=O)ⁱPr | 6-Cl | 3-Cl | (E)—CH=CH— | 2-methyl-4-pyridyl— |
| 1.1426 | —Me | —Me | —(C=O)ⁱPr | 6-Cl | 3-Cl | (E)—CH=CH— | 2-trifluoromethyl-4-pyridyl— |
| 1.1427 | —Me | —Me | —(C=O)ⁱPr | 6-Cl | 3-Cl | (E)—CH=CH— | 2-amino-4-pyridyl— |
| 1.1428 | —Me | —Me | —(C=O)ⁱPr | 6-Cl | 3-Cl | (E)—CH=CH— | 2-fluoro-4-pyridyl— |
| 1.1429 | —Me | —Me | —(C=O)ⁱPr | 6-Cl | 3-Cl | (E)—CH=CH— | 4-pyridyl— |
| 1.1430 | —Me | —Me | —(C=O)ⁱPr | 6-Cl | 3-Cl | (E)—CH=CH— | 4-(methylamino)-phenyl— |
| 1.1431 | —Me | —Me | —(C=O)ⁱPr | 6-Cl | 3-Cl | (E)—CH=CH— | 4-amino-phenyl— |
| 1.1432 | —Me | —Me | —(C=O)ⁱPr | 6-Cl | 3-Cl | (E)—CH=CH— | 4-(dimethylamino)-phenyl— |
| 1.1433 | —Me | —Me | —(C=O)ⁱPr | 6-Cl | 3-Cl | (E)—CH=CH— | 3-methyl-4-amino-phenyl— |
| 1.1434 | —Me | —Me | —(C=O)ⁱPr | 6-Cl | 3-Cl | (E)—CH=CH— | thiophen-3-yl— |
| 1.1435 | —Me | —Me | —(C=O)ⁱPr | 6-Cl | 3-Cl | (E)—CH=CH— | 1-methyl-pyrazol-4-yl— |
| 1.1436 | —Me | —Me | —(C=O)ⁱPr | 6-Cl | 3-Cl | (E)—CH=CH— | 2-methyl-triazol-4-yl— |
| 1.1437 | —Me | —Me | —(C=O)ⁱPr | 6-Cl | 3-Cl | (E)—CH=CH— | 5-methyl-1,3,4-oxadiazol-2-yl— |
| 1.1438 | —Me | —Me | —(C=O)ⁱPr | 6-Cl | 3-Cl | (E)—CH=CH— | 5-methyl-3-pyridyl— |
| 1.1439 | —Me | —Me | —(C=O)ⁱPr | 6-Cl | 3-Cl | (E)—CH=CH— | 5-methyl-2-pyridyl— |
| 1.1440 | —Me | —Me | —(C=O)ⁱPr | 6-Cl | 3-Cl | (E)—CH=CH— | 6-methyl-2-pyridyl— |
| 1.1441 | —Me | —Me | —(C=O)ⁱPr | 6-Cl | 3-Cl | (E)—CH=CH— | 3-methyl-2-pyridyl— |
| 1.1442 | —Me | —Me | —(C=O)ⁱPr | 6-Cl | 3-Cl | (E)—CH=CH— | 6-chloro-3-pyridyl— |
| 1.1443 | —Me | —Me | —(C=O)ⁱPr | 6-Cl | 3-Cl | (E)—CH=CH— | 3-trifluoromethyl-3-pyridyl— |
| 1.1444 | —Me | —Me | —(C=O)ⁱPr | 6-Cl | 3-Cl | (E)—CH=CH— | 3,5-difluoro-phenyl— |
| 1.1445 | —Me | —Me | —(C=O)ⁱPr | 6-Cl | 3-Cl | (E)—CH=CH— | 4-methyl-2-pyridyl— |
| 1.1446 | —Me | —Me | —(C=O)ⁱPr | 6-Cl | 3-Cl | (E)—CH=CH— | 2-acetamidothiazol-5-yl— |
| 1.1447 | —Me | —Me | —H | 6-F | 3-Cl | —C≡C— | —Ph |
| 1.1448 | —Me | —Me | —H | 6-F | 3-Cl | —C≡C— | 4-chloro-phenyl— |
| 1.1449 | —Me | —Me | —H | 6-F | 3-Cl | —C≡C— | 4-trifluoromethyl-phenyl— |
| 1.1450 | —Me | —Me | —H | 6-F | 3-Cl | —C≡C— | 4-cyano-phenyl— |
| 1.1451 | —Me | —Me | —H | 6-F | 3-Cl | —C≡C— | 4-chloro-3-pyridyl— |
| 1.1452 | —Me | —Me | —H | 6-F | 3-Cl | —C≡C— | 2-chlorothiazol-5-yl— |
| 1.1453 | —Me | —Me | —H | 6-F | 3-Cl | —C≡C— | 4-trifluoromethyl-3-pyridyl— |
| 1.1454 | —Me | —Me | —H | 6-F | 3-Cl | —C≡C— | 4-fluoro-phenyl— |
| 1.1455 | —Me | —Me | —H | 6-F | 3-Cl | —C≡C— | 3-pyridyl— |
| 1.1456 | —Me | —Me | —H | 6-F | 3-Cl | —C≡C— | 3,4-difluoro-phenyl— |
| 1.1457 | —Me | —Me | —H | 6-F | 3-Cl | —C≡C— | 2-trifluoromethyl-phenyl— |
| 1.1458 | —Me | —Me | —H | 6-F | 3-Cl | —C≡C— | 4-tolyl— |
| 1.1459 | —Me | —Me | —H | 6-F | 3-Cl | —C≡C— | 4-(trifluoromethoxy)-phenyl— |
| 1.1460 | —Me | —Me | —H | 6-F | 3-Cl | —C≡C— | 2-chloro-3-pyridyl— |
| 1.1461 | —Me | —Me | —H | 6-F | 3-Cl | —C≡C— | 2-chloro-4-pyridyl— |
| 1.1462 | —Me | —Me | —H | 6-F | 3-Cl | —C≡C— | 3-chloro-4-fluoro-phenyl— |
| 1.1463 | —Me | —Me | —H | 6-F | 3-Cl | —C≡C— | 3-chloro-4-pyridyl— |
| 1.1464 | —Me | —Me | —H | 6-F | 3-Cl | —C≡C— | 4-hydroxy-phenyl— |
| 1.1465 | —Me | —Me | —H | 6-F | 3-Cl | —C≡C— | 4-cyclopropyl-phenyl— |
| 1.1466 | —Me | —Me | —H | 6-F | 3-Cl | —C≡C— | 1-methyl-3-(trifluoromethyl)pyrazol-4-yl— |
| 1.1467 | —Me | —Me | —H | 6-F | 3-Cl | —C≡C— | thiazol-2-yl— |
| 1.1468 | —Me | —Me | —H | 6-F | 3-Cl | —C≡C— | pyrimidin-5-yl— |

TABLE 1-continued

Herbicidal compounds of the present invention. The numbering system used to describe the positions of X and Y is shown for the purposes of clarity only.

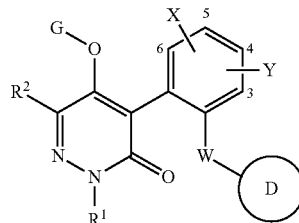

(I)

| Cmpd. No. | R¹ | R² | G | X | Y | W | D |
|---|---|---|---|---|---|---|---|
| 1.1469 | —Me | —Me | —H | 6-F | 3-Cl | —C≡C— | 4-(tert-butoxy)-phenyl— |
| 1.1470 | —Me | —Me | —H | 6-F | 3-Cl | —C≡C— | thiazol-5-yl— |
| 1.1471 | —Me | —Me | —H | 6-F | 3-Cl | —C≡C— | 2-cyano-phenyl— |
| 1.1472 | —Me | —Me | —H | 6-F | 3-Cl | —C≡C— | 3-cyano-phenyl— |
| 1.1473 | —Me | —Me | —H | 6-F | 3-Cl | —C≡C— | 3-trifluoromethyl-phenyl— |
| 1.1474 | —Me | —Me | —H | 6-F | 3-Cl | —C≡C— | 2-tolyl— |
| 1.1475 | —Me | —Me | —H | 6-F | 3-Cl | —C≡C— | 3-tolyl— |
| 1.1476 | —Me | —Me | —H | 6-F | 3-Cl | —C≡C— | 2-methyl-4-pyridyl— |
| 1.1477 | —Me | —Me | —H | 6-F | 3-Cl | —C≡C— | 2-trifluoromethyl-4-pyridyl— |
| 1.1478 | —Me | —Me | —H | 6-F | 3-Cl | —C≡C— | 2-amino-4-pyridyl— |
| 1.1479 | —Me | —Me | —H | 6-F | 3-Cl | —C≡C— | 2-fluoro-4-pyridyl— |
| 1.1480 | —Me | —Me | —H | 6-F | 3-Cl | —C≡C— | 4-pyridyl— |
| 1.1481 | —Me | —Me | —H | 6-F | 3-Cl | —C≡C— | 4-(methylamino)-phenyl— |
| 1.1482 | —Me | —Me | —H | 6-F | 3-Cl | —C≡C— | 4-amino-phenyl— |
| 1.1483 | —Me | —Me | —H | 6-F | 3-Cl | —C≡C— | 4-(dimethylamino)-phenyl— |
| 1.1484 | —Me | —Me | —H | 6-F | 3-Cl | —C≡C— | 3-methyl-4-amino-phenyl— |
| 1.1485 | —Me | —Me | —H | 6-F | 3-Cl | —C≡C— | thiophen-3-yl— |
| 1.1486 | —Me | —Me | —H | 6-F | 3-Cl | —C≡C— | 1-methyl-pyrazol-4-yl— |
| 1.1487 | —Me | —Me | —H | 6-F | 3-Cl | —C≡C— | 2-methyl-triazol-4-yl— |
| 1.1488 | —Me | —Me | —H | 6-F | 3-Cl | —C≡C— | 5-methyl-1,3,4-oxadiazol-2-yl— |
| 1.1489 | —Me | —Me | —H | 6-F | 3-Cl | —C≡C— | 5-methyl-3-pyridyl— |
| 1.1490 | —Me | —Me | —H | 6-F | 3-Cl | —C≡C— | 5-methyl-2-pyridyl— |
| 1.1491 | —Me | —Me | —H | 6-F | 3-Cl | —C≡C— | 6-methyl-2-pyridyl— |
| 1.1492 | —Me | —Me | —H | 6-F | 3-Cl | —C≡C— | 3-methyl-2-pyridyl— |
| 1.1493 | —Me | —Me | —H | 6-F | 3-Cl | —C≡C— | 6-chloro-3-pyridyl— |
| 1.1494 | —Me | —Me | —H | 6-F | 3-Cl | —C≡C— | 3-trifluoromethyl-3-pyridyl— |
| 1.1495 | —Me | —Me | —H | 6-F | 3-Cl | —C≡C— | 3,5-difluoro-phenyl— |
| 1.1496 | —Me | —Me | —H | 6-F | 3-Cl | —C≡C— | 4-methyl-2-pyridyl— |
| 1.1497 | —Me | —Me | —H | 6-F | 3-Cl | —C≡C— | 2-acetamidothiazol-5-yl— |
| 1.1498 | —Me | —Me | —H | 6-Cl | 3-Cl | —C≡C— | —Ph |
| 1.1499 | —Me | —Me | —H | 6-Cl | 3-Cl | —C≡C— | 4-chloro-phenyl— |
| 1.1500 | —Me | —Me | —H | 6-Cl | 3-Cl | —C≡C— | 4-trifluoromethyl-phenyl— |
| 1.1501 | —Me | —Me | —H | 6-Cl | 3-Cl | —C≡C— | 4-cyano-phenyl— |
| 1.1502 | —Me | —Me | —H | 6-Cl | 3-Cl | —C≡C— | 4-chloro-3-pyridyl— |
| 1.1503 | —Me | —Me | —H | 6-Cl | 3-Cl | —C≡C— | 2-chlorothiazol-5-yl— |
| 1.1504 | —Me | —Me | —H | 6-Cl | 3-Cl | —C≡C— | 4-trifluoromethyl-3-pyridyl— |
| 1.1505 | —Me | —Me | —H | 6-Cl | 3-Cl | —C≡C— | 4-fluoro-phenyl— |
| 1.1506 | —Me | —Me | —H | 6-Cl | 3-Cl | —C≡C— | 3-pyridyl— |
| 1.1507 | —Me | —Me | —H | 6-Cl | 3-Cl | —C≡C— | 3,4-difluoro-phenyl— |
| 1.1508 | —Me | —Me | —H | 6-Cl | 3-Cl | —C≡C— | 2-trifluoromethyl-phenyl— |
| 1.1509 | —Me | —Me | —H | 6-Cl | 3-Cl | —C≡C— | 4-tolyl— |
| 1.1510 | —Me | —Me | —H | 6-Cl | 3-Cl | —C≡C— | 4-(trifluoromethoxy)-phenyl— |
| 1.1511 | —Me | —Me | —H | 6-Cl | 3-Cl | —C≡C— | 2-chloro-3-pyridyl— |
| 1.1512 | —Me | —Me | —H | 6-Cl | 3-Cl | —C≡C— | 2-chloro-4-pyridyl— |
| 1.1513 | —Me | —Me | —H | 6-Cl | 3-Cl | —C≡C— | 3-chloro-4-fluoro-phenyl— |
| 1.1514 | —Me | —Me | —H | 6-Cl | 3-Cl | —C≡C— | 3-chloro-4-pyridyl— |
| 1.1515 | —Me | —Me | —H | 6-Cl | 3-Cl | —C≡C— | 4-hydroxy-phenyl— |
| 1.1516 | —Me | —Me | —H | 6-Cl | 3-Cl | —C≡C— | 4-cyclopropyl-phenyl— |
| 1.1517 | —Me | —Me | —H | 6-Cl | 3-Cl | —C≡C— | 1-methyl-3-(trifluoromethyl)pyrazol-4-yl— |
| 1.1518 | —Me | —Me | —H | 6-Cl | 3-Cl | —C≡C— | thiazol-2-yl— |
| 1.1519 | —Me | —Me | —H | 6-Cl | 3-Cl | —C≡C— | pyrimidin-5-yl— |
| 1.1520 | —Me | —Me | —H | 6-Cl | 3-Cl | —C≡C— | 4-(tert-butoxy)-phenyl— |
| 1.1521 | —Me | —Me | —H | 6-Cl | 3-Cl | —C≡C— | thiazol-5-yl— |
| 1.1522 | —Me | —Me | —H | 6-Cl | 3-Cl | —C≡C— | 2-cyano-phenyl— |
| 1.1523 | —Me | —Me | —H | 6-Cl | 3-Cl | —C≡C— | 3-cyano-phenyl— |
| 1.1524 | —Me | —Me | —H | 6-Cl | 3-Cl | —C≡C— | 3-trifluoromethyl-phenyl— |
| 1.1525 | —Me | —Me | —H | 6-Cl | 3-Cl | —C≡C— | 2-tolyl— |
| 1.1526 | —Me | —Me | —H | 6-Cl | 3-Cl | —C≡C— | 3-tolyl— |
| 1.1527 | —Me | —Me | —H | 6-Cl | 3-Cl | —C≡C— | 2-methyl-4-pyridyl— |
| 1.1528 | —Me | —Me | —H | 6-Cl | 3-Cl | —C≡C— | 2-trifluoromethyl-4-pyridyl— |
| 1.1529 | —Me | —Me | —H | 6-Cl | 3-Cl | —C≡C— | 2-amino-4-pyridyl— |

TABLE 1-continued

Herbicidal compounds of the present invention. The numbering system used to describe the
positions of X and Y is shown for the purposes of clarity only.

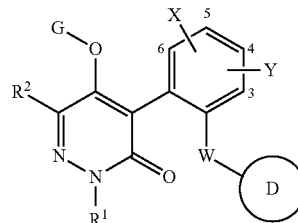

(I)

| Cmpd. No. | R¹ | R² | G | X | Y | W | D |
|---|---|---|---|---|---|---|---|
| 1.1530 | —Me | —Me | —H | 6-Cl | 3-Cl | —C≡C— | 2-fluoro-4-pyridyl— |
| 1.1531 | —Me | —Me | —H | 6-Cl | 3-Cl | —C≡C— | 4-pyridyl— |
| 1.1532 | —Me | —Me | —H | 6-Cl | 3-Cl | —C≡C— | 4-(methylamino)-phenyl— |
| 1.1533 | —Me | —Me | —H | 6-Cl | 3-Cl | —C≡C— | 4-amino-phenyl— |
| 1.1534 | —Me | —Me | —H | 6-Cl | 3-Cl | —C≡C— | 4-(dimethylamino)-phenyl— |
| 1.1535 | —Me | —Me | —H | 6-Cl | 3-Cl | —C≡C— | 3-methyl-4-amino-phenyl— |
| 1.1536 | —Me | —Me | —H | 6-Cl | 3-Cl | —C≡C— | thiophen-3-yl— |
| 1.1537 | —Me | —Me | —H | 6-Cl | 3-Cl | —C≡C— | 1-methyl-pyrazol-4-yl— |
| 1.1538 | —Me | —Me | —H | 6-Cl | 3-Cl | —C≡C— | 2-methyl-triazol-4-yl— |
| 1.1539 | —Me | —Me | —H | 6-Cl | 3-Cl | —C≡C— | 5-methyl-1,3,4-oxadiazol-2-yl— |
| 1.1540 | —Me | —Me | —H | 6-Cl | 3-Cl | —C≡C— | 5-methyl-3-pyridyl— |
| 1.1541 | —Me | —Me | —H | 6-Cl | 3-Cl | —C≡C— | 5-methyl-2-pyridyl— |
| 1.1542 | —Me | —Me | —H | 6-Cl | 3-Cl | —C≡C— | 6-methyl-2-pyridyl— |
| 1.1543 | —Me | —Me | —H | 6-Cl | 3-Cl | —C≡C— | 3-methyl-2-pyridyl— |
| 1.1544 | —Me | —Me | —H | 6-Cl | 3-Cl | —C≡C— | 6-chloro-3-pyridyl— |
| 1.1545 | —Me | —Me | —H | 6-Cl | 3-Cl | —C≡C— | 3-trifluoromethyl-3-pyridyl— |
| 1.1546 | —Me | —Me | —H | 6-Cl | 3-Cl | —C≡C— | 3,5-difluoro-phenyl— |
| 1.1547 | —Me | —Me | —H | 6-Cl | 3-Cl | —C≡C— | 4-methyl-2-pyridyl— |
| 1.1548 | —Me | —Me | —H | 6-Cl | 3-Cl | —C≡C— | 2-acetamidothiazol-5-yl— |
| 1.1549 | —Me | —Me | —(C═O)ⁱPr | 6-F | 3-Cl | —C≡C— | —Ph |
| 1.1550 | —Me | —Me | —(C═O)ⁱPr | 6-F | 3-Cl | —C≡C— | 4-chloro-phenyl— |
| 1.1551 | —Me | —Me | —(C═O)ⁱPr | 6-F | 3-Cl | —C≡C— | 4-trifluoromethyl-phenyl— |
| 1.1552 | —Me | —Me | —(C═O)ⁱPr | 6-F | 3-Cl | —C≡C— | 4-cyano-phenyl— |
| 1.1553 | —Me | —Me | —(C═O)ⁱPr | 6-F | 3-Cl | —C≡C— | 4-chloro-3-pyridyl— |
| 1.1554 | —Me | —Me | —(C═O)ⁱPr | 6-F | 3-Cl | —C≡C— | 2-chlorothiazol-5-yl— |
| 1.1555 | —Me | —Me | —(C═O)ⁱPr | 6-F | 3-Cl | —C≡C— | 4-trifluoromethyl-3-pyridyl— |
| 1.1556 | —Me | —Me | —(C═O)ⁱPr | 6-F | 3-Cl | —C≡C— | 4-fluoro-phenyl— |
| 1.1557 | —Me | —Me | —(C═O)ⁱPr | 6-F | 3-Cl | —C≡C— | 3-pyridyl— |
| 1.1558 | —Me | —Me | —(C═O)ⁱPr | 6-F | 3-Cl | —C≡C— | 3,4-difluoro-phenyl— |
| 1.1559 | —Me | —Me | —(C═O)ⁱPr | 6-F | 3-Cl | —C≡C— | 2-trifluoromethyl-phenyl— |
| 1.1560 | —Me | —Me | —(C═O)ⁱPr | 6-F | 3-Cl | —C≡C— | 4-tolyl— |
| 1.1561 | —Me | —Me | —(C═O)ⁱPr | 6-F | 3-Cl | —C≡C— | 4-(trifluoromethoxy)-phenyl— |
| 1.1562 | —Me | —Me | —(C═O)ⁱPr | 6-F | 3-Cl | —C≡C— | 2-chloro-3-pyridyl— |
| 1.1563 | —Me | —Me | —(C═O)ⁱPr | 6-F | 3-Cl | —C≡C— | 2-chloro-4-pyridyl— |
| 1.1564 | —Me | —Me | —(C═O)ⁱPr | 6-F | 3-Cl | —C≡C— | 3-chloro-4-fluoro-phenyl— |
| 1.1565 | —Me | —Me | —(C═O)ⁱPr | 6-F | 3-Cl | —C≡C— | 3-chloro-4-pyridyl— |
| 1.1566 | —Me | —Me | —(C═O)ⁱPr | 6-F | 3-Cl | —C≡C— | 4-hydroxy-phenyl— |
| 1.1567 | —Me | —Me | —(C═O)ⁱPr | 6-F | 3-Cl | —C≡C— | 4-cyclopropyl-phenyl— |
| 1.1568 | —Me | —Me | —(C═O)ⁱPr | 6-F | 3-Cl | —C≡C— | 1-methyl-3-(trifluoromethyl)pyrazol-4-yl— |
| 1.1569 | —Me | —Me | —(C═O)ⁱPr | 6-F | 3-Cl | —C≡C— | thiazol-2-yl— |
| 1.1570 | —Me | —Me | —(C═O)ⁱPr | 6-F | 3-Cl | —C≡C— | pyrimidin-5-yl— |
| 1.1571 | —Me | —Me | —(C═O)ⁱPr | 6-F | 3-Cl | —C≡C— | 4-(tert-butoxy)-phenyl— |
| 1.1572 | —Me | —Me | —(C═O)ⁱPr | 6-F | 3-Cl | —C≡C— | thiazol-5-yl— |
| 1.1573 | —Me | —Me | —(C═O)ⁱPr | 6-F | 3-Cl | —C≡C— | 2-cyano-phenyl— |
| 1.1574 | —Me | —Me | —(C═O)ⁱPr | 6-F | 3-Cl | —C≡C— | 3-cyano-phenyl— |
| 1.1575 | —Me | —Me | —(C═O)ⁱPr | 6-F | 3-Cl | —C≡C— | 3-trifluoromethyl-phenyl— |
| 1.1576 | —Me | —Me | —(C═O)ⁱPr | 6-F | 3-Cl | —C≡C— | 2-tolyl— |
| 1.1577 | —Me | —Me | —(C═O)ⁱPr | 6-F | 3-Cl | —C≡C— | 3-tolyl— |
| 1.1578 | —Me | —Me | —(C═O)ⁱPr | 6-F | 3-Cl | —C≡C— | 2-methyl-4-pyridyl— |
| 1.1579 | —Me | —Me | —(C═O)ⁱPr | 6-F | 3-Cl | —C≡C— | 2-trifluoromethyl-4-pyridyl— |
| 1.1580 | —Me | —Me | —(C═O)ⁱPr | 6-F | 3-Cl | —C≡C— | 2-amino-4-pyridyl— |
| 1.1581 | —Me | —Me | —(C═O)ⁱPr | 6-F | 3-Cl | —C≡C— | 2-fluoro-4-pyridyl— |
| 1.1582 | —Me | —Me | —(C═O)ⁱPr | 6-F | 3-Cl | —C≡C— | 4-pyridyl— |
| 1.1583 | —Me | —Me | —(C═O)ⁱPr | 6-F | 3-Cl | —C≡C— | 4-(methylamino)-phenyl— |
| 1.1584 | —Me | —Me | —(C═O)ⁱPr | 6-F | 3-Cl | —C≡C— | 4-amino-phenyl— |
| 1.1585 | —Me | —Me | —(C═O)ⁱPr | 6-F | 3-Cl | —C≡C— | 4-(dimethylamino)-phenyl— |
| 1.1586 | —Me | —Me | —(C═O)ⁱPr | 6-F | 3-Cl | —C≡C— | 3-methyl-4-amino-phenyl— |
| 1.1587 | —Me | —Me | —(C═O)ⁱPr | 6-F | 3-Cl | —C≡C— | thiophen-3-yl— |
| 1.1588 | —Me | —Me | —(C═O)ⁱPr | 6-F | 3-Cl | —C≡C— | 1-methyl-pyrazol-4-yl— |
| 1.1589 | —Me | —Me | —(C═O)ⁱPr | 6-F | 3-Cl | —C≡C— | 2-methyl-triazol-4-yl— |
| 1.1590 | —Me | —Me | —(C═O)ⁱPr | 6-F | 3-Cl | —C≡C— | 5-methyl-1,3,4-oxadiazol-2-yl— |

TABLE 1-continued

Herbicidal compounds of the present invention. The numbering system used to describe the positions of X and Y is shown for the purposes of clarity only.

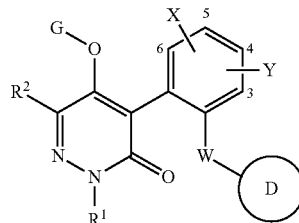

(I)

| Cmpd. No. | R¹ | R² | G | X | Y | W | D |
|---|---|---|---|---|---|---|---|
| 1.1591 | —Me | —Me | —(C=O)ⁱPr | 6-F | 3-Cl | —C≡C— | 5-methyl-3-pyridyl— |
| 1.1592 | —Me | —Me | —(C=O)ⁱPr | 6-F | 3-Cl | —C≡C— | 5-methyl-2-pyridyl— |
| 1.1593 | —Me | —Me | —(C=O)ⁱPr | 6-F | 3-Cl | —C≡C— | 6-methyl-2-pyridyl— |
| 1.1594 | —Me | —Me | —(C=O)ⁱPr | 6-F | 3-Cl | —C≡C— | 3-methyl-2-pyridyl— |
| 1.1595 | —Me | —Me | —(C=O)ⁱPr | 6-F | 3-Cl | —C≡C— | 6-chloro-3-pyridyl— |
| 1.1596 | —Me | —Me | —(C=O)ⁱPr | 6-F | 3-Cl | —C≡C— | 3-trifluoromethyl-3-pyridyl— |
| 1.1597 | —Me | —Me | —(C=O)ⁱPr | 6-F | 3-Cl | —C≡C— | 3,5-difluoro-phenyl— |
| 1.1598 | —Me | —Me | —(C=O)ⁱPr | 6-F | 3-Cl | —C≡C— | 4-methyl-2-pyridyl— |
| 1.1599 | —Me | —Me | —(C=O)ⁱPr | 6-F | 3-Cl | —C≡C— | 2-acetamidothiazol-5-yl— |
| 1.1600 | —Me | —Me | —(C=O)ⁱPr | 6-Cl | 3-Cl | —C≡C— | —Ph |
| 1.1601 | —Me | —Me | —(C=O)ⁱPr | 6-Cl | 3-Cl | —C≡C— | 4-chloro-phenyl— |
| 1.1602 | —Me | —Me | —(C=O)ⁱPr | 6-Cl | 3-Cl | —C≡C— | 4-trifluoromethyl-phenyl— |
| 1.1603 | —Me | —Me | —(C=O)ⁱPr | 6-Cl | 3-Cl | —C≡C— | 4-cyano-phenyl— |
| 1.1604 | —Me | —Me | —(C=O)ⁱPr | 6-Cl | 3-Cl | —C≡C— | 4-chloro-3-pyridyl— |
| 1.1605 | —Me | —Me | —(C=O)ⁱPr | 6-Cl | 3-Cl | —C≡C— | 2-chlorothiazol-5-yl— |
| 1.1606 | —Me | —Me | —(C=O)ⁱPr | 6-Cl | 3-Cl | —C≡C— | 4-trifluoromethyl-3-pyridyl— |
| 1.1607 | —Me | —Me | —(C=O)ⁱPr | 6-Cl | 3-Cl | —C≡C— | 4-fluoro-phenyl— |
| 1.1608 | —Me | —Me | —(C=O)ⁱPr | 6-Cl | 3-Cl | —C≡C— | 3-pyridyl— |
| 1.1609 | —Me | —Me | —(C=O)ⁱPr | 6-Cl | 3-Cl | —C≡C— | 3,4-difluoro-phenyl— |
| 1.1610 | —Me | —Me | —(C=O)ⁱPr | 6-Cl | 3-Cl | —C≡C— | 2-trifluoromethyl-phenyl— |
| 1.1611 | —Me | —Me | —(C=O)ⁱPr | 6-Cl | 3-Cl | —C≡C— | 4-tolyl— |
| 1.1612 | —Me | —Me | —(C=O)ⁱPr | 6-Cl | 3-Cl | —C≡C— | 4-(trifluoromethoxy)-phenyl— |
| 1.1613 | —Me | —Me | —(C=O)ⁱPr | 6-Cl | 3-Cl | —C≡C— | 2-chloro-3-pyridyl— |
| 1.1614 | —Me | —Me | —(C=O)ⁱPr | 6-Cl | 3-Cl | —C≡C— | 2-chloro-4-pyridyl— |
| 1.1615 | —Me | —Me | —(C=O)ⁱPr | 6-Cl | 3-Cl | —C≡C— | 3-chloro-4-fluoro-phenyl— |
| 1.1616 | —Me | —Me | —(C=O)ⁱPr | 6-Cl | 3-Cl | —C≡C— | 3-chloro-4-pyridyl— |
| 1.1617 | —Me | —Me | —(C=O)ⁱPr | 6-Cl | 3-Cl | —C≡C— | 4-hydroxy-phenyl— |
| 1.1618 | —Me | —Me | —(C=O)ⁱPr | 6-Cl | 3-Cl | —C≡C— | 4-cyclopropyl-phenyl— |
| 1.1619 | —Me | —Me | —(C=O)ⁱPr | 6-Cl | 3-Cl | —C≡C— | 1-methyl-3-(trifluoromethyl)pyrazol-4-yl— |
| 1.1620 | —Me | —Me | —(C=O)ⁱPr | 6-Cl | 3-Cl | —C≡C— | thiazol-2-yl— |
| 1.1621 | —Me | —Me | —(C=O)ⁱPr | 6-Cl | 3-Cl | —C≡C— | pyrimidin-5-yl— |
| 1.1622 | —Me | —Me | —(C=O)ⁱPr | 6-Cl | 3-Cl | —C≡C— | 4-(tert-butoxy)-phenyl— |
| 1.1623 | —Me | —Me | —(C=O)ⁱPr | 6-Cl | 3-Cl | —C≡C— | thiazol-5-yl— |
| 1.1624 | —Me | —Me | —(C=O)ⁱPr | 6-Cl | 3-Cl | —C≡C— | 2-cyano-phenyl— |
| 1.1625 | —Me | —Me | —(C=O)ⁱPr | 6-Cl | 3-Cl | —C≡C— | 3-cyano-phenyl— |
| 1.1626 | —Me | —Me | —(C=O)ⁱPr | 6-Cl | 3-Cl | —C≡C— | 3-trifluoromethyl-phenyl— |
| 1.1627 | —Me | —Me | —(C=O)ⁱPr | 6-Cl | 3-Cl | —C≡C— | 2-tolyl— |
| 1.1628 | —Me | —Me | —(C=O)ⁱPr | 6-Cl | 3-Cl | —C≡C— | 3-tolyl— |
| 1.1629 | —Me | —Me | —(C=O)ⁱPr | 6-Cl | 3-Cl | —C≡C— | 2-methyl-4-pyridyl— |
| 1.1630 | —Me | —Me | —(C=O)ⁱPr | 6-Cl | 3-Cl | —C≡C— | 2-trifluoromethyl-4-pyridyl— |
| 1.1631 | —Me | —Me | —(C=O)ⁱPr | 6-Cl | 3-Cl | —C≡C— | 2-amino-4-pyridyl— |
| 1.1632 | —Me | —Me | —(C=O)ⁱPr | 6-Cl | 3-Cl | —C≡C— | 2-fluoro-4-pyridyl— |
| 1.1633 | —Me | —Me | —(C=O)ⁱPr | 6-Cl | 3-Cl | —C≡C— | 4-pyridyl— |
| 1.1634 | —Me | —Me | —(C=O)ⁱPr | 6-Cl | 3-Cl | —C≡C— | 4-(methylamino)-phenyl— |
| 1.1635 | —Me | —Me | —(C=O)ⁱPr | 6-Cl | 3-Cl | —C≡C— | 4-amino-phenyl— |
| 1.1636 | —Me | —Me | —(C=O)ⁱPr | 6-Cl | 3-Cl | —C≡C— | 4-(dimethylamino)-phenyl— |
| 1.1637 | —Me | —Me | —(C=O)ⁱPr | 6-Cl | 3-Cl | —C≡C— | 3-methyl-4-amino-phenyl— |
| 1.1638 | —Me | —Me | —(C=O)ⁱPr | 6-Cl | 3-Cl | —C≡C— | thiophen-3-yl— |
| 1.1639 | —Me | —Me | —(C=O)ⁱPr | 6-Cl | 3-Cl | —C≡C— | 1-methyl-pyrazol-4-yl— |
| 1.1640 | —Me | —Me | —(C=O)ⁱPr | 6-Cl | 3-Cl | —C≡C— | 2-methyl-triazol-4-yl— |
| 1.1641 | —Me | —Me | —(C=O)ⁱPr | 6-Cl | 3-Cl | —C≡C— | 5-methyl-1,3,4-oxadiazol-2-yl— |
| 1.1642 | —Me | —Me | —(C=O)ⁱPr | 6-Cl | 3-Cl | —C≡C— | 5-methyl-3-pyridyl— |
| 1.1643 | —Me | —Me | —(C=O)ⁱPr | 6-Cl | 3-Cl | —C≡C— | 5-methyl-2-pyridyl— |
| 1.1644 | —Me | —Me | —(C=O)ⁱPr | 6-Cl | 3-Cl | —C≡C— | 6-methyl-2-pyridyl— |
| 1.1645 | —Me | —Me | —(C=O)ⁱPr | 6-Cl | 3-Cl | —C≡C— | 3-methyl-2-pyridyl— |
| 1.1646 | —Me | —Me | —(C=O)ⁱPr | 6-Cl | 3-Cl | —C≡C— | 6-chloro-3-pyridyl— |
| 1.1647 | —Me | —Me | —(C=O)ⁱPr | 6-Cl | 3-Cl | —C≡C— | 3-trifluoromethyl-3-pyridyl— |
| 1.1648 | —Me | —Me | —(C=O)ⁱPr | 6-Cl | 3-Cl | —C≡C— | 3,5-difluoro-phenyl— |
| 1.1649 | —Me | —Me | —(C=O)ⁱPr | 6-Cl | 3-Cl | —C≡C— | 4-methyl-2-pyridyl— |
| 1.1650 | —Me | —Me | —(C=O)ⁱPr | 6-Cl | 3-Cl | —C≡C— | 2-acetamidothiazol-5-yl— |
| 1.1651 | —Me | —Me | —(C=O)Me | 6-F | 3-Cl | —CH₂—CH₂— | p-tolyl |

TABLE 1-continued

Herbicidal compounds of the present invention. The numbering system used to describe the positions of X and Y is shown for the purposes of clarity only.

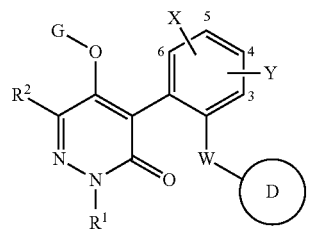

(I)

| Cmpd. No. | $R^1$ | $R^2$ | G | X | Y | W | D |
|---|---|---|---|---|---|---|---|
| 1.1652 | —Me | —Me | —(C=O)O$^t$Bu | 6-F | 3-Cl | —$CH_2$—$CH_2$— | p-tolyl |
| 1.1653 | —Me | —Me | —(C=O)OMe | 6-F | 3-Cl | —$CH_2$—$CH_2$— | p-tolyl |
| 1.1654 | —Me | —Me | —(C=O)tBu | 6-F | 3-Cl | —$CH_2$—$CH_2$— | p-tolyl |
| 1.1655 | —Me | —Me | —(C=O)Ph | 6-F | 3-Cl | —$CH_2$—$CH_2$— | p-tolyl |
| 1.1656 | —Me | —Me | —(C=O)4-morpholino | 6-F | 3-Cl | —$CH_2$—$CH_2$— | p-tolyl |

As stated hereinbefore, a compound of formula (I) according to the invention may comprise any combination of the values of $R^1$, $R^2$, $R^3$, $R^4$, $R^5$, $R^6$, $R^8$, $R^9$, $R^{10}$, $R^{11}$, $R^{12}$, $R^{13}$, $R^{14}$, $R^{15}$, W, D, Dp, G, X, Y, $Z^1$, $Z^2$, $Z^3$, $Z^4$, $Z^5$ and m as set out above. However, the following combinations constitute specific sets of embodiments contemplated within the invention.

One preferred combination of substituents provides a compound of formula (I) wherein: $R^1$ is methyl, —$CH_2$—C≡CH, or cyclopropyl; $R^2$ is methyl, G is H, —C(O)$C_1$-$C_4$alkyl, —C(O)O$C_1$-$C_4$alkyl, —C(O)-4-morpholino, or —C(O)-phenyl; X is hydrogen, halogen or $C_1$-haloalkyl; Y is hydrogen or halogen; W is —$CH_2$—$CH_2$—, (E) —CH=CH—, or —C≡C—; D is either DP, wherein $Z^1$, $Z^2$, $Z^3$, $Z^4$, and $Z^5$ are each independently selected from the group consisting of hydrogen, cyano, amino, di-$C_1$-$C_3$alkylamino, hydroxy, $C_1$-$C_3$ alkyl, $C_1$-$C_4$ alkoxy, $C_1$-$C_3$haloalkyl, $C_1$-$C_3$haloalkoxy, and halogen, or D is a substituted or unsubstituted pyridyl, pyrazolyl, thiazolyl, pyrimidinyl, thienyl, triazolyl or oxadiazolyl ring, which ring when substituted, is substituted by 1 or 2 $R^8$; and each $R^8$ is independently selected from the group consisting of halogen, amino, —NHC(O)$C_1$-$C_3$alkyl, $C_1$-$C_4$alkyl and $C_1$-$C_4$haloalkyl.

A further preferred combination of substituents provides a compound of formula (I) wherein: $R^1$ is methyl, —$CH_2$—C≡CH, or cyclopropyl; $R^2$ is methyl, G is H, —C(O)methyl, —C(O)iPr, —C(O)$^t$-Bu, —C(O)Omethyl, —C(O)O$^t$Bu, —C(O)-4-morpholino, or —C(O)-phenyl; X is hydrogen, halogen or $C_1$-haloalkyl; Y is hydrogen or halogen; W is —$CH_2$—$CH_2$—, (E) —CH=CH—, or —C≡C—; D is either DP, wherein $Z^1$, $Z^2$, $Z^3$, $Z^4$, and $Z^5$ are each independently selected from the group consisting of hydrogen, cyano, amino, di-methylamino, hydroxy, methyl, methoxy, halomethyl, $C_1$-$C_3$haloalkoxy, and halogen, or D is a substituted or unsubstituted pyridyl, pyrazolyl, thiazolyl, pyrimidinyl, or thienyl, ring, which ring when substituted, is substituted by 1 or 2 $R^8$; and each $R^8$ is independently selected from the group consisting of halogen, amino, —NHC(O)$C_1$-$C_3$alkyl, methyl and halomethyl.

Yet another preferred combination of substituents provides a compound of formula (I) wherein: $R^1$ is methyl, —$CH_2$—C≡CH, or cyclopropyl; $R^2$ is methyl, G is H or —C(O)$^i$Pr; X is hydrogen, halogen or C1-haloalkyl; Y is hydrogen or halogen; W is —$CH_2$—$CH_2$—, or (E) —CH=CH—; D is either DP, wherein $Z^1$, $Z^2$, $Z^3$, $Z^4$, and $Z^5$ are each independently selected from the group consisting of hydrogen, cyano, halogen, $C_1$-$C_3$alkyl or $C_1$-$C_3$haloalkyl, or D is a substituted or unsubstituted pyridyl or thiazolyl ring, which ring when substituted, is substituted by 1 or 2 $R^8$; and each $R^8$ is independently selected from the group consisting of halogen, $C_1$-$C_3$alkyl or $C_1$-$C_3$haloalkyl.

Yet another preferred combination of substituents provides a compound of formula (I) wherein: $R^1$ is methyl, —$CH_2$—C≡CH, or cyclopropyl; $R^2$ is methyl, G is H or —C(O)$^i$Pr; X is fluoro or chloro; Y is hydrogen or chloro; W is —$CH_2$—$CH_2$—, or (E) —CH=CH—; D is either DP, wherein $Z^1$, $Z^2$, $Z^3$, $Z^4$, and $Z^5$ are each independently selected from the group consisting of hydrogen, cyano, halogen, methyl, or halomethyl, or D is a substituted or unsubstituted pyridyl or thiazolyl ring, which ring when substituted, is substituted by 1 or 2 $R^8$; and each $R^8$ is independently selected from the group consisting of halogen, methyl, and halomethyl.

Typical abbreviations used herein include:
br=broadDba
$^t$Bu=tert-butyl
d=doublet
dba=dibenzylideneacetone
DCM=dichloromethane
DMSO=dimethylsulfoxide
DPPA=diphenylphosphoryl azide
$Et_2O$=diethyl ether
EtOAc=ethyl acetate
m=multiplet
Me=methyl
MeOH=methanol
Ph=phenyl
$^i$Pr=isopropyl
rt=room temperature
s=singlet
t=triplet
THF=tetrahydrofuran The compounds of the present invention may be prepared according to the following schemes, in which the substituents $R^1$, $R^2$, $R^3$, $R^4$, $R^5$, $R^6$, $R^8$, $R^9$, $R^{10}$, $R^{11}$, $R^{12}$, $R^{13}$, $R^{14}$, $R^{15}$, W, D, Dp, G, X, Y, $Z^1$, $Z^2$, $Z^3$, $Z^4$, $Z^5$ and m have (unless otherwise stated explicitly) the definitions described hereinbefore.

Certain compounds (I-ii) of the present invention may be prepared from compounds (2) as shown in Reaction scheme 1. Compounds (I-ii) are compounds of formula (I) in which W is —$CH_2$—$CH_2$—.

Reaction scheme 1

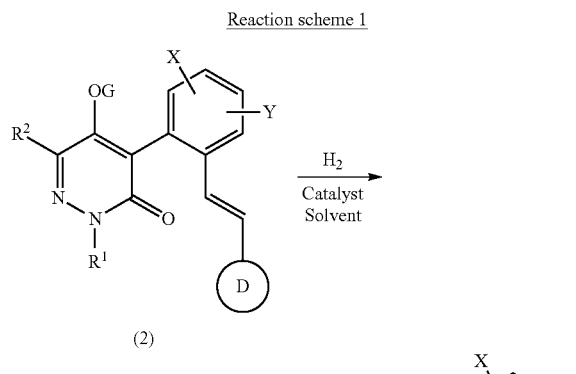

Compounds (I-ii) may be prepared by catalytic hydrogenation of compounds (2) with hydrogen gas in a suitable solvent [such as tetrahydrofuran, methanol, ethanol, acetic acid or ethyl acetate] in the presence of a suitable catalyst [such as Pd/C, Pd/$CaCO_3$, Rh/$Al_2O_3$ or sponge nickel] at a temperature between −10 and 100° C.

Compounds (2) may be prepared from compounds (3) and compounds (4) as shown in Reaction scheme 2, according to either the Suzuki Protocol or the Heck Protocol described. When employing the Suzuki Protocol, compounds (4) are organoboron compounds such as boronic acids, boronic esters or trifluoroborate potassium salts. When employing the Heck Protocol, compounds (4) are styrenes.

Reaction scheme 2

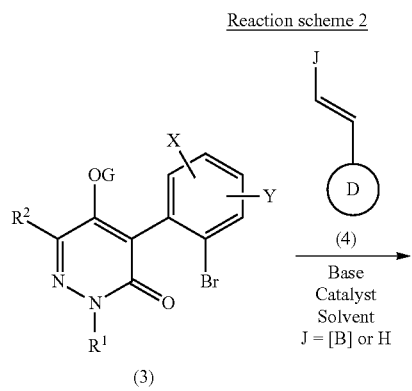

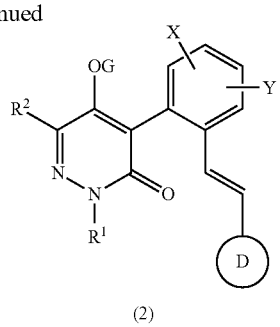

Suzuki Protocol

Compounds (2) may be prepared by treatment of compounds (3) with compounds (4) in the presence of a suitable base and a suitable catalyst in a suitable solvent at a temperature between 10 and 150° C. Examples of suitable bases include potassium carbonate, potassium phosphate, sodium carbonate, sodium bicarbonate and potassium fluoride. Examples of suitable catalysts include 1,1'-bis(diphenylphosphino)ferrocene]dichloropalladium(II) dichloromethane complex [$PdCl_2$(dppf).DCM], tetrakis (triphenylphosphine)palladium(0) [Pd($PPh_3$)$_4$], and a catalytic system formed in-situ from a mixture of palladium (II)acetate and triphenylphosphine. Examples of suitable solvents include 1,4-dioxane, tetrahydrofuran, acetonitrile and toluene. Many compounds (4) are commercially available [such as trans-2-phenylvinylboronic acid, trans-2-(4-trifluoromethyl-phenyl)vinylboronic acid and trans-2-(4-chlorophenyl)vinylboronic acid] or can be made by known methods. Examples of compounds (3) with particular utility in the Suzuki Protocol are isobutyryl esters (3-i) wherein G is isobutyryl.

The skilled man will appreciate that the conditions of the Suzuki Protocol are liable to cleave ester groups, so that Reaction scheme 2 may also describe a reaction wherein starting material (3) contains an ester moiety [such that G is an acyl group], but product (2) does not [such that G is hydrogen].

Heck Protocol

Compounds (2) may be prepared by treatment of compounds (3) with compounds (4) in the presence of a suitable base and a suitable catalyst at a temperature between 10 and 150° C. An additional solvent may optionally be included. Examples of suitable bases include triethylamine, morpholine, N-methylmorpholine, diisopropylethylamine and pyridine. Examples of suitable catalysts include tetrakis(triphenylphosphine)palladium(0) [Pd($PPh_3$)$_4$], a catalytic system formed in-situ from a mixture of palladium(II)acetate and triphenylphosphine, and a catalytic system formed in-situ from a mixture of tris(dibenzylideneacetone)dipalladium(0) and tri-tertbutylphosphonium tetrafluoroborate. Examples of the optional additional solvent include 1,4-dioxane, tetrahydrofuran, acetonitrile and toluene. Many compounds (4) are commercially available [such as 2-(trifluoromethyl)-5-vinyl-pyridine, 4-fluorostyrene, 4-cyanostyrene and 4-trifluoromethyl styrene] or can be made by known methods. Examples of compounds (3) with particular utility in the Heck Protocol are isobutyryl esters (3-i) wherein G is isobutyryl.

Compounds (3-i) may be prepared from compounds (5) as shown in Reaction scheme 3.

Reaction scheme 3

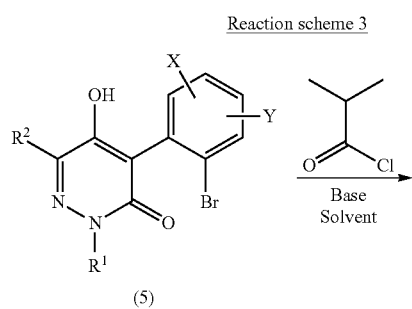

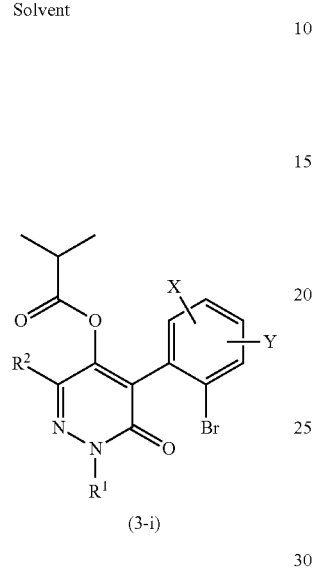

Compounds (3-i) may be prepared by treatment of compounds (5) with isobutyryl chloride in a suitable solvent [such as dichloromethane, acetonitrile or toluene] in the presence of a suitable base [such as triethylamine, diisopropylethylamine or pyridine] at a temperature between −10 and 60° C. A catalyst [such as 4-(dimethylamino)pyridine] may optionally be included.

Compounds (5) may be prepared from compounds (6) as shown in Reaction scheme 4, by heating compounds (6) with a base (such as 1,8-diazabicyclo[5.4.0]undec-7-ene, sodium hexamethyldisilazide or lithium hexamethyldisilazide) in a solvent [such as acetonitrile, N,N-dimethylformamide or toluene] at a temperature between 50 and 200° C. Conventional heating or microwave heating may be used.

Reaction scheme 4

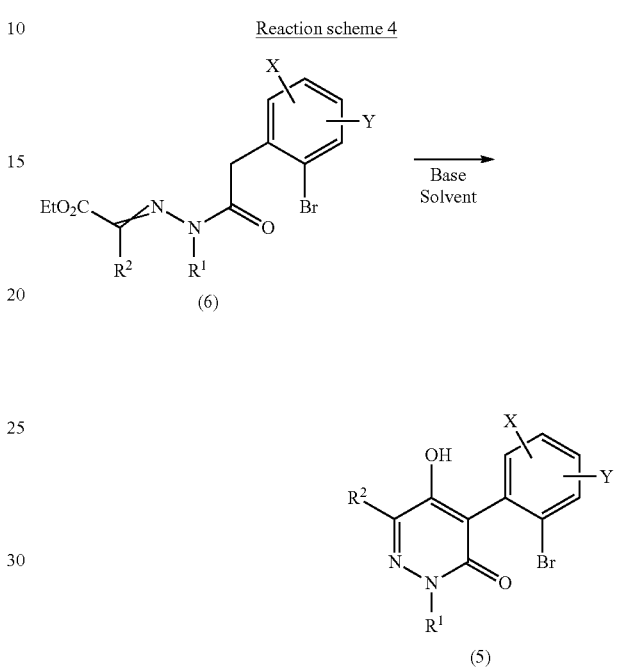

Compounds (6) may be prepared from phenylacetic acids (7) as shown in Reaction scheme 5.

Reaction scheme 5

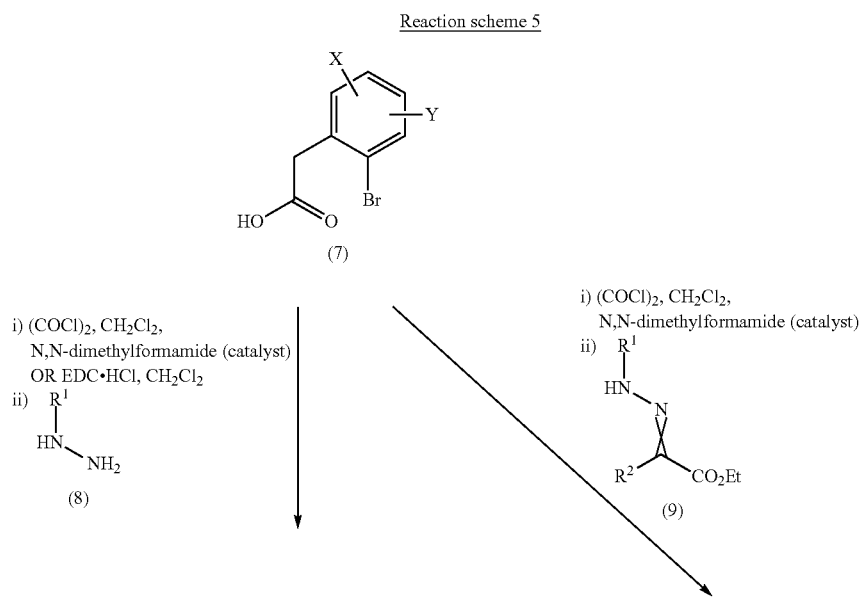

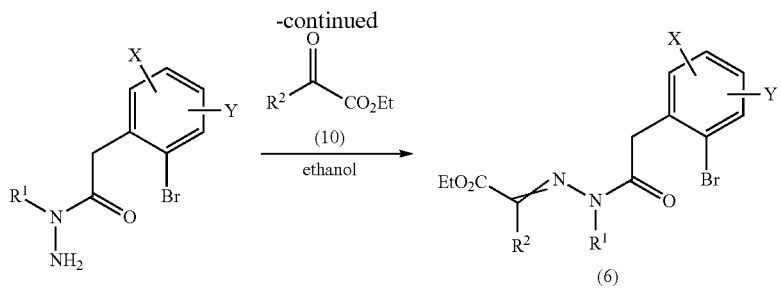

With respect to Reaction scheme 5, an example of a hydrazine (8) is methylhydrazine, and an example of a ketoester (10) is ethyl pyruvate. An example of a hydrazone (9) is ethyl(2E/Z)-2-(methylhydrazono)propanoate, prepared according to methods described in PCT patent publication No. WO2016/008816. An example of a phenylacetic acid (7) is (2-bromo-6-fluoro-phenyl)acetic acid, which may be synthesised according to Reaction scheme 10. A further example of a phenylacetic acid (7) is (2-bromo-3-chloro-6-fluoro-phenyl)acetic acid, which may be synthesised according to Reaction scheme 11.

Certain compounds (I-iii) of the present invention may be prepared from compounds (11) as shown in Reaction scheme 6 or from compounds (I-iv) as shown in Reaction scheme 12. Compounds (I-iii) are compounds of formula (I) in which W is —CH$_2$—CH$_2$— and G is hydrogen.

Reaction scheme 6

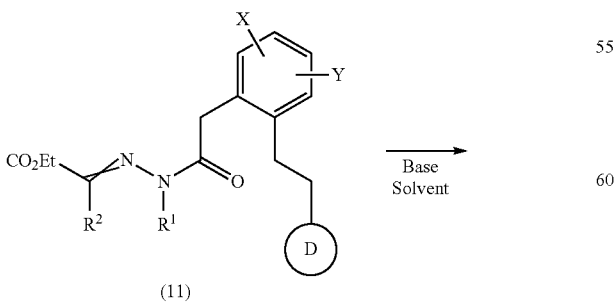

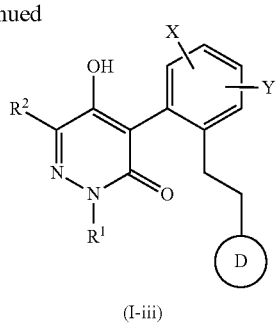

Compounds (I-iii) may be prepared by heating compounds (11) with a base (such as 1,8-diazabicyclo[5.4.0]undec-7-ene, sodium hexamethyldisilazide or lithium hexamethyldisilazide) in a solvent [such as acetonitrile, N,N-dimethylformamide or toluene] at a temperature between 50 and 200° C. Conventional heating or microwave heating may be used.

Reaction scheme 7
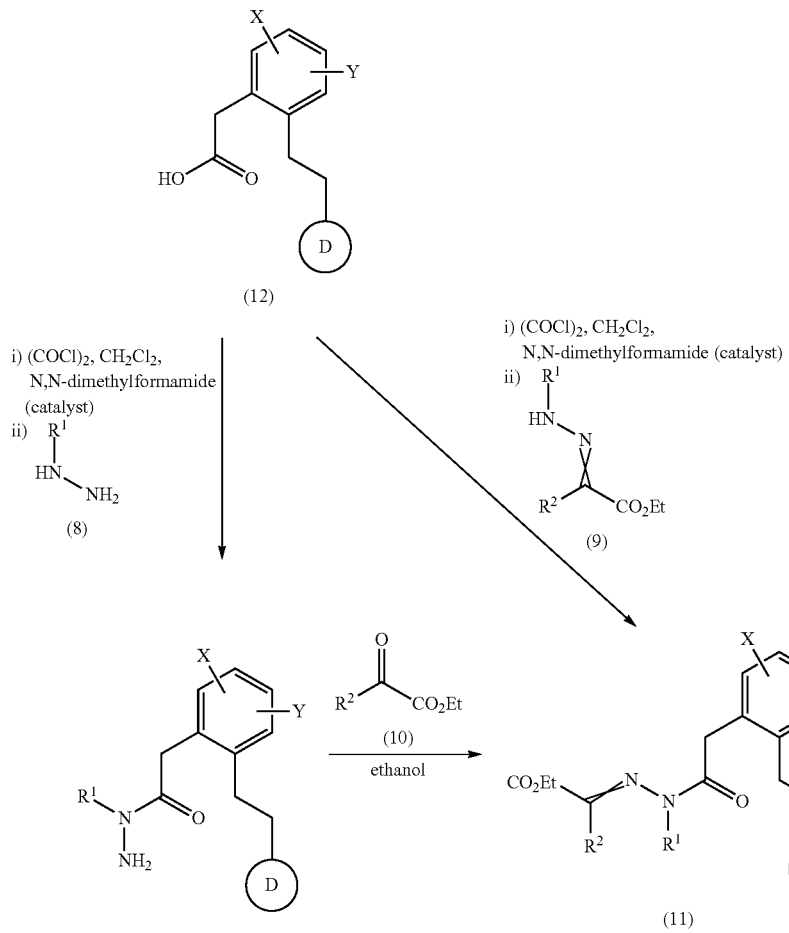
Compounds (11) may be prepared from compounds (12) as shown in Reaction scheme 7 above.
Compounds (12) can be prepared from compounds (13) as shown in Reaction scheme 8. Many compounds (13) are commercially available [such as methyl 2-phenylacetate and methyl 2-(2-fluorophenyl)acetate].
Reaction scheme 8
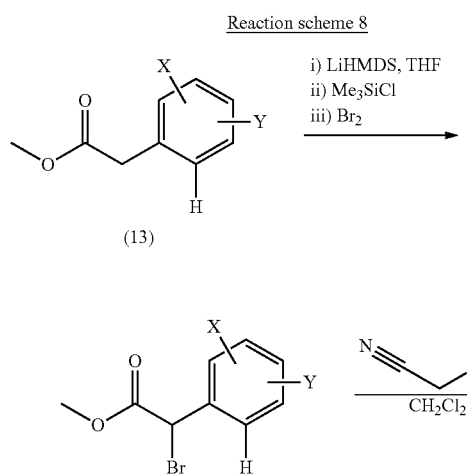
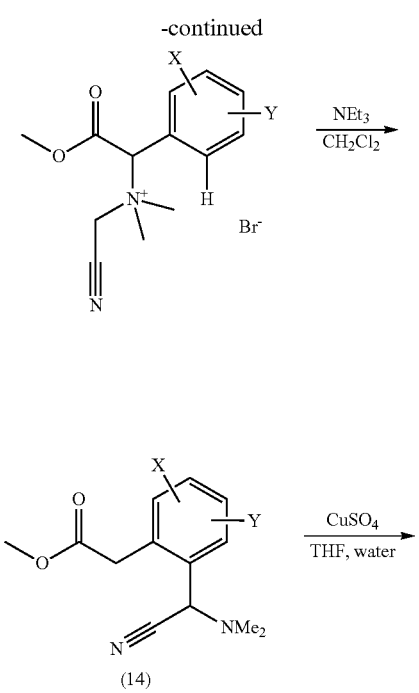

Reaction scheme 10

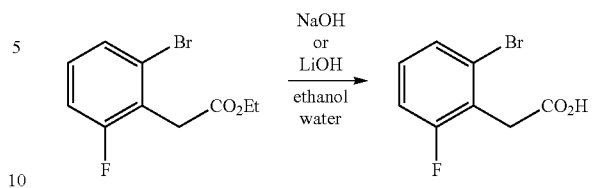

With respect to Reaction scheme 10, (2-Bromo-6-fluorophenyl)acetic acid ethyl ester may be prepared as described in Lundgren et al. *JACS* 2016, 138, 13826-13829.

Reaction scheme 8 (continued)

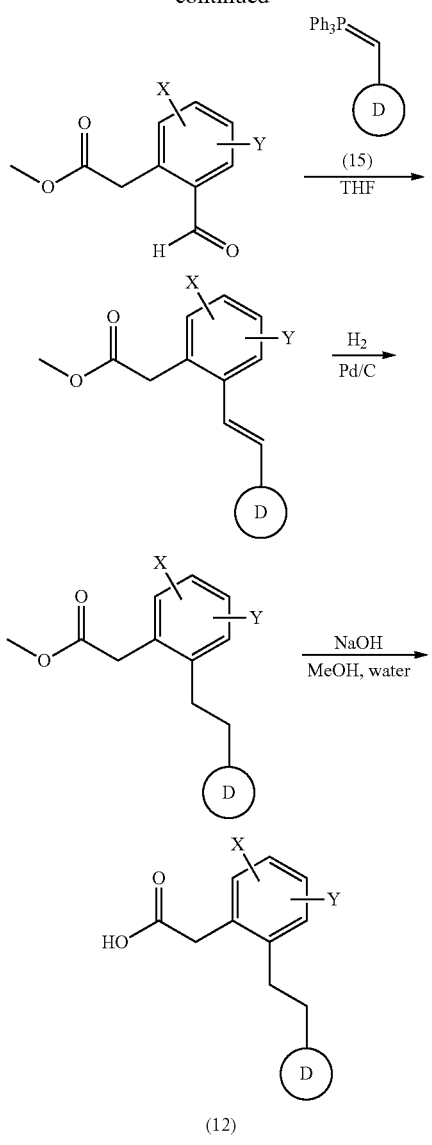

Reaction scheme 11

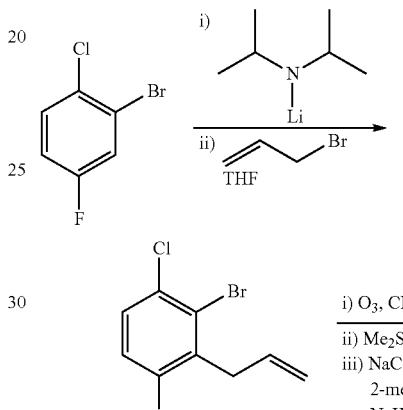

With respect to Reaction scheme 11, 2-bromo-1-chloro-4-fluoro-benzene is commercially available.

With respect to Reaction scheme 8, phosphoranes (15) can be made according to Reaction scheme 9.

Reaction scheme 9

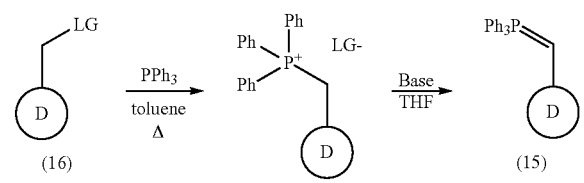

With respect to Reaction scheme 9, examples of suitable bases are sodium hydride, sodium hexamethyldisilazide and potassium tert-butoxide. Compounds (16) are electrophiles wherein LG is a Leaving Group [such as chloride, bromide, iodide, tosylate or mesylate]. Many compounds (16) are commercially available [such as 4-chlorobenzyl bromide or 2-chloro-5-chloromethylthiazole].

Reaction scheme 12

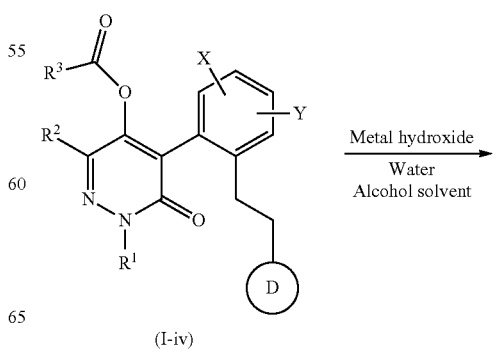

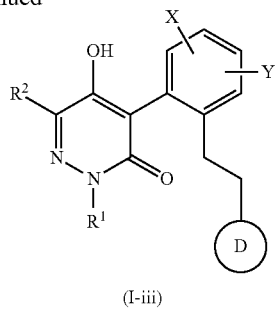

(I-iii)

Compounds (I-iii) may be prepared by treating compounds (I-iv) with a metal hydroxide [such as sodium hydroxide, lithium hydroxide or potassium hydroxide] in a mixture of water and an alcohol solvent [such as methanol or ethanol] at a temperature between 0° C. and 100° C. Compounds (I-iv) are compounds of formula (I) in which W is —CH$_2$—CH$_2$— and G is C(O)R$^3$.

Compounds (2) may be prepared from compounds (14) and compounds (15) as shown in Reaction scheme 13, according to either the Suzuki Protocol or the Heck Protocol described. When employing the Suzuki Protocol, compounds (14) are organoboron compounds such as boronic acids, boronic esters or trifluoroborate potassium salts and compounds (15) are halide or pseudo-halide compounds such as chlorides, bromides, iodides or triflates. When employing the Heck Protocol, compounds (14) are styrenes and compounds (15) are halide or pseudo-halide compounds such as chlorides, bromides, iodides or triflates.

Reaction scheme 13

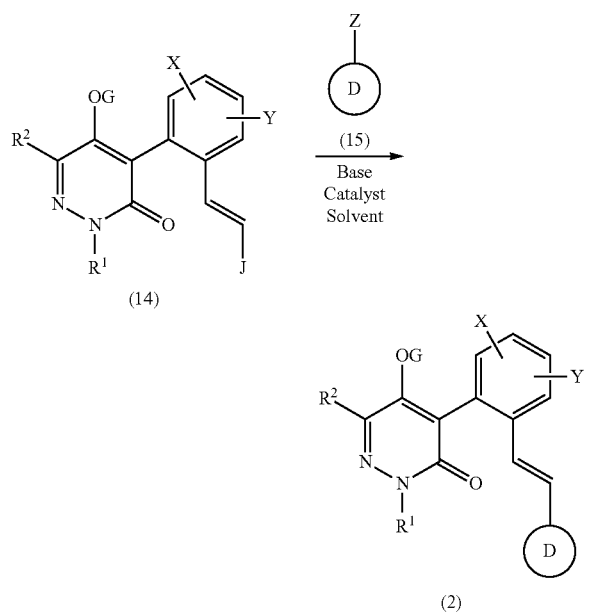

J = [B] or H
Z = halide or pseudo-halide

Suzuki Protocol

Compounds (2) may be prepared by treatment of compounds (14) with compounds (15) in the presence of a suitable base and a suitable catalyst in a suitable solvent at a temperature between 10 and 150° C. Examples of suitable bases include potassium carbonate, potassium phosphate, sodium carbonate, sodium bicarbonate and potassium fluoride. Examples of suitable catalysts include 1,1'-bis(diphenylphosphino)ferrocene]dichloropalladium(II) dichloromethane complex [PdCl$_2$(dppf).DCM], tetrakis(triphenylphosphine)palladium(0) [Pd(PPh$_3$)$_4$], and a catalytic system formed in-situ from a mixture of palladium (II)acetate and triphenylphosphine. Examples of suitable solvents include 1,4-dioxane, tetrahydrofuran, acetonitrile and toluene. Many compounds (15) are commercially available or can be made by known methods. Examples of compounds (14) with particular utility in the Suzuki Protocol are isobutyryl esters (14-i) wherein G is isobutyryl.

The skilled man will appreciate that the conditions of the Suzuki Protocol are liable to cleave ester groups, so that Reaction scheme 13 may also describe a reaction wherein starting material (14) contains an ester moiety [such that G is an acyl group], but product (2) does not [such that G is hydrogen].

Heck Protocol

Compounds (2) may be prepared by treatment of compounds (14) with compounds (15) in the presence of a suitable base and a suitable catalyst at a temperature between 10 and 150° C. An additional solvent may optionally be included. Examples of suitable bases include triethylamine, morpholine, N-methylmorpholine, diisopropylethylamine and pyridine. Examples of suitable catalysts include tetrakis(triphenylphosphine)palladium(0) [Pd(PPh$_3$)$_4$], a catalytic system formed in-situ from a mixture of palladium (II)acetate and triphenylphosphine, and a catalytic system formed in-situ from a mixture of tris(dibenzylideneacetone)dipalladium(0) and tri-tertbutylphosphonium tetrafluoroborate. Examples of the optional additional solvent include 1,4-dioxane, tetrahydrofuran, acetonitrile and toluene. Many compounds (15) are commercially available or can be made by known methods. Examples of compounds (14) with particular utility in the Heck Protocol are isobutyryl esters (14-i) wherein G is isobutyryl.

Compounds (14-ii), wherein J is an organoboron species such as a boronic ester, may be prepared from compounds (3) and compounds (16) as shown in Reaction scheme 14.

Reaction scheme 14

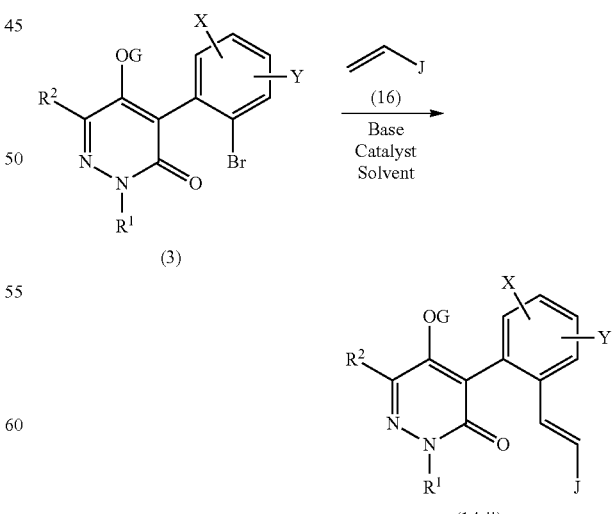

J = [B]

Compounds (14-ii) may be prepared by treatment of compounds (3) with compounds (16) in the presence of a suitable base and a suitable catalyst at a temperature between 10 and 150° C. An additional solvent may optionally be included. Examples of suitable bases include triethylamine, morpholine, N-methylmorpholine, diisopropylethylamine and pyridine. Examples of suitable catalysts include tetrakis(triphenylphosphine)palladium(0) [Pd(PPh$_3$)$_4$], a catalytic system formed in-situ from a mixture of palladium (II)acetate and triphenylphosphine, and a catalytic system formed in-situ from a mixture of tris(dibenzylideneacetone)dipalladium(0) and tri-tertbutylphosphonium tetrafluoroborate. Examples of the optional additional solvent include 1,4-dioxane, tetrahydrofuran, acetonitrile and toluene. Many compounds (16) are commercially available, such as vinylboronic acid MIDA ester or vinylboronic acid pinacol ester, or can be made by known methods. Examples of compounds (3) with particular utility in the Heck Protocol are isobutyryl esters (3-i) wherein G is isobutyryl.

Compounds (14-iii), wherein J is hydrogen, may be prepared from compounds (3) as shown in Reaction scheme 15.

Reaction scheme 15

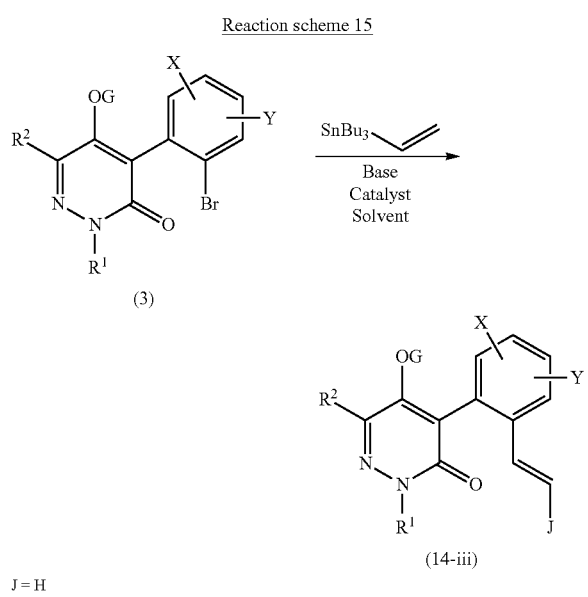

(3)

(14-iii)

J = H

Compounds (14-iii) may be prepared by treatment of compounds (3) with tributyl(vinyl)stannane, optionally in the presence of a suitable base, in the presence of a suitable catalyst at a temperature between 10 and 150° C. in a suitable solvent. Examples of the optional base include triethylamine, morpholine, N-methylmorpholine, diisopropylethylamine and pyridine. Examples of suitable catalysts include 1,1'-bis(diphenylphosphino)ferrocene]dichloropalladium(II) dichloromethane complex [PdCl$_2$(dppf).DCM], tetrakis(triphenylphosphine)palladium(0) [Pd(PPh$_3$)$_4$], a catalytic system formed in-situ from a mixture of palladium (II)acetate and triphenylphosphine, a catalytic system formed in-situ from a mixture of tris(dibenzylideneacetone)dipalladium(0) and tri-tertbutylphosphonium tetrafluoroborate, and a catalytic system formed in-situ from a palladacycle pre-catalyst such as chloro[(tri-tert-butylphosphine)-2-(2-aminobiphenyl)] palladium(II). Examples of suitable solvents include 1,4-dioxane, tetrahydrofuran, acetonitrile and toluene. Examples of compounds (3) with particular utility are isobutyryl esters (3-i) wherein G is isobutyryl.

Compounds (18) may be prepared from compounds (3) through a Sonogashira reaction as shown in Reaction scheme 16.

Reaction scheme 16

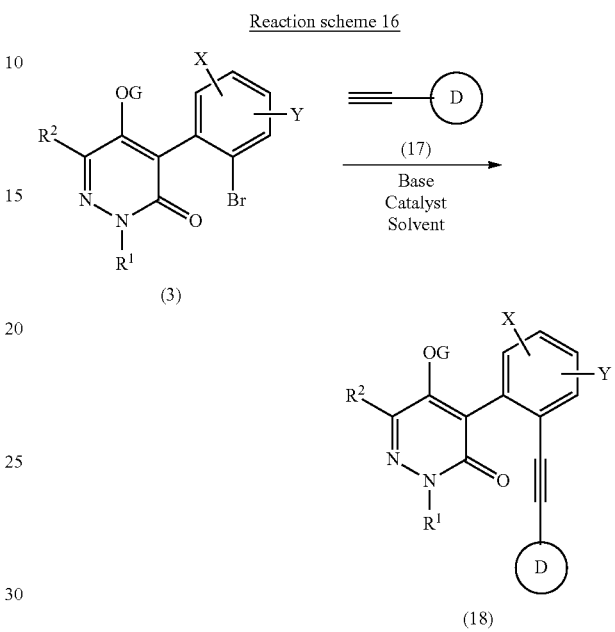

Compounds (18) may be prepared by treatment of compounds (3) with compounds (17) in the presence of a suitable base and suitable catalyst(s) at a temperature between 10 and 150° C. Optionally an additional solvent may be added. Examples of suitable bases include triethylamine, morpholine, N-methylmorpholine, diisopropylamine, diisopropylethylamine and pyridine. Examples of suitable catalysts include bis(triphenylphosphine)palladium(II) dichloride [Pd(PPh$_3$)Cl$_2$], a catalytic system formed in-situ from a mixture of palladium(II)acetate and triphenylphosphine, a catalytic system formed in-situ from a mixture of tris(dibenzylideneacetone)dipalladium(0) and tri-tertbutylphosphonium tetrafluoroborate, and a catalytic system formed in-situ from a palladacycle pre-catalyst such as chloro[(tri-tert-butylphosphine)-2-(2-aminobiphenyl)] palladium(II). Optionally a copper catalysts, such as copper (I) iodide, may also be added. Examples of suitable additional solvents include 1,4-dioxane, tetrahydrofuran, acetonitrile, toluene and N,N-dimethylformamide. Examples of compounds (3) with particular utility are isobutyryl esters (3-i) wherein G is isobutyryl.

The skilled man will appreciate that the conditions of the Sonogashira reaction are liable to cleave ester groups, so that Reaction scheme 16 may also describe a reaction wherein starting material (3) contains an ester moiety [such that G is an acyl group], but product (18) does not [such that G is hydrogen].

Compounds (19) may be prepared from compounds (3) and compounds (20) as shown in Reaction scheme 17, through a Suzuki reaction, wherein compound (20) is a suitable organoboron species, such as a bornic acid, boronate ester or potassium trifluoroborate salt.

Reaction scheme 17

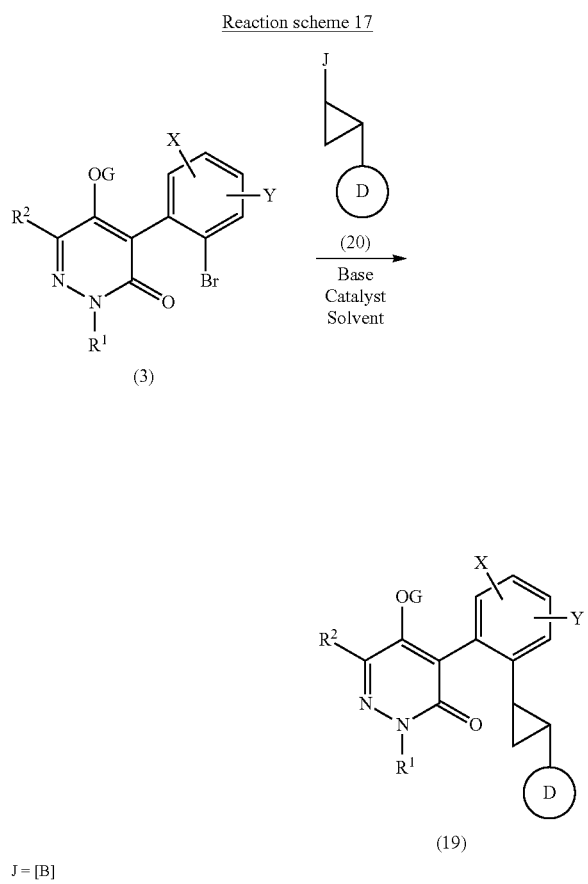

J = [B]

Compounds (19) may be prepared by treatment of compounds (3) with compounds (20) in the presence of a suitable base and a suitable catalyst in a suitable solvent at a temperature between 10 and 150° C. Examples of suitable bases include potassium carbonate, potassium phosphate, sodium carbonate, sodium bicarbonate and potassium fluoride. Examples of suitable catalysts include 1,1'-bis(diphenylphosphino)ferrocene]dichloropalladium(II) dichloromethane complex [PdCl$_2$(dppf).DCM], a catalytic system formed in-situ from a mixture of tris(dibenzylideneacetone)dipalladium(0) and tri-tertbutylphosphonium tetrafluoroborate, a catalytic system formed in-situ from a mixture of tris(dibenzylideneacetone)dipalladium(0) and tricyclohexylphosphine, a catalytic system formed in-situ from a palladacycle pre-catalyst such as chloro[(tri-tert-butylphosphine)-2-(2-aminobiphenyl)] palladium(II), and a catalytic system formed in-situ from a palladacycle pre-catalyst such as chloro[(tricyclohexylphosphine)-2-(2'-aminobiphenyl)] palladium(II). Examples of suitable solvents include 1,4-dioxane, tetrahydrofuran, acetonitrile and toluene. Some compounds (20) are commercially available [such as 4,4,5,5-tetramethyl-2-(2-phenyl-cyclopropyl)-[1,3,2]dioxaborolane] or can be made by known methods (see for example methods described in Org. Process Res. Dev. 2012, 16, 87-95). Examples of compounds (3) with particular utility in the Suzuki reaction are benzyl ethers (3-ii) wherein G is benzyl.

Reaction scheme 18

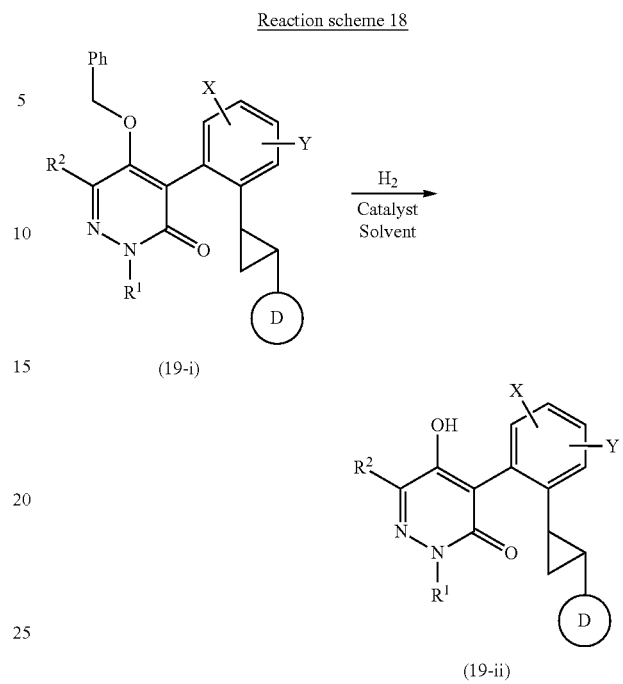

Compounds (I9-ii) may be prepared by catalytic hydrogenation of compounds (19-i) with hydrogen gas in a suitable solvent [such as tetrahydrofuran, methanol, ethanol, acetic acid or ethyl acetate] in the presence of a suitable catalyst [such as Pd/C, Pd/CaCO$_3$, Rh/Al$_2$CO$_3$ or sponge nickel] at a temperature between −10 and 100° C.

The skilled man will appreciate that certain intermediates described herein are also novel, and as such these form further aspects of the invention. In particular, certain of compounds (7), (7a) and (12) are novel and the invention thus encompasses compounds of formulae (7), (7a) and (12) as defined in the schemes above.

The compounds of Formula (I) according to the invention can be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound according to any one of the previous claims and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces: resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octyl-cresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The composition of the present may further comprise at least one additional pesticide. For example, the compounds according to the invention can also be used in combination with other herbicides or plant growth regulators. In a preferred embodiment the additional pesticide is a herbicide and/or herbicide safener. Specific examples of such mixtures include (wherein "I" represents a compound of Formula (I)): I+acetochlor; I+acifluorfen (including acifluorfen-sodium); I+aclonifen; I+alachlor; I+alloxydim; I+ametryn; I+amicarbazone; I+amidosulfuron; I+aminocyclopyrachlor; I+aminopyralid; I+amitrole; I+asulam; I+atrazine; I+bensulfuron (including bensulfuron-methyl); I+bentazone; I+bicyclopyrone; I+bilanafos; I+bifenox; I+bispyribac-sodium; I+bixlozone; I+bromacil; I+bromoxynil; I+butachlor; I+butafenacil; I+cafenstrole; I+carfentrazone (including carfentrazone-ethyl); cloransulam (including cloransulam-methyl); I+chlorimuron (including chlorimuron-ethyl); I+chlorotoluron; I+cinosulfuron; I+chlorsulfuron; I+cinmethylin; I+clacyfos; I+clethodim; I+clodinafop (including clodinafop-propargyl); I+clomazone; I+clopyralid; I+cyclopyranil; I+cyclopyrimorate; I+cyclosulfamuron; I+cyhalofop (including cyhalofop-butyl); I+2,4-D (including the choline salt and 2-ethylhexyl ester thereof); I+2,4-DB; I+daimuron; I+desmedipham; I+dicamba (including the aluminum, aminopropyl, bis-aminopropylmethyl, choline, dichloroprop, diglycolamine, dimethylamine, dimethylammonium, potassium and sodium salts thereof); I+diclofop-methyl; I+diclosulam; I+diflufenican; I+difenzoquat; I+diflufenican; I+diflufenzopyr; I+dimethachlor; I+dimethenamid-P; I+diquat dibromide; I+diuron; I+esprocarb; I+ethalfluralin; I+ethofumesate; I+fenoxaprop (including fenoxaprop-P-ethyl); I+fenoxasulfone; I+fenquinotrione; I+fentrazamide; I+flazasulfuron; I+florasulam; I+florpyrauxifen; I+fluazifop (including fluazifop-P-butyl); I+flucarbazone (including flucarbazone-sodium); I+flufenacet; I+flumetralin; I+flumetsulam; I+flumioxazin; I+flupyrsulfuron (including flupyrsulfuron-methyl-sodium); I+fluroxypyr (including fluroxypyr-meptyl); I+fluthiacet-methyl; I+fomesafen; I+foramsulfuron; I+glufosinate (including the ammonium salt thereof); I+glyphosate (including the diammonium, isopropylammonium and potassium salts thereof); I+halauxifen (including halauxifen-methyl); I+halosulfuron-methyl; I+haloxyfop (including haloxyfop-methyl); I+hexazinone; I+hydantocidin; I+imazamox; I+imazapic; I+imazapyr; I+imazaquin; I+imazethapyr; I+indaziflam; I+iodosulfuron (including iodosulfuron-methyl-sodium); I+iofensulfuron; I+iofensulfuron-sodium; I+ioxynil; I+ipfencarbazone; I+isoproturon; I+isoxaben; I+isoxaflutole; I+lactofen; I+lancotrione; I+linuron; I+MCPA; I+MCPB; I+mecoprop-P; I+mefenacet; I+mesosulfuron; I+mesosulfuron-methyl; I+mesotrione; I+metamitron; I+metazachlor; I+methiozolin; I+metobromuron; I+metolachlor; I+metosulam; I+metoxuron; I+metribuzin; I+metsulfuron; I+molinate; I+napropamide; I+nicosulfuron; I+norflurazon; I+orthosulfamuron; I+oxadiargyl; I+oxadiazon; I+oxasulfuron; I+oxyfluorfen; I+paraquat dichloride; I+pendimethalin; I+penoxsulam; I+phenmedipham; I+picloram; I+picolinafen; I+pinoxaden; I+pretilachlor; I+primisulfuron-methyl; I+prodiamine; I+prometryn; I+propachlor; I+propanil; I+propaquizafop; I+propham; I+propyrisulfuron, I+propyzamide; I+prosulfocarb; I+prosulfuron; I+pyraclonil; I+pyraflufen (including pyraflufen-ethyl): I+pyrasulfotole; I+pyrazolynate, I+pyrazosulfuron-ethyl; I+pyribenzoxim; I+pyridate; I+pyriftalid; I+pyrimisulfan, I+pyrithiobac-sodium; I+pyroxasulfone; I+pyroxsulam; I+quinclorac; I+quinmerac; I+quizalofop (including quizalofop-P-ethyl and quizalofop-P-tefuryl); I+rimsulfuron; I+saflufenacil; I+sethoxydim; I+simazine; I+S-metolachlor; I+sulcotrione; I+sulfentrazone; I+sulfosulfuron; I+tebuthiuron; I+tefuryltrione; I+tembotrione; I+terbuthylazine; I+terbutryn; I+thiencarbazone; I+thifensulfuron; I+tiafenacil; I+tolpyralate; I+topramezone; I+tralkoxydim; I+triafamone; I+triallate; I+triasulfuron; I+tribenuron (including tribenuron-methyl); I+triclopyr; I+trifloxysulfuron (including trifloxysulfuron-sodium); I+trifludimoxazin; I+trifluralin; I+triflusulfuron; I+tritosulfuron; I+4-hydroxy-1-methoxy-5-methyl-3-[4-(trifluoromethyl)-2-pyridyl]imidazolidin-2-one; I+4-hydroxy-1,5-dimethyl-3-[4-(trifluoromethyl)-2-pyridyl]imidazolidin-2-one; I+5-ethoxy-4-hydroxy-1-methyl-3-[4-(trifluoromethyl)-2-pyridyl]imidazolidin-2-one; I+4-hydroxy-1-methyl-3-[4-(trifluoromethyl)-2-pyridyl]imidazolidin-2-one; I+4-hydroxy-1,5-dimethyl-3-[1-methyl-5-(trifluoromethyl) pyrazol-3-yl]imidazolidin-2-one; I+(4R)1-(5-tert-butylisoxazol-3-yl)-4-ethoxy-5-hydroxy-3-methyl-imidazolidin-2-one; I+3-[2-(3,4-dimethoxyphenyl)-6-methyl-3-oxo-pyridazine-4-carbonyl]bicyclo[3.2.1]octane-2,4-dione; I+2-[2-(3,4-dimethoxyphenyl)-6-methyl-3-oxo-pyridazine-4-carbonyl]-5-methyl-cyclohexane-1,3-dione;

I+2-[2-(3,4-dimethoxyphenyl)-6-methyl-3-oxo-pyridazine-4-carbonyl]cyclohexane-1,3-dione; I+2-[2-(3,4-dimethoxyphenyl)-6-methyl-3-oxo-pyridazine-4-carbonyl]-5,5-dimethyl-cyclohexane-1,3-dione; I+6-[2-(3,4-dimethoxyphenyl)-6-methyl-3-oxo-pyridazine-4-carbonyl]-2,2,4,4-tetramethyl-cyclohexane-1,3,5-trione; I+2-[2-(3,4-dimethoxyphenyl)-6-methyl-3-oxo-pyridazine-4-carbonyl]-5-ethyl-cyclohexane-1,3-dione; I+2-[2-(3,4-dimethoxyphenyl)-6-methyl-3-oxo-pyridazine-4-carbonyl]-4,4,6,6-tetramethyl-cyclohexane-1,3-dione; I+2-[6-cyclopropyl-2-(3,4-dimethoxyphenyl)-3-oxo-pyridazine-4-carbonyl]-5-methyl-cyclohexane-1,3-dione; I+3-[6-cyclopropyl-2-(3,4-dimethoxyphenyl)-3-oxo-pyridazine-4-carbonyl]bicyclo[3.2.1]octane-2,4-dione; I+2-[6-cyclopropyl-2-(3,4-dimethoxyphenyl)-3-oxo-pyridazine-4-carbonyl]-5,5-dimethyl-cyclohexane-1,3-dione; I+6-[6-cyclopropyl-2-(3,4-dimethoxyphenyl)-3-oxo-pyridazine-4-carbonyl]-2,2,4,4-tetramethyl-cyclohexane-1,3,5-trione; I+2-[6-cyclopropyl-2-(3,4-dimethoxyphenyl)-3-oxo-pyridazine-4-carbonyl]cyclohexane-1,3-dione; I+4-[2-(3,4-dimethoxyphenyl)-6-methyl-3-oxo-pyridazine-4-carbonyl]-2,2,6,6-tetramethyl-tetrahydropyran-3,5-dione and I+4-[6-cyclopropyl-2-(3,4-dimethoxyphenyl)-3-oxo-pyridazine-4-carbonyl]-2,2,6,6-tetramethyl-tetrahydropyran-3,5-dione.

The mixing partners of the compound of Formula (I) may also be in the form of esters or salts, as mentioned e.g. in The Pesticide Manual, Fourteenth Edition, British Crop Protection Council, 2006.

The compound of Formula (I) can also be used in mixtures with other agrochemicals such as fungicides, nematicides or insecticides, examples of which are given in The Pesticide Manual.

The mixing ratio of the compound of Formula (I) to the mixing partner is preferably from 1:100 to 1000:1.

The mixtures can advantageously be used in the above-mentioned formulations (in which case "active ingredient" relates to the respective mixture of compound of Formula (I) with the mixing partner).

Compounds of Formula (I) of the present invention may also be combined with herbicide safeners. Preferred combinations (wherein "I" represents a compound of Formula (I)) include:—I+benoxacor, I+cloquintocet (including cloquintocet-mexyl); I+cyprosulfamide; I+dichlormid; I+fenchlorazole (including fenchlorazole-ethyl); I+fenclorim; I+fluxofenim; I+furilazole I+isoxadifen (including isoxadifen-ethyl); I+mefenpyr (including mefenpyr-diethyl); I+metcamifen; I+N-(2-methoxybenzoyl)-4-[(methyl-aminocarbonyl)amino] benzenesulfonamide and I+oxabetrinil.

Particularly preferred are mixtures of a compound of Formula (I) with cyprosulfamide, isoxadifen (including isoxadifen-ethyl), cloquintocet (including cloquintocet-mexyl) and/or N-(2-methoxybenzoyl)-4-[(methyl-aminocarbonyl)amino]benzenesulfonamide.

The safeners of the compound of Formula (I) may also be in the form of esters or salts, as mentioned e.g. in The Pesticide Manual, 14$^{th}$ Edition (BCPC), 2006. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of Formula (I) to safener is from 100:1 to 1:10, especially from 20:1 to 1:1.

The compound of Formula (I) can also be used in mixtures with other agrochemicals such as fungicides, nematicides or insecticides, examples of which are given in The Pesticide Manual.

The mixing ratio of the compound of Formula (I) to the mixing partner is preferably from 1:100 to 1000:1.

The mixtures can advantageously be used in the above-mentioned formulations (in which case "active ingredient" relates to the respective mixture of compound of Formula I with the mixing partner).

The present invention still further provides a method of selectively controlling weeds at a locus comprising crop plants and weeds, wherein the method comprises application to the locus of a weed controlling amount of a composition according to the present invention. 'Controlling' means killing, reducing or retarding growth or preventing or reducing germination. Generally the plants to be controlled are unwanted plants (weeds). 'Locus' means the area in which the plants are growing or will grow.

The rates of application of compounds of Formula (I) may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®. In a particularly preferred aspect, the crop plant has been engineered to overexpress homogentisate solanesyltransferase as taught in, for example, WO2010/029311.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled include both monocotyledonous species, for example *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*, and dicotyledonous species, for example *Abutilon, Amaranthus, Ambrosia, Chenopodium, Chrysanthemum, Conyza, Galium, Ipomoea, Nasturtium, Sida, Sinapis, Solanum, Stellaria, Veronica, Viola* and *Xanthium*. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

Various aspects and embodiments of the present invention will now be illustrated in more detail by way of example. It will be appreciated that modification of detail may be made without departing from the scope of the invention.

PREPARATION EXAMPLES

Example 1 Preparation of 4-(3-chloro-6-fluoro-2-phenethyl-phenyl)-5-hydroxy-2,6-dimethyl-pyridazin-3-one

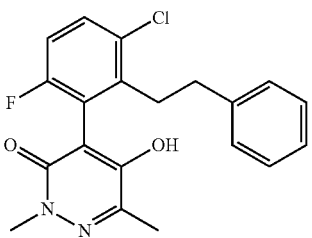 [SMILES: Cc1nn(C)c(=O)c(-c2c(F)ccc(Cl)c2CCc2ccccc2)c1O]

1.1 3-allyl-2-bromo-1-chloro-4-fluoro-benzene

A solution of lithium diisopropylamide (2M in tetrahydrofuran, 3.6 ml, 7.2 mmol) was cooled to −78° C. under $N_2$. A solution of 2-bromo-1-chloro-4-fluoro-benzene (1.0 g, 4.8 mmol) in tetrahydrofuran was added dropwise at −78° C. The mixture was stirred for 45 minutes at the same temperature before being treated with allyl bromide (0.3 ml, 5.7 mmol). The reaction was continued at −78° C. for 2 h then allowed to warm to rt. The reaction was quenched with sat. $NH_4Cl$ (aq) and extracted with ethyl acetate. The organics were separated and kept, then washed with brine. The organics were dried over sodium sulfate and concentrated under reduced pressure to give 3-allyl-2-bromo-1-chloro-4-fluoro-benzene (1.2 g, 100%) as an oil.

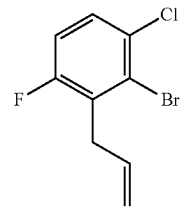

$^1H$ NMR (400 MHz, $CDCl_3$) $δ_H$: 7.34-7.30 (m, 1H), 7.01-6.96 (m, 1H), 5.94-5.83 (m, 1H), 5.10-5.00 (m, 2H), 3.64-3.58 (m, 2H).

1.2 2-(2-bromo-3-chloro-6-fluoro-phenyl)acetic Acid

A solution of 3-allyl-2-bromo-1-chloro-4-fluoro-benzene (15.0 g, 60.1 mmol) in dichloromethane (200 mL) in a 2-necked flask was cooled to −78° C. One side neck was connected to a trap containing an aqueous solution of KI. Ozone was bubbled through the solution until the starting material was fully consumed (5 hours). Air was bubbled through the solution for 10 minutes to remove excess ozone. Dimethyl sulfide (44 ml, 601 mmol) was added and the mixture allowed to warm to rt. The reaction was continued for 16 h at rt.

The mixture was washed with brine (2×100 mL) and the organic layer kept. The organics were dried over $Na_2SO_4$, filtered and concentrated under reduced pressure to give crude 2-(2-bromo-3-chloro-6-fluoro-phenyl)acetaldehyde (15.3 g) which was used for the next step without further purification.

Crude 2-(2-bromo-3-chloro-6-fluoro-phenyl)acetaldehyde (15.3 g, 60.8 mmol) was dissolved in a mixture of tert-butanol (92 mL) and water (46 mL) then cooled to 0° C. 2-methylbut-2-ene (64.5 mL, 608 mmol), sodium dihydrogen phosphate (34.6 g, 243 mmol) and sodium chlorite (16.5 g, 163 mmol) were added. The mixture was stirred for 2 h then diluted with brine (150 mL) and 2M hydrochloric acid (150 mL). The mixture was extracted with ethyl acetate (3×100 mL). The combined organic extracts were washed with a saturated aqueous solution of sodium metabisulfite (100 mL) then dried over $Na_2SO_4$, filtered and concentrated under reduced pressure to provide a pale yellow solid. The crude solid was dissolved in a mixture of water (100 mL) and 2.0M NaOH (30 mL). The aqueous solution was washed with ethyl acetate (100 mL) and the organics discarded. The aqueous layer was acidified by addition of concentrated hydrochloric acid (20 mL) resulting in the formation of a white suspension. The mixture was extracted with ethyl acetate (3×200 mL). The combined organics were washed with brine, dried over $Na_2SO_4$, filtered and evaporated to provide 2-(2-bromo-3-chloro-6-fluoro-phenyl)acetic acid (8.0 g, 49%) as a white solid.

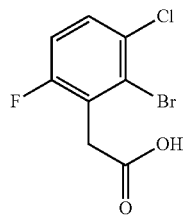

¹H NMR (400 MHz, DMSO-d6) $\delta_H$: 12.79 (br.s, 1H), 7.67-7.59 (m, 1H), 7.39-7.31 (m, 1H), 3.82 (s, 2H).

1.3 2-(2-bromo-3-chloro-6-fluoro-phenyl)-N-methyl-acetohydrazide

To a stirred solution of 2-(2-bromo-3-chloro-6-fluoro-phenyl)acetic acid (2.0 g, 7.5 mmol) in dichloromethane (20 ml) at 0° C. was added N-(3-Dimethylaminopropyl)-N'-ethylcarbodiimide hydrochloride [EDC.HCl] (1.4 g, 9.0 mmol), followed by dropwise addition of methyl hydrazine (0.4 ml, 7.5 mmol). The temperature of the reaction mixture was maintained at 0° C. for 3 h. The reaction was then quenched with water and extracted into dichloromethane. The organics were separated, washed with brine and dried over Na₂SO₄. Concentration under reduced pressure gave crude 2-(2-bromo-3-chloro-6-fluoro-phenyl)-N-methyl-acetohydrazide (1.8 g, 81%) which was used in the next step without further purification.

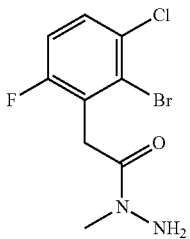

¹H NMR (400 MHz, DMSO-d6) $\delta_H$: 7.59 (dd, J=8.9 and 5.4, 1H), 7.30 (t, J=8.9, 1H), 4.91 (s, 2H), 4.10 (br. s, 2H), 3.02 (s, 3H).

1.4 2-{[2-(2-Bromo-3-chloro-6-fluoro-phenyl)-acetyl]-methyl-hydrazono}-propionic Acid Ethyl Ester To a stirred solution of 2-(2-bromo-3-chloro-6-fluoro-phenyl)-N-methyl-acetohydrazide (1.8 g, 6.09 mmol) in ethanol (5 ml) was added ethyl pyruvate (0.7 ml, 6.7 mmol) dropwise. The reaction was heated at 80° C. for 4 h. The reaction mixture was then allowed to cool to rt, and evaporated under reduced pressure. The residue was purified by column chromatography on silica gel (eluent an ethyl acetate/hexane gradient) to give the desired compound 2-{[2-(2-Bromo-3-chloro-6-fluoro-phenyl)-acetyl]-methyl-hydrazono}-propionic acid ethyl ester (1.8 g, 75%) as an off-white solid.

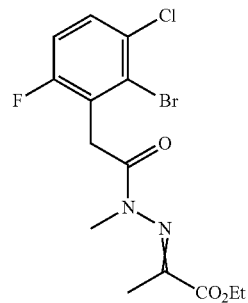 [SMILES: CCOC(=O)C(C)=NN(C)C(=O)Cc1c(F)ccc(Cl)c1Br]

¹H NMR (400 MHz, CDCl₃) $\delta_H$: 7.40-7.35 (m, 1H), 7.04-6.98 (m, 1H), 4.32 (q, J=7.1, 2H), 4.24 (s, 2H), 3.41 (s, 3H), 2.32 (s, 3H), 1.36 (t, J=7.1, 3H).

1.5 4-(2-bromo-3-chloro-6-fluoro-phenyl)-5-hydroxy-2,6-dimethyl-pyridazin-3-one 2-{[2-(2-Bromo-3-chloro-6-fluoro-phenyl)-acetyl]-methyl-hydrazono}-propionic acid ethyl ester (500 mg, 1.27 mmol) was dissolved in acetonitrile (2.5 ml) and treated with 1,8-diazabicyclo[5.4.0]undec-7-ene [DBU] (0.47 ml, 3.2 mmol). The mixture was heated to 125° C. using microwave irradiation for 1 h. The reaction mixture was then evaporated under reduced pressure. The residue was dissolved in water and acidified to pH 1 with 2N hydrochloric acid. The mixture was extracted with DCM, the organics separated and washed with brine solution. The organic solution was dried over Na₂SO₄ and concentrated under reduced pressure to give crude product. The crude was purified by column chromatography on silica gel (eluent an ethyl acetate/hexane gradient) to give 4-(2-bromo-3-chloro-6-fluoro-phenyl)-5-hydroxy-2,6-dimethyl-pyridazin-3-one (340 mg, 77.1%) as an off-white solid.

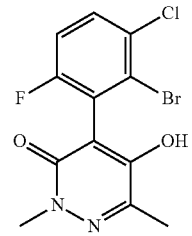 [SMILES: Cc1nn(C)c(=O)c(-c2c(F)ccc(Cl)c2Br)c1O]

¹H NMR (400 MHz, DMSO-d6) $\delta_H$: 11.01 (s, 1H), 7.77-7.73 (m, 1H), 7.39 (t, J=8.7, 1H), 3.58 (s, 3H), 2.24 (s, 3H).

1.6 [5-(2-bromo-3-chloro-6-fluoro-phenyl)-1,3-dimethyl-6-oxo-pyridazin-4-yl] 2-methylpropanoate To a stirred solution of 4-(2-bromo-3-chloro-6-fluoro-phenyl)-5-hydroxy-2,6-dimethyl-pyridazin-3-one (1.4 g, 4.02 mmol) in dichloromethane (32 ml) at rt were added triethylamine (1.1 ml, 8.06 mmol), 4-(dimethylamino)pyridine [DMAP] (49 mg, 0.40 mmol) and isobutyryl chloride (0.6 ml, 4.83 mmol).

Once judged complete, the reaction was diluted with dichloromethane and water. The organic layer was separated, dried over Na₂SO₄, and concentrated under reduced pressure to give crude product. The crude was purified by column chromatography on silica gel (eluent an ethyl acetate/hexane gradient) to give [5-(2-bromo-3-chloro-6-fluoro-phenyl)-1,3-dimethyl-6-oxo-pyridazin-4-yl] 2-methylpropanoate (1.47 g, 87%).

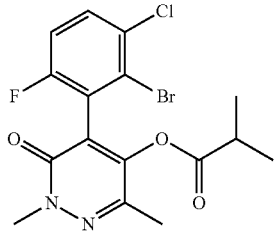 [SMILES: Cc1nn(C)c(=O)c(-c2c(F)ccc(Cl)c2Br)c1OC(=O)C(C)C]

¹H NMR (400 MHz, CDCl₃) δ$_H$: 7.51-7.47 (m, 1H), 7.10-7.05 (m, 1H), 3.82 (s, 3H), 2.60-2.55 (m, 1H), 2.25 (s, 3H), 1.02-0.98 (m, 6H).

1.7 4-[3-chloro-6-fluoro-2-[(E)-styryl]phenyl]-5-hydroxy-2,6-dimethyl-pyridazin-3-one Solid K₂CO₃ (298 mg, 2.16 mmol), trans-2-phenylvinylboronic acid (213 mg, 1.43 mmol) and PdCl₂(dppf).DCM (118 mg, 0.143 mmol) were placed under argon atmosphere. A solution of [5-(2-bromo-3-chloro-6-fluoro-phenyl)-1,3-dimethyl-6-oxo-pyridazin-4-yl] 2-methylpropanoate (250 mg, 0.72 mmol) in 1,4-dioxane (4 ml) was added and the mixture stirred at 95° C. for 18 h.

The reaction mixture was evaporated directly under reduced pressure to give a residue which was purified by column chromatography on silica gel (eluent an ethyl acetate/hexane gradient) to give 4-[3-chloro-6-fluoro-2-[(E)-styryl]phenyl]-5-hydroxy-2,6-dimethyl-pyridazin-3-one (160 mg, 72%).

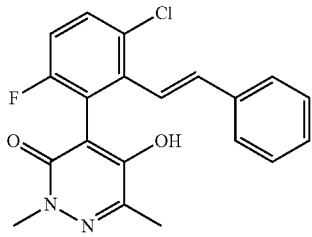 [SMILES: Cc1nn(C)c(=O)c(-c2c(F)ccc(Cl)c2/C=C/c2ccccc2)c1O]

¹H NMR (DMSO-d6) δ$_H$: 10.8 (s, 1H), 7.62 (m, 1H), 7.37-7.24 (m, 6H), 6.94 (d, J=16.5, 1H), 6.57 (d, J=16.5, 1H), 6.53 (s, 3H), 2.18 (s, 3H).

1.8 4-(3-chloro-6-fluoro-2-phenethyl-phenyl)-5-hydroxy-2,6-dimethyl-pyridazin-3-one A stirred mixture of 4-[3-chloro-6-fluoro-2-[(E)-styryl]phenyl]-5-hydroxy-2,6-dimethyl-pyridazin-3-one (200 mg, 0.54 mmol) and Pd/C (40 mg) in tetrahydrofuran (10 ml) was treated with hydrogen under balloon pressure for 21 h.

The catalyst was removed by filtration and the reaction solution evaporated to dryness. The residue was purified by flash column chromatography on silica gel (eluent an ethyl acetate/hexanes gradient) to give 4-(3-chloro-6-fluoro-2-phenethyl-phenyl)-5-hydroxy-2,6-dimethyl-pyridazin-3-one (110 mg, 55%) as a white solid.

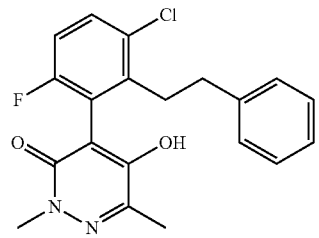 [SMILES: Cc1nn(C)c(=O)c(-c2c(F)ccc(Cl)c2CCc2ccccc2)c1O]

¹H NMR (DMSO-d6) δ$_H$: 10.85 (s, 1H), 7.57-7.53 (m, 1H), 7.27-7.15 (m, 4H), 7.0 (d, J=7.2, 2H), 3.60 (s, 3H), 2.73-2.50 (m, 4H), 2.25 (s, 3H).

Example 2 Preparation of 4-[3-chloro-6-fluoro-2-[2-(4-fluorophenyl)ethyl]-phenyl]-5-hydroxy-2,6-dimethyl-pyridazin-3-one

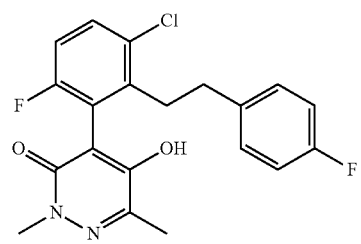 [SMILES: Cc1nn(C)c(=O)c(-c2c(F)ccc(Cl)c2CCc2ccc(F)cc2)c1O]

2.1 [5-[3-chloro-6-fluoro-2-[(E)-2-(4-fluorophenyl)vinyl]phenyl]-1,3-dimethyl-6-oxo-pyridazin-4-yl] 2-methylpropanoate A mixture of [5-(2-bromo-3-chloro-6-fluoro-phenyl)-1,3-dimethyl-6-oxo-pyridazin-4-yl] 2-methylpropanoate (0.50 g, 1.20 mmol, 1.0 equiv.) [prepared as described in Example 1], tris(dibenzylideneacetone)dipalladium(0) (27 mg, 0.030 mmol, 0.025 equiv.) and tri-tertbutylphosphonium tetrafluoroborate (35 mg, 0.12 mmol, 0.1 equiv.) was treated with degassed triethylamine (12 mL). 1-fluoro-4-vinyl-benzene (0.43 mL, 0.44 g, 3.59 mmol, 3.0 equiv.) was added and the mixture heated to 95° C. for 18.5 hrs.

Heating was halted and LC/MS analysis showed high conversion to the target stilbene. The reaction mixture was diluted with dichloromethane and filtered through Celite™, washing with further dichloromethane. The liquors were concentrated to dryness. The crude product was partially purified by flash column chromatography (silica, eluent ethyl acetate/isohexane) to afford desired stilbene [5-[3-chloro-6-fluoro-2-[(E)-2-(4-fluorophenyl)vinyl]phenyl]-1,3-dimethyl-6-oxo-pyridazin-4-yl] 2-methylpropanoate (0.36 g, 0.774 mmol, 65% yield) as a colourless gum.

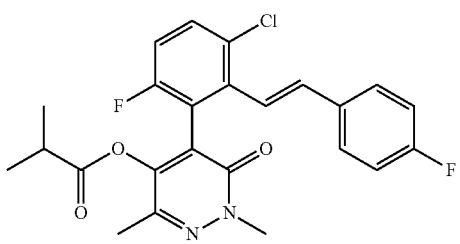 [SMILES: Cc1nn(C)c(=O)c(-c2c(F)ccc(Cl)c2/C=C/c2ccc(F)cc2)c1OC(=O)C(C)C]

¹H NMR (400 MHz, CDCl₃) $\delta_H$=7.45-7.41 (m, 1H), 7.35-7.30 (m, 2H), 7.04-6.98 (m, 3H), 6.93 (d, 1H), 6.61 (d, 1H), 3.71 (s, 3H), 2.64 (sept, 1H), 2.23 (s, 3H), 1.09 (dd, 6H).

2.2 [5-[3-chloro-6-fluoro-2-[2-(4-fluorophenyl)ethyl]phenyl]-1,3-dimethyl-6-oxo-pyridazin-4-yl] 2-methylpropanoate

[5-[3-chloro-6-fluoro-2-[(E)-2-(4-fluorophenyl)vinyl]phenyl]-1,3-dimethyl-6-oxo-pyridazin-4-yl] 2-methylpropanoate (130 mg, 0.283 mmol) was subjected to catalytic hydrogenation in tetrahydrofuran (3 mL) over 5% Pd/C catalyst (60 mg) at 3 bar H₂.

After 1.5 hrs, LC/MS showed complete reaction. The reaction mixture was filtered through a pad of Celite™, washing with ethyl acetate. The liquors were concentrated in-vacuo to afford a crude residue.

The residue was adsorbed onto silica and purified by flash column chromatography (silica, eluent ethyl acetate/isohexane) to give [5-[3-chloro-6-fluoro-2-[2-(4-fluorophenyl)ethyl]phenyl]-1,3-dimethyl-6-oxo-pyridazin-4-yl] 2-methylpropanoate (85 mg, 65% yield) as a colourless gum.

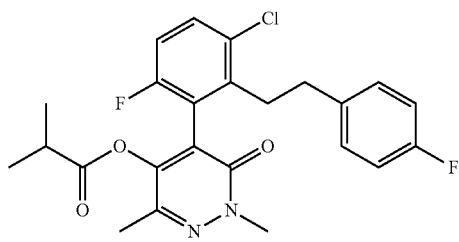

¹H NMR (400 MHz, CDCl₃) $\delta_H$=7.42 (dd, 1H), 7.11-7.06 (m, 2H), 6.99 (t, 1H), 6.97-6.90 (m, 2H), 3.84 (s, 3H), 2.86-2.68 (m, 4H), 2.55 (sept, 1H), 2.26 (s, 3H), 0.98 (dd, 6H).

2.3 4-[3-chloro-6-fluoro-2-[2-(4-fluorophenyl)ethyl]phenyl]-5-hydroxy-2,6-dimethyl-pyridazin-3-one

[5-[3-chloro-6-fluoro-2-[2-(4-fluorophenyl)ethyl]phenyl]-1,3-dimethyl-6-oxo-pyridazin-4-yl]2-methylpropanoate (108 mg, 0.234 mmol, 1.0 equiv.) was dissolved in ethanol (7.5 mL). The mixture was treated with a solution of lithium hydroxide (17 mg, 0.703 mmol, 3.0 equiv.) in water (2.5 mL). The reaction was stirred at rt for 2 hrs.

LC/MS showed complete conversion. The reaction mixture was concentrated in-vacuo to remove ethanol. The remaining aqueous solution was acidified with 1M HCl (30 mL) and extracted with EtOAc (3×30 mL). The combined organics were dried over MgSO₄, filtered and concentrated in-vacuo to afford crude product.

Purification by flash column chromatography (silica, eluent ethyl acetate/isohexane) gave 4-[3-chloro-6-fluoro-2-[2-(4-fluorophenyl)ethyl]phenyl]-5-hydroxy-2,6-dimethyl-pyridazin-3-one (83 mg, 91% yield) as a white solid.

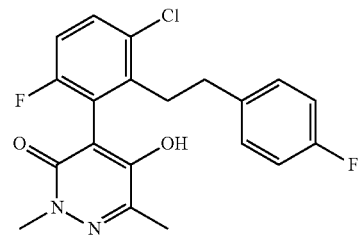 [SMILES: Cc1nn(C)c(=O)c(-c2c(F)ccc(Cl)c2CCc2ccc(F)cc2)c1O]

¹H NMR (400 MHz, CDCl₃) $\delta_H$=7.44 (dd, 1H), 7.01-6.88 (m, 5H), 5.91 (br s, 1H), 3.73 (s, 3H), 2.81-2.65 (m 4H), 2.30 (s, 3H).

Example 3 Preparation of 4-[3-chloro-6-fluoro-2-[2-[6-(trifluoromethyl)-3-pyridyl]ethyl]phenyl]-5-hydroxy-2,6-dimethyl-pyridazin-3-one

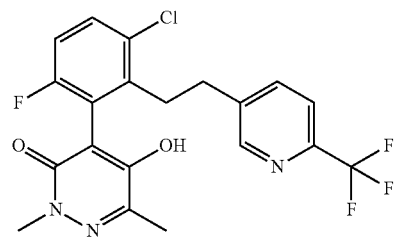 [SMILES: Cc1nn(C)c(=O)c(-c2c(F)ccc(Cl)c2CCc2ccc(C(F)(F)F)nc2)c1O]

3.1 [5-[3-chloro-6-fluoro-2-[(E)-2-[6-(trifluoromethyl)-3-pyridyl]vinyl]phenyl]-1,3-dimethyl-6-oxo-pyridazin-4-yl] 2-methylpropanoate Triethylamine (12 mL) was sparged with nitrogen for 2 minutes. It was then added to a mixture of [5-(2-bromo-3-chloro-6-fluoro-phenyl)-1,3-dimethyl-6-oxo-pyridazin-4-yl] 2-methylpropanoate (1.65 g, 3.95 mmol, 1.0 eq.) [prepared as described in Example 1], Pd₂(dba)₃ (90 mg, 0.099 mmol, 0.025 eq.) and tri tert-butylphosphonium tetrafluoroborate (115 mg, 0.40 mmol, 0.1 eq.). 2-(trifluoromethyl)-5-vinyl-pyridine (1.71 g, 9.88 mmol, 2.5 eq.) was added and the mixture heated at 95° C. for 6 hours.

The mixture was allowed to cool to room temperature then diluted with dichloromethane (20 mL). The mixture was washed with hydrochloric acid (20 mL, 2.0 M). The organics were dried over MgSO₄, filtered and concentrated in vacuo. The crude product was purified by flash column chromatography to provide [5-[3-chloro-6-fluoro-2-[(E)-2-[6-(trifluoromethyl)-3-pyridyl]vinyl]phenyl]-1,3-dimethyl-6-oxo-pyridazin-4-yl] 2-methylpropanoate (1.41 g, 2.76 mmol, 70% yield) as an orange oil.

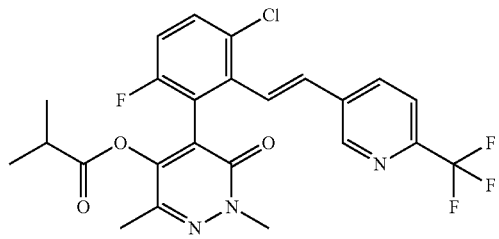 [SMILES: Cc1nn(C)c(=O)c(-c2c(F)ccc(Cl)c2/C=C/c2ccc(C(F)(F)F)nc2)c1OC(=O)C(C)C]

¹H NMR (400 MHz, CDCl₃) δH: 8.65 (d, J=1.6, 1H), 7.87 (dd, J=8.2 and 2.1, 1H), 7.64 (d, J=8.2, 1H), 7.47 (dd, J=8.9 and 5.0, 1H), 7.17 (d, J=16.5, 1H), 7.08 (t, J=8.7, 1H), 6.75 (d, J=16.5, 1H), 3.71 (s, 3H), 2.66 (spt, J=7.0, 1H), 2.24 (s, 3H), 1.11 (d, J=7.0, 3H), 1.08 (d, J=7.1, 3H).

3.2 [5-[3-chloro-6-fluoro-2-[2-[6-(trifluoromethyl)-3-pyridyl]ethyl]phenyl]-1,3-dimethyl-6-oxo-pyridazin-4-yl] 2-methylpropanoate Tetrahydrofuran (12 mL) was added to a mixture of [5-[3-chloro-6-fluoro-2-[(E)-2-[6-(trifluoromethyl)-3-pyridyl]vinyl]phenyl]-1,3-dimethyl-6-oxo-pyridazin-4-yl] 2-methylpropanoate (1.2 g, 2.4 mmol, 1.0 eq.) and 10% palladium on activated charcoal catalyst (0.25 g) under nitrogen atmosphere. The mixture was subjected to hydrogenation at 4 bar hydrogen for 16 hours.

The mixture was filtered through Celite™, washing with further tetrahydrofuran, and the filtrate was concentrated in vacuo. The crude product was purified by flash column chromatography to provide [5-[3-chloro-6-fluoro-2-[2-[6-(trifluoromethyl)-3-pyridyl]ethyl]phenyl]-1,3-dimethyl-6-oxo-pyridazin-4-yl] 2-methylpropanoate (1.1 g, 91% yield) as a colourless oil.

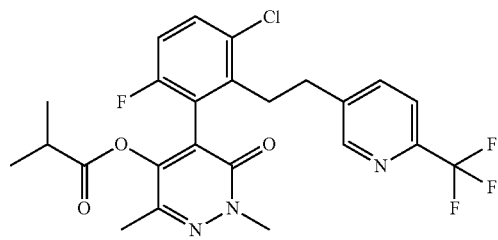 [SMILES: Cc1nn(C)c(=O)c(-c2c(F)ccc(Cl)c2CCc2ccc(C(F)(F)F)nc2)c1OC(=O)C(C)C]

¹H NMR (400 MHz, CDCl₃) δH: 8.53 (d, J=1.2, 1H), 7.69-7.63 (m, 1H), 7.62-7.55 (m, 1H), 7.44 (dd, J=8.8 and 5.1, 1H), 7.02 (t, J=8.6, 1H), 3.86 (s, 3H), 3.10-2.98 (m, 1H), 2.97-2.81 (m, 2H), 2.76-2.64 (m, 1H), 2.55 (spt, J=7.0, 1H), 2.26 (s, 3H), 0.99 (d, J=7.0, 3H), 0.95 (d, J=7.0, 3H).

3.3 4-[3-chloro-6-fluoro-2-[2-[6-(trifluoromethyl)-3-pyridyl]ethyl]phenyl]-5-hydroxy-2,6-dimethyl-pyridazin-3-one Lithium hydroxide (0.13 g, 5.3 mmol, 3.0 eq.) was added to a solution of [5-[3-chloro-6-fluoro-2-[2-[6-(trifluoromethyl)-3-pyridyl]ethyl]phenyl]-1,3-dimethyl-6-oxo-pyridazin-4-yl] 2-methylpropanoate (0.90 g, 1.8 mmol, 1.0 eq.) in a mixture of ethanol (13 mL) and water (4.4 mL). The mixture was stirred at room temperature for 2 days.

The mixture was concentrated in vacuo. The mixture was acidified to pH 1 by addition of hydrochloric acid (6.0 mL, 2.0 M) resulting in formation of a precipitate. The solid was isolated by filtration and re-dissolved in dichloromethane (40 mL). The dichloromethane solution was dried over MgSO₄, filtered and concentrated in vacuo to afford crude product. Purification by flash column chromatography gave impure title compound as a white foam. The material was further purified by reverse phase column chromatography to provide 4-[3-chloro-6-fluoro-2-[2-[6-(trifluoromethyl)-3-pyridyl]ethyl]phenyl]-5-hydroxy-2,6-dimethyl-pyridazin-3-one (0.232 g, 0.525 mmol, 30% yield) as a white foam.

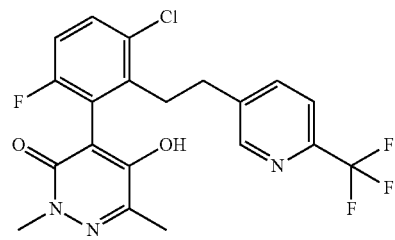 [SMILES: Cc1nn(C)c(=O)c(-c2c(F)ccc(Cl)c2CCc2ccc(C(F)(F)F)nc2)c1O]

¹H NMR (400 MHz, CDCl₃) δH: 8.30 (s, 1H), 7.54 (d, J=1.2, 2H), 7.37 (dd, J=8.8 and 5.1, 1H), 6.95 (t, J=8.5, 1H), 3.69 (s, 3H), 2.92-2.65 (m, 4H), 2.28 (s, 3H).

Example 4 Preparation of 4-[3-chloro-2-[2-(2-chloro-4-pyridyl)ethyl]-6-fluoro-phenyl]-5-hydroxy-2,6-dimethyl-pyridazin-3-one

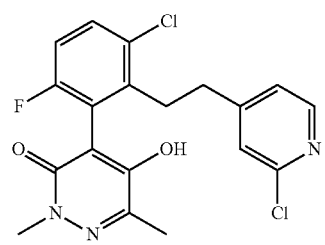 [SMILES: Cc1nn(C)c(=O)c(-c2c(F)ccc(Cl)c2CCc2ccnc(Cl)c2)c1O]

4.1 [5-[3-chloro-6-fluoro-2-[(E)-2-(6-methyl-4,8-dioxo-1,3,6,2-dioxazaborocan-2-yl)vinyl]phenyl]-1,3-dimethyl-6-oxo-pyridazin-4-yl] 2-methylpropanoate

[5-(2-bromo-3-chloro-6-fluoro-phenyl)-1,3-dimethyl-6-oxo-pyridazin-4-yl] 2-methylpropanoate (5.00 g, 11.97 mmol, 1.0 eq), 6-methyl-2-vinyl-1,3,6,2-dioxazaborocane-4,8-dione (2.63 g, 14.36 mmol, 1.2 eq) and chloro[(tri-tert-butylphosphine)-2-(2-aminobiphenyl)] palladium(II) (307 mg, 0.60 mmol, 0.05 eq) were charged into a 250 ml round bottom flask fitted with a condenser, stirrer bar and nitrogen bubbler. THF (100 mL) was added followed by N,N-diisopropylethylamine (4.2 mL, 23.94 mmol, 2.0 eq) against a flow of nitrogen and the mixture heated to reflux for 3 h.

The reaction mixture was allowed to cool to room temperature then diluted in DCM and filtered through Celite™, washing with further portions of DCM. The eluent was then concentrated to dryness.

The crude product purified by flash column chromatography to afford [5-[3-chloro-6-fluoro-2-[(E)-2-(6-methyl-4,8-dioxo-1,3,6,2-dioxazaborocan-2-yl)vinyl]phenyl]-1,3-dimethyl-6-oxo-pyridazin-4-yl] 2-methylpropanoate (5.91 g, 11.4 mmol, 95% yield) as an off white solid.

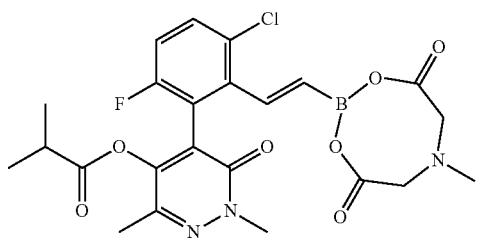 [SMILES: Cc1nn(C)c(=O)c(-c2c(F)ccc(Cl)c2/C=C/B2OC(=O)CN(C)CC(=O)O2)c1OC(=O)C(C)C]

¹H NMR (400 MHz, DMSO-d₆) δ=7.63 (dd, J=5.1, 8.9 Hz, 1H), 7.31 (t, J=8.9 Hz, 1H), 6.65 (d, J=18.3 Hz, 1H), 5.68 (d, J=18.3 Hz, 1H), 4.24 (dd, J=11.9, 17.2 Hz, 2H), 3.95-3.83 (m, 2H), 3.70 (s, 3H), 2.66 (spt, J=7.0 Hz, 1H), 2.16 (s, 3H), 0.90 (d, J=7.0 Hz, 3H), 0.89 (d, J=7.0 Hz, 3H)

4.2 4-[3-chloro-2-[(E)-2-(2-chloro-4-pyridyl)vinyl]-6-fluoro-phenyl]-5-hydroxy-2,6-dimethyl-pyridazin-3-one

[5-[3-Chloro-6-fluoro-2-[(E)-2-(6-methyl-4,8-dioxo-1,3,6,2-dioxazaborocan-2-yl)vinyl]phenyl]-1,3-dimethyl-6-oxo-pyridazin-4-yl] 2-methylpropanoate (10.0 g, 19.24 mmol, 1.0 eq), potassium carbonate (8.06 g, 3.0 eq) and 1,1-bis(diphenylphosphino)ferrocene]dichloropalladium(II) dichloromethane complex [PdCl2(dppf).DCM] (786 mg, 0.96 mmol, 0.05 eq) were charged into a 250 mL flask equipped with a stirrer bar, condenser and nitrogen inlet. The reaction vessel was evacuated and back-filled with nitrogen three times. Acetonitrile (192 mL, de-oxygenated by sparging with N₂(g)) was added by cannula followed by 4-bromo-2-chloro-pyridine (5.55 g, 1.5 eq) and water (6.93 mL, 20 eq). The reaction mixture was then heated at reflux for 17 hrs.

The reaction mixture was allowed to cool to room temperature then concentrated in vacuo. The residue was diluted with water (50 mL) and DCM (100 mL) and the aqueous phase carefully acidified to pH 3 by slow addition of 2M HCl (aq.). The organic layer was separated and the aqueous phase extracted with a further two portions of DCM (50 mL). The combined organic extracts were dried by passing through a phase separation cartridge then concentrated in vacuo.

The crude product was purified by flash column chromatography to afford 4-[3-chloro-2-[(E)-2-(2-chloro-4-pyridyl)vinyl]-6-fluoro-phenyl]-5-hydroxy-2,6-dimethyl-pyridazin-3-one (5.79 g, 74% yield) as a pink solid.

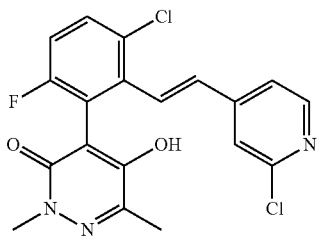 [SMILES: Cc1nn(C)c(=O)c(-c2c(F)ccc(Cl)c2/C=C/c2ccnc(Cl)c2)c1O]

¹H NMR (500 MHz, DMSO-d₆) δ=10.85 (br s, 1H), 8.34 (d, J=5.1 Hz, 1H), 7.63 (dd, J=5.1, 8.9 Hz, 1H), 7.54 (d, J=1.4 Hz, 1H), 7.39 (dd, J=1.4, 5.1 Hz, 1H), 7.33 (t, J=8.9 Hz, 1H), 7.31 (d, J=16.5 Hz, 1H), 6.56 (d, J=16.5 Hz, 1H), 3.53 (s, 3H), 2.19 (s, 3H)

4.3 4-[3-chloro-2-[2-(2-chloro-4-pyridyl)ethyl]-6-fluoro-phenyl]-5-hydroxy-2,6-dimethyl-pyridazin-3-one 4-[3-Chloro-2-[(E)-2-(2-chloro-4-pyridyl)vinyl]-6-fluoro-phenyl]-5-hydroxy-2,6-dimethyl-pyridazin-3-one (5.00 g) was subjected to catalytic hydrogenation in a 2:1 mixture of EtOAc:MeOH (150 mL) over 5% Rh/Al₂O₃ catalyst (1.27 g) at 4 bar H₂.

After 8.5 hrs, the reaction mixture was filtered through a pad of Celite™, washing with ethyl acetate/methanol (1:1). The filtrate was concentrated in-vacuo to afford a crude residue.

The crude product was purified by flash column chromatography to afford 4-[3-chloro-2-[2-(2-chloro-4-pyridyl)ethyl]-6-fluoro-phenyl]-5-hydroxy-2,6-dimethyl-pyridazin-3-one (2.33 g, 46% yield) as a white solid.

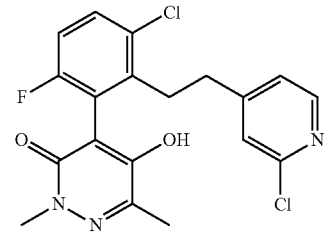 [SMILES: Cc1nn(C)c(=O)c(-c2c(F)ccc(Cl)c2CCc2ccnc(Cl)c2)c1O]

¹H NMR (400 MHz, DMSO-d₆) δ=10.83 (br s, 1H), 8.24 (d, J=5.1 Hz, 1H), 7.54 (dd, J=5.3, 8.9 Hz, 1H), 7.23 (t, J=8.9 Hz, 1H), 7.16 (br s, 1H), 7.08 (dd, J=1.4, 5.1 Hz, 1H), 3.60 (s, 3H), 2.84-2.65 (m, 4H), 2.25 (s, 3H)

Example 5 Preparation of [5-[3-chloro-2-[(E)-2-(4-cyclopropylphenyl)vinyl]-6-fluoro-phenyl]-1,3-dimethyl-6-oxo-pyridazin-4-yl] 2-methylpropanoate

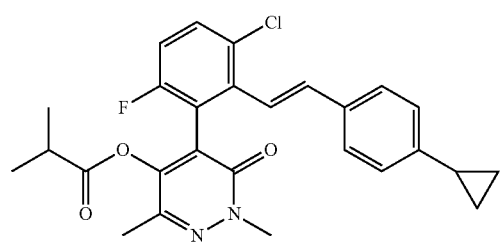 [SMILES: Cc1nn(C)c(=O)c(-c2c(F)ccc(Cl)c2/C=C/c2ccc(C3CC3)cc2)c1OC(=O)C(C)C]

5.1 [5-(3-chloro-6-fluoro-2-vinyl-phenyl)-1,3-dimethyl-6-oxo-pyridazin-4-yl] 2-methylpropanoate

[5-(2-bromo-3-chloro-6-fluoro-phenyl)-1,3-dimethyl-6-oxo-pyridazin-4-yl] 2-methylpropanoate (4.177 g, 10.00 mmol, 1.0 eq) and tributyl(vinyl)stannane (4.384 mL, 15.00 mmol, 1.50 eq) were dissolved in toluene (60.00 mL) then 1,1-bis(diphenylphosphino)ferrocene]dichloropalladium(II) dichloromethane complex [PdCl2(dppf).DCM] (408 mg, 0.50 mmol, 0.05 eq) was added. The reaction mixture was heated at reflux overnight.

The reaction mixture was allowed to cool to room temperature then concentrated in vacuo. The crude product was then purified by flash column chromatography to afford [5-(3-chloro-6-fluoro-2-vinyl-phenyl)-1,3-dimethyl-6-oxo-pyridazin-4-yl] 2-methylpropanoate as an off-white solid (3.02 g, 83% yield).

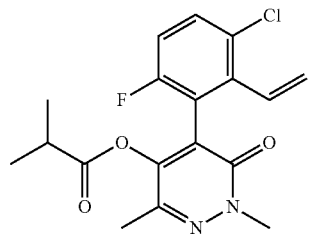 [SMILES: C=Cc1c(Cl)ccc(F)c1-c1c(OC(=O)C(C)C)c(C)nn(C)c1=O]

¹H NMR (400 MHz, CDCl₃) δ=7.40 (dd, J=5.1, 8.7 Hz, 1H), 6.99 (t, J=8.7 Hz, 1H), 6.65 (dd, J=11.6, 17.6 Hz, 1H), 5.37-5.30 (m, 2H), 3.79 (s, 3H), 2.59 (spt, J=7.0 Hz, 1H), 2.23 (s, 3H), 1.04 (d, J=7.0 Hz, 4H), 1.03 (d, J=7.0 Hz, 1H)

5.2 [5-[3-chloro-2-[(E)-2-(4-cyclopropylphenyl) vinyl]-6-fluoro-phenyl]-1,3-dimethyl-6-oxo-pyridazin-4-yl] 2-methylpropanoate A stirred mixture of [5-(3-chloro-6-fluoro-2-vinyl-phenyl)-1,3-dimethyl-6-oxo-pyridazin-4-yl] 2-methylpropanoate (300 mg, 1.0 eq), chloro[(tri-tert-butylphosphine)-2-(2-aminobiphenyl)]palladium(II) (21 mg, 0.05 eq), 1-bromo-4-cyclopropylbenzene (243 mg, 1.5 eq) and N,N-diisopropylethylamine (0.29 mL, 2.0 eq) in toluene (5 mL) under $N_2$ was heated at reflux for 3 hrs.

The reaction mixture was allowed to cool to room temperature then diluted with DCM and filtered through a pad of Celite™, eluting with further portions of DCM. The filtrate was concentrated in vacuo to give the crude product.

The crude product was purified by flash column chromatography to give [5-[3-chloro-2-[(E)-2-(4-cyclopropylphenyl)vinyl]-6-fluoro-phenyl]-1,3-dimethyl-6-oxo-pyridazin-4-yl] 2-methylpropanoate (285 mg, 72% yield) as a pale yellow gum.

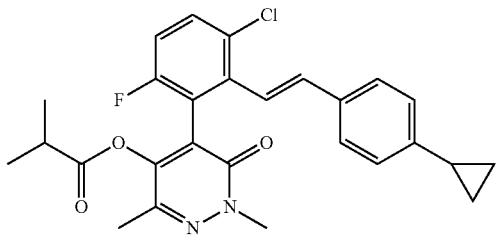 [SMILES: Cc1nn(C)c(=O)c(-c2c(F)ccc(Cl)c2/C=C/c2ccc(C3CC3)cc2)c1OC(=O)C(C)C]

$^1$H NMR (400 MHz, CDCl$_3$) δ=7.41 (dd, J=5.1, 8.9 Hz, 1H), 7.26-7.22 (m, 2H), 7.02-6.98 (m, 2H), 6.99 (t, J=8.9 Hz, 1H), 6.93 (d, J=16.5 Hz, 1H), 6.59 (d, J=16.5 Hz, 1H), 3.71 (s, 3H), 2.62 (spt, J=7.0 Hz, 1H), 2.19 (s, 3H), 1.87 (tt, J=5.0, 8.4 Hz, 1H), 1.07 (d, J=7.0 Hz, 3H), 1.06 (d, J=7.0 Hz, 1H), 0.99-0.93 (m, J=2.0, 8.4 Hz, 2H), 0.73-0.64 (m, 2H).

Example 6 Preparation of 4-[3-chloro-6-fluoro-2-(2-phenylethynyl)phenyl]-5-hydroxy-2,6-dimethyl-pyridazin-3-one A stirred mixture of [5-(2-bromo-3-chloro-6-fluoro-phenyl)-1,3-dimethyl-6-oxo-pyridazin-4-yl] 2-methylpropanoate (400 mg, 1.0 eq), copper (1) iodide (11 mg, 0.06 eq), chloro[(tri-tert-butylphosphine)-2-(2-aminobiphenyl)] palladium(II) (37 mg, 0.075 eq) and diisopropylamine (9 mL) was heated at 120° C. for 1 hr in a sealed vessel under microwave irradiation.

After cooling to room temperature the reaction mixture was concentrated in vacuo then diluted with DCM before filtering through a pad of Celite™. The filtrate was concentrated in vacuo to give the crude product.

The crude product was purified by mass-directed reverse-phase prep HPLC to afford [5-[3-chloro-6-fluoro-2-(2-phenylethynyl)phenyl]-1,3-dimethyl-6-oxo-pyridazin-4-yl] 2-methylpropanoate (57 mg, 14% yield).

[5-[3-chloro-6-fluoro-2-(2-phenylethynyl)phenyl]-1,3-dimethyl-6-oxo-pyridazin-4-yl] 2-methylpropanoate was dissolved in ethanol (5 mL) then water (0.9 mL) and lithium hydroxide monohydrate (15 mg, 3.0 eq) were added. The reaction mixture was stirred at room temperature for 2 hrs, then concentrated in vacuo to remove the ethanol. The remaining aqueous phase was acidified to pH 3 by addition of 2M HCl then extracted with DCM (10 mL then 2×5 mL). The combined organics were dried by passage through a phase separating cartridge then concentrated in vacuo to give the crude product.

The crude product was purified by flash column chromatography to afford 4-[3-chloro-6-fluoro-2-(2-phenylethynyl) phenyl]-5-hydroxy-2,6-dimethyl-pyridazin-3-one (30 mg, 69% yield) as a white solid.

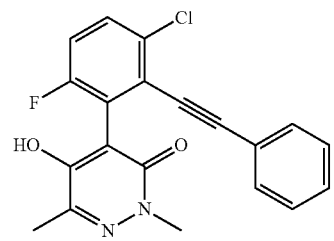 [SMILES: Cc1nn(C)c(=O)c(-c2c(F)ccc(Cl)c2C#Cc2ccccc2)c1O]

$^1$H NMR (400 MHz, CDCl$_3$) δ ppm 7.35 (dd, J=8.00, 5.00 Hz, 1H), 7.33-7.27 (m, 5H), 6.98 (t, J=8.60 Hz, 1H), 3.71-3.63 (m, 3H), 2.32-2.26 (m, 3H).

Compounds 1.0001, 1.0002, 1.0012, 1.0018, 1.0024, 1.0042, 1.0048, 1.0054, 1.0060, 1.0066, 1.0072, 1.0089, 1.0101, 1.0119, 1.0095, 1.0143, 1.0125, 1.0327, 1.0333, 1.0339, 1.0345, 1.0351, 1.0357, 1.0363, 1.0369, 1.0375, 1.0387, 1.0417, 1.0429, 1.0441, 1.0597, 1.0603, 1.0609, 1.0615, 1.0621, 1.0627, 1.0633, 1.0639, 1.0645, 1.0651, 1.0657, 1.0663, 1.0669, 1.0675, 1.0681, 1.0687, 1.0693, 1.0789, 1.0885, 1.0891, 1.0897, 1.0903, 1.0915, 1.0921, 1.0933, 1.0149, 1.0969, 1.0975, 1.0975, 1.0981, 1.0993, 1.0999, 1.1005, 1.1011, 1.1185, 1.1191, 1.1257, 1.1258, 1.1259, 1.1261, 1.1265, 1.1267, 1.1269, 1.1270, 1.1271, 1.1282, 1.1293, 1.1294, 1.1348, 1.1351, 1.1352, 1.1357, 1.1363, 1.1367, 1.1369, 1.1370, 1.1371, 1.1372, 1.1373, 1.1383, 1.1387, 1.1391, 1.1392, 1.1393, 1.1394, 1.1447, 1.1454, 1.1457, 1.1458, 1.1556, 1.1560, 1.1651, 1.1652, 1.1653, 1.1654, 1.1655, 1.1656 were prepared using the general methods as described supra. Table 2 below shows the structure of these compounds and NMR characterising data.

TABLE 2

Preparation examples of compounds of formula (I). The numbering system used to describe the positions of X and Y is shown for the purposes of clarity only.

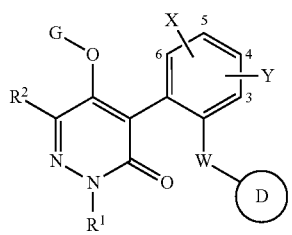

(I)

| Cmpd | R¹ | R² | G | X | Y | W | D | NMR details |
|------|----|----|---|---|---|---|---|-------------|
| 1.001 | —Me | —Me | —H | 6-F | 3-Cl | —CH$_2$—CH$_2$— | —Ph | ¹H NMR (DMSO-d6) $\delta_H$: 10.85 (s, 1H), 7.57-7.53 (m, 1H), 7.27-7.15 (m, 4H), 7.0 (d, J = 7.2, 2H), 3.60 (s, 3H), 2.73-2.50 (m, 4H), 2.25 (s, 3H). |
| 1.0002 | —Me | —Me | —H | 6-F | 3-Cl | (E)-CH=CH— | —Ph | ¹H NMR (DMSO-d6) $\delta_H$: 10.8 (s, 1H), 7.62 (m, 1H), 7.37-7.24 (m, 6H), 6.94 (d, J = 16.5, 1H), 6.57 (d, J = 16.5, 1H), 6.53 (s, 3H), 2.18 (s, 3H). |
| 1.0012 | —Me | —Me | —H | 6-F | 3-Cl | —CH$_2$—CH$_2$— | 4-chloro-phenyl- | ¹H NMR (400 MHz, chloroform) δ = 7.51-7.44 (m, 1H), 7.21-7.15 (m, 2H), 7.07-6.98 (m, 1H), 6.93 (d, J = 8.4 Hz, 2H), 5.43-5.18 (m, 1H), 3.76 (s, 3H), 2.86-2.67 (m, 4H), 2.31 (s, 3H). |
| 1.0018 | —Me | —Me | —H | 6-F | 3-Cl | —CH$_2$—CH$_2$— | 4-trifluoro-methyl-phenyl- | ¹H NMR (400 MHz, CDCl$_3$) δ ppm 2.29 (d, J = 4.16 Hz, 3 H) 2.70-2.93 (m, 4 H) 3.65-3.81 (m, 3 H) 6.95-7.06 (m, 1 H) 7.12 (br d, J = 6.48 Hz, 2 H) 7.48 (d, J = 8.07 Hz, 3 H). |
| 1.0024 | —Me | —Me | —H | 6-F | 3-Cl | —CH$_2$—CH$_2$— | 4-cyano-phenyl- | ¹H NMR (400 MHz, CDCl3) δ ppm 7.46-7.51 (m, 2 H) 7.26-7.31 (m, 1 H) 7.08 (d, J = 8.19 Hz, 2 H) 6.86 (t, J = 8.50 Hz, 1 H) 3.63 (s, 3 H) 2.61-2.77 (m, 4 H) 2.24 (s, 3 H). |
| 1.0042 | —Me | —Me | —H | 6-F | 3-Cl | —CH$_2$—CH$_2$— | 4-trifluoro-methyl-3-pyridyl- | ¹H NMR (400 MHz, CDCl$_3$) δ = 8.30 (s, 1H), 7.54 (d, J = 1.2, 2H), 7.37 (dd, J = 8.8 and 5.1, 1H), 6.95 (t, J = 8.5, 1H), 3.69 (s, 3H), 2.92-2.65 (m, 4H), 2.28 (s, 3H). |
| 1.0048 | —Me | —Me | —H | 6-F | 3-Cl | —CH$_2$—CH$_2$— | 4-fluoro-phenyl- | ¹H NMR (400 MHz, CDCl$_3$) δ ppm 7.44 (dd, 1H), 7.01-6.88 (m, 5H), 5.91 (br s, 1H), 3.73 (s, 3H), 2.81-2.65 (m, 4H), 2.30 (s, 3H). |
| 1.0054 | —Me | —Me | —H | 6-F | 3-Cl | —CH$_2$—CH$_2$— | 3-pyridyl- | ¹H NMR (400 MHz, DMSO-d6) δ ppm 2.26 (s, 3 H) 2.58-2.82 (m, 4 H) 3.61 (s, 3 H) 7.22 (t, J = 8.80 Hz, 1 H) 7.26-7.32 (m, 1 H) 7.46 (dt, J = 7.79, 1.79 Hz, 1 H) 7.43-7.49 (m, 1 H) 7.53 (dd, J = 8.86, 5.20 Hz, 1 H) 8.24 (s, 1 H) 8.40 (br d, J = 3.79 Hz, 1 H). |
| 1.0060 | —Me | —Me | —H | 6-F | 3-Cl | —CH$_2$—CH$_2$— | 3,4-difluoro-phenyl- | ¹H NMR (400 MHz, CDCl$_3$) δ = 7.44 (dd, J = 5.2, 8.6 Hz, 1H), 7.04-6.95 (m, 2H), 6.86-6.77 (m, 1H), 6.77-6.63 (m, 1H), 3.78-3.70 (m, 3H), 2.83-2.64 (m, 4H), 2.31 (s, 3H). |
| 1.0066 | —Me | —Me | —H | 6-F | 3-Cl | —CH$_2$—CH$_2$— | 2-trifluoro-methyl-phenyl- | ¹H NMR (400 MHz, CDCl$_3$) δ = 7.53 (br. d, J = 7.5 Hz, 1H), 7.43 (br. t, J = 7.5 Hz, 1H), 7.33 (dd, J = 5.1, 8.5 Hz, 1H), 7.29-7.22 (m, 2H), 6.89 (t, J = 8.5 Hz, 1H), 3.65 (s, 3H), 2.83-2.65 (m, 4H), 2.26 (s, 3H). |
| 1.0072 | —Me | —Me | —(C=O)$^i$Pr | 6-F | 3-Cl | —CH$_2$—CH$_2$— | 4-chloro-phenyl- | ¹H NMR (400 MHz, CDCl$_3$) δ = 7.41 (dd, J = 5.1, 8.9 Hz, 1H), 7.23-7.18 (m, 2H), 7.07-7.03 (m, 2H), 6.98 (t, J = 8.6 Hz, 1H), 3.83 (s, 3H), 2.86-2.67 (m, 4H), 2.54 (m, 1H), 2.24 (s, 3H), 0.97 (d, J = 7.0 Hz, 3H), 0.96 (d, J = 7.0 Hz, 3H). |

TABLE 2-continued

Preparation examples of compounds of formula (I). The numbering system used to describe the positions of X and Y is shown for the purposes of clarity only.

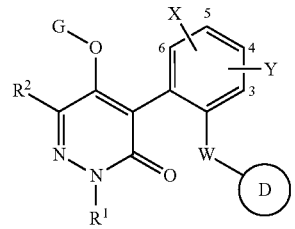

(I)

| Cmpd | R¹ | R² | G | X | Y | W | D | NMR details |
|---|---|---|---|---|---|---|---|---|
| 1.0089 | —Me | —Me | —(C═O)ⁱPr | 6-F | 3-Cl | —CH₂—CH₂— | 4-chloro-phenyl- | ¹H NMR (400 MHz, CDCl₃) δ = 7.41 (dd, J = 5.1, 8.9 Hz, 1H), 7.23-7.18 (m, 2H), 7.07-7.03 (m, 2H), 6.98 (t, J = 8.6 Hz, 1H), 3.83 (s, 3H), 2.86-2.67 (m, 4H), 2.54 (m, 1H), 2.24 (s, 3H), 0.97 (d, J = 7.0 Hz, 3H), 0.96 (d, J = 7.0 Hz, 3H). |
| 1.0101 | —Me | —Me | —(C═O)ⁱPr | 6-F | 3-Cl | —CH₂—CH₂— | 4-fluoro-phenyl- | ¹H NMR (400 MHz, CDCl₃) δ = 7.42 (dd, 1H), 7.11-7.06 (m, 2H), 6.99 (t, 1H), 6.97-6.90 (m, 2H), 3.84 (s, 3H), 2.86-2.68 (m, 4H), 2.55 (sept, 1H), 2.26 (s, 3H), 0.98 (dd, 6H). |
| 1.0119 | —Me | —Me | —(C═O)ⁱPr | 6-F | 3-Cl | —CH₂—CH₂— | 4-tolyl- | ¹H NMR (400 MHz, CDCl₃) δ = 7.41 (dd, J = 8.8 & 5.1, 1H), 7.10-6.92 (m, 5H), 3.83 (s, 3H), 2.86-2.68 (m, 4H), 2.54 (sep, J = 7.0, 1H), 2.31 (s, 3H), 2.24 (s, 3H), 0.96 (d, J = 7.0, 6H). |
| 1.0095 | —Me | —Me | —(C═O)ⁱPr | 6-F | 3-Cl | —CH₂—CH₂— | 4-trifluoro-methyl-phenyl- | ¹H NMR (400 MHz, CDCl₃) dₕ = 7.50 (d, J = 8.0, 2H), 7.43 (dd, J = 8.9 & 5.1, 1H), 7.24 (d, J = 8.0, 2H), 7.00 (t, J = 8.6 Hz, 1H), 3.84 (s, 3H), 2.99-2.80 (m, 3H), 2.73 (dd, J = 11.0 & 6.2, 1H), 2.54 (hep, J = 7.0, 1H), 2.25 (s, 3H), 0.98 (d, J = 7.0, 3H), 0.95 (d, J = 7.0, 3H). |
| 1.0143 | —Me | —Me | —(C═O)ⁱPr | 6-F | 3-Cl | —CH₂—CH₂— | 2-trifluoro-methyl-phenyl | ¹H NMR (400 MHz, chloroform) δ = 7.56 (d, J = 7.8 Hz, 1H), 7.49-7.37 (m, 3H), 7.28 (t, J = 7.2 Hz, 1H), 7.00 (t, J = 8.6 Hz, 1H), 3.84 (s, 3H), 2.99-2.77 (m, 4H), 2.53 (spt, J = 7.0 Hz, 1H), 2.26 (s, 3H), 0.96 (app. t, J = 7.0 Hz, 6H) |
| 1.0125 | —Me | —Me | —(C═O)ⁱPr | 6-F | 3-Cl | —CH₂—CH₂— | 4-fluoro-phenyl- | ¹H NMR (400 MHz, CDCl₃) δ = 7.42 (dd, 1H), 7.11-7.06 (m, 2H), 6.99 (t, 1H), 6.97-6.90 (m, 2H), 3.84 (s, 3H), 2.86-2.68 (m, 4H), 2.55 (sept, 1H), 2.26 (s, 3H), 0.98 (dd, 6H). |
| 1.0327 | —Me | —Me | H | 6-F | 3-Cl | —CH₂—CH₂— | 3-chloro-4-fluoro-phenyl | ¹H NMR (400 MHz, chloroform) δ = 7.34 (dd, J = 5.1, 8.9 Hz, 1H), 6.99 (dd, J = 2.0, 7.3 Hz, 1H), 6.96 (t, J = 8.6 Hz, 1H), 6.90 (t, J = 8.9 Hz, 1H), 6.82 (ddd, J = 2.0, 4.8, 8.6 Hz, 1H), 3.66 (s, 3H), 2.75-2.55 (m, 4H), 2.25 (s, 3H) |
| 1.0333 | —Me | —Me | H | 6-F | 3-Cl | —CH₂—CH₂— | 3-chloro-4-pyridyl | ¹H NMR (400 MHz, chloroform) δ = 8.14 (d, J = 5.0 Hz, 1H), 7.38 (dd, J = 5.1, 8.9 Hz, 1H), 7.01 (d, J = 1.2 Hz, 1H), 6.98 (t, J = 8.9 Hz, 1H), 6.89 (dd, J = 1.2, 5.0 Hz, 1H), 3.74 (s, 3H), 2.89-2.65 (m, 4H), 2.32 (s, 3H) |
| 1.0339 | —Me | —Me | H | 6-F | 3-Cl | —CH₂—CH₂— | 4-hydroxy-phenyl | ¹H NMR (400 MHz, DMSO-d6) δ = 10.82 (br s, 1H), 9.17 (s, 1H), 7.54 (dd, J = 5.2, 8.9 Hz, 1H), 7.20 (t, J = 8.9 Hz, 1H), 6.82-6.75 (m, 2H), 6.65-6.60 (m, 2H), 3.61 (s, 3H), , 2.69-2.43 (m, 4H), 2.26 (s, 3H) |
| 1.0345 | —Me | —Me | H | 6-F | 3-Cl | —CH₂—CH₂— | 4-cyclo-propyl-phenyl | ¹H NMR (400 MHz, chloroform) δ = 7.37 (dd, J = 5.2, 8.8 Hz, 1H), 6.96-6.88 (m, 2H), 6.91 (t, J = 8.8 Hz, 1H), 6.88-6.83 (m, 2H), 3.67 (s, 3H), 2.82-2.62 (m, 4H), 2.25 (s, 3H), 1.84 (tt, J = 5.0, 8.5 Hz, 1H), 0.95-0.88 (m, 2H), 0.68-0.60 (m, 2H) |

TABLE 2-continued

Preparation examples of compounds of formula (I). The numbering system used to describe the positions of X and Y is shown for the purposes of clarity only.

(I)

| Cmpd | R¹ | R² | G | X | Y | W | D | NMR details |
|---|---|---|---|---|---|---|---|---|
| 1.0351 | —Me | —Me | H | 6-F | 3-Cl | —CH$_2$—CH$_2$— | 1-methyl-3-(trifluoro-methyl)-pyrazol-4-yl | $^1$H NMR (400 MHz, chloroform) δ ppm 7.39-7.27 (m, 1H), 7.08 (br s, 1H), 6.96-6.79 (m, 1H), 3.86-3.76 (m, 3H), 3.71-3.52 (m, 3H), 2.75-2.40 (m, 4H), 2.32-3.16 (m, 3H) |
| 1.0357 | —Me | —Me | H | 6-F | 3-Cl | —CH$_2$—CH$_2$— | thiazol-2-yl | $^1$H NMR (400 MHz, chloroform) δ ppm 7.38 (d, J = 3.30 Hz, 1 H), 7.16-7.11 (m, 2H), 6.89 (t, J = 8.50 Hz, 1 H), 3.52-3.39 (m, 2 H), 3.22-3.08 (m, 1H), 3.06-2.94 (m, 1H), 2.35 (s, 3H) |
| 1.0363 | —Me | —Me | H | 6-F | 3-Cl | —CH$_2$—CH$_2$— | pyrimidin-5-yl | $^1$H NMR (400 MHz, methanol) δ = 8.95 (s, 1H), 8.46 (s, 2H), 7.46 (dd, J = 5.2, 8.8 Hz, 1H), 7.11 (t, J = 8.7 Hz, 1H), 3.72 (s, 3H), 2.99-2.75 (m, 4H), 2.32 (s, 3H) |
| 1.0369 | —Me | —Me | H | 6-F | 3-Cl | —CH$_2$—CH$_2$— | 4-(tert-butoxy)-phenyl | $^1$H NMR (400 MHz, chloroform) δ = 7.28 (dd, J = 5.2, 8.9 Hz, 1H), 6.82 (s, 5H), 3.62 (s, 3H), 2.73-2.50 (m, 4H), 2.23 (s, 3H) |
| 1.0375 | —Me | —Me | H | 6-F | 3-Cl | —CH$_2$—CH$_2$— | thiazol-5-yl | $^1$H NMR (400 MHz, chloroform) δ ppm 8.54 (s, 1 H), 7.38 (s, 2H), 7.03-6.91 (m, 1H), 3.70 (s, 3H), 3.04-2.93 (m, 2H), 2.87-2.79 (m, 2H), 2.28 (s, 3H) |
| 1.0387 | —Me | —Me | —(C=O)$^i$Pr | 6-F | 3-Cl | —CH$_2$—CH$_2$— | 2-chloro-3-pyridyl | $^1$H NMR (400 MHz, chloroform) δ = 8.23 (dd, J = 1.9, 4.7 Hz, 1H), 7.51 (dd, J = 1.9, 7.5 Hz, 1H), 7.41 (dd, J = 5.1, 8.6 Hz, 1H), 7.13 (dd, J = 4.7, 7.5 Hz, 1H), 7.00 (t, J = 8.6 Hz, 1H), 3.84 (s, 3H), 2.98-2.76 (m, 4H), 2.54 (spt, J = 7.0 Hz, 1H), 2.26 (s, 3H), 0.97 (d, J = 7.0 Hz, 3H), 0.96 (d, J = 7.0 Hz, 1H) |
| 1.0417 | —Me | —Me | —(C=O)$^i$Pr | 6-F | 3-Cl | —CH$_2$—CH$_2$— | 4-cyclo-propyl-phenyl | $^1$H NMR (400 MHz, chloroform) δ = 7.41 (dd, J = 5.2, 8.8 Hz, 1H), 7.04-7.00 (m, 2H), 6.98-6.94 (m, 2H), 6.97 (t, J = 8.8 Hz, 1H), 3.83 (s, 3H), 2.84-2.67 (m, 4H), 2.53 (spt, J = 7.0 Hz, 1H), 2.24 (s, 3H), 1.85 (tt, J = 5.1, 8.4 Hz, 1H), 0.96 (d, J = 7.0 Hz, 3H), 0.96 (d, J = 7.0 Hz, 3H), 0.94-0.88 (m, J = 1.9, 8.5 Hz, 2H), 0.68-0.61 (m, 2H) |
| 1.0429 | —Me | —Me | —(C=O)$^i$Pr | 6-F | 3-Cl | —CH$_2$—CH$_2$— | thiazol-2-yl | $^1$H NMR (400 MHz, chloroform) δ ppm 7.65 (d, J = 3.30 Hz, 1 H), 7.43 (dd, J = 8.93, 5.14 Hz, 1 H), 7.17 (d, J = 3.30 Hz, 1 H), 7.04-6.97 (m, 1H), 3.83 (s, 3H), 3.30 (ddd, J = 10.82, 7.03, 5.87 Hz, 2 H), 3.19-3006 (m, 1H), 2.98-2.87 (m, 1H), 2.60-2.50 (m, 1H), 2.25 (s 3H), 0.97 (dd, J = 6.97, 2.57 Hz, 6 H) |
| 1.0441 | —Me | —Me | —(C=O)$^i$Pr | 6-F | 3-Cl | —CH$_2$—CH$_2$— | 4-(tert-butoxy)-phenyl | $^1$H NMR (400 MHz, chloroform) δ = 7.40 (dd, J = 5.1, 8.8 Hz, 1H), 7.03-6.99 (m, 2H), 6.97 (t, J = 8.8 Hz, 1H), 6.90-6.83 (m, 2H), 3.84 (s, 3H), 2.85-2.68 (m, 4H), 2.55 (spt, J = 7.0 Hz, 1H), 2.25 (s, 3H), 1.32 (s, 9H), 0.97 (d, J = 7.0 Hz, 3H), 0.97 (d, J = 7.0 Hz, 3H) |

TABLE 2-continued

Preparation examples of compounds of formula (I). The numbering system used to describe the positions of X and Y is shown for the purposes of clarity only.

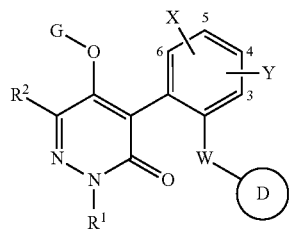

(I)

| Cmpd | R¹ | R² | G | X | Y | W | D | NMR details |
|---|---|---|---|---|---|---|---|---|
| 1.0597 | —Me | —Me | H | 6-F | 3-Cl | —CH₂—CH₂— | 2-cyano-phenyl | ¹H NMR (400 MHz, chloroform) δ = 7.51-7.44 (m, 2H), 7.33-7.24 (m, 3H + CHCl3 peak), 6.95 (t, J = 8.6 Hz, 1H), 3.69 (s, 3H), 2.95-2.79 (m, 4H), 2.30 (s, 3H). |
| 1.0603 | —Me | —Me | H | 6-F | 3-Cl | —CH₂—CH₂— | 3-cyano-phenyl | ¹H NMR (400 MHz, chloroform) δ = 7.46 (td, J = 1.4, 7.6 Hz, 1H), 7.37 (dd, J = 5.2, 8.9 Hz, 1H), 7.35-7.28 (m, 2H), 7.26-7.23 (m, 1H), 6.95 (t, J = 8.6 Hz, 1H), 3.69 (s, 3H), 2.82-2.63 (m, 4H), 2.28 (s, 3H). |
| 1.0609 | —Me | —Me | H | 6-F | 3-Cl | —CH₂—CH₂— | 3-trifluoromethyl-phenyl | ¹H NMR (400 MHz, chloroform) δ = 7.46-7.38 (m, 2H), 7.33 (t, J = 7.6 Hz, 1H), 7.25-7.16 (m, 2H), 6.98 (t, J = 8.5 Hz, 1H), 6.13 (br s, 1H), 3.71 (s, 3H), 2.92-2.66 (m, 4H), 2.28 (s, 3H). |
| 1.0615 | —Me | —Me | H | 6-F | 3-Cl | —CH₂—CH₂— | o-tolyl | ¹H NMR (400 MHz, chloroform) δ = 7.37 (dd, J = 5.1, 8.8 Hz, 1H), 7.11-7.02 (m, 3H), 6.97-6.87 (m, 2H), 3.67 (s, 3H), 2.76-2.58 (m, 4H), 2.26 (s, 3H), 2.05 (s, 3H). |
| 1.0621 | —Me | —Me | H | 6-F | 3-Cl | —CH₂—CH₂— | m-tolyl | ¹H NMR (400 MHz, chloroform) δ = 7.40 (dd, J = 5.1, 8.8 Hz, 1H), 7.14-7.07 (m, 1H), 7.01-6.90 (m, 2H), 6.83-6.74 (m, 2H), 6.21 (brd s, 1H), 3.70 (s, 3H), 2.86-2.59 (m, 4H), 2.28 (s, 3H), 2.26 (s, 3H). |
| 1.0627 | —Me | —Me | H | 6-F | 3-Cl | —CH₂—CH₂— | 2-methyl-4-pyridyl | ¹H NMR (400 MHz, chloroform) δ ppm 8.41 (d, J = 5.99 Hz, 1 H), 7.36 (dd, J = 8.86, 5.07 Hz, 1 H), 7.30 (d, J = 5.99 Hz, 1H), 7.23 (s, 1H), 6.98 (t, J = 8.56 Hz, 1H), 3.69 (s, 3H), 3.03 (s, 2H), 2.97-2.82 (m, 2H), 2.67 (s, 3H), 2.27 (s, 3H) |
| 1.0633 | —Me | —Me | H | 6-F | 3-Cl | —CH₂—CH₂— | 2-trifluoromethyl-4-pyridyl | ¹H NMR (400 MHz, chloroform) δ = 8.48 (d, J = 5.0 Hz, 1H), 7.26 (dd, J = 5.6, 8.5 Hz, 1H), 7.26 (br s, 1H), 7.13 (d, J = 5.0 Hz, 1H), 6.85 (t, J = 8.5 Hz, 1H), 3.63 (s, 3H), 2.82-2.69 (m, 3H), 2.69-2.56 (m, 1H), 2.24 (s, 3H) |
| 1.0639 | —Me | —Me | H | 6-F | 3-Cl | —CH₂—CH₂— | 2-amino-4-pyridyl | ¹H NMR (400 MHz, DMSO-d6) δ ppm 7.73 (d, J = 5.26 Hz, 1 H) 7.50 (dd, J = 8.86, 5.20 Hz, 1 H) 7.16 (t, J = 8.62 Hz, 1 H) 6.18 (s, 2 H) 3.57 (s, 3 H) 2.60-2.69 (m, 2 H) 2.40-2.47 (m, 2 H) 2.20 (s, 3 H) |
| 1.0645 | —Me | —Me | H | 6-F | 3-Cl | —CH₂—CH₂— | 2-fluoro-4-pyridyl | ¹H NMR (400 MHz, chloroform) δ ppm 8.01 (d, J = 5.13 Hz, 1 H) 7.42 (dd, J = 8.86, 5.20 Hz, 1 H) 6.98-7.07 (m, 1 H) 6.84-6.90 (m, 1 H) 6.62 (s, 1 H) 3.74 (s, 3 H) 2.71-2.94 (m, 4 H) 2.31 (s, 3 H) |
| 1.0651 | —Me | —Me | H | 6-F | 3-Cl | —CH₂—CH₂— | 4-pyridyl | ¹H NMR (400 MHz, DMSO-d6) δ = 8.66 (d, J = 6.4 Hz, 2H), 7.55 (d, J = 6.4 Hz, 2H), 7.54 (dd, J = 5.0, 8.8 Hz, 1H), 7.23 (t, J = 8.8 Hz, 1H), 3.59 (s, 3H), 2.98-2.75 (m, 4H), 2.26 (s, 3H) |

TABLE 2-continued

Preparation examples of compounds of formula (I). The numbering system used to describe the positions of X and Y is shown for the purposes of clarity only.

(I)

| Cmpd | R¹ | R² | G | X | Y | W | D | NMR details |
|---|---|---|---|---|---|---|---|---|
| 1.0657 | —Me | —Me | H | 6-F | 3-Cl | —CH₂—CH₂— | 4-(methyl-amino)-phenyl | ¹H NMR (400 MHz, chloroform) δ ppm 7.43 (dd, J = 8.86, 5.20 Hz, 1 H), 6.97 (t, J = 8.56 Hz, 1 H), 6.81 (d, J = 8.44 Hz, 2 H), 6.48 (d, J = 8.44 Hz, 2 H), 3.72 (s, 3H), 2.80 (s, 4H), 2.75-2.56 (m, 3H), 2.28 (s, 3H) |
| 1.0663 | —Me | —Me | H | 6-F | 3-Cl | —CH₂—CH₂— | 4-amino-phenyl | ¹H NMR (400 MHz, chloroform) δ ppm 7.37 (dd, J = 8.80, 5.26 Hz, 1 H), 6.95 (s, 1 H), 6.80 (d, J = 8.31 Hz, 2 H), 6.55 (d, J = 8.31 Hz, 2 H), 3.70 (s, 3 H), 2.71 (br s, 2 H), 2.59 (s, 2 H), 2.28 (s, 3 H) |
| 1.0669 | —Me | —Me | —(C═O)ⁱPr | 6-F | 3-Cl | —CH₂—CH₂— | 2-cyano-phenyl | ¹H NMR (400 MHz, chloroform) δ = 7.56 (dd, J = 1.1, 7.7 Hz, 1H), 7.51-7.46 (m, 1H), 7.43 (dd, J = 5.1, 8.8 Hz, 1H), 7.32 (d, J = 7.7 Hz, 1H), 7.30-7.26 (m, 1H + CHCl3 peak), 7.01 (t, J = 8.6 Hz, 1H), 3.85 (s, 3H), 3.15-3.05 (m, 1H), 3.04-2.80 (m, 3H), 2.55 (spt, J = 7.0 Hz, 1H), 2.27 (s, 3H), 0.97 (dd, J = 1.1, 7.0 Hz, 6H). |
| 1.0675 | —Me | —Me | —(C═O)ⁱPr | 6-F | 3-Cl | —CH₂—CH₂— | 3-cyano-phenyl | ¹H NMR (400 MHz, chloroform) δ = 7.50-7.46 (m, 1H), 7.46-7.37 (m, 3H), 7.37-7.31 (m, 1H), 7.00 (t, J = 8.6 Hz, 1H), 3.86 (s, 3H), 3.00-2.78 (m, 3H), 2.73-2.63 (m, 1H), 2.55 (quin, J = 7.0 Hz, 1H), 2.26 (s, 3H), 0.97 (d, J = 7.0, 13.5 Hz, 6H). |
| 1.0681 | —Me | —Me | —(C═O)ⁱPr | 6-F | 3-Cl | —CH₂—CH₂— | 3-trifluoro-methyl-phenyl | ¹H NMR (400 MHz, chloroform) δ = 7.47-7.39 (m, 2H), 7.39-7.30 (m, 3H), 7.00 (t, J = 8.6 Hz, 1H), 3.86 (s, 3H), 2.96-2.83 (m, 3H), 2.74-2.65 (m, 1H), 2.55 (spt, J = 7.0 Hz, 1H), 2.26 (s, 3H), 0.97 (t, J = 7.2 Hz, 6H). |
| 1.0687 | —Me | —Me | —(C═O)ⁱPr | 6-F | 3-Cl | —CH₂—CH₂— | o-tolyl | ¹H NMR (400 MHz, chloroform) δ = 7.43 (dd, J = 5.1, 8.8 Hz, 1H), 7.15-7.04 (m, 4H), 6.99 (t, J = 8.6 Hz, 1H), 3.84 (s, 3H), 2.88-2.64 (m, 4H), 2.54 (spt, J = 7.0 Hz, 1H), 2.25 (s, 3H), 2.18 (s, 3H), 0.96 (d, J = 7.0 Hz, 6H). |
| 1.0693 | —Me | —Me | —(C═O)ⁱPr | 6-F | 3-Cl | —CH₂—CH₂— | m-tolyl | ¹H NMR (400 MHz, chloroform) δ = 7.42 (dd, J = 5.1, 8.8 Hz, 1H), 7.18-7.11 (m, 1H), 7.02-6.89 (m, 4H), 3.84 (s, 3H), 2.88-2.65 (m, 4H), 2.54 (spt, J = 7.0 Hz, 1H), 2.31 (s, 3H), 2.25 (s, 3H), 0.97 (d, J = 7.0 Hz, 6H). |
| 1.0789 | —Me | —Me | H | 6-F | H | —CH₂—CH₂— | 2-fluoro-4-pyridyl | ¹H NMR (400 MHz, chloroform) δ ppm 8.02 (d, J = 5.14 Hz, 1 H), 7.33 (dd, J = 7.89, 5.93 Hz, 1 H), 7.09-6.98 (m, 2 H), 6.89 (d, J = 5.01 Hz, 1 H), 6.64 (s, 1H), 3.76 (s, 3H), 2.95-2.68 (m, 4H), 2.33 (s, 3H) |
| 1.0885 | —Me | —Me | H | 6-F | 3-Cl | —CH₂—CH₂— | 4-(dimethyl-amino)-phenyl | ¹H NMR (400 MHz, chloroform) δ ppm 7.42 (dd, J = 8.80, 5.14 Hz, 1 H), 6.96 (t, J = 8.56 Hz, 1 H), 6.86 (d, J = 8.68 Hz, 2 H), 6.65-6.59 (m, 2H), 3.72 (s, 3H), 2.90 (s, 6H), 2.87-2.80 (m, 1H), 2.77-2.62 (m, 3H), 2.27 (s, 3H) |
| 1.0891 | —Me | —Me | H | 6-F | 3-Cl | —CH₂—CH₂— | 3-methyl-4-amino-phenyl | ¹H NMR (400 MHz, chloroform) δ ppm 7.38 (dd, J = 8.86, 5.20 Hz, 1 H), 6.93 (t, J = 8.56 Hz, 1 H), 6.73-6.59 |

TABLE 2-continued

Preparation examples of compounds of formula (I). The numbering system used to describe the positions of X and Y is shown for the purposes of clarity only.

(I)

| Cmpd | R¹ | R² | G | X | Y | W | D | NMR details |
|---|---|---|---|---|---|---|---|---|
| | | | | | | | | (m, 2H), 6.52 (d, J = 7.83 Hz, 1 H), 3.70 (s, 3H), 2.83-2.50 (m, 4H), 2.27 (s, 3H), 2.09 (s, 3H) |
| 1.0897 | —Me | —Me | H | 6-F | 3-Cl | —CH$_2$—CH$_2$— | thiophen-3-yl | $^1$H NMR (400 MHz, chloroform) δ = 7.39 (dd, J = 5.2, 8.9 Hz, 1H), 7.19 (dd, J = 2.9, 4.9 Hz, 1H), 6.95 (t, J = 8.6 Hz, 1H), 6.84-6.79 (m, 1H), 6.74 (dd, J = 1.2, 4.9 Hz, 1H), 6.42 (br s, 1H), 3.68 (s, 3H), 2.88-2.63 (m, 4H), 2.27 (s, 3H). |
| 1.0903 | —Me | —Me | H | 6-F | 3-Cl | —CH$_2$—CH$_2$— | 1-methyl-pyrazol-4-yl | $^1$H NMR (400 MHz, DMSO-d6) δ = 7.54 (dd, J = 5.3, 8.9 Hz, 1H), 7.35 (s, 1H), 7.20 (t, J = 8.9 Hz, 1H), 7.05 (s, 1H), 3.73 (s, 3H), 3.59 (s, 3H), 2.70-2.57 (m, 2H), 2.53-2.37 (m, 2H), 2.24 (s, 3H) |
| 1.0915 | —Me | —Me | H | 6-F | 3-Cl | —CH$_2$—CH$_2$— | 5-methyl-1,3,4-oxadiazol-2-yl | $^1$H NMR (400 MHz, chloroform) δ ppm 7.34-7.27 (m, 1 H), 7.03-6.94 (m, 1H), 3.76-3.68 (m, 3H), 3.22 (s, 4H), 2.47 (s, 3H), 2.36-2.27 (m, 3H) |
| 1.0921 | —Me | —Me | H | 6-F | 3-Cl | —CH$_2$—CH$_2$— | 5-methyl-3-pyridyl | $^1$H NMR (400 MHz, chloroform) δ ppm 7.64-7.84 (m, 2 H) 7.34 (s, 1 H) 7.09-7.19 (m, 1 H) 6.79 (br s, 1 H) 3.74 (s, 3 H) 2.65-2.87 (m, 4 H) 2.34 (s, 3 H) 2.28 (s, 3 H) |
| 1.0933 | —Me | —Me | H | 6-F | 3-Cl | —CH$_2$—CH$_2$— | 6-methyl-2-pyridyl | $^1$H NMR (400 MHz, chloroform) δ ppm 7.49-7.64 (m, 1 H) 7.21 (br s, 1 H) 6.99 (br d, J = 3.67 Hz, 2 H) 6.84 (s, 1 H) 3.76 (s, 4 H) 3.39-3.54 (m, 1 H) 3.05-3.19 (m, 1 H) 2.81-3.02 (m, 2 H) 2.36 (s, 4 H) 2.24 (br s, 3 H) |
| 1.0149 | —Me | —Me | —(C=O)$^i$Pr | 6-F | 3-Cl | —CH$_2$—CH$_2$— | 4-tolyl- | $^1$H NMR (400 MHz, CDCl$_3$) δ = 7.41 (dd, J = 8.8 & 5.1, 1H), 7.10-6.92 (m, 5H), 3.83 (s, 3H), 2.86-2.68 (m, 4H), 2.54 (sep, J = 7.0, 1H), 2.31 (s, 3H), 2.24 (s, 3H), 0.96 (d, J = 7.0, 6H). |
| 1.0969 | —Me | —Me | —(C=O)$^i$Pr | 6-F | 3-Cl | —CH$_2$—CH$_2$— | thiophen-3-yl | $^1$H NMR (400 MHz, chloroform) δ = 7.41 (dd, J = 5.1, 8.8 Hz, 1H), 7.22 (dd, J = 2.9, 4.9 Hz, 1H), 6.98 (t, J = 8.6 Hz, 1H), 6.94-6.91 (m, 1H), 6.88 (dd, J = 1.2, 4.9 Hz, 1H), 3.83 (s, 3H), 2.92-2.72 (m, 4H), 2.55 (spt, J = 7.0 Hz, 1H), 2.25 (s, 3H), 0.97 (dd, J = 3.9, 7.0 Hz, 6H). |
| 1.0975 | —Me | —Me | —(C=O)$^i$Pr | 6-F | 3-Cl | —CH$_2$—CH$_2$— | 1-methyl-pyrazol-4-yl | $^1$H NMR (400 MHz, chloroform) δ ppm 7.41 (dd, J = 8.93, 5.14 Hz, 1 H), 7.21 (d, J = 2.20 Hz, 1 H), 6.97 (t, J = 8.62 Hz, 1 H), 5.95 (d, J = 2.20 Hz, 1 H), 3.82 (d, J = 1.83 Hz, 6 H), 2.78-3.00 (m, 5 H), 2.49-2.62 (m, 1 H), 2.24 (s, 3 H), 0.97 (t, J = 7.15 Hz, 6 H) |
| 1.0975 | —Me | —Me | —(C=O)$^i$Pr | 6-F | 3-Cl | —CH$_2$—CH$_2$— | 1-methyl-pyrazol-4-yl | $^1$H NMR (400 MHz, chloroform) δ = 7.40 (dd, J = 5.2, 8.9 Hz, 1H), 7.23 (s, 1H), 7.10 (s, 1H), 6.97 (t, J = 8.9 Hz, 1H), 3.83 (s, 3H), 3.82 (s, 3H), 2.86-2.75 (m, 1H), 2.74-2.59 (m, 3H), 2.55 (spt, J = 7.0 Hz, 1H), 2.24 (s, 3H), 0.98 (d, J = 7.0 Hz, 3H), 0.97 (d, J = 7.0 Hz, 1H) |
| 1.0981 | —Me | —Me | —(C=O)$^i$Pr | 6-F | 3-Cl | —CH$_2$—CH$_2$— | 2-methyl-triazol-4-yl | $^1$H NMR (400 MHz, chloroform) δ ppm 7.42 (dd, J = 8.93, 5.14 Hz, 1 H), 7.26 (s, 1 H), 6.99 (t, J = 8.62 Hz, 1 H), |

TABLE 2-continued

Preparation examples of compounds of formula (I). The numbering system used to describe the positions of X and Y is shown for the purposes of clarity only.

(I)

| Cmpd | $R^1$ | $R^2$ | G | X | Y | W | D | NMR details |
|---|---|---|---|---|---|---|---|---|
| | | | | | | | | 3.83 (s, 3 H), 4.12 (s, 3 H), 2.72-3.01 (m, 4 H), 2.47-2.63 (m, 1 H), 2.25 (s, 3 H), 0.97 (dd, J = 6.97, 2.20 Hz, 6 H) |
| 1.0993 | —Me | —Me | —(C=O)$^i$Pr | 6-F | 3-Cl | —CH$_2$—CH$_2$— | 5-methyl-3-pyridyl | $^1$H NMR (400 MHz, chloroform) δ ppm 8.25 (d, J = 1.47 Hz, 1 H) 8.18 (d, J = 1.71 Hz, 1 H) 7.42 (dd, J = 8.80, 5.14 Hz, 1 H) 7.26 (s, 1 H) 7.00 (t, J = 8.62 Hz, 1 H) 3.85 (s, 3 H) 2.64-2.91 (m, 4 H) 2.54 (d, J = 6.97 Hz, 1 H) 2.29 (s, 3 H) 2.25 (s, 3 H) 0.97 (dd, J = 8.01, 7.03 Hz, 6 H) |
| 1.0999 | —Me | —Me | —(C=O)$^i$Pr | 6-F | 3-Cl | —CH$_2$—CH$_2$— | 5-methyl-2-pyridyl | $^1$H NMR (400 MHz, chloroform) δ ppm 8.30 (dd, J = 1.53, 0.67 Hz, 1 H) 7.40 (dd, J = 8.80, 5.14 Hz, 1 H) 7.32-7.37 (m, 1 H) 6.91-7.00 (m, 2 H) 3.81 (s, 3 H) 2.81-3.07 (m, 4 H) 2.54 (quin, J = 6.97 Hz, 1 H) 2.28 (s, 3 H) 2.24 (s, 3 H) 0.96 (dd, J = 6.97, 5.01 Hz, 6 H) |
| 1.1005 | —Me | —Me | —(C=O)$^i$Pr | 6-F | 3-Cl | —CH$_2$—CH$_2$— | 6-methyl-2-pyridyl | $^1$H NMR (400 MHz, chloroform) δ ppm 7.36-7.45 (m, 2 H) 6.97 (t, J = 8.62 Hz, 1 H) 6.93 (d, J = 7.58 Hz, 1 H) 6.82 (d, J = 7.58 Hz, 1 H) 3.81 (s, 3 H) 2.92 (s, 4 H) 2.50-2.61 (m, 1 H) 2.47 (s, 3 H) 2.25 (s, 3 H) 0.98 (dd, J = 8.25, 7.03 Hz, 6 H) |
| 1.1011 | —Me | —Me | —(C=O)$^i$Pr | 6-F | 3-Cl | —CH$_2$—CH$_2$— | 3-methyl-2-pyridyl | $^1$H NMR (400 MHz, chloroform) δ ppm 8.34 (dd, J = 4.77, 1.22 Hz, 1 H) 7.42 (dd, J = 8.93, 5.14 Hz, 1 H) 7.35 (dd, J = 7.58, 0.86 Hz, 1 H) 6.94-7.02 (m, 2 H) 3.79 (s, 3 H) 2.97 (t, J = 7.95 Hz, 4 H) 2.46-2.60 (m, 1 H) 2.23 (s, 3 H) 2.13 (s, 3 H) 0.97 (dd, J = 7.03, 3.97 Hz, 6 H) |
| 1.1185 | —Me | —Me | H | 6-F | 3-Cl | —CH$_2$—CH$_2$— | 2-acetamido-thiazol-5-yl | $^1$H NMR (400 MHz, chloroform) δ ppm 7.41 (dd, J = 8.86, 5.07 Hz, 1 H) 6.97-7.03 (m, 2 H) 3.73 (s, 3 H) 2.84-3.06 (m, 3 H) 2.72 (s, 1 H) 2.37 (s, 3 H) 2.30 (s, 4 H) |
| 1.1191 | —Me | —Me | —(C=O)$^i$Pr | 6-F | 3-Cl | —CH$_2$—CH$_2$— | 3,5-difluoro-phenyl | $^1$H NMR (400 MHz, chloroform) δ = 7.42 (dd, J = 5.1, 8.9 Hz, 1H), 6.99 (t, J = 8.9 Hz, 1H), 6.69-6.58 (m, 3H), 3.87-3.84 (m, 3H), 2.93-2.77 (m, 3H), 2.75-2.62 (m, 1H), 2.54 (spt, J = 7.0 Hz, 1H), 2.25 (s, 3H), 0.98 (d, J = 7.0 Hz, 3H), 0.95 (d, J = 7.0 Hz, 3H) |
| 1.1257 | —Me | —Me | H | 6-F | 3-Cl | (E)-CH=CH— | 2-chloro-3-pyridyl | $^1$H NMR (400 MHz, DMSO-d6) δ = 10.94 (br s, 1H), 8.33 (dd, J = 1.6, 4.6 Hz, 1H), 8.17 (dd, J = 1.7, 7.3 Hz, 1H), 7.64 (dd, J = 5.1, 8.8 Hz, 1H), 7.46 (dd, J = 4.6, 7.3 Hz, 1H), 7.33 (t, J = 8.8 Hz, 1H), 7.17 (d, J = 16.5 Hz, 1H), 6.76 (d, J = 16.5 Hz, 1H), 3.53 (s, 3H), 2.19 (s, 3H) |

TABLE 2-continued

Preparation examples of compounds of formula (I). The numbering system used to describe the positions of X and Y is shown for the purposes of clarity only.

(I)

| Cmpd | R¹ | R² | G | X | Y | W | D | NMR details |
|---|---|---|---|---|---|---|---|---|
| 1.1258 | —Me | —Me | H | 6-F | 3-Cl | (E)-CH=CH— | 2-chloro-4-pyridyl | ¹H NMR (400 MHz, chloroform) δ = 8.20 (d, J = 5.3 Hz, 1H), 7.29 (dd, J = 5.3, 8.5 Hz, 1H), 7.14 (d, J = 1.3 Hz, 1H), 7.10 (d, J = 16.5 Hz, 1H), 7.05 (dd, J = 1.3, 5.3 Hz, 1H), 6.91 (t, J = 8.5 Hz, 1H), 6.44 (d, J = 16.5 Hz, 1H), 3.61 (s, 3H), 2.24 (s, 3H) |
| 1.1259 | —Me | —Me | H | 6-F | 3-Cl | (E)-CH=CH— | 3-chloro-4-fluoro-phenyl | ¹H NMR (400 MHz, chloroform) δ = 7.39 (dd, J = 5.1, 8.9 Hz, 1H), 7.30 (dd, J = 2.2, 6.9 Hz, 1H), 7.11 (ddd, J = 2.2, 5.0, 8.6 Hz, 1H), 7.06 (t, J = 8.6 Hz, 1H), 6.97 (t, J = 8.9 Hz, 1H), 6.82 (d, J = 16.5 Hz, 1H), 6.44 (d, J = 16.5 Hz, 1H), 3.63 (s, 3H), 2.24 (s, 3H) |
| 1.1261 | —Me | —Me | H | 6-F | 3-Cl | (E)-CH=CH— | 4-hydroxy-phenyl | ¹H NMR (400 MHz, DMSO-d6) δ = 10.75 (br s, 1H), 9.67 (s, 1H), 7.58 (dd, J = 5.3, 8.8 Hz, 1H), 7.23 (t, J = 8.8 Hz, 1H), 7.19-7.13 (m, 2H), 6.75-6.72 (m, 2H), 6.73 (d, J = 16.5 Hz, 1H), 6.48 (d, J = 16.5 Hz, 1H), 3.55 (s, 3H), 2.19 (s, 3H) |
| 1.1265 | —Me | —Me | H | 6-F | 3-Cl | (E)-CH=CH— | pyrimidin-5-yl | ¹H NMR (400 MHz, DMSO-d6) δ = 9.08 (s, 1H), 8.86 (s, 2H), 7.63 (dd, J = 5.2, 8.9 Hz, 1H), 7.32 (t, J = 8.9 Hz, 1H), 7.23 (d, J = 16.8 Hz, 1H), 6.60 (d, J = 16.8 Hz, 1H), 3.54 (s, 3H), 2.19 (s, 3H) |
| 1.1267 | —Me | —Me | H | 6-F | 3-Cl | (E)-CH=CH— | thiazol-5-yl | ¹H NMR (400 MHz, chloroform) δ ppm 8.66 (s, 1 H), 7.67 (s, 1 H), 7.49 (dd, J = 8.86, 5.20 Hz, 1 H), 7.36-7.29 (m, 3H), 7.13-7.05 (m, 3H), 6.89-6.81 (m, 1H). 6.78-6.63 (m, 1H), 4.77-4.55 (m, 2H), 3.75 (s, 3H), 2.24 (s, 3H) |
| 1.1269 | —Me | —Me | H | 6-F | 3-Cl | (E)-CH=CH— | 3-cyano-phenyl | ¹H NMR (400 MHz, chloroform) δ = 7.56-7.47 (m, 3H), 7.44-7.38 (m, 2H), 7.04-6.93 (m, 2H), 6.53 (d, J = 16.5 Hz, 1H), 3.64 (s, 3H), 2.25 (s, 3H). |
| 1.1270 | —Me | —Me | H | 6-F | 3-Cl | (E)-CH=CH— | 3-trifluoro-methyl-phenyl | ¹H NMR (400 MHz, chloroform) δ = 7.55-7.49 (m, 2H), 7.46-7.39 (m, 3H), 7.05-6.94 (m, 2H), 6.60 (d, J = 16.4 Hz, 2H), 3.65 (s, 3H), 2.25 (s, 3H). |
| 1.1271 | —Me | —Me | H | 6-F | 3-Cl | | o-tolyl | ¹H NMR (400 MHz, chloroform) δ = 7.43 (dd, J = 3.7, 5.4 Hz, 1H), 7.37 (dd, J = 5.1, 8.8 Hz, 1H), 7.21-7.13 (m, 2H), 7.12-7.05 (m, 1H), 6.94 (t, J = 8.6 Hz, 1H), 6.84 (d, J = 1.0 Hz, 1H), 6.77 (d, J = 1.0 Hz, 1H), 6.70 (br s, 1H), 3.64 (s, 3H), 2.23 (s, 3H), 2.04 (s, 3H). |
| 1.1282 | —Me | —Me | H | 6-F | 3-Cl | (E)-CH=CH— | thiophen-3-yl | ¹H NMR (400 MHz, chloroform) δ = 7.39 (dd, J = 5.2, 8.9 Hz, 1H), 7.29-7.24 (m, 1H + CHCl3 peak), 7.17 (dd, J = 1.0, 5.0 Hz, 1H), 7.10 (dd, J = 1.1, 2.8 Hz, 1H), 6.95 (t, J = 8.6 Hz, 1H), 6.82-6.73 (m, 1H), 6.65-6.58 (m, 1H), 3.65 (s, 3H), 2.24 (s, 3H). |
| 1.1293 | —Me | —Me | H | 6-F | 3-Cl | (E)-CH=CH— | 4-methyl-2-pyridyl | ¹H NMR (400 MHz, chloroform) δ ppm 8.09 (d, J = 5.26 Hz, 1 H) 7.22 (d, J = 16.63 Hz, 1 H) 7.19 (br s, 1 H) 7.01 |

TABLE 2-continued

Preparation examples of compounds of formula (I). The numbering system used to describe the positions of X and Y is shown for the purposes of clarity only.

(I)

| Cmpd | R¹ | R² | G | X | Y | W | D | NMR details |
|---|---|---|---|---|---|---|---|---|
| 1.1294 | —Me | —Me | H | 6-F | 3-Cl | (E)-CH=CH— | 2-acetamido-thiazol-5-yl | (dd, J = 8.74, 5.32 Hz, 1 H) 6.95 (d, J = 5.87 Hz, 1 H) 6.53-6.66 (m, 2 H) 3.64 (s, 4 H) 2.35 (d, J = 9.17 Hz, 6 H) ¹H NMR (400 MHz, chloroform) δ ppm 7.44 (dd, J = 8.93, 5.14 Hz, 1 H) 7.16-7.21 (m, 1 H) 7.04 (t, J = 8.56 Hz, 1 H) 6.71 (d, J = 4.65 Hz, 2 H) 3.72 (s, 3 H) 2.28 (s, 3 H) 2.26 (s, 3 H) |
| 1.1348 | —Me | —Me | —(C=O)ⁱPr | 6-F | 3-Cl | (E)-CH=CH— | 4-cyano-phenyl | ¹H NMR (400 MHz, chloroform) δ = 7.62-7.55 (m, 2H), 7.45 (dd, J = 5.0, 8.5 Hz, 1H), 7.45-7.40 (m, 1H), 7.13 (d, J = 16.5 Hz, 1H), 7.05 (t, J = 8.5 Hz, 1H), 6.68 (d, J = 16.5 Hz, 1H), 3.69 (s, 3H), 2.65 (spt, J = 7.0 Hz, 1H), 2.23 (s, 3H), 1.11 (d, J = 7.0 Hz, 3H), 1.07 (d, J = 7.0 Hz, 3H) |
| 1.1351 | —Me | —Me | —(C=O)ⁱPr | 6-F | 3-Cl | (E)-CH=CH— | 4-trifluoro-methyl-3-pyridyl- | ¹H NMR (400 MHz, CDCl3) δH: 8.65 (d, J = 1.6, 1H), 7.87 (dd, J = 8.2 and 2.1, 1H), 7.64 (d, J = 8.2, 1H), 7.47 (dd, J = 8.9 and 5.0, 1H), 7.17 (d, J = 16.5 Hz, 1H), 7.08 (t, J = 8.7, 1H), 6.75 (d, J = 16.5 Hz, 1H), 3.71 (s, 3H), 2.66 (spt, J = 7.0, 1H), 2.24 (s, 3H), 1.11 (d, J = 7.0, 3H), 1.08 (d, J = 7.1, 3H). |
| 1.1352 | —Me | —Me | —(C=O)ⁱPr | 6-F | 3-Cl | (E)-CH=CH— | 4-fluoro-phenyl | ¹H NMR (400 MHz, CDCl3) δ ppm 7.45 (dd, 1 H) 7.29-7.37 (m, 2 H) 6.96-7.07 (m, 3 H) 6.92 (d, 1 H) 6.59 (d, 1 H) 3.75 (s, 3 H) 2.66 (sept, 1 H) 2.26 (s, 3 H) 1.09 (dd, 6 H). |
| 1.1357 | —Me | —Me | —(C=O)ⁱPr | 6-F | 3-Cl | (E)-CH=CH— | 4-(trifluoro-methoxy)phenyl | ¹H NMR (400 MHz, chloroform) δ = 7.43 (dd, J = 5.1, 8.9 Hz, 1H), 7.40-7.34 (m, 2H), 7.18-7.11 (m, J = 7.9 Hz, 2H), 7.03 (t, J = 8.9 Hz, 1H), 6.98 (d, J = 16.5 Hz, 1H), 6.64 (d, J = 16.5 Hz, 1H), 3.71 (s, 3H), 2.64 (spt, J = 7.0 Hz, 1H), 2.22 (s, 3H), 1.09 (d, J = 7.0 Hz, 3H), 1.07 (d, J = 7.0 Hz, 3H) |
| 1.1363 | —Me | —Me | —(C=O)ⁱPr | 6-F | 3-Cl | (E)-CH=CH— | 4-cyclo-propyl-phenyl | ¹H NMR (400 MHz, chloroform) δ = 7.41 (dd, J = 5.1, 8.9 Hz, 1H), 7.26-7.22 (m, 2H), 7.02-6.98 (m, 2H), 6.99 (t, J = 8.9 Hz, 1H), 6.93 (d, J = 16.5 Hz, 1H), 6.59 (d, J = 16.5 Hz, 1H), 3.71 (s, 3H), 2.62 (spt, J = 7.0 Hz, 1H), 2.19 (s, 3H), 1.87 (tt, J = 5.0, 8.4 Hz, 1H), 1.07 (d, J = 7.0 Hz, 3H), 1.06 (d, J = 7.0 Hz, 1H), 0.99-0.93 (m, J = 2.0, 8.4 Hz, 2H), 0.73-0.64 (m, 2H) |
| 1.1367 | —Me | —Me | —(C=O)ⁱPr | 6-F | 3-Cl | (E)-CH=CH— | 4-(tert-butoxy)-phenyl | ¹H NMR (400 MHz, chloroform) δ = 7.41 (dd, J = 5.0, 8.6 Hz, 1H), 7.26-7.23 (m, 2H), 6.99 (t, J = 8.6 Hz, 1H), 6.94-6.90 (m, 1H), 6.91 (d, J = 16.5 Hz, 1H), 6.60 (d, J = 16.5 Hz, 1H), 3.71 (s, 3H), 2.63 (spt, J = 7.0 Hz, 1H), 2.22 (s, 3H), 1.35 (s, 9H), 1.08 (d, J = 7.0 Hz, 3H), 1.06 (d, J = 7.0 Hz, 1H) |
| 1.1369 | —Me | —Me | —(C=O)ⁱPr | 6-F | 3-Cl | (E)-CH=CH— | 2-cyano-phenyl | ¹H NMR (400 MHz, chloroform) δ = 7.70 (d, J = 8.1 Hz, 1H), 7.61-7.53 (m, 2H), 7.46 (dd, J = 5.1, 8.9 Hz, 1H), 7.34 (dt, J = 1.0, 7.6 Hz, 1H), |

TABLE 2-continued

Preparation examples of compounds of formula (I). The numbering system used to describe the positions of X and Y is shown for the purposes of clarity only.

(I)

| Cmpd | R¹ | R² | G | X | Y | W | D | NMR details |
|------|-----|-----|---------------|-----|------|-------------|-----------------------|-------------|
| 1.1370 | —Me | —Me | —(C=O)$^i$Pr | 6-F | 3-Cl | (E)-CH=CH— | 3-cyano-phenyl | 7.24 (d, J = 16.5 Hz, 1H), 7.10-6.97 (m, 2H), 3.76 (s, 3H), 2.65 (spt, J = 7.0 Hz, 1H), 2.26 (s, 3H), 1.08 (dd, J = 3.0, 7.0 Hz, 6H). ¹H NMR (400 MHz, chloroform) δ = 7.63-7.55 (m, 2H), 7.55-7.50 (m, 1H), 7.48-7.38 (m, 2H), 7.12-7.00 (m, 2H), 6.65 (d, J = 16.5 Hz, 1H), 3.70 (s, 3H), 2.65 (spt, J = 7.0 Hz, 1H), 2.24 (s, 3H), 1.09 (dd, J = 7.0, 12.5 Hz, 6H). |
| 1.1371 | —Me | —Me | —(C=O)$^i$Pr | 6-F | 3-Cl | (E)-CH=CH— | 3-trifluoro-methyl-phenyl | ¹H NMR (400 MHz, chloroform) δ = 7.57 (s, 1H), 7.54-7.48 (m, 2H), 7.47-7.39 (m, 2H), 7.10-7.00 (m, 2H), 6.68 (d, J = 16.5 Hz, 1H), 3.72 (s, 3H), 2.65 (spt, J = 7.0 Hz, 1H), 2.24 (s, 3H), 1.09 (t, J = 7.4 Hz, 6H). |
| 1.1372 | —Me | —Me | —(C=O)$^i$Pr | 6-F | 3-Cl | (E)-CH=CH— | o-tolyl | ¹H NMR (400 MHz, chloroform) δ = 7.51-7.39 (m, 2H), 7.22-7.13 (m, 2H), 7.13-7.08 (m, 1H), 7.01 (t, J = 8.7 Hz, 1H), 6.94-6.78 (m, 2H), 3.75 (s, 3H), 2.61 (spt, J = 7.0 Hz, 1H), 2.22 (s, 3H), 2.12 (s, 3H), 1.06 (dd, J = 0.6, 7.0 Hz, 6H). |
| 1.1373 | —Me | —Me | —(C=O)$^i$Pr | 6-F | 3-Cl | (E)-CH=CH— | m-tolyl | ¹H NMR (400 MHz, chloroform) δ = 7.42 (dd, J = 5.1, 8.9 Hz, 1H), 7.23-7.10 (m, 3H), 7.07 (d, J = 7.3 Hz, 1H), 7.04-6.94 (m, 2H), 6.59 (d, J = 16.5 Hz, 1H), 3.73 (s, 3H), 2.63 (quin, J = 7.0 Hz, 1H), 2.34 (s, 3H), 2.21 (s, 3H), 1.08 (dd, J = 2.8, 7.0 Hz, 6H). |
| 1.1383 | —Me | —Me | —(C=O)$^i$Pr | 6-F | 3-Cl | (E)-CH=CH— | thiophen-3-yl | ¹H NMR (400 MHz, chloroform) δ = 7.42 (dd, J = 5.1, 8.8 Hz, 1H), 7.30-7.21 (m, 2H + CHCl3 peak), 7.15 (dd, J = 1.2, 2.8 Hz, 1H), 7.00 (t, J = 8.7 Hz, 1H), 6.89-6.80 (m, 1H), 6.69-6.61 (m, 1H), 3.74 (s, 3H), 2.62 (spt, J = 7.0 Hz, 1H), 2.23 (s, 3H), 1.06 (dd, J = 5.5, 7.0 Hz, 6H). |
| 1.1387 | —Me | —Me | —(C=O)$^i$Pr | 6-F | 3-Cl | (E)-CH=CH— | 5-methyl-3-pyridyl | ¹H NMR (400 MHz, chloroform) δ ppm 8.32 (s, 2 H), 7.52 (s, 1 H), 7.44 (dd, J = 8.93, 5.14 Hz, 1 H), 7.10-6.99 (m, 2 H), 6.63 (d, J = 16.51 Hz, 1 H), 3.71 (s, 3 H), 2.65 (quin, J = 7.00 Hz, 1 H), 2.34 (s, 3 H) 2.23 (s, 3 H) 1.09 (t, J = 7.15 Hz, 6 H) |
| 1.1391 | —Me | —Me | —(C=O)$^i$Pr | 6-F | 3-Cl | (E)-CH=CH— | 6-chloro-3-pyridyl | ¹H NMR (400 MHz, chloroform) δ ppm 8.28 (d, J = 2.45 Hz, 1 H) 7.68 (dd, J = 8.31, 2.45 Hz, 1 H) 7.45 (dd, J = 8.86, 5.07 Hz, 1 H) 7.26-7.29 (m, 1 H) 7.00-7.10 (m, 2 H) 6.64 (d, J = 16.63 Hz, 1 H) 3.70 (s, 3 H) 2.54-2.74 (m, 1 H) 2.23 (s, 3 H) 1.08 (dd, J = 11.80, 7.03 Hz, 6 H) |

TABLE 2-continued

Preparation examples of compounds of formula (I). The numbering system used to describe the positions of X and Y is shown for the purposes of clarity only.

(I)

| Cmpd | R¹ | R² | G | X | Y | W | D | NMR details |
|---|---|---|---|---|---|---|---|---|
| 1.1392 | —Me | —Me | —(C═O)ⁱPr | 6-F | 3-Cl | (E)-CH═CH— | 2-trifluoro-methyl-3-pyridyl | ¹H NMR (400 MHz, chloroform) δ = 8.57 (dd, J = 1.2, 4.7 Hz, 1H), 8.05 (dd, J = 1.2, 7.9 Hz, 1H), 7.50 (dd, J = 4.7, 7.9 Hz, 1H), 7.46 (dd, J = 5.1, 8.9 Hz, 1H), 7.11 (d, J = 16.2 Hz, 1H), 7.07 (t, J = 8.9 Hz, 1H), 7.03 (qd, J = 2.0, 16.2 Hz, 1H), 3.74 (s, 3H), 2.63 (spt, J = 7.0 Hz, 1H), 2.24 (s, 3H), 1.07 (d, J = 7.0 Hz, 6H) |
| 1.1393 | —Me | —Me | —(C═O)ⁱPr | 6-F | 3-Cl | (E)-CH═CH— | 3,5-difluoro-phenyl | ¹H NMR (400 MHz, chloroform) δ = 7.44 (dd, J = 5.1, 8.9 Hz, 1H), 7.04 (t, J = 8.9 Hz, 1H), 7.01 (d, J = 16.4 Hz, 1H), 6.89-6.83 (m, 2H), 6.69 (tt, J = 2.3, 8.8 Hz, 1H), 6.58 (d, J = 16.4 Hz, 1H), 3.72 (s, 3H), 2.64 (spt, J = 7.0 Hz, 1H), 2.23 (s, 3H), 1.10 (d, J = 7.0 Hz, 3H), 1.07 (d, J = 7.0 Hz, 3H) |
| 1.1394 | —Me | —Me | —(C═O)ⁱPr | 6-F | 3-Cl | (E)-CH═CH— | 4-methyl-2-pyridyl | ¹H NMR (400 MHz, chloroform) δ ppm 8.41 (d, J = 5.01 Hz, 1 H) 7.50 (d, J = 16.26 Hz, 1 H) 7.43 (dd, J = 8.86, 5.07 Hz, 1 H) 6.93-7.07 (m, 3 H) 6.68 (d, J = 16.26 Hz, 1 H) 3.74 (s, 3 H) 2.62 (dt, J = 13.94, 6.97 Hz, 1 H) 2.32 (s, 3 H) 2.21 (s, 3 H) 1.06 (dd, J = 6.97, 5.62 Hz, 6 H) |
| 1.1447 | —Me | —Me | H | 6-F | 3-Cl | —C≡C— | phenyl | ¹H NMR (400 MHz, chloroform) δ ppm 7.35 (dd, J = 8.00, 5.00 Hz, 1 H), 7.33-7.27 (m, 5H), 6.98 (t, J = 8.60 Hz, 1H), 3.71-3.63 (m, 3H), 2.32-2.26 (m, 3H) |
| 1.1454 | —Me | —Me | H | 6-F | 3-Cl | —C≡C— | 4-fluoro-phenyl | ¹H NMR (400 MHz, chloroform) δ ppm 7.47 (dd, J = 8.93, 5.01 Hz, 1 H), 7/35-7/28 (m, 2H), 7.10 (t, J = 8.50 Hz, 1H), 7.05-6.98 (m, 2H), 3.73 (s, 3H), 2.34 (s, 3H) |
| 1.1457 | —Me | —Me | H | 6-F | 3-Cl | —C≡C— | 2-trifluoro-methyl-phenyl | ¹H NMR (400 MHz, chloroform) δ ppm 7.61-7.37 (m, 4 H), 7.23 (dd, J = 8.00, 5.00 Hz, 1 H), 6.88 (br t, J = 8.44 Hz, 1 H), 3.58 (s, 3H), 2.22 (s, 3H) |
| 1.1458 | —Me | —Me | H | 6-F | 3-Cl | —C≡C— | p-tolyl | ¹H NMR (400 MHz, chloroform) δ ppm 7.36 (dd, J = 9.00, 5.00 Hz, 1 H), 7.22-7.16 (m, 2H), 7.14-7.08 (m, 2H), 6.98 (t, J = 8.50 Hz, 1H), 3.68 (s, 3H), 2.35 (s, 3H), 2.29 (s, 3H) |
| 1.1556 | —Me | —Me | —(C═O)ⁱPr | 6-F | 3-Cl | —C≡C— | 4-fluoro-phenyl | ¹H NMR (400 MHz, CDCl3) δ ppm 7.46 (dd, 1 H) 7.31-7.38 (m, 2 H) 7.08 (t, 1 H) 6.99-7.06 (m, 2 H) 3.83 (s, 3 H) 2.61 (sept, 1 H) 2.28 (s, 3 H) 1.04 (dd, 6 H). |
| 1.1560 | —Me | —Me | —(C═O)ⁱPr | 6-F | 3-Cl | —C≡C— | p-tolyl | ¹H NMR (400 MHz, chloroform) δ ppm 7.44 (dd, J = 9.00, 5.00 Hz, 1 H), 7.26-7.20 (m, 2H), 7.16-7.09 (m, 2H), 7.06 (t, J = 8.50 Hz, 1 H), 3.82 (s, £H), 2.60 (spt, J = 7.00 Hz, 1H), 2.35 (s, 3H), 2.27 (s, 3H), 1.04 (d, J = 7.00 Hz, 3 H), 1.03 (d, J = 7.00 Hz, 3 H) |
| 1.1651 | —Me | —Me | —(C═O)Me | 6-F | 3-Cl | —CH₂—CH₂— | p-tolyl | ¹H NMR (400 MHz, chloroform) δ ppm 7.44 (dd, J = 8.86, 5.20 Hz, 1 H), 7.11-6.94 (m, 5H), 3.84 (s, £H), 2.89-2.69 (m, 4H), 2.32 (s, 3H), 2.06 (s, 3H) |

TABLE 2-continued

Preparation examples of compounds of formula (I). The numbering system used to describe the positions of X and Y is shown for the purposes of clarity only.

(I)

| Cmpd | R¹ | R² | G | X | Y | W | D | NMR details |
|---|---|---|---|---|---|---|---|---|
| 1.1652 | —Me | —Me | —(C=O)OtBu | 6-F | 3-Cl | —CH₂—CH₂— | p-tolyl | ¹H NMR (400 MHz, chloroform) δ ppm 7.42 (dd, J = 8.80, 5.14 Hz, 1 H), 7.10-7.04 (m, 2H), 7.04-6.94 (m, 3H), 3.78 (s, 3H), 2.88 (br d, J = 7.83 Hz, 2 H), 2.69 (td, J = 12.72, 11.37 Hz, 2 H), 2.36 (s, 3 H), 2.31 (s, 3 H), 1.10 (s, 9 H) |
| 1.1653 | —Me | —Me | —(C=O)O-me | 6-F | 3-Cl | —CH₂—CH₂— | p-tolyl | ¹H NMR (400 MHz, chloroform) δ ppm 7.44 (dd, J = 8.86, 5.20 Hz, 1 H), 7.12-6.94 (m, 5H), 3.83 (s, 3H), 3.76 (s, 3H), 2.88-2.70 (m, 4H), 2.38-2.24 (m, 6H) |
| 1.1654 | —Me | —Me | —(C=O)tBu | 6-F | 3-Cl | —CH₂—CH₂— | p-tolyl | ¹H NMR (400 MHz, chloroform) δ ppm 7.42 (dd, J = 8.80, 5.14 Hz, 1 H), 7.11-6.94 (m, 5H), 3.85 (s, 3H), 2.90-2.68 (m, 4H), 2.32 (s, 3H), 2.24 (s, 3H), 1.03 (s, 9H) |
| 1.1655 | —Me | —Me | —(C=O)Ph | 6-F | 3-Cl | —CH₂—CH₂— | p-tolyl | ¹H NMR (400 MHz, chloroform) δ ppm 7.90 (dd, J = 8.38, 1.28 Hz, 2 H), 7.65-7.57 (m, 1H), 7.48-7.39 (m, 2H), 7.32 (dd, J = 8.80, 5.14 Hz, 1 H), 7.13-7.02 (m, 4H), 6.91 (t, J = 8.68 Hz, 1 H), 3.87 (s, 3H), 2.92-2.70 (m, 4H), 2.28-2.23 (m, 6H) |
| 1.1656 | —Me | —Me | —(C=O)4-morph-olino | 6-F | 3-Cl | —CH₂—CH₂— | p-tolyl | ¹H NMR (400 MHz, chloroform) δ ppm 7.46 (dd, J = 8.86, 5.20 Hz, 1 H), 7.11-6.96 (m, 5H), 3.85 (s, 3H), 3.59-3.20 (m, 8H), 2.96-2.67 (m, 4H), 2.40-2.22 (m, 6H) |

Biological Examples

B1 Post-Emergence Efficacy—Test 1

Seeds of a variety of test species are sown in standard soil in pots:—*Solanum nigrum* (SOLNI), *Amaranthus retoflexus* (AMARE), *Setaria faberi* (SETFA), *Alopecurus myosuroides* (ALOMY), *Echinochloa crus-galli* (ECHCG), *Ipomoea hederacea* (IPOHE), *Lolium perenne* (LOLPE). After 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethylene sorbitan monolaurate, CAS RN 9005-64-5). Compounds are applied at 1000 g/ha. The test plants are then grown in a glasshouse under controlled conditions in a glasshouse (at 24/16° C., day/night; 14 hours light; 65% humidity) and watered twice daily. After 13 days, the test is evaluated for the percentage damage caused to the plant. The biological activities are assessed on a five point scale (5=80-100%; 4=60-79%; 3=40-59%; 2=20-39%; 1=0-19%). A blank value in the table is indicative that the compound was not tested on that species.

TABLE 3

Control of weed species by compounds of formula (I) after post-emergence application

| Compound | AMARE | SOLNI | SETFA | LOLPE | ECHCG | IPOHE |
|---|---|---|---|---|---|---|
| 1.0001 | 5 | 5 | 5 | 5 | 5 | 5 |
| 1.0002 | 4 | 5 | 3 | 4 | 4 | 5 |
| 1.0012 | 5 | 5 | 5 | 5 | 5 | 5 |
| 1.0018 | 5 | 5 | 5 | 5 | 5 | 5 |
| 1.0024 | 5 | 5 | 5 | 5 | 5 | 5 |
| 1.0042 | 5 | 5 | 5 | 5 | 5 | 5 |
| 1.0048 | 5 | 5 | 5 | 5 | 5 | 5 |
| 1.0054 | 5 | 5 | 5 | 5 | 5 | 5 |
| 1.0060 | 5 | 5 | 5 | 5 | 5 | 5 |
| 1.0066 | 5 | 5 | 5 | 4 | 5 | 5 |
| 1.0089 | 5 | 5 | 5 | 5 | 5 | 5 |
| 1.0095 | 5 | 5 |   | 5 | 5 | 5 |
| 1.0125 | 5 | 5 | 5 | 5 | 5 | 5 |
| 1.0149 | 5 | 5 | 5 | 5 | 5 | 5 |

B2 Post-Emergence Efficacy—Test 2

Seeds of a variety of test species are sown in standard soil in pots:—*Solanum nigrum* (SOLNI), *Amaranthus retoflexus* (AMARE), *Setaria faberi* (SETFA), *Alopecurus myosuroides* (ALOMY), *Echinochloa crus-galli* (ECHCG), *Ipomoea hederacea* (IPOHE), *Lolium perenne* (LOLPE). After 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethylene sorbitan monolaurate, CAS RN 9005-64-5). Compounds are applied at 250 g/ha. The test plants are then grown in a glasshouse under controlled conditions in a glasshouse (at 24/16° C., day/night; 14 hours light; 65% humidity) and watered twice daily. After 13 days, the test is evaluated for the percentage damage caused to the plant. The biological activities are assessed on a five point scale (5=80-100%; 4=60-79%; 3=40-59%; 2=20-39%; 1=0-19%). A blank value in the table is indicative that the compound was not tested on that species.

TABLE 4

Control of weed species by compounds of formula (I) after post-emergence application

| Compound | AMARE | SOLNI | SETFA | LOLPE | ECHCG | IPOHE |
|---|---|---|---|---|---|---|
| 1.0001 | 4 | 5 | 5 | 5 | 5 | 5 |
| 1.0002 | 1 | 5 | 1 | 1 | 0 | 5 |
| 1.0012 | 4 | 5 | 5 | 5 | 5 | 5 |
| 1.0018 | 5 | 5 | 5 | 5 | 5 | 5 |
| 1.0024 | 5 | 5 | 5 | 5 | 5 | 5 |
| 1.0042 | 5 | 5 | 5 | 5 | 5 | 5 |
| 1.0048 | 4 | 5 | 5 | 5 | 5 | 5 |
| 1.0054 | 4 | 5 | 5 | 4 | 4 | 3 |
| 1.0060 | 4 | 5 | 5 | 5 | 5 | 5 |
| 1.0066 | 5 | 5 | 4 | 2 | 3 | 5 |
| 1.0072 | 5 | 5 | 5 | 5 | 5 | 5 |
| 1.0089 | 4 | 5 | 5 | 5 | 5 | 5 |
| 1.0101 | 5 | 5 | 4 | 4 | 4 | 5 |
| 1.0119 | 3 | 5 | 4 | 4 | 3 | 4 |
| 1.0095 | 5 | 5 |   | 5 | 5 | 5 |
| 1.0143 | 5 | 5 | 2 | 2 | 2 | 5 |
| 1.0125 | 3 | 5 | 5 | 5 | 5 | 5 |
| 1.0327 | 5 | 5 | 5 | 5 | 5 | 5 |
| 1.0333 | 5 | 5 | 5 | 5 | 5 | 5 |
| 1.0339 | 1 | 5 | 5 | 1 | 3 | 5 |
| 1.0345 | 5 | 5 | 5 | 5 | 5 | 5 |
| 1.0351 | 5 | 5 | 5 | 5 | 5 | 5 |
| 1.0363 | 4 | 5 | 5 | 5 | 5 | 4 |
| 1.0369 | 4 | 5 | 4 | 4 | 4 | 4 |
| 1.0375 | 5 | 5 | 5 | 5 | 5 | 5 |
| 1.0387 | 5 | 5 | 5 | 5 | 5 | 5 |
| 1.0417 | 5 | 5 | 5 | 5 | 2 | 5 |
| 1.0429 | 5 | 5 | 5 | 5 | 5 | 5 |
| 1.0441 | 5 | 5 | 5 | 5 | 4 | 5 |
| 1.0597 | 4 | 5 | 4 | 4 | 2 | 5 |
| 1.0603 | 4 | 5 | 4 | 5 | 4 | 5 |
| 1.0609 | 5 | 5 | 2 | 4 | 3 | 5 |
| 1.0615 | 4 | 5 | 5 | 5 | 4 | 5 |
| 1.0621 | 5 | 5 | 4 | 4 | 4 | 5 |
| 1.0627 | 5 | 5 | 5 | 5 | 5 | 5 |
| 1.0633 | 5 | 5 | 5 | 5 | 5 | 5 |
| 1.0639 | 4 | 5 | 2 | 2 | 2 | 1 |
| 1.0645 | 5 | 5 | 5 | 5 | 5 | 5 |
| 1.0651 | 4 | 5 | 4 | 4 | 4 | 5 |
| 1.0657 | 5 | 5 | 5 | 5 | 1 | 5 |
| 1.0663 | 5 | 5 | 5 | 4 | 2 | 5 |
| 1.0669 | 4 | 5 | 2 | 2 | 1 | 5 |
| 1.0675 | 5 | 5 | 5 | 4 | 2 | 5 |
| 1.0681 | 3 | 5 | 2 | 3 | 3 | 5 |
| 1.0687 | 4 | 5 | 5 | 5 | 5 | 5 |
| 1.0693 | 4 | — | 4 | 4 | 4 | 4 |
| 1.0789 | 5 | 5 | 5 | 5 | 5 | 5 |
| 1.0885 | 5 | 5 | 5 | 5 | 4 | 5 |
| 1.0891 | 5 | 5 | 4 | 4 | 4 | 4 |
| 1.0897 | 4 | 5 | 4 | 4 | 4 | 5 |
| 1.0149 | 4 | 5 | 5 | 5 | 5 | 5 |
| 1.0969 | 5 | 5 | 4 | 4 | 4 | 4 |
| 1.0999 | 5 | 5 | 5 | 5 | 4 | 5 |
| 1.1005 | 4 | 5 | 5 | 4 | 3 | 3 |
| 1.1257 | 4 | 5 | 5 | 5 | 5 | 4 |

TABLE 4-continued

Control of weed species by compounds of formula (I) after post-emergence application

| Compound | AMARE | SOLNI | SETFA | LOLPE | ECHCG | IPOHE |
|---|---|---|---|---|---|---|
| 1.1258 | 3 | 5 | 5 | 5 | 5 | 5 |
| 1.1259 | 1 | 5 | 1 | 2 | 2 | 2 |
| 1.1265 | 2 | 5 | 1 | 2 | 2 | 3 |
| 1.1267 | 4 | 5 | 0 | 1 | 1 | 3 |
| 1.1269 | 3 | 4 | 0 | 1 | 0 | 4 |
| 1.1270 | 2 | 4 | 0 | 0 | 0 | 0 |
| 1.1271 | 0 | 5 | 1 | 1 | 0 | 4 |
| 1.1348 | 2 | 5 | 1 | 3 | 3 | 4 |
| 1.1351 | 3 | 5 | 4 | 4 | 4 | 4 |
| 1.1352 | 2 | 4 | 2 | 2 | 3 | 4 |
| 1.1357 | 2 | 5 | 3 | 2 | 5 | 3 |
| 1.1363 | 1 | 5 | 0 | 1 | 1 | 2 |
| 1.1367 | 1 | 3 | 0 | 0 | 0 | 3 |
| 1.1369 | 4 | 4 | 0 | 1 | 1 | 4 |
| 1.1370 | 2 | 3 | 0 | 1 | 1 | 3 |
| 1.1372 | 1 | — | 1 | 2 | 2 | 5 |
| 1.1383 | 2 | 5 | 0 | 0 | 0 | 4 |
| 1.1387 | 0 | 0 | 0 | 0 | 0 | 2 |
| 1.1454 | 4 | 5 | 4 | 5 | 5 | 5 |
| 1.1457 | 4 | 5 | 1 | 1 | 1 | 4 |
| 1.1556 | 3 | 5 | 4 | 5 | 5 | 5 |
| 1.1651 | 4 | 5 | 5 | 5 | 5 | 4 |
| 1.1652 | 3 | 3 | 3 | 1 | 0 | 1 |
| 1.1653 | 4 | 5 | 5 | 5 | 5 | 5 |
| 1.1654 | 4 | 5 | 5 | 3 | 5 | 5 |
| 1.1655 | 3 | 5 | 2 | 1 | 3 | 1 |
| 1.1656 | 3 | 5 | 2 | 1 | 2 | 4 |

B3 Post-Emergence Efficacy—Test 3

Seeds of a variety of test species (see Table B1) were sown in standard soil in pots. After cultivation for 12 days (post-emergence) under controlled conditions in a glasshouse (at 24/18° C. or 20/16° C., at day/night; 16 hours light; 65% humidity), the plants were sprayed with an aqueous spray solution derived from the formulation of the technical active ingredient dissolved in IF50 (see Table B2 for composition) and adjuvant (Genapol XO80) was added to the spray solution at a rate of 0.2% v/v.

TABLE B1

Plant species under test and abbreviations used

|  | Abbreviation |
|---|---|
| Cool climate plant species: | |
| *Hordeum vulgare* | HORVW |
| *Triticum aestivum* | TRZAW |
| *Brassica napus* | BRSNN |
| *Beta vulgaris* | BEAVA |
| *Alopecurus myosuroides* | ALOMY |
| *Avena fatua* | AVEFA |
| *Bromus tectorum* | BROTE |
| *Lolium perenne* | LOLPE |
| *Poa annua* | POAAN |
| *Chenopodium album* | CHEAL |
| *Galium aparine* | GALAP |
| *Kochia scoparia* | KSHSC |
| *Polygonum convolvulus* | POLCO |
| *Sinapis arvensis* | SINAR |
| *Stellaria media* | STEME |
| *Veronica persica* | VERPE |
| Warm climate species: | |
| *Orysa sativa* | ORYSA |
| *Zea mays* | ZEAMX |
| *Glycine max* | GLXMA |
| *Brachiaria plantaginea* | BRAPL |
| *Digitaria sanguinalis* | DIGSA |
| *Echinochloa crus galli* | ECHCG |

TABLE B1-continued

Plant species under test and abbreviations used

|  | Abbreviation |
|---|---|
| *Eleisine indica* | ELEIN |
| *Panicum miliaceum* | PANMI |
| *Setaria faberi* | SETFA |
| *Sorghum bicolour* | SORVU |
| *Abutilon theophrasti* | ABUTH |
| *Amaranthus retroflexus* | AMARE |
| *Bidens pilosa* | BIDPI |
| *Euphorbia hetrophylla* | EPHHL |
| *Ipomoea hederacea* | IPOHE |
| *Sida spinosa* | SIDSP |
| *Xanthium strumarium* | XANST |
| *Cyperus esculentus* | CYPES |

TABLE B2

Chemical composition of IF50

| Component | Chemical description | Function | CAS Registry number | Amount (% w/w) |
|---|---|---|---|---|
| Emulsogen EL360 ™ | Castor oil ethoxylate | Emulsifier | 61791-12-6 | 11.12 |
| N-methyl-pyrrolidone | 1-Methyl-2-pyrrolidone | Solvent | 872-50-4 | 44.44 |
| Dowanol DPM glycol ether | Dipropylene glycol monomethyl ether | Solvent | 34590-94-8 | 44.44 |

After application, the test plants were grown in a glasshouse under controlled conditions (as above) and watered twice daily. Herbicidal activity was evaluated 15 days after application on a 0-100 scale. The results, where 0=no damage to test plant and 100=total kill of test plant are shown below in Tables 5 to 8. A blank value in the table is indicative that the compound was not tested on that species.

TABLE 5

Control of warm season plant species by compounds of Formula (I) after post-emergence application

| Compound ID | Rate (g/Ha) | ZEAMX | GLXMA | ORYSA | SETFA | PANMI | SORVU | DIGSA | ECHCG | BRAPL | ELEIN |
|---|---|---|---|---|---|---|---|---|---|---|---|
| 1.0001 | 500 | 20 | 90 | 0 | 90 | 100 | 20 | 70 | 90 | 80 | 30 |
|  | 250 | 10 | 80 | 0 | 90 | 90 | 10 | 70 | 80 | 70 |  |
|  | 125 | 10 | 80 | 0 | 80 | 80 | 10 | 70 | 80 | 50 |  |
|  | 60 | 10 | 80 | 0 | 80 | 80 | 0 |  | 80 | 50 |  |
|  | 30 | 0 | 60 | 0 | 70 | 70 | 0 |  | 70 |  | 30 |
|  | 15 | 0 | 0 | 40 | 50 | 0 | 50 | 70 | 50 | 30 |  |
| 1.0012 | 500 | 100 | 100 | 30 | 100 | 100 | 90 | 70 | 100 | 100 | 80 |
|  | 250 | 70 | 90 | 10 | 80 | 100 | 80 | 50 | 90 | 90 | 80 |
|  | 125 | 50 | 90 | 0 | 70 | 80 | 70 | 20 | 90 | 80 | 60 |
|  | 60 | 50 | 90 | 0 | 40 | 30 | 70 | 20 | 80 | 80 | 60 |
|  | 30 | 10 | 80 | 0 | 40 | 20 | 30 | 10 | 80 | 60 | 50 |
|  | 15 | 0 | 70 | 0 | 0 | 0 | 0 | 0 | 60 | 20 | 0 |
| 1.0018 | 500 | 70 | 90 | 40 | 90 | 100 | 100 | 70 | 90 | 100 | 80 |
|  | 250 | 30 | 90 | 20 | 90 | 100 | 90 | 70 | 90 | 70 | 70 |
|  | 125 | 20 | 70 | 10 | 80 | 80 | 80 | 40 | 90 | 80 | 70 |
|  | 60 | 20 | 70 | 0 | 70 | 60 | 60 | 20 | 90 |  | 70 |
|  | 30 | 20 | 40 | 0 | 70 | 50 | 20 | 20 | 80 | 60 | 20 |
|  | 15 | 0 | 20 | 0 | 0 | 0 | 0 | 0 | 20 | 0 | 0 |
| 1.0024 | 500 | 90 | 100 | 50 | 100 | 100 | 100 | 90 | 100 | 90 | 90 |
|  | 250 | 70 | 100 | 20 | 90 | 100 | 90 | 80 | 100 | 90 | 80 |
|  | 125 | 60 | 90 | 0 | 90 | 90 | 90 | 70 | 90 | 90 | 80 |
|  | 60 | 20 | 90 | 0 | 90 | 80 | 80 | 70 | 90 | 90 | 70 |
|  | 30 | 10 | 80 | 0 | 80 | 60 | 70 | 60 | 90 | 80 | 70 |
|  | 15 | 0 | 60 | 0 | 40 | 10 | 0 | 0 | 80 | 80 | 0 |
| 1.0042 | 500 | 100 | 100 | 40 | 100 | 100 | 100 | 90 | 100 | 90 | 80 |
|  | 250 | 70 | 100 | 20 | 90 | 90 | 90 | 90 | 90 | 70 | 80 |
|  | 125 | 40 | 90 | 0 | 90 | 90 | 80 | 80 | 90 | 70 | 60 |
|  | 60 | 20 | 90 | 0 | 80 | 80 | 70 | 40 | 80 | 70 | 40 |
|  | 30 | 10 | 80 | 0 | 70 | 70 | 10 | 20 | 80 | 60 | 40 |
|  | 15 | 0 | 70 | 0 | 20 | 0 | 0 | 0 | 70 | 30 | 0 |
| 1.0048 | 500 | 100 | 100 | 50 | 80 | 90 | 90 | 30 | 100 | 90 | 90 |
|  | 250 | 90 | 100 | 20 | 60 | 80 | 90 | 40 | 90 | 90 | 90 |
|  | 125 | 30 |  | 10 | 60 | 60 | 90 | 10 | 90 |  | 80 |
|  | 60 | 30 | 80 | 0 | 30 | 50 | 70 | 0 | 80 |  | 70 |
|  | 30 | 20 | 70 | 0 | 20 | 20 | 60 | 0 | 80 | 90 | 0 |
|  | 15 | 0 |  | 0 | 0 | 0 | 0 | 0 | 80 | 80 | 0 |
| 1.0066 | 500 | 60 | 90 | 10 | 10 | 50 | 10 | 10 | 80 | 10 | 0 |
|  | 250 | 40 | 90 | 0 | 0 | 20 | 10 | 0 | 60 | 0 | 0 |
|  | 125 | 30 | 80 | 0 | 0 | 0 | 10 | 0 | 60 | 0 | 0 |
|  | 60 | 20 | 80 | 0 | 0 | 0 | 0 | 0 | 40 | 0 | 0 |
|  | 30 | 10 | 40 | 0 | 0 | 0 | 0 | 0 | 30 | 0 | 0 |
|  | 15 | 10 | 40 | 0 | 0 | 0 | 0 | 0 | 10 | 0 | 0 |

TABLE 5-continued

Control of warm season plant species by compounds of Formula (I) after post-emergence application

| Compound ID | Rate (g/Ha) | ZEAMX | GLXMA | ORYSA | SETFA | PANMI | SORVU | DIGSA | ECHCG | BRAPL | ELEIN |
|---|---|---|---|---|---|---|---|---|---|---|---|
| 1.0072 | 500 | 20 | 40 | 0 | 80 | 70 | 0 | 20 | 70 | 40 | 0 |
|  | 250 | 0 | 40 | 0 | 60 | 20 | 0 | 10 | 60 | 20 | 0 |
|  | 125 | 0 | 30 | 0 | 30 | 10 |  | 0 | 60 | 10 | 0 |
|  | 60 | 0 | 30 | 0 | 20 | 0 | 0 | 0 | 50 | 10 | 0 |
|  | 30 | 0 | 20 | 0 | 0 | 0 |  | 0 | 40 | 20 | 0 |
|  | 15 | 0 | 10 | 0 | 0 | 0 |  | 0 | 0 | 0 | 0 |
| 1.0095 | 500 | 30 | 50 | 30 | 60 | 70 | 60 | 60 | 80 | 80 | 30 |
|  | 250 | 10 | 50 | 10 | 40 | 40 | 50 | 30 | 80 | 70 |  |
|  | 125 | 0 | 40 | 0 | 40 | 10 |  | 40 | 70 | 70 |  |
|  | 60 | 0 | 30 | 0 | 20 | 20 |  | 50 | 60 | 60 | 20 |
|  | 30 | 0 | 20 | 0 | 10 | 10 | 20 | 10 | 50 | 50 |  |
|  | 15 | 0 | 10 | 0 | 0 | 0 |  | 0 | 30 | 10 |  |
| 1.0101 | 500 | 10 | 90 | 20 | 90 | 70 | 70 | 70 | 50 | 80 | 20 |
|  | 250 | 0 | 80 | 0 | 50 | 70 | 0 | 10 | 60 | 60 |  |
|  | 125 | 0 | 40 | 0 | 50 | 0 | 0 | 0 | 40 | 70 | 10 |
|  | 60 | 0 | 50 | 0 | 30 | 30 | 0 | 0 |  | 60 | 0 |
|  | 30 | 0 | 30 | 0 | 20 | 60 | 0 | 0 | 40 | 60 |  |
|  | 15 | 0 | 30 | 0 | 0 | 0 |  | 0 | 30 | 40 |  |
| 1.0125 | 500 | 70 | 90 | 0 | 100 | 80 | 90 | 70 | 100 | 80 | 80 |
|  | 250 | 40 | 90 | 0 | 20 | 70 | 80 | 30 | 90 | 70 | 80 |
|  | 125 | 20 |  | 0 | 20 | 50 | 70 | 10 | 80 | 80 | 70 |
|  | 60 | 30 | 70 | 0 | 20 | 50 | 50 | 0 | 80 | 80 | 70 |
|  | 30 | 20 | 70 | 0 | 10 | 30 | 50 | 0 | 80 |  | 40 |
|  | 15 | 0 | 40 | 0 | 0 | 20 | 0 | 0 | 70 | 80 | 40 |
| 1.0149 | 500 | 0 | 40 | 10 | 20 | 40 | 0 | 10 | 80 | 10 | 0 |
|  | 250 | 0 | 30 | 10 | 20 | 40 | 0 | 10 | 70 | 10 | 0 |
|  | 125 | 0 | 30 | 0 | 10 | 10 | 0 | 0 | 70 | 0 | 0 |
|  | 60 | 0 | 20 | 0 | 0 | 0 | 0 | 0 | 70 | 0 | 0 |
|  | 30 | 0 | 20 | 0 | 0 | 0 | 0 | 0 | 70 | 0 | 0 |
|  | 15 | 0 | 10 | 0 | 0 | 0 | 0 | 0 | 60 | 0 | 0 |
| 1.0327 | 500 | 70 | 90 | 0 | 80 | 90 | 80 | 30 | 90 | 90 | 40 |
|  | 250 | 10 | 90 | 0 | 60 | 70 |  | 40 | 70 | 80 | 30 |
|  | 125 | 0 | 80 | 0 | 30 | 10 |  | 10 | 50 |  | 20 |
|  | 60 | 0 | 60 | 0 | 20 | 10 |  | 10 | 30 | 40 |  |
|  | 30 | 0 | 40 | 0 | 0 | 80 | 20 | 0 | 20 | 30 |  |
|  | 15 | 0 | 20 | 0 | 0 | 0 |  | 0 | 10 | 0 |  |
| 1.0333 | 500 | 90 | 90 | 0 | 90 | 100 | 90 | 90 | 90 | 90 | 70 |
|  | 250 | 70 | 90 | 0 | 80 | 90 | 80 | 50 | 80 | 80 |  |
|  | 125 | 40 | 90 | 0 | 80 | 100 | 70 | 40 | 80 | 80 |  |
|  | 60 | 10 | 80 | 0 | 60 | 70 |  | 10 | 60 | 70 | 10 |
|  | 30 | 0 | 80 | 0 | 30 | 80 | 20 | 0 | 60 | 70 |  |
|  | 15 | 0 | 70 | 0 | 0 | 0 | 10 | 0 | 30 | 70 | 0 |
| 1.0345 | 500 | 20 | 60 | 30 | 50 | 10 | 20 | 0 | 30 | 0 | 30 |
|  | 250 | 0 | 30 | 20 | 30 | 20 |  | 0 |  | 0 | 20 |
|  | 125 | 0 | 40 | 0 | 0 | 0 | 10 | 0 | 20 | 0 | 20 |
|  | 60 | 0 | 40 | 0 | 0 | 0 |  | 0 | 20 | 0 | 20 |
|  | 30 | 0 | 20 | 0 | 0 | 0 | 0 | 0 | 0 | 0 | 0 |
|  | 15 | 0 | 10 | 0 | 0 | 0 | 0 | 0 | 0 | 0 |  |
| 1.0351 | 500 | 20 | 80 | 10 | 80 | 100 | 50 | 0 | 70 | 60 | 20 |
|  | 250 | 10 | 70 | 10 | 70 | 90 |  | 0 | 40 | 50 | 10 |
|  | 125 | 0 | 60 | 0 | 60 | 50 | 0 | 0 | 50 | 60 |  |
|  | 60 | 0 | 40 | 0 | 40 | 60 | 0 | 0 | 50 | 60 |  |
|  | 30 | 0 | 20 | 0 | 30 | 100 | 0 | 0 | 40 | 0 |  |
|  | 15 | 0 | 10 | 0 | 0 | 10 | 0 | 0 | 0 | 0 |  |
| 1.0387 | 500 | 60 | 90 | 0 | 100 | 100 | 90 | 100 | 100 | 100 | 50 |
|  | 250 | 40 | 90 | 0 | 90 | 80 | 70 | 80 | 90 | 100 | 50 |
|  | 125 | 20 | 90 | 0 | 90 | 70 | 60 | 40 | 90 | 100 | 40 |
|  | 60 | 10 | 90 | 0 | 90 | 70 | 40 |  |  | 90 | 30 |
|  | 30 | 0 | 90 | 0 | 80 | 60 | 30 | 30 | 80 | 90 | 20 |
|  | 15 | 0 | 90 | 0 | 80 | 60 | 10 | 0 | 60 | 90 | 10 |
| 1.0417 | 500 | 30 | 40 | 0 | 0 | 0 | 0 | 0 | 0 | 10 | 10 |
|  | 250 | 0 | 20 | 0 | 0 | 0 | 0 | 0 | 0 | 0 |  |
|  | 125 | 0 | 10 | 0 | 0 | 0 | 0 | 0 | 0 | 0 | 10 |
|  | 60 | 0 | 10 | 0 | 0 | 0 | 0 | 0 | 0 | 0 | 10 |
|  | 30 | 0 | 10 | 0 | 0 | 0 | 0 | 0 | 0 | 0 |  |
|  | 15 | 0 | 10 | 0 | 0 | 0 | 0 | 0 | 0 | 0 |  |

TABLE 5-continued

Control of warm season plant species by compounds
of Formula (I) after post-emergence application

| Compound ID | Rate (g/Ha) | ZEAMX | GLXMA | ORYSA | SETFA | PANMI | SORVU | DIGSA | ECHCG | BRAPL | ELEIN |
|---|---|---|---|---|---|---|---|---|---|---|---|
| 1.0429 | 500 | 20 | 60 | 30 | 90 | 70 | 0 | 0 | 60 | 70 | 30 |
|  | 250 | 0 | 50 | 20 | 60 | 80 | 0 | 0 | 50 | 30 | 20 |
|  | 125 | 0 | 40 | 0 | 50 | 20 | 0 | 0 | 30 |  | 10 |
|  | 60 | 0 | 20 | 0 | 20 | 0 | 0 | 0 |  | 20 | 0 |
|  | 30 | 0 | 10 | 0 | 30 | 0 | 0 | 0 | 10 | 0 | 10 |
|  | 15 | 0 | 10 | 0 | 10 | 0 | 0 | 0 | 0 | 0 |  |
| 1.0615 | 500 | 50 | 50 | 30 | 80 | 60 | 20 | 30 | 80 | 90 | 0 |
|  | 250 | 10 | 40 | 20 | 70 | 50 | 10 | 30 | 70 | 80 | 0 |
|  | 125 | 0 | 30 | 0 | 50 | 40 | 0 | 30 | 60 | 70 | 0 |
|  | 60 | 20 | 20 | 0 | 40 | 30 | 0 | 20 | 60 | 60 | 0 |
|  | 30 | 0 | 10 | 0 | 30 | 20 | 0 | 20 | 60 |  | 0 |
|  | 15 | 0 | 10 | 0 | 10 | 10 | 0 | 0 |  | 10 | 0 |
| 1.0633 | 500 | 40 | 100 | 30 | 90 | 70 | 80 | 90 | 100 | 100 | 50 |
|  | 250 | 30 | 90 | 20 | 80 | 60 | 70 | 80 | 90 | 100 | 50 |
|  | 125 | 20 | 80 | 10 | 70 | 60 | 70 | 80 | 80 | 90 |  |
|  | 60 | 10 | 80 | 10 | 70 | 50 | 50 | 50 | 80 | 90 | 30 |
|  | 30 | 0 | 70 | 0 |  | 10 | 30 | 20 | 80 | 80 | 20 |
|  | 15 | 0 | 40 | 0 | 20 | 0 | 0 | 10 | 80 |  | 0 |
| 1.1653 | 500 | 10 | 30 | 0 | 40 | 10 | 30 | 0 | 40 | 30 | 10 |
|  | 250 | 0 | 10 | 0 | 30 | 60 | 0 | 0 | 30 | 0 |  |
|  | 125 | 0 | 10 | 0 | 20 | 80 |  | 0 | 40 | 0 |  |
|  | 60 | 0 | 10 | 0 | 60 | 10 | 0 | 0 |  | 0 | 0 |
|  | 30 | 0 | 10 | 0 | 50 | 0 | 0 | 0 |  | 0 |  |
|  | 15 | 0 | 10 | 0 | 20 | 0 | 0 | 0 | 40 | 0 |  |

TABLE 6

Control of warm season plant species by compounds of
Formula (I) after post-emergence application

| Compound ID | Rate (g/Ha) | ZEAMX | GLXMA | ORYSA | EPHHL | SIDSP | ABUTH | XANST | IPOHE | BIDPI | AMARE |
|---|---|---|---|---|---|---|---|---|---|---|---|
| 1.0001 | 500 | 100 | 70 | 100 | 90 | 90 | 90 | 80 | 100 | 70 | 100 |
|  | 250 | 90 | 60 | 90 | 90 | 80 | 50 | 70 | 90 | 60 | 90 |
|  | 125 | 90 | 60 | 90 | 90 | 80 | 40 | 70 | 90 | 60 | 90 |
|  | 60 | 80 | 60 | 90 | 90 | 80 | 40 | 70 | 80 | 60 | 90 |
|  | 30 | 30 | 60 | 90 | 90 | 80 | 30 | 70 | 30 | 60 | 90 |
|  | 15 | 20 | 40 | 80 | 90 | 80 | 20 | 60 | 20 | 40 | 80 |
| 1.0012 | 500 | 100 | 90 | 100 | 100 | 100 | 100 | 100 | 100 | 90 | 100 |
|  | 250 | 100 | 90 | 90 | 90 | 100 | 100 | 100 | 100 | 90 | 90 |
|  | 125 | 90 | 90 | 90 | 90 | 100 | 70 | 90 | 90 | 90 | 90 |
|  | 60 | 90 | 80 | 90 | 90 | 100 | 70 | 90 | 90 | 80 | 90 |
|  | 30 | 70 | 80 | 80 |  | 80 | 70 | 80 | 80 | 80 | 80 |
|  | 15 | 50 | 80 | 60 |  | 70 | 70 | 60 | 50 | 80 | 60 |
| 1.0018 | 500 | 100 | 100 | 100 | 100 | 100 | 90 | 100 | 100 | 100 | 100 |
|  | 250 | 100 | 90 | 90 | 100 | 100 | 90 | 100 | 100 | 90 | 90 |
|  | 125 | 90 | 90 | 90 |  | 100 | 80 | 100 | 90 | 90 | 90 |
|  | 60 | 80 | 80 | 50 | 90 | 90 | 70 | 90 | 80 | 80 | 50 |
|  | 30 | 70 | 80 | 50 |  | 90 | 60 | 90 | 70 | 80 | 50 |
|  | 15 | 60 | 40 | 20 |  | 70 | 50 | 90 | 60 | 40 | 20 |
| 1.0024 | 500 | 100 | 100 | 100 | 100 | 100 | 90 | 100 | 100 | 100 | 100 |
|  | 250 | 100 | 100 | 100 | 100 | 100 | 80 | 100 | 100 | 100 | 100 |
|  | 125 | 100 |  | 100 | 90 | 100 | 70 | 100 | 100 |  | 100 |
|  | 60 | 90 | 100 | 100 |  | 100 | 70 | 100 | 90 | 100 | 100 |
|  | 30 | 90 | 90 | 90 |  | 100 | 70 | 100 | 90 | 90 | 90 |
|  | 15 | 80 | 90 | 80 | 80 | 100 | 70 |  | 80 | 90 | 80 |
| 1.0042 | 500 | 100 | 100 | 100 | 100 | 100 | 90 | 100 | 100 | 100 | 100 |
|  | 250 | 100 | 100 | 100 |  | 100 | 80 | 100 | 100 | 100 | 100 |
|  | 125 | 90 | 100 | 100 | 80 | 100 | 80 | 100 | 90 | 100 | 100 |
|  | 60 | 90 | 90 | 100 | 80 | 100 | 80 | 90 | 90 | 90 | 100 |
|  | 30 | 90 | 90 | 90 |  | 100 | 80 | 90 | 90 | 90 | 90 |
|  | 15 | 70 | 80 | 90 |  |  | 80 | 80 | 70 | 80 | 90 |
| 1.0048 | 500 | 100 | 100 | 100 | 100 | 100 | 100 | 100 | 100 | 100 | 100 |
|  | 250 | 100 | 100 | 100 | 90 | 100 | 80 | 100 | 100 | 100 | 100 |
|  | 125 | 100 | 100 | 100 | 90 | 100 | 80 | 100 | 100 | 100 | 100 |
|  | 60 | 100 | 90 | 100 | 80 | 100 | 70 | 90 | 100 | 90 | 100 |
|  | 30 | 100 | 80 | 90 | 90 | 100 | 60 | 80 | 100 | 80 | 90 |
|  | 15 | 80 |  | 70 |  | 100 | 70 | 80 | 80 |  | 70 |

TABLE 6-continued

Control of warm season plant species by compounds of Formula (I) after post-emergence application

| Compound ID | Rate (g/Ha) | ZEAMX | GLXMA | ORYSA | EPHHL | SIDSP | ABUTH | XANST | IPOHE | BIDPI | AMARE |
|---|---|---|---|---|---|---|---|---|---|---|---|
| 1.0066 | 500 | 70 | 90 | 90 | 80 | 90 | 70 | 80 | 70 | 90 | 90 |
|  | 250 | 70 | 90 | 80 | 80 | 90 | 50 | 80 | 70 | 90 | 80 |
|  | 125 | 60 | 80 | 80 | 80 | 80 | 50 | 80 | 60 | 80 | 80 |
|  | 60 | 60 | 80 | 80 | 70 | 80 | 40 | 70 | 60 | 80 | 80 |
|  | 30 | 30 | 60 | 70 | 70 | 80 | 40 | 80 | 30 | 60 | 70 |
|  | 15 | 30 | 60 | 60 | 70 | 60 | 40 | 80 | 30 | 60 | 60 |
| 1.0072 | 500 | 70 | 50 | 90 |  | 90 | 60 | 80 | 70 | 50 | 90 |
|  | 250 | 70 |  | 80 |  | 90 | 10 | 80 | 70 |  | 80 |
|  | 125 | 60 | 20 | 80 |  | 80 | 10 | 80 | 60 | 20 | 80 |
|  | 60 |  |  | 80 |  | 70 | 10 | 70 |  |  | 80 |
|  | 30 | 20 | 10 | 70 |  | 60 | 0 | 50 | 20 | 10 | 70 |
|  | 15 | 10 |  | 70 |  | 30 | 0 | 40 | 10 |  | 70 |
| 1.0095 | 500 | 90 | 70 | 80 |  | 70 | 30 | 80 | 90 | 70 | 80 |
|  | 250 | 60 |  | 40 |  | 30 | 0 | 80 | 60 |  | 40 |
|  | 125 | 50 | 30 | 60 |  | 30 | 0 | 80 | 50 | 30 | 60 |
|  | 60 | 50 | 20 | 60 |  | 40 | 0 | 80 | 50 | 20 | 60 |
|  | 30 | 40 |  | 40 |  | 20 | 0 | 70 | 40 |  | 40 |
|  | 15 | 40 |  | 20 |  | 10 | 0 | 70 | 40 |  | 20 |
| 1.0101 | 500 | 70 | 70 | 90 |  | 90 | 30 | 80 | 70 | 70 | 90 |
|  | 250 | 50 | 60 | 80 |  | 80 | 0 | 80 | 50 | 60 | 80 |
|  | 125 | 40 |  | 80 |  | 60 | 0 | 80 | 40 |  | 80 |
|  | 60 |  |  | 80 |  | 80 | 0 | 80 |  |  | 80 |
|  | 30 | 50 | 30 | 70 |  | 90 | 0 | 80 | 50 | 30 | 70 |
|  | 15 | 20 | 30 | 70 |  | 80 | 0 | 80 | 20 | 30 | 70 |
| 1.0125 | 500 | 100 | 100 | 100 | 100 | 100 | 100 | 100 | 100 | 100 | 100 |
|  | 250 | 100 | 90 | 100 | 90 | 100 | 80 | 100 | 100 | 90 | 100 |
|  | 125 | 100 | 90 | 90 | 90 | 100 | 70 | 100 | 100 | 90 | 90 |
|  | 60 | 100 | 80 | 90 | 90 | 100 | 70 | 90 | 100 | 80 | 90 |
|  | 30 | 90 |  | 90 | 90 | 100 | 60 | 90 | 90 |  | 90 |
|  | 15 | 90 |  | 80 |  | 90 | 60 | 80 | 90 |  | 80 |
| 1.0149 | 500 | 80 | 50 | 80 | 80 | 60 | 60 | 90 | 80 | 50 | 80 |
|  | 250 | 70 | 50 | 70 | 70 | 70 | 50 | 80 | 70 | 50 | 70 |
|  | 125 | 70 | 40 | 70 | 70 | 70 | 40 | 80 | 70 | 40 | 70 |
|  | 60 | 60 | 50 | 70 | 60 | 50 | 40 | 80 | 60 | 50 | 70 |
|  | 30 | 40 | 50 | 70 | 60 | 30 | 30 | 70 | 40 | 50 | 70 |
|  | 15 | 40 | 40 | 70 | 60 | 30 | 30 | 50 | 40 | 40 | 70 |
| 1.0327 | 500 | 80 | 90 | 90 |  | 90 | 70 | 80 | 80 | 90 | 90 |
|  | 250 | 80 | 20 | 80 |  | 90 | 40 | 70 | 80 | 20 | 80 |
|  | 125 | 60 | 30 | 80 |  | 90 | 20 | 50 | 60 | 30 | 80 |
|  | 60 | 60 | 20 | 80 |  | 90 | 10 | 50 | 60 | 20 | 80 |
|  | 30 | 40 |  | 40 |  | 30 | 0 | 40 | 40 |  | 40 |
|  | 15 | 20 | 10 | 20 |  | 20 | 0 | 30 | 20 | 10 | 20 |
| 1.0333 | 500 | 100 | 80 | 100 |  | 90 | 60 | 90 | 100 | 80 | 100 |
|  | 250 | 80 | 80 | 90 |  | 90 | 40 | 90 | 80 | 80 | 90 |
|  | 125 | 70 | 80 | 90 |  | 90 | 30 | 90 | 70 | 80 | 90 |
|  | 60 | 60 | 30 | 80 |  | 90 | 0 | 80 | 60 | 30 | 80 |
|  | 30 | 50 |  | 80 |  | 90 |  | 80 | 50 |  | 80 |
|  | 15 | 50 |  | 70 |  | 90 |  | 80 | 50 |  | 70 |
| 1.0345 | 500 | 80 | 40 | 80 |  | 80 | 30 | 80 | 80 | 40 | 80 |
|  | 250 | 70 |  | 70 |  | 80 |  | 80 | 70 |  | 70 |
|  | 125 | 60 |  | 60 |  | 70 |  | 80 | 60 |  | 60 |
|  | 60 | 50 | 40 | 60 |  | 60 | 0 | 80 | 50 | 40 | 60 |
|  | 30 | 30 |  | 50 |  | 40 | 0 | 80 | 30 |  | 50 |
|  | 15 | 30 |  | 20 |  | 20 | 0 | 80 | 30 |  | 20 |
| 1.0351 | 500 | 80 | 80 | 90 |  | 90 | 30 | 80 | 80 | 80 | 90 |
|  | 250 | 60 | 20 | 80 |  | 90 | 20 | 70 | 60 | 20 | 80 |
|  | 125 | 60 | 20 | 80 |  | 90 | 10 | 60 | 60 | 20 | 80 |
|  | 60 | 70 |  | 60 |  | 80 | 0 | 60 | 70 |  | 60 |
|  | 30 | 50 |  | 60 |  | 90 | 0 | 50 | 50 |  | 60 |
|  | 15 | 40 |  | 10 |  | 80 | 0 | 50 | 40 |  | 10 |
| 1.0387 | 500 | 100 | 90 | 90 |  | 100 | 50 | 90 | 100 | 90 | 90 |
|  | 250 | 90 | 80 | 90 |  | 90 | 40 | 90 | 90 | 80 | 90 |
|  | 125 | 90 | 70 | 90 |  | 90 | 30 | 90 | 90 | 70 | 90 |
|  | 60 | 80 | 60 | 90 |  | 90 | 20 | 90 | 80 | 60 | 90 |
|  | 30 | 70 | 50 | 80 |  | 90 | 10 | 80 | 70 | 50 | 80 |
|  | 15 | 50 |  | 80 |  | 90 | 10 | 80 | 50 |  | 80 |

TABLE 6-continued

Control of warm season plant species by compounds of
Formula (I) after post-emergence application

| Compound ID | Rate (g/Ha) | ZEAMX | GLXMA | ORYSA | EPHHL | SIDSP | ABUTH | XANST | IPOHE | BIDPI | AMARE |
|---|---|---|---|---|---|---|---|---|---|---|---|
| 1.0417 | 500 | 60 | 60 | 60 |  | 80 | 0 | 70 | 60 | 60 | 60 |
|  | 250 | 60 | 0 | 70 |  | 70 | 0 | 60 | 60 | 0 | 70 |
|  | 125 | 40 | 0 | 60 |  | 60 | 0 | 50 | 40 | 0 | 60 |
|  | 60 | 30 |  | 50 |  | 10 | 0 | 40 | 30 |  | 50 |
|  | 30 | 30 |  | 40 |  | 0 | 0 | 50 | 30 |  | 40 |
|  | 15 | 20 |  | 0 |  | 0 | 0 | 30 | 20 |  | 0 |
| 1.0429 | 500 | 70 | 50 | 90 |  | 90 | 40 | 80 | 70 | 50 | 90 |
|  | 250 | 40 | 60 | 80 |  | 90 | 30 | 80 | 40 | 60 | 80 |
|  | 125 | 30 |  | 80 |  | 90 | 10 | 70 | 30 |  | 80 |
|  | 60 | 20 |  | 70 |  | 90 | 0 | 50 | 20 |  | 70 |
|  | 30 | 10 | 0 | 70 |  | 90 | 0 | 50 | 10 | 0 | 70 |
|  | 15 | 0 | 0 | 60 |  | 90 | 0 | 40 | 0 | 0 | 60 |
| 1.0615 | 500 | 80 | 60 | 90 |  | 100 | 60 | 70 | 80 | 60 | 90 |
|  | 250 | 70 | 50 | 80 |  | 90 | 40 | 60 | 70 | 50 | 80 |
|  | 125 | 50 | 40 | 80 |  | 90 | 30 | 40 | 50 | 40 | 80 |
|  | 60 | 40 | 20 | 80 |  | 90 | 20 |  | 40 | 20 | 80 |
|  | 30 | 30 | 20 | 70 |  | 80 | 10 | 40 | 30 | 20 | 70 |
|  | 15 | 20 |  | 50 |  | 60 | 10 | 30 | 20 |  | 50 |
| 1.0633 | 500 | 90 | 90 | 90 |  | 100 | 70 | 90 | 90 | 90 | 90 |
|  | 250 | 80 | 90 | 90 |  | 100 | 50 | 80 | 80 | 90 | 90 |
|  | 125 | 70 | 80 | 80 |  | 90 |  | 80 | 70 | 80 | 80 |
|  | 60 | 60 | 80 | 70 |  | 90 | 40 | 80 | 60 | 80 | 70 |
|  | 30 | 40 | 60 | 70 |  | 90 | 20 | 60 | 40 | 60 | 70 |
|  | 15 | 40 | 50 | 60 |  | 80 | 10 | 60 | 40 | 50 | 60 |
| 1.1653 | 500 | 60 | 30 | 80 |  | 90 | 90 | 70 | 60 | 30 | 80 |
|  | 250 | 60 | 20 | 70 |  | 80 | 40 | 80 | 60 | 20 | 70 |
|  | 125 | 40 |  | 70 |  |  | 30 | 60 | 40 |  | 70 |
|  | 60 | 40 |  | 70 |  | 70 | 20 | 60 | 40 |  | 70 |
|  | 30 | 30 | 10 | 70 |  | 70 | 10 | 50 | 30 | 10 | 70 |
|  | 15 | 20 |  | 70 |  | 50 | 10 | 40 | 20 |  | 70 |

TABLE 7

Control of cool season plant species by compounds
of Formula (I) after post-emergence application

| Compound ID | Rate (g/Ha) | HORVW | TRZAW | BRSNN | BEAVA | ALOMY | AVEFA | BROTE | LOLPE | POAAN | CHEAL |
|---|---|---|---|---|---|---|---|---|---|---|---|
| 1.0001 | 500 | 20 | 20 | 100 | 100 | 80 | 90 | 60 | 80 | 60 | 100 |
|  | 250 | 10 | 20 | 100 | 100 | 60 | 80 | 40 | 80 | 30 | 100 |
|  | 125 | 0 | 10 | 100 | 100 | 30 | 70 | 20 | 80 | 10 | 100 |
|  | 60 | 0 | 0 | 100 | 90 | 20 | 60 | 10 | 70 | 10 | 100 |
|  | 30 | 0 | 0 | 90 | 90 | 0 | 50 | 20 | 70 | 0 | 100 |
|  | 15 | 0 | 0 | 90 | 100 | 0 | 30 | 20 | 60 | 0 |  |
| 1.0012 | 500 | 30 | 40 | 90 | 70 | 50 | 70 | 30 | 60 | 50 | 100 |
|  | 250 | 20 | 30 | 90 | 50 | 50 | 50 | 20 | 40 | 30 | 80 |
|  | 125 | 10 | 10 | 80 | 50 | 20 | 40 | 0 | 50 | 10 | 80 |
|  | 60 | 0 | 10 | 80 | 50 | 10 | 30 | 0 | 50 | 10 | 70 |
|  | 30 | 0 | 0 | 80 | 40 | 10 | 20 | 0 | 30 | 20 | 50 |
|  | 15 | 0 | 0 | 80 | 30 | 20 | 10 | 0 | 30 | 10 |  |
| 1.0018 | 500 | 0 | 0 | 100 | 100 | 0 | 10 | 20 | 50 | 10 | 80 |
|  | 250 | 0 | 0 | 100 | 100 | 0 | 10 | 20 | 50 | 0 | 70 |
|  | 125 | 0 | 0 | 100 | 100 | 0 | 0 | 0 | 40 | 0 | 70 |
|  | 60 | 0 | 0 | 80 | 80 | 0 | 0 | 0 | 40 | 0 | 30 |
|  | 30 | 0 | 0 | 60 | 80 | 0 | 0 | 0 | 20 | 0 |  |
|  | 15 | 0 | 0 | 40 | 80 | 0 | 0 |  | 0 | 0 |  |
| 1.0024 | 500 | 40 | 50 | 100 | 60 | 60 | 60 | 30 | 70 | 90 | 90 |
|  | 250 | 20 | 30 | 90 | 50 | 50 | 50 | 10 | 70 | 80 | 90 |
|  | 125 | 10 | 20 | 90 | 40 | 30 | 30 | 0 | 40 | 50 | 80 |
|  | 60 | 0 | 10 | 80 | 30 | 20 | 10 | 0 | 30 | 10 | 50 |
|  | 30 | 0 | 10 | 80 | 20 | 0 | 0 | 0 | 10 | 0 | 10 |
|  | 15 | 0 | 0 | 70 | 0 | 0 | 0 | 0 | 0 | 0 | 0 |
| 1.0042 | 500 |  |  |  |  |  |  |  |  |  |  |
|  | 250 | 0 | 0 | 40 | 20 | 10 | 0 | 0 | 10 | 10 | 10 |
|  | 125 | 0 | 0 | 20 | 10 | 10 | 0 | 0 | 0 | 0 | 0 |
|  | 60 | 0 | 0 | 30 | 0 | 0 | 0 | 0 | 0 | 0 | 0 |
|  | 30 | 0 | 0 | 30 | 0 | 0 | 0 | 0 | 0 | 0 | 0 |
|  | 15 | 0 | 0 | 30 | 0 | 0 | 0 | 0 | 0 | 0 | 0 |

TABLE 7-continued

Control of cool season plant species by compounds of Formula (I) after post-emergence application

| Compound ID | Rate (g/Ha) | HORVW | TRZAW | BRSNN | BEAVA | ALOMY | AVEFA | BROTE | LOLPE | POAAN | CHEAL |
|---|---|---|---|---|---|---|---|---|---|---|---|
| 1.0048 | 500 | 30 | 60 | 90 | 70 | 10 | 20 | 10 | 40 | 20 | 80 |
| | 250 | 10 | 40 | 80 | 50 | 0 | 30 | 10 | 50 | 10 | 70 |
| | 125 | 0 | 10 | 90 | 60 | 0 | 20 | 0 | 50 | 10 | 50 |
| | 60 | 0 | 20 | 80 | 50 | 0 | 20 | 0 | 30 | 0 | 60 |
| | 30 | 0 | 0 | 80 | 50 | 0 | 10 | 0 | 20 | 0 | 10 |
| | 15 | 0 | 0 | 80 | 40 | 0 | 0 | 0 | 10 | 0 | 0 |
| 1.0066 | 500 | 10 | 0 | 100 | 60 | 10 | 10 | 10 | 20 | 20 | 80 |
| | 250 | 10 | 0 | 90 | 50 | 10 | 0 | 0 | 30 | 0 | 50 |
| | 125 | 0 | 0 | 90 | 30 | 0 | 0 | 0 | 10 | 0 | 40 |
| | 60 | 0 | 0 | 90 | 10 | 0 | 0 | 0 | 10 | 0 | 20 |
| | 30 | 0 | 0 | 90 | 0 | 0 | 0 | 0 | 0 | 0 | 0 |
| | 15 | 0 | 0 | 70 | 0 | 0 | 0 | 0 | 0 | 0 | 0 |
| 1.0072 | 500 | 50 | 70 | 90 | 80 | 90 | 80 | 40 | 90 | 90 | 100 |
| | 250 | 30 | 60 | 90 | 70 | 80 | 70 | 50 | 90 | 90 | 100 |
| | 125 | 10 | 60 | 90 | 60 | 80 | 70 | 30 | 90 | 80 | 90 |
| | 60 | 20 | 40 | 90 | 50 | 60 | 60 | 10 | 80 | 50 | 90 |
| | 30 | 0 | 30 | 80 | 40 | 30 | 40 | 0 | 70 | 40 | 90 |
| | 15 | 0 | 0 | 80 | 40 | 10 | 10 | 0 | 50 | 10 | 60 |
| 1.0095 | 500 | 60 | 70 | 90 | 100 | 90 | 90 | 20 | 90 | 90 | 90 |
| | 250 | 30 | 50 | 90 | 70 | 80 | 80 | 10 | 80 | 90 | 90 |
| | 125 | 20 | 50 | 80 | 60 | 70 | 70 | 0 | 60 | 90 | |
| | 60 | 10 | 20 | 90 | 70 | 70 | 50 | 0 | 50 | 80 | 80 |
| | 30 | 0 | 20 | 80 | 70 | 40 | 20 | 0 | 40 | 70 | 70 |
| | 15 | 0 | 0 | 70 | 50 | 10 | 0 | 0 | 20 | 10 | |
| 1.0101 | 500 | 0 | 10 | 90 | 40 | 50 | 20 | 10 | 60 | 50 | 80 |
| | 250 | 0 | 10 | 80 | 40 | 40 | 10 | 0 | 40 | 50 | 80 |
| | 125 | 0 | 0 | 80 | 20 | 30 | 0 | 0 | 30 | 30 | 60 |
| | 60 | 0 | 0 | 60 | 10 | 20 | 0 | 0 | 20 | 10 | 20 |
| | 30 | 0 | 0 | 40 | 10 | 0 | 0 | 0 | 0 | 0 | 10 |
| | 15 | 0 | 0 | 30 | 0 | 0 | 0 | 0 | 0 | 0 | 0 |
| 1.0125 | 500 | 20 | 70 | 90 | 100 | 70 | 80 | 70 | 90 | 90 | 100 |
| | 250 | 10 | 60 | 90 | 80 | 70 | 70 | 40 | 90 | 80 | 90 |
| | 125 | 10 | 30 | 90 | 80 | 70 | 60 | 20 | 90 | 80 | 90 |
| | 60 | 10 | 20 | 90 | 80 | 50 | 30 | 10 | 70 | 30 | 90 |
| | 30 | 10 | 0 | 90 | 70 | 30 | 20 | 0 | 70 | 20 | 90 |
| | 15 | 0 | 0 | 80 | 70 | 10 | 10 | 0 | 10 | 10 | 60 |
| 1.0149 | 500 | 30 | 0 | 100 | 80 | 20 | 30 | 40 | 20 | 10 | 90 |
| | 250 | 10 | 0 | 100 | 50 | 10 | 20 | 10 | 20 | 10 | 90 |
| | 125 | 0 | 0 | 90 | 40 | 0 | 10 | 10 | 10 | 0 | 100 |
| | 60 | 0 | 0 | 80 | 40 | 0 | 10 | 0 | 10 | 0 | 100 |
| | 30 | 0 | 0 | 80 | 40 | 0 | 10 | 0 | 10 | 0 | 80 |
| | 15 | 0 | 0 | 80 | | 0 | 0 | 0 | 0 | 0 | 80 |
| 1.0327 | 500 | 20 | 0 | 90 | 40 | 20 | 10 | 0 | 70 | 30 | 90 |
| | 250 | 20 | 0 | 90 | 40 | 10 | 10 | 0 | 20 | 10 | 90 |
| | 125 | 0 | 0 | 80 | 40 | 10 | 0 | 0 | 10 | 0 | 50 |
| | 60 | 0 | 0 | 50 | 20 | 0 | 0 | 0 | 10 | 0 | 40 |
| | 30 | 0 | 0 | 40 | 30 | 0 | 0 | 0 | 0 | 0 | 0 |
| | 15 | 0 | 0 | 30 | 30 | 0 | 0 | 0 | 0 | 0 | 0 |
| 1.0333 | 500 | 80 | 80 | 90 | 90 | 90 | 90 | 90 | 90 | 90 | 100 |
| | 250 | 80 | 80 | 90 | 90 | 90 | 90 | 80 | 90 | 90 | 100 |
| | 125 | 40 | 70 | 90 | 90 | 80 | 80 | 80 | 90 | 90 | 90 |
| | 60 | 20 | 60 | 90 | 80 | 80 | 80 | 70 | 70 | 80 | 90 |
| | 30 | 20 | 30 | 90 | 70 | 60 | 60 | 30 | 70 | 70 | 90 |
| | 15 | 10 | 20 | 90 | 80 | 20 | 30 | 20 | 60 | 20 | |
| 1.0345 | 500 | 80 | 80 | 90 | 90 | 90 | 90 | 70 | 90 | 90 | 100 |
| | 250 | 40 | 50 | 90 | 90 | 80 | 90 | 60 | 90 | 90 | 90 |
| | 125 | 40 | 20 | 90 | 90 | 80 | 80 | 50 | 90 | 80 | 70 |
| | 60 | 10 | 20 | 90 | 80 | 70 | 60 | 20 | 90 | 80 | |
| | 30 | 10 | 10 | 90 | 80 | 30 | 30 | 10 | 40 | 30 | |
| | 15 | 10 | 0 | 90 | 70 | 20 | 10 | 0 | 20 | 30 | |
| 1.0351 | 500 | 90 | 80 | 90 | 90 | 90 | 90 | 90 | 100 | 90 | 100 |
| | 250 | 80 | 70 | 90 | 80 | 90 | 90 | 80 | 90 | 90 | 100 |
| | 125 | 70 | 60 | 90 | 80 | 80 | 90 | 70 | 90 | 90 | 90 |
| | 60 | 20 | 40 | 90 | 80 | 70 | 40 | 60 | 80 | 80 | 90 |
| | 30 | 10 | 10 | 90 | 80 | 50 | 20 | 20 | 20 | 70 | 90 |
| | 15 | 0 | 0 | 90 | 80 | 20 | 0 | 0 | 10 | 20 | |
| 1.0387 | 500 | 60 | 70 | 90 | 90 | 90 | 90 | 70 | 90 | 70 | 100 |
| | 250 | 30 | 60 | 90 | 90 | 80 | 90 | 60 | 90 | 80 | 100 |
| | 125 | 20 | 30 | 90 | 80 | 80 | 80 | 30 | 90 | 90 | 100 |
| | 60 | 20 | 20 | 90 | 80 | 50 | 70 | 10 | 80 | 70 | 90 |
| | 30 | 10 | 0 | 80 | 80 | 50 | 70 | 0 | 70 | 40 | 90 |
| | 15 | 10 | 0 | 80 | 90 | 20 | 30 | 0 | 40 | 20 | 80 |

TABLE 7-continued

Control of cool season plant species by compounds of Formula (I) after post-emergence application

| Compound ID | Rate (g/Ha) | HORVW | TRZAW | BRSNN | BEAVA | ALOMY | AVEFA | BROTE | LOLPE | POAAN | CHEAL |
|---|---|---|---|---|---|---|---|---|---|---|---|
| 1.0417 | 500 | 10 | 50 | 90 | 70 | 40 | 80 | 10 | 90 | 60 | 90 |
| | 250 | 10 | 30 | 90 | 70 | 60 | 70 | 10 | 80 | 70 | 90 |
| | 125 | 10 | 20 | 90 | 70 | 30 | 70 | 0 | 70 | 60 | 90 |
| | 60 | 10 | 10 | 80 | 60 | 30 | 60 | 0 | 60 | 20 | 90 |
| | 30 | 0 | 10 | 80 | 60 | 10 | 40 | 0 | 50 | 10 | 90 |
| | 15 | 0 | 0 | 80 | 70 | 10 | 30 | 0 | 40 | 0 | 90 |
| 1.0429 | 500 | 20 | 50 | 90 | 80 | 60 | 60 | 20 | 40 | 80 | 80 |
| | 250 | 20 | 0 | 90 | 60 | 70 | 60 | 10 | 50 | 70 | 70 |
| | 125 | 0 | 0 | 90 | 50 | 40 | 40 | 0 | 40 | 80 | 80 |
| | 60 | 0 | 0 | 90 | 40 | 50 | 40 | 0 | 50 | 80 | 80 |
| | 30 | 0 | 0 | 70 | 40 | 50 | 30 | 0 | 40 | 70 | 60 |
| | 15 | 0 | 0 | 80 | 30 | 10 | 10 | 0 | 30 | 50 | 60 |
| 1.0615 | 500 | 50 | 60 | 100 | 100 | 50 | 90 | | 60 | 70 | |
| | 250 | 30 | 40 | 100 | 100 | 30 | 90 | | 40 | 70 | |
| | 125 | 10 | 30 | 90 | 100 | 20 | 70 | | 30 | 60 | |
| | 60 | 10 | 10 | 80 | 100 | 20 | 60 | | 40 | 40 | |
| | 30 | 0 | 0 | 60 | 100 | 10 | 30 | | 30 | 40 | |
| | 15 | 0 | 0 | 50 | 80 | 0 | 0 | | 0 | 20 | |
| 1.0633 | 500 | | | | | | | | | | |
| | 250 | 10 | 50 | 90 | 70 | 40 | 70 | 20 | 40 | 70 | 80 |
| | 125 | 0 | 50 | 90 | 50 | 20 | 50 | 10 | 20 | 50 | 70 |
| | 60 | 0 | 20 | 80 | 50 | 10 | 20 | 0 | 20 | 20 | |
| | 30 | 0 | 0 | 80 | 50 | 0 | 10 | 0 | 0 | 0 | 80 |
| | 15 | 0 | 0 | 60 | 40 | 0 | 0 | 0 | 0 | 0 | |
| 1.1653 | 500 | 20 | 40 | 100 | 100 | 20 | 70 | 30 | 60 | 80 | 90 |
| | 250 | 0 | 30 | 100 | 100 | 30 | 60 | 40 | 60 | 80 | 90 |
| | 125 | 0 | 40 | 90 | 80 | 20 | 20 | 40 | 30 | 60 | 80 |
| | 60 | 0 | 0 | 90 | 70 | 0 | 10 | 0 | 10 | 50 | 80 |
| | 30 | 0 | 0 | 70 | 70 | 0 | 0 | 0 | 0 | 10 | 70 |
| | 15 | 0 | 0 | 60 | 70 | 0 | 0 | 0 | 0 | 0 | |

TABLE 8

Control of cool season plant species by compounds of Formula (I) after post-emergence application

| Compound ID | Rate (g/Ha) | HORVW | TRZAW | POLCO | KCHSC | SINAR | STEME | GALAP | VERPE |
|---|---|---|---|---|---|---|---|---|---|
| 1.0001 | 500 | 20 | 20 | 100 | 80 | 100 | 100 | 90 | 90 |
| | 250 | 10 | 20 | 100 | 80 | 100 | 100 | 90 | 90 |
| | 125 | 0 | 10 | 100 | 70 | 90 | 100 | 80 | 80 |
| | 60 | 0 | 0 | 100 | 50 | 90 | | 80 | 80 |
| | 30 | 0 | 0 | 100 | 40 | 90 | 100 | | 70 |
| | 15 | 0 | 0 | 90 | 30 | 90 | 100 | 20 | 60 |
| 1.0012 | 500 | 30 | 40 | 100 | 70 | 90 | 90 | 80 | 90 |
| | 250 | 20 | 30 | 100 | 60 | 80 | 80 | 40 | 80 |
| | 125 | 10 | 10 | 90 | 30 | 80 | 70 | 50 | 70 |
| | 60 | 0 | 10 | 90 | 10 | 80 | 80 | 30 | 60 |
| | 30 | 0 | 0 | 90 | 0 | | 70 | 20 | 60 |
| | 15 | 0 | 0 | 100 | 0 | 80 | | 0 | 60 |
| 1.0018 | 500 | 0 | 0 | 100 | 60 | 100 | 100 | 90 | 90 |
| | 250 | 0 | 0 | 100 | 60 | 90 | 90 | 90 | 90 |
| | 125 | 0 | 0 | 100 | 40 | 90 | 90 | 60 | 80 |
| | 60 | 0 | 0 | 90 | 10 | 40 | 90 | | 80 |
| | 30 | 0 | 0 | 100 | 10 | 20 | 90 | 20 | 70 |
| | 15 | 0 | 0 | 80 | 0 | 20 | 80 | 0 | 40 |
| 1.0024 | 500 | 40 | 50 | 100 | 80 | 100 | 90 | 50 | 90 |
| | 250 | 20 | 30 | 100 | 80 | 90 | 80 | 60 | 70 |
| | 125 | 10 | 20 | 80 | 80 | 90 | 80 | 30 | 60 |
| | 60 | 0 | 10 | 80 | 50 | 80 | 80 | | 30 |
| | 30 | 0 | 10 | 80 | 30 | 80 | 70 | | 20 |
| | 15 | 0 | 0 | 70 | 10 | 80 | 50 | | 10 |
| 1.0042 | 500 | | | | | | | | |
| | 250 | 0 | 0 | 40 | 20 | 20 | 50 | 30 | 40 |
| | 125 | 0 | 0 | 20 | 10 | 10 | 60 | 40 | 30 |
| | 60 | 0 | 0 | 30 | 10 | | 60 | 20 | 30 |
| | 30 | 0 | 0 | 30 | 0 | 10 | 60 | 20 | 20 |
| | 15 | 0 | 0 | 0 | 0 | 0 | 30 | 0 | 20 |

TABLE 8-continued

Control of cool season plant species by compounds of Formula (I) after post-emergence application

| Compound ID | Rate (g/Ha) | HORVW | TRZAW | POLCO | KCHSC | SINAR | STEME | GALAP | VERPE |
|---|---|---|---|---|---|---|---|---|---|
| 1.0048 | 500 | 30 | 60 | 90 | 40 | 90 | 90 | 60 | 80 |
|  | 250 | 10 | 40 | 90 | 50 | 80 | 80 | 70 | 80 |
|  | 125 | 0 | 10 | 90 | 40 | 80 | 80 | 70 | 70 |
|  | 60 | 0 | 20 | 80 | 20 |  | 70 | 50 | 60 |
|  | 30 | 0 | 0 | 80 | 30 | 70 | 70 | 50 | 40 |
|  | 15 | 0 | 0 | 50 | 10 |  | 70 | 20 | 20 |
| 1.0066 | 500 | 10 | 0 | 80 | 70 | 80 | 70 | 40 | 40 |
|  | 250 | 10 | 0 | 60 | 60 | 80 | 70 | 50 | 20 |
|  | 125 | 0 | 0 |  | 50 | 80 | 70 | 30 | 20 |
|  | 60 | 0 | 0 |  | 20 |  | 60 | 40 | 10 |
|  | 30 | 0 | 0 |  | 0 | 70 | 50 | 30 | 0 |
|  | 15 | 0 | 0 |  | 0 | 40 | 30 | 20 | 0 |
| 1.0072 | 500 | 50 | 70 | 100 | 90 | 90 | 90 | 90 | 100 |
|  | 250 | 30 | 60 | 100 | 90 | 90 | 90 | 90 | 100 |
|  | 125 | 10 | 60 | 100 | 80 | 80 | 90 | 50 | 90 |
|  | 60 | 20 | 40 |  | 70 | 70 | 80 | 60 | 80 |
|  | 30 | 0 | 30 | 90 | 30 | 70 |  | 20 | 70 |
|  | 15 | 0 | 0 | 90 | 20 |  | 70 | 30 | 60 |
| 1.0095 | 500 | 60 | 70 | 100 | 60 | 100 | 100 | 90 | 90 |
|  | 250 | 30 | 50 | 100 | 30 | 80 | 90 | 70 | 90 |
|  | 125 | 20 | 50 | 100 | 30 | 70 | 80 | 60 | 80 |
|  | 60 | 10 | 20 | 90 | 20 |  | 80 | 40 | 80 |
|  | 30 | 0 | 20 | 90 | 0 | 70 | 70 |  | 50 |
|  | 15 | 0 | 0 | 90 | 0 | 50 | 80 | 30 | 30 |
| 1.0101 | 500 | 0 | 10 | 80 | 90 | 70 | 70 | 70 | 80 |
|  | 250 | 0 | 10 | 90 | 70 | 50 | 80 | 50 | 70 |
|  | 125 | 0 | 0 | 80 | 70 | 40 | 70 |  | 70 |
|  | 60 | 0 | 0 | 70 | 30 |  | 60 | 20 | 50 |
|  | 30 | 0 | 0 | 50 | 10 | 0 | 60 |  |  |
|  | 15 | 0 | 0 | 0 | 0 | 0 | 30 |  | 20 |
| 1.0125 | 500 | 20 | 70 | 100 | 20 | 100 | 100 | 90 | 100 |
|  | 250 | 10 | 60 | 90 | 10 | 90 | 90 | 90 | 100 |
|  | 125 | 10 | 30 | 90 | 10 |  | 90 | 60 | 80 |
|  | 60 | 10 | 20 | 90 | 0 | 80 | 90 | 20 | 90 |
|  | 30 | 10 | 0 |  | 0 | 80 | 90 | 20 | 80 |
|  | 15 | 0 | 0 | 80 | 0 | 80 | 90 |  | 80 |
| 1.0149 | 500 | 30 | 0 | 90 | 70 | 100 | 100 | 70 | 100 |
|  | 250 | 10 | 0 | 90 | 50 | 90 | 100 | 40 | 80 |
|  | 125 | 0 | 0 | 90 | 50 | 80 | 90 | 40 | 80 |
|  | 60 | 0 | 0 | 80 | 30 | 80 | 90 | 40 | 80 |
|  | 30 | 0 | 0 | 30 | 0 | 60 | 90 | 40 | 60 |
|  | 15 | 0 | 0 | 20 | 0 | 50 | 80 | 20 | 40 |
| 1.0327 | 500 | 20 | 0 | 70 | 60 | 60 | 90 | 30 | 70 |
|  | 250 | 20 | 0 | 30 | 50 | 40 | 70 | 30 | 50 |
|  | 125 | 0 | 0 | 20 | 40 | 40 | 70 | 30 | 40 |
|  | 60 | 0 | 0 | 20 | 30 | 30 | 40 | 30 | 40 |
|  | 30 | 0 | 0 | 10 | 20 | 20 | 40 | 20 | 30 |
|  | 15 | 0 | 0 | 10 | 10 | 0 | 20 | 10 | 20 |
| 1.0333 | 500 | 80 | 80 | 100 | 60 | 90 | 100 | 90 | 100 |
|  | 250 | 80 | 80 | 90 | 30 | 90 | 100 | 80 | 100 |
|  | 125 | 40 | 70 | 90 | 20 | 90 | 100 | 80 | 100 |
|  | 60 | 20 | 60 | 90 | 10 | 90 | 90 | 60 | 100 |
|  | 30 | 20 | 30 | 80 | 10 | 90 | 100 | 30 | 90 |
|  | 15 | 10 | 20 | 80 | 0 | 80 | 100 | 10 | 80 |
| 1.0345 | 500 | 80 | 80 | 90 | 80 | 90 | 100 | 80 | 100 |
|  | 250 | 40 | 50 | 90 | 50 | 90 | 100 | 60 | 100 |
|  | 125 | 40 | 20 | 90 | 20 | 90 | 100 | 60 | 80 |
|  | 60 | 10 | 20 | 90 | 10 | 80 | 90 | 50 | 90 |
|  | 30 | 10 | 10 | 70 | 0 | 80 | 90 | 30 | 80 |
|  | 15 | 10 | 0 | 60 | 0 | 40 | 90 | 20 | 60 |
| 1.0351 | 500 | 90 | 80 | 100 | 20 | 90 | 100 | 90 | 100 |
|  | 250 | 80 | 70 | 100 | 20 | 90 | 90 | 30 | 100 |
|  | 125 | 70 | 60 | 90 | 10 | 90 | 90 | 20 | 100 |
|  | 60 | 20 | 40 | 90 | 0 | 80 | 90 | 20 | 100 |
|  | 30 | 10 | 10 | 80 | 0 | 60 | 60 | 20 | 90 |
|  | 15 | 0 | 0 | 70 | 0 | 60 | 80 | 20 | 80 |

TABLE 8-continued

Control of cool season plant species by compounds of Formula (I) after post-emergence application

| Compound ID | Rate (g/Ha) | HORVW | TRZAW | POLCO | KCHSC | SINAR | STEME | GALAP | VERPE |
|---|---|---|---|---|---|---|---|---|---|
| 1.0387 | 500 | 60 | 70 | | 60 | 90 | 90 | 90 | 100 |
| | 250 | 30 | 60 | | 60 | 90 | 90 | 30 | 100 |
| | 125 | 20 | 30 | | 60 | 90 | 90 | 30 | 90 |
| | 60 | 20 | 20 | | 50 | 90 | 90 | | 90 |
| | 30 | 10 | 0 | | 20 | 80 | 90 | 20 | 80 |
| | 15 | 10 | 0 | | 10 | 70 | 90 | 10 | 70 |
| 1.0417 | 500 | 10 | 50 | 90 | 70 | 90 | 90 | 70 | 90 |
| | 250 | 10 | 30 | 90 | 60 | 90 | 90 | 40 | 80 |
| | 125 | 10 | 20 | 90 | 50 | 90 | 90 | 30 | 80 |
| | 60 | 10 | 10 | 90 | 30 | 80 | 90 | 20 | 70 |
| | 30 | 0 | 10 | 90 | 20 | 60 | 90 | 20 | 70 |
| | 15 | 0 | 0 | 90 | 0 | 60 | 90 | | 70 |
| 1.0429 | 500 | 20 | 50 | 100 | 30 | 60 | 80 | 20 | 90 |
| | 250 | 20 | 0 | 90 | 20 | 70 | 80 | 10 | 60 |
| | 125 | 0 | 0 | 90 | 20 | 60 | 70 | 20 | 60 |
| | 60 | 0 | 0 | 90 | 10 | 40 | 70 | 20 | 70 |
| | 30 | 0 | 0 | 60 | 0 | | | | 60 |
| | 15 | 0 | 0 | 0 | 0 | 40 | 70 | 20 | 60 |
| 1.0615 | 500 | 50 | 60 | 100 | 100 | 100 | 100 | 100 | 90 |
| | 250 | 30 | 40 | 100 | 100 | 100 | 100 | 100 | 80 |
| | 125 | 10 | 30 | 100 | 100 | 100 | 100 | | 60 |
| | 60 | 10 | 10 | 90 | 80 | | 100 | | 60 |
| | 30 | 0 | 0 | 100 | 80 | | 100 | | 50 |
| | 15 | 0 | 0 | 100 | 70 | 60 | 100 | | 40 |
| 1.0633 | 500 | | | | | | | | |
| | 250 | 10 | 50 | 90 | 80 | 90 | 80 | 70 | 80 |
| | 125 | 0 | 50 | 90 | 80 | 80 | 80 | 60 | 70 |
| | 60 | 0 | 20 | 80 | 60 | 70 | 80 | 60 | 60 |
| | 30 | 0 | 0 | 90 | 60 | | 90 | 50 | 50 |
| | 15 | 0 | 0 | 80 | 20 | 40 | 80 | 10 | 20 |
| 1.1653 | 500 | 20 | 40 | 100 | 70 | 90 | 100 | 80 | 90 |
| | 250 | 0 | 30 | 100 | 60 | 100 | 100 | 50 | 80 |
| | 125 | 0 | 40 | 90 | 50 | 90 | 100 | 50 | 70 |
| | 60 | 0 | 0 | 100 | 40 | 90 | 90 | 40 | 60 |
| | 30 | 0 | 0 | 100 | | 30 | 90 | 40 | 50 |
| | 15 | 0 | 0 | 90 | | 20 | 80 | 20 | 30 |

What is claimed is:

1. A compound of formula (I)

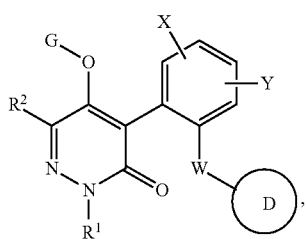

(I)

or a salt or N-oxide thereof, wherein

R¹ is selected from the group consisting of $C_1$-$C_4$ alkyl, $C_3$-$C_6$cycloalkyl, $C_3$-$C_6$alkoxy, $C_1$-$C_2$ alkoxy-$C_1$-$C_2$ alkyl, $C_2$-$C_4$ alkenyl, $C_1$-$C_4$ haloalkyl, cyano-$C_1$-$C_4$alkyl, $C_2$-$C_4$ haloalkenyl, $C_2$-$C_4$ alkynyl and $C_2$-$C_4$ haloalkynyl;

R² is selected from the group consisting of hydrogen, halogen, cyano, $C_1$-$C_6$alkyl, $C_1$-$C_6$haloalkyl, $C_1$-$C_6$haloalkoxy, $C_1$-$C_3$haloalkoxy-$C_1$-$C_3$alkyl-, $C_1$-$C_6$alkoxy, $C_1$-$C_3$alkoxy-$C_1$-$C_3$alkyl, $C_1$-$C_3$alkoxy-$C_1$-$C_3$alkoxy-$C_1$-$C_3$alkyl-, $C_3$-$C_6$cycloalkyl, $C_2$-$C_6$ alkenyl, $C_2$-$C_6$ haloalkenyl, $C_2$-$C_6$ alkynyl, $C_1$-$C_6$hydroxyalkyl-, $C_1$-$C_6$alkylcarbonyl-, —S(O)$_m$$C_1$-$C_6$alkyl, amino, $C_1$-$C_6$alkylamino, $C_1$-$C_6$dialkylamino, —C($C_1$-$C_3$alkyl)=N—O—$C_1$-$C_3$alkyl and $C_2$-$C_6$ haloalkynyl;

G is hydrogen, or C(O)R³;

R³ is selected from the group consisting of $C_1$-$C_6$alkyl, $C_2$-$C_6$alkenyl, $C_2$-$C_6$alkynyl, $C_1$-$C_6$alkyl-S—, $C_1$-$C_6$alkoxy, —NR⁴R⁵ and phenyl optionally substituted by one or more R⁶;

R⁴ and R⁵ are independently selected from the group consisting of $C_1$-$C_6$ alkyl and $C_1$-$C_6$ alkoxy, or R⁴ and R⁵ together can form a morpholinyl ring; and, R⁶ is selected from the group consisting of halogen, cyano, nitro, $C_1$-$C_3$alkyl, $C_1$-$C_3$haloalky, $C_1$-$C_3$alkoxy and $C_1$-$C_3$haloalkoxy;

X and Y are each independently hydrogen, $C_1$-$C_3$ alkyl, $C_1$-$C_3$ alkoxy, $C_1$-$C_3$haloalkyl, $C_1$-$C_3$haloalkoxy, or halogen;

D is a substituted or unsubstituted monocyclic heteroaryl ring containing 1, 2, or 3 heteroatoms independently selected from oxygen, nitrogen and sulphur, and wherein when D is substituted it is substituted on at least one ring carbon atom with R⁸ and/or on a ring nitrogen atom with R⁹;

each R⁸ is independently oxygen, hydroxyl, halogen, cyano, $C_1$-$C_6$alkyl, $C_1$-$C_6$haloalkyl, $C_1$-$C_6$haloalkoxy, $C_1$-$C_3$haloalkoxy-$C_1$-$C_3$alkyl-, $C_1$-$C_6$alkoxy, $C_1$-$C_3$alkoxy-$C_1$-$C_3$alkyl, $C_1$-$C_3$alkoxy-$C_1$-$C_3$alkoxy- $C_1$-$C_3$alkyl-, $C_3$-$C_6$cycloalkyl, $C_2$-$C_6$ alkenyl, $C_2$-$C_6$ haloalkenyl, $C_2$-$C_6$ alkynyl, $C_1$-$C_6$hydroxyalkyl-, $C_1$-$C_6$alkylcarbonyl-, $C_1$-$C_6$alkyl-S(O)$_m$—, amino, $C_1$-$C_6$alkylamino, $C_1$-$C_6$dialkylamino, —C($C_1$-$C_3$alkyl)=N—O—$C_1$-$C_3$alkyl and $C_2$-$C_6$ haloalkynyl;

m is an integer of 0, 1, or 2; and each $R^9$ is independently, $C_1$-$C_4$ alkyl, $C_3$-$C_6$alkoxy, $C_1$-$C_2$ alkoxy-$C_1$-$C_2$ alkyl, $C_2$-$C_4$ alkenyl, $C_1$-$C_4$ haloalkyl, $C_2$-$C_4$ haloalkenyl, $C_2$-$C_4$ alkynyl or $C_2$-$C_4$ haloalkynyl;

or D is a substituted or unsubstituted phenyl ring (Dp),

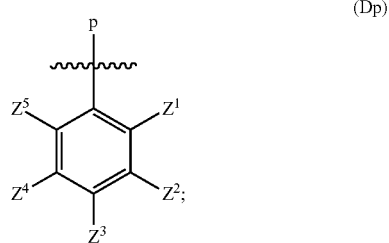

wherein p denotes the point of attachment of (Dp) to the rest of the molecule;

$Z^1$, $Z^2$, $Z^3$, $Z^4$, and $Z^5$ are each independently selected from the group consisting of hydrogen, cyano, amino, $C_1$-$C_3$dialkylamino, hydroxy, $C_1$-$C_3$ alkyl, $C_1$-$C_4$ alkoxy, $C_1$-$C_3$haloalkyl, $C_1$-$C_3$haloalkoxy, and halogen;

and,

W is either

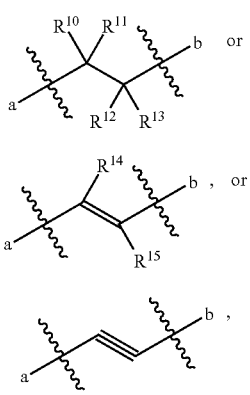

wherein

"a" denotes the point of attachment to the phenyl-pyridazine dione/phenyl-pyridazinone moiety, "b" denotes the point of attachment to ring D, $R^{10}$, $R^{12}$, $R^{14}$ and $R^{15}$ are each independently hydrogen, $C_1$-$C_3$alkyl, or $C_1$-$C_3$haloalkyl;

or $R^{10}$ and $R^{12}$ together with the carbon atoms to which they are joined form a $C_3$-$C_6$ carbocyclic ring;

$R^{11}$ and $R^{13}$ are each independently hydrogen, halogen, $C_1$-$C_3$alkyl, or $C_1$-$C_3$haloalkyl, provided that when one of $R^{11}$ or $R^{13}$ is halogen, $C_1$-$C_3$alkyl or $C_1$-$C_3$ haloalkyl, the other is hydrogen.

2. The compound according to claim 1, wherein G is hydrogen or —C(O)$R^3$, and $R^3$ is $C_1$-$C_4$ alkyl, $C_2$-$C_3$alkenyl, $C_2$-$C_3$alkynyl,—$C_1$-$C_4$alkoxy, —NR$^4$R$^5$ wherein R$^4$ and R$^5$ together form a morpholinyl ring, or phenyl.

3. The compound according to claim 1, wherein G is hydrogen or C(O)$R^3$ wherein $R^3$ is isopropyl, t-butyl, methyl, ethyl, propargyl, methoxy, ethoxy, or tert-butoxy.

4. The compound of claim 1 wherein X is hydrogen, halogen, or $C_1$haloalkyl.

5. The compound of claim 1 wherein Y is hydrogen, $C_1$-$C_3$ alkyl, $C_1$-$C_3$haloalkyl, or halogen.

6. The compound according to claim 1 wherein $R^1$ is methyl, ethyl, n-propyl, cyclopropyl, propargyl, or $C_1$haloalkyl.

7. The compound according to claim 1 wherein $R^2$ is selected from the group consisting of hydrogen, $C_1$-$C_6$alkyl, $C_1$-$C_6$haloalkyl, $C_1$-$C_6$alkoxy, $C_1$-$C_3$alkoxy-$C_1$-$C_3$alkyl, $C_3$-$C_6$cycloalkyl, $C_2$-$C_6$ alkenyl, $C_2$-$C_6$ haloalkenyl, $C_2$-$C_6$ alkynyl and $C_2$-$C_6$ haloalkynyl.

8. The compound according to claim 1 wherein D is a substituted or unsubstituted furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyridonyl, pyrimidinyl, pyridazinyl, pyrazinyl, 1,2,3-triazinyl, 1,2,4-triazinyl, or 1,3,5-triazinyl ring.

9. The compound according to claim 1 wherein each $R^8$ is independently oxo, $C_1$-$C_4$alkyl, $C_1$-$C_4$haloalkyl, halogen, cyano, hydroxyl, $C_1$-$C_4$alkoxy, or $C_1$-$C_4$alkylthio.

10. The compound according to claim 1 wherein D is Dp and each Z is independently selected from hydrogen, cyano, halogen, methyl, methoxy, and trifluoromethyl.

11. The compound according to claim 1 wherein W is W1 and each of $R^{10}$, $R^{11}$, $R^{12}$, and $R^{13}$ is hydrogen.

12. The compound according to claim 1 wherein W is W2 and each of $R^{14}$ and $R^{15}$ is hydrogen.

13. The compound according to claim 1 wherein W is W3.

14. The compound according to claim 2, wherein G is hydrogen or C(O)$R^3$ wherein $R^3$ is isopropyl, t-butyl, methyl, ethyl, propargyl, methoxy, ethoxy, or tert-butoxy.

15. A herbicidal composition comprising a herbicidal compound according to claim 1 and an agriculturally acceptable formulation adjuvant.

16. A herbicidal composition according to claim 15, further comprising at least one additional pesticide.

17. A herbicidal composition according to claim 16, wherein the additional pesticide is a herbicide or herbicide safener.

18. A method of controlling unwanted plant growth, comprising applying a compound of formula (I) as defined in claim 1, to the unwanted plants or to the locus thereof.

19. A method of controlling unwanted plant growth, comprising applying a herbicidal composition according to claim 15, to the unwanted plants or to the locus thereof.

* * * * *